US012767661B2

(12) United States Patent
Kai et al.

(10) Patent No.: US 12,767,661 B2
(45) Date of Patent: Oct. 20, 2026

(54) ORGANIC ELECTROLUMINESCENT ELEMENT

(71) Applicant: NIPPON STEEL CHEMICAL & MATERIAL CO., LTD., Tokyo (JP)

(72) Inventors: Takahiro Kai, Tokyo (JP); Kentaro Hayashi, Tokyo (JP); Junya Ogawa, Tokyo (JP); Yuji Ikenaga, Tokyo (JP); Ayaka Terada, Tokyo (JP); Kazunari Yoshida, Tokyo (JP); Ikumi Kitahara, Tokyo (JP); Haruka Izumi, Tokyo (JP); Katsuhide Noguchi, Tokyo (JP); Atsushi Kawada, Tokyo (JP)

(73) Assignee: NIPPON STEEL CHEMICAL & MATERIAL CO., LTD., Tokyo (JP)

(*) Notice: Subject to any disclaimer, the term of this patent is extended or adjusted under 35 U.S.C. 154(b) by 972 days.

(21) Appl. No.: 18/012,379

(22) PCT Filed: Jun. 29, 2021

(86) PCT No.: PCT/JP2021/024526
§ 371 (c)(1),
(2) Date: Dec. 22, 2022

(87) PCT Pub. No.: WO2022/004709
PCT Pub. Date: Jan. 6, 2022

(65) Prior Publication Data
US 2023/0284526 A1 Sep. 7, 2023

(30) Foreign Application Priority Data
Jun. 30, 2020 (JP) ................................. 2020-112859

(51) Int. Cl.
*H10K 101/00* (2023.01)
*C07D 487/04* (2006.01)
*H10K 71/16* (2023.01)
*H10K 85/60* (2023.01)
*H10K 50/12* (2023.01)
*H10K 101/30* (2023.01)

(52) U.S. Cl.
CPC ........... *C07D 487/04* (2013.01); *H10K 71/16* (2023.02); *H10K 85/6572* (2023.02); *H10K 85/6574* (2023.02); *H10K 85/6576* (2023.02); *H10K 50/12* (2023.02); *H10K 2101/30* (2023.02); *H10K 2101/90* (2023.02)

(58) Field of Classification Search
None
See application file for complete search history.

(56) References Cited

U.S. PATENT DOCUMENTS

| | | | | |
|---|---|---|---|---|
| 12,473,256 | B2 * | 11/2025 | Kim | H10K 85/654 |
| 2012/0241732 | A1 | 9/2012 | Endo et al. | |
| 2013/0112952 | A1 | 5/2013 | Adamovich et al. | |
| 2014/0306207 | A1 | 10/2014 | Nishimura et al. | |
| 2014/0374728 | A1 | 12/2014 | Adamovich et al. | |
| 2015/0041785 | A1 | 2/2015 | Sannomiya et al. | |
| 2017/0098778 | A1 | 4/2017 | Oh et al. | |
| 2018/0083201 | A1 | 3/2018 | Ogawa et al. | |
| 2018/0138420 | A1 | 5/2018 | Tada et al. | |
| 2019/0036055 | A1 * | 1/2019 | Lin | H10K 85/346 |
| 2020/0266357 | A1 * | 8/2020 | Lui | H10K 85/653 |
| 2020/0266358 | A1 * | 8/2020 | Yang | H10K 85/6574 |
| 2021/0009616 | A1 * | 1/2021 | Kim | H10K 85/346 |
| 2021/0083195 | A1 * | 3/2021 | Ogawa | H10K 85/342 |
| 2021/0143340 | A1 * | 5/2021 | Ogawa | H10K 85/654 |
| 2021/0376245 | A1 * | 12/2021 | Kim | H10K 85/615 |
| 2021/0376252 | A1 * | 12/2021 | Sun | C09K 11/06 |
| 2022/0006029 | A1 * | 1/2022 | Seo | H10K 85/654 |

(Continued)

FOREIGN PATENT DOCUMENTS

| | | | |
|---|---|---|---|
| CN | 110492009 | A | 11/2019 |
| KR | 10-2020-0017727 | A | 2/2020 |

(Continued)

OTHER PUBLICATIONS

Zhang, Gang, and Charles B. Musgrave. "Comparison of DFT methods for molecular orbital eigenvalue calculations." The journal of physical chemistry A 111.8 (2007): 1554-1561. (Year: 2007).*

(Continued)

*Primary Examiner* — Robert S Loewe

(74) *Attorney, Agent, or Firm* — Birch, Stewart, Kolasch & Birch, LLP

(57) ABSTRACT

To provide an organic electroluminescent device having long lifetime characteristics while having a low driving voltage and high power efficiency. The organic electroluminescent device includes one or more light-emitting layers between an anode and a cathode opposed to each other, wherein at least one of the light-emitting layers contains a host material including a first host material, a second host material and a third host material, and a light-emitting dopant material. A LUMO energy of the first host material is −1.95 eV or less, and LM2≥LM3≥LM1 is satisfied under the assumption that LUMO energies of the first host material, the second host material and the third host material are LM1, LM2 and LM3, respectively. A suitable first host material is an indolocarbazole compound represented by general formula (1), a suitable second host material is, for example, a biscarbazole compound represented by general formula (2), and a suitable third host material is an indolocarbazole compound represented by general formula (5).

18 Claims, 1 Drawing Sheet

(56) References Cited

U.S. PATENT DOCUMENTS

| | | | | |
|---|---|---|---|---|
| 2022/0123246 A1* | 4/2022 | Syn | C09K 11/06 | |
| 2022/0199913 A1* | 6/2022 | Ogawa | C09K 11/06 | |
| 2022/0199914 A1* | 6/2022 | Ogawa | C07D 487/04 | |
| 2023/0033529 A1* | 2/2023 | Shiomi | H10K 85/654 | |
| 2023/0119201 A1* | 4/2023 | Kim | H10K 85/6572 | 257/40 |
| 2023/0172065 A1* | 6/2023 | Park | C07D 487/04 | 257/40 |
| 2023/0200229 A1* | 6/2023 | Suh | C09K 11/06 | 257/40 |
| 2023/0240140 A1* | 7/2023 | Han | H10K 85/6572 | |
| 2023/0263054 A1* | 8/2023 | Hwang | H10K 85/633 | 257/40 |
| 2023/0301183 A1* | 9/2023 | Lee | H10K 85/6574 | 257/40 |

FOREIGN PATENT DOCUMENTS

| | | | |
|---|---|---|---|
| WO | WO 2011/070963 A1 | 6/2011 | |
| WO | WO 2011/136755 A1 | 11/2011 | |
| WO | WO 2013/062075 A1 | 5/2013 | |
| WO | WO-2016068458 A1 * | 5/2016 | H10K 50/12 |
| WO | WO 2016/158191 A1 | 10/2016 | |
| WO | WO 2016/194604 A1 | 12/2016 | |
| WO | WO 2018/198844 A1 | 11/2018 | |
| WO | WO-2020032424 A1 * | 2/2020 | H10K 50/00 |

OTHER PUBLICATIONS

Document published by Ossila "Understanding HOMO and LUMO", no author listed, 9 pages. (Year: 2026).*

Cai et al., "High-Efficiency Solution-Processed Small Molecule Electrophosphorescent Organic Light-Emitting Diodes", Advanced Materials, 2011, vol. 23, p. 3590-3596.

International Preliminary Report on Patentability, issued in PCT/JP2021/024526, PCT/IPEA/409, dated Jun. 21, 2022.

International Search Report, issued in PCT/JP2021/024526, PCT/ISA/210, dated Aug. 24, 2021.

Written Opinion of the International Searching Authority, issued in PCT/JP2021/024526, PCT/ISA/237, dated Aug. 24, 2021.

* cited by examiner

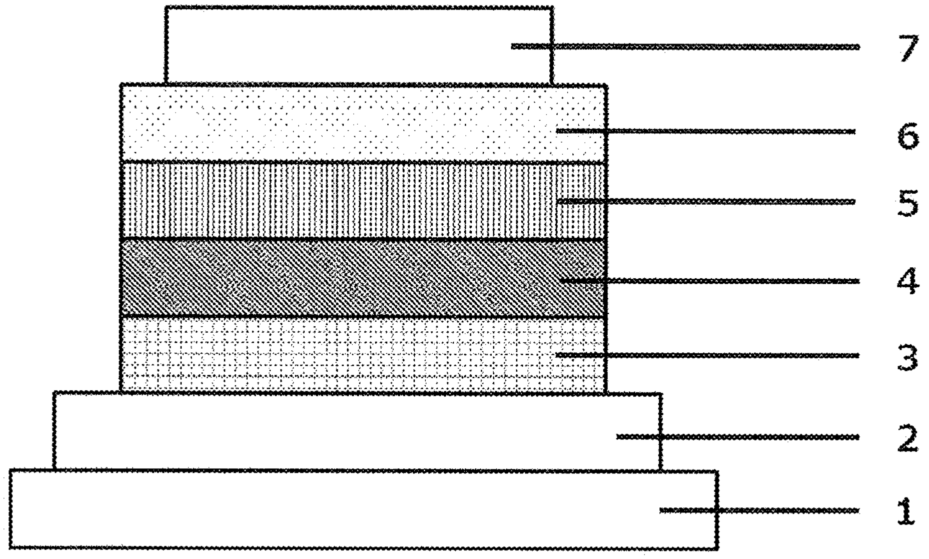
7
6
5
4
3
2
1

ORGANIC ELECTROLUMINESCENT ELEMENT

TECHNICAL FIELD

The present invention relates to an organic electroluminescent device (organic EL device).

BACKGROUND ART

Application of a voltage to an organic electroluminescent device allows injection of holes and electrons from an anode and a cathode, respectively, into a light-emitting layer. Then, in the light-emitting layer, injected holes and electrons recombine to generate excitons. At this time, according to statistical rules of electron spins, singlet excitons and triplet excitons are generated at a ratio of 1:3. Regarding a fluorescence-emitting organic electroluminescent device using light emission from singlet excitons, it is said that the internal quantum efficiency thereof has a limit of 25%. Meanwhile, regarding a phosphorescent organic electroluminescent device using light emission from triplet excitons, it is known that intersystem crossing is efficiently performed from singlet excitons, the internal quantum efficiency is enhanced to 100%.

Recently, highly efficient organic electroluminescent devices utilizing delayed fluorescence have been developed. There is known, for example, an organic electroluminescent device utilizing a TTF (Triplet-Triplet Fusion) mechanism, which is one of delayed fluorescence mechanisms. The TTF mechanism utilizes a phenomenon in which singlet excitons are generated due to collision of two triplet excitons, and it is thought that the internal quantum efficiency can be theoretically raised to 40%. However, since the efficiency is lower compared to phosphorescent organic electroluminescent devices, further improvement in efficiency is required.

Patent Literature 1 discloses an organic electroluminescent device utilizing a TADF (Thermally Activated Delayed Fluorescence) mechanism. The TADF mechanism utilizes a phenomenon in which reverse intersystem crossing from triplet excitons to singlet excitons is generated in a material having a small energy difference between a singlet level and a triplet level, and it is thought that the internal quantum efficiency can be theoretically raised to 100%. Devices utilizing fluorescent materials or phosphorescent materials, and devices utilizing TADF mechanism, which are currently in practical use, are respectively demanded to be further enhanced in efficiency characteristics, voltage characteristics and driving lifetime, and demanded to realize characteristics at practical levels.

CITATION LIST

Patent Literature

Patent Literature 1: WO2011/070963A
Patent Literature 2: WO2013/062075A
Patent Literature 3: US2014/0374728A
Patent Literature 4: WO2011/136755A
Patent Literature 5: WO2016/194604A
Patent Literature 6: WO2018/0198844A
Patent Literature 7: US2017/098778A
Patent Literature 8: KR2020-017727A

Non Patent Literature

Non Patent Literature 1: Adv. Mater, 2011, 23, 3590-3596

Patent Literatures 2 and 3 disclose use of a biscarbazole compound as a mixed host material.

Patent Literature 4 discloses use of a host material in which a plurality of host materials containing an indolocarbazole compound is premixed.

Patent Literatures 5 and 6 disclose use of a mixed host material containing an indolocarbazole compound and a biscarbazole compound.

Patent Literatures 7 and 8, and Non Patent Literature 1 disclose use of a mixed host material containing three host materials.

However, none of these can be said to be sufficient, and further improvement is desired.

SUMMARY OF INVENTION

In order to apply organic electroluminescent devices to display devices such as flat panel displays, or light sources, it is necessary to improve the driving voltage and the luminous efficiency of devices and at the same time, to sufficiently secure the stability during driving. An object of the present invention is to provide an organic electroluminescent device exhibiting long driving lifetime characteristics while having a low driving voltage and high efficiency, and a material for organic electroluminescent device suitable therefor.

It is effective for enhancements in lifetime characteristics of organic electroluminescent devices to not only enhance the stability in a more active state than the ground state, for example, the charged state or excited state of materials used, but also reduce the frequency of the active state per molecule, namely, to disperse the active state to many molecules. It is important particularly for dispersion of the excited state to suitably adjust the injection ability and the transport ability of electrons and holes into light-emitting layers, namely, adjust the charge balance. Furthermore, the charge balance is adjusted to thereby reduce leakage of electrons, holes and excitons to surrounding layers, also leading to an enhancement in lifetime and furthermore allowing the effect of enhancing efficiency to be obtained.

In order to realize them, a procedure is currently adopted mainly for a phosphorescent layer, in which the charge balance is optimized by mixing two host materials of a combination of an electron injecting/transporting host and a hole injecting/transporting host, and adjusting the mixing ratio. On the other hand, mixing of two host materials, while results in enhancements in lifetime characteristics, has the problem of causing deterioration in charge injection/transport ability and thus an increase in driving voltage.

As a result of intensive studies, the present inventors have found that use of a specific first host material, a second host material, and a third host material provides an organic electroluminescent device exhibiting excellent characteristics, and have completed the present invention.

The present invention is an organic electroluminescent device including one or more light-emitting layers between an anode and a cathode opposed to each other, wherein at least one of the light-emitting layers contains a host material including a first host material, a second host material and a third host material, and a light-emitting dopant material, a LUMO energy of the first host material is −1.95 eV or less, and $LM2 \geq LM3 \geq LM1$ is satisfied under the assumption that LUMO energies of the first host material, the second host material and the third host material are LM1, LM2 and LM3, respectively.

In a preferred aspect, the LUMO energy of the second host material is −1.54 eV or more, the LUMO energy of the third host material is −1.94 to −1.77 eV, or triplet excitation (T1) energies of the first host material, the second host material and the third host material are each 2.55 eV or more.

In a preferred aspect, at least three materials of the first host material, the second host material and the third host material, and the light-emitting dopant material are vapor deposited from one vapor deposition source, or the first host material, the second host material and the third host material are vapor deposited from one vapor deposition source.

Examples of the light-emitting dopant material include a material emitting fluorescence including thermally activated delayed fluorescence, or a phosphorescence-emitting material.

The first host material can be a compound represented by the following general formula (1).

[C 1]

(1)

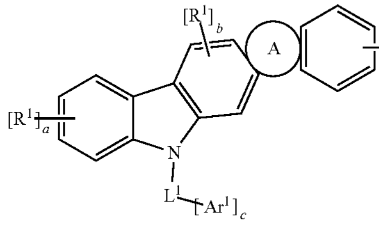

(1a)

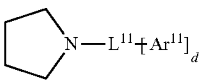

In the formula, a ring A is a heterocycle represented by formula (1a) and the ring A is fused to an adjacent ring at any position,

- $R^1$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other,
- a, c and d each independently represent an integer of 0 to 4, and b represents an integer of 0 to 2, and
- $L^1$ and $L^{11}$ independently represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group.
- $Ar^1$ and $Ar^{11}$ each independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other.

It is preferred that at least one of $L^1$ and $L^{11}$ represents a substituted or unsubstituted nitrogen-containing 6-membered ring group, or a substituted or unsubstituted ring-fused aromatic heterocyclic group containing a nitrogen-containing 6-membered ring.

The compound represented by the general formula (1) is a compound represented by the following formula (11), formula (12) or formula (13).

[C 2]

(11)

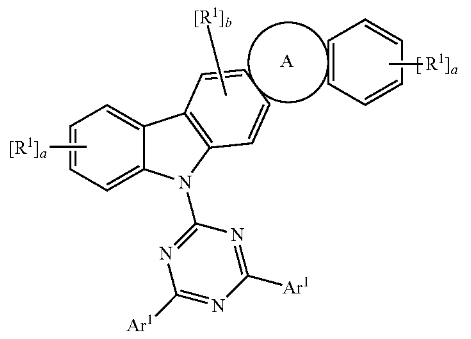

[C 3]

(12)

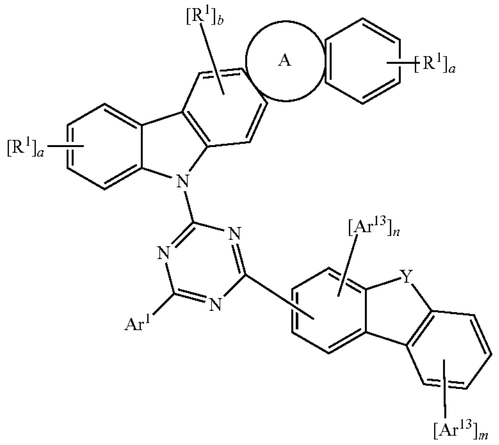

(13)

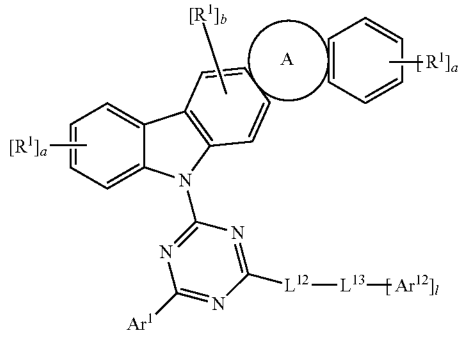

In the formulas, $R^1$, a ring A, $Ar^1$, a and b are as defined for the general formula (1),

- Y represents O, S, $NAr^{14}$, or $CAr^{15}Ar^{16}$,
- $Ar^{13}$, $Ar^{14}$, $Ar^{15}$, and $Ar^{16}$ each independently represent an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, and
- m represents an integer of 0 to 4, n represents an integer of 0 to 3, and l represents an integer of 0 to 4.

$L^{12}$ represents a substituted or unsubstituted aromatic hydrocarbon group having 6 to 30 carbon atoms, $L^{13}$ represents a nitrogen-containing 6-membered ring group, and $Ar^{12}$ independently represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other.

The second host material can be a compound represented by the following general formula (2), general formula (3), or general formula (4).

[C 4]

(2)

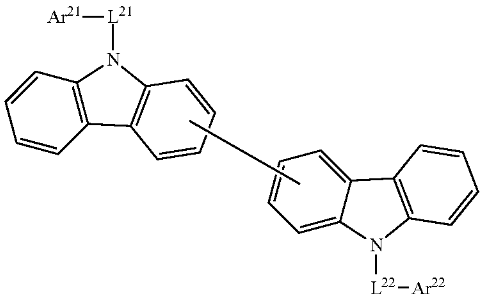

In the formula, $Ar^{21}$ and $Ar^{22}$ independently represent hydrogen, deuterium, a substituted or unsubstituted aromatic hydrocarbon group having 6 to 14 carbon atoms, an aromatic heterocyclic group having 3 to 17 carbon atoms, or a substituted or unsubstituted linked aromatic group in which two of these aromatic rings are linked to each other. $L^{21}$ and $L^{22}$ independently represent a direct bond or a phenylene group.

[C 5]

(3)

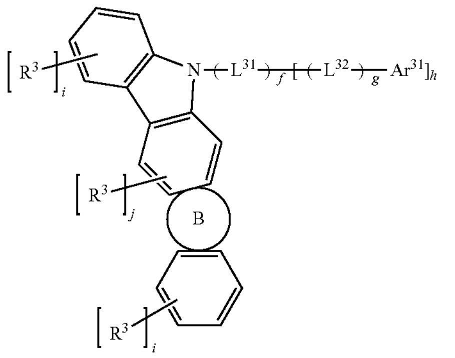

(3a)

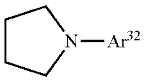

In the formula, a ring B is a heterocycle represented by formula (3a) and the ring B is fused to an adjacent ring at any position, $R^3$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, $L^{31}$ independently represents a substituted or unsubstituted aromatic hydrocarbon group having 6 to 30 carbon atoms, or a substituted or unsubstituted aromatic heterocyclic group having 3 to 17 carbon atoms, $L^{32}$ independently represents a substituted or unsubstituted aromatic hydrocarbon group having 6 to 10 carbon atoms, $A^{31}$ represents a substituted or unsubstituted aromatic hydrocarbon group having 6 to 10 carbon atoms, a substituted or unsubstituted carbazolyl group, or a substituted or unsubstituted linked aromatic group in which two to five of these aromatic rings are linked to each other, $Ar^{32}$ represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, i represents an integer of 0 to 4, and j represents an integer of 0 to 2, f is the number of repetitions, and represents an integer of 1 to 3, g is the number of repetitions and independently represents an integer of 0 to 3, and h represents the number of substitutions and represents an integer of 0 to 7.

[C 6]

(4)

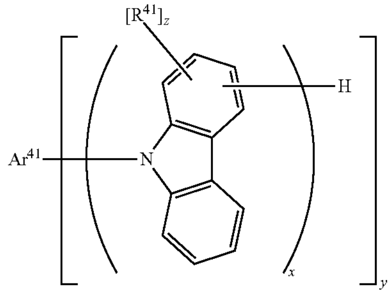

In the formula, $Ar^{41}$ represents a substituted or unsubstituted aromatic hydrocarbon group having 6 to 30 carbon atoms, a substituted or unsubstituted aromatic heterocyclic group having 3 to 17 carbon atoms, or a linked aromatic group in which two to five of these aromatic rings are linked. When $Ar^{41}$ has a hydrogen atom, the hydrogen atom may be replaced by deuterium.

$R^{41}$ each independently represents, deuterium, an aliphatic hydrocarbon group having 1 to 10 carbon atoms, a substituted or unsubstituted aromatic hydrocarbon group having 6 to 30 carbon atoms, or a substituted or unsubstituted aromatic heterocyclic group having 3 to 17 carbon atoms, provided that $R^{41}$ is not a carbazolyl group. x is the number of repetitions and independently represents an integer of 1 to 4, provided that at least one x is an integer of 2 to 4. y is the number of substitutions and represents an integer of 1 to 4. When x and y are each 2 or more, a plurality of carbazolyl groups in the formula may be the same or different. z is an integer of 0 to 3.

The third host material can be a compound represented by the following general formula (5).

[C 7]

(5)

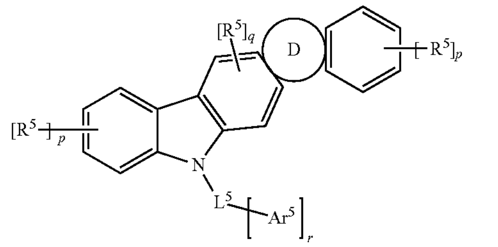

(5a)

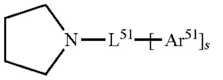

In the formula, a ring D is a heterocycle represented by formula (5a) and the ring D is fused to an adjacent ring at any position, $R^5$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, p, r and s each independently represent an integer of 0 to 4, and q represents an integer of 0 to 2, $L^5$ and $L^{51}$ represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group.

$Ar^5$ and $Ar^{51}$ each independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other.

In a preferred aspect, at least one of $L^5$ and $L^{51}$ represents a substituted or unsubstituted nitrogen-containing 6-membered ring or ring-fused aromatic heterocyclic group containing a nitrogen-containing 6-membered ring.

The third host material can be a compound represented by the following formula (51).

[C 8]

(51)

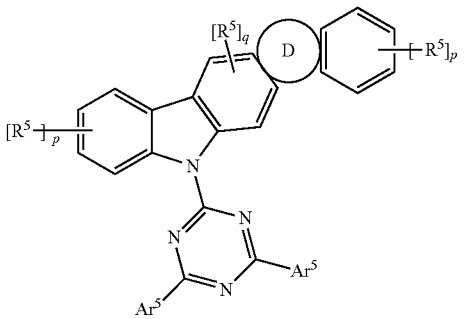

In the formula, $R^5$, D, $Ar^5$, p, and q are as defined for the general formula (5).

The proportion of the first host material can be larger than 1.0 wt % and less than 30 wt % and the proportion of the third host material can be larger than 5.0 wt % and less than 80 wt % based on the first host material, the second host material and the third host material in total.

The present invention is also a method for producing an organic electroluminescent device including one or more light-emitting layers between an anode and a cathode opposed to each other, at least one of the light-emitting layers including a host material and a light-emitting dopant material, the method including forming each of the light-emitting layers by vapor depositing the light-emitting dopant material and a host material composition in which the host material includes a first host material, a second host material and a third host material and a LUMO energy of the first host material is −1.95 eV or less. Furthermore, the present invention is a host material composition for use in the method for producing an organic electroluminescent device.

Use of a mixture of two host materials, which is currently in practical use mainly for phosphorescence-emitting devices, results in enhancements in lifetime characteristics, but has the problem of causing deterioration in charge injection/transport ability and thus an increase in driving voltage. In other words, lifetime characteristics and driving voltage are often in a trade-off relationship.

On the contrary, the present invention can allow for an improvement in driving voltage with favorable efficiency and lifetime characteristics being kept, by use of a mixed host material of three host materials including a host material having a low LUMO energy.

A conventional method in which two hosts of an electron transporting host and a hole transporting host are mixed for optimization of the charge balance effective for enhancements in lifetime characteristics has caused particularly reductions in transport rates of electrons and holes, resulting in an increase in driving voltage. It is considered that a proper amount of a host material low in LUMO energy can be further mixed to thereby result in an improvement in electron injection ability and a reduction in driving voltage with the charge balance being still optimized and favorable efficiency characteristics and lifetime characteristics being kept.

BRIEF DESCRIPTION OF DRAWING

The FIGURE is a schematic cross-sectional view showing one example of an organic electroluminescent device.

DESCRIPTION OF EMBODIMENTS

An organic electroluminescent device of the present invention has an organic layer comprising a plurality of layers between an anode and a cathode opposed to each other; and at least one layer of the plurality of layers is a light-emitting layer, and there may be a plurality of light-emitting layers. Then, at least one of the light-emitting layers contains a first host material, a second host material and a third host material, and a light-emitting dopant material. The light-emitting layer is preferably comprising a vapor deposition layer.

In the present specification, materials including the first host material, the second host material and the third host material herein are collectively referred to as "host material". The material containing the first host material, the second host material and the third host material, used for formation of the light-emitting layer by a vapor deposition method, is referred to as "host material composition".

Under the assumption that the LUMO energies of the first host material, the second host material and the third host material are LM1, LM2 and LM3, respectively, LM2≥LM3≥LM1 is satisfied. LM2>LM3>LM1 is preferably satisfied.

The LUMO energy LM1 of the first host material is −1.95 eV or less. The energy is preferably −1.97 eV or less and further preferably −2.00 eV or less.

The LUMO energy LM2 of the second host material may be −1.54 eV or more, and is preferably −1.30 eV or more and further preferably −1.07 eV or more.

The LUMO energy LM3 of the third host material may be −1.94 to −1.77 eV, and is preferably −1.94 to −1.83 eV and further preferably −1.94 to −1.87 eV.

The triplet excitation (T1) energies of the first host material, the second host material and the third host material are each preferably 2.55 eV or more, more preferably 2.60 eV or more, further preferably 2.65 eV or more.

The first host material, the second host material and the third host material may satisfy the characteristics, and the following compounds are preferred.

The compound suitable as the first host material is the compound represented by the general formula (1).

In the general formula (1), $Ar^1$ and $Ar^{11}$ each independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other. Preferred is a substituted or unsubstituted aromatic hydrocarbon group having 6 to 10 carbon atoms, a substituted or unsubstituted aromatic heterocyclic group having 3 to 12 carbon atoms, or a substituted or unsubstituted linked aromatic group in which two to seven of these aromatic rings are linked to each other.

In the case of $Ar^1$ and $Ar^{11}$ being each an unsubstituted aromatic hydrocarbon group, an unsubstituted aromatic heterocyclic group or an unsubstituted linked aromatic group, specific examples thereof include a group generated by removing one hydrogen from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, indolizine, indole, isoindole, indazole, purine, quinolizine, isoquinoline, imidazole, naphthyridine, phthalazine, carbazole, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisooxazole, benzisothiazole, or a compound formed by linking two to seven of these to each other. Preferred is a group generated from pyridine, pyrimidine, triazine, dibenzofuran, dibenzothiophene, carbazole, benzene, naphthalene, or a compound formed by linking two to seven of these to each other.

$R^1$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other. Preferred is an aliphatic hydrocarbon group having 1 to 6 carbon atoms, a substituted or unsubstituted aromatic hydrocarbon group having 6 to 10 carbon atoms, or a substituted or unsubstituted aromatic heterocyclic group having 3 to 12 carbon atoms.

When $R^1$ represents an aliphatic hydrocarbon group, the group may be linear, branched or cyclic, and is preferably an aliphatic hydrocarbon group having 1 to 8 carbon atoms and further preferably an alkyl group having 1 to 6 carbon atoms.

Specific examples of the aliphatic hydrocarbon group include methyl, ethyl, propyl, butyl, t-butyl, pentyl, hexyl, cyclohexyl, heptyl, octyl, nonyl, or decyl. The group is preferably methyl, ethyl, propyl, butyl, t-butyl, pentyl, hexyl, cyclohexyl, heptyl, or octyl, and further preferably methyl, ethyl, propyl, butyl, t-butyl, pentyl, hexyl, and cyclohexyl.

In the case of $R^1$ being an unsubstituted aromatic hydrocarbon group having 6 to 30 carbon atoms, an unsubstituted aromatic heterocyclic group having 3 to 17 carbon atoms, or an unsubstituted linked aromatic group, specific examples thereof are the same as in the case of $Ar^1$ and $Ar^{11}$ except that two to five of the aromatic rings in the linked aromatic group are linked to each other.

a, b, c and d each represent the number of substitutions, a, c and d each independently represent an integer of 0 to 4, preferably an integer of 0 to 3 and further preferably 0 to 1. b represents an integer of 0 to 2, preferably represents 0 to 1.

In the present specification, the linked aromatic group refers to an aromatic group in which respective aromatic rings of the aromatic group are bound and linked to each other by a single bond. Two or more aromatic groups linked to each other are here intended, and may be each linear or branched. These aromatic groups may be each an aromatic hydrocarbon group or an aromatic heterocyclic group, and may be the same or different.

In the present specification, the above unsubstituted aromatic hydrocarbon group, aromatic heterocyclic group, nitrogen-containing 6-membered ring group, fused aromatic heterocyclic group, carbazolyl group, or linked aromatic group each has a substituent. When the group has a substituent, the substituent is an aliphatic hydrocarbon group having 1 to 10 carbon atoms, an alkoxy group having 1 to 5 carbon atoms, an alkenyl group having 2 to 5 carbon atoms, a diarylamino group having 12 to 44 carbon atoms, deuterium, halogen, or a cyano group.

The number of substituents is 0 to 5 and preferably 0 to 3. When the aromatic hydrocarbon group and the aromatic heterocyclic group each have a substituent, the number of carbon atoms is calculated with not including the number of carbon atoms of the substituent. However, it is preferred to satisfy the above range by the number of carbon atoms including the number of carbon atoms of the substituent.

Specific examples of the substituent include cyano, methyl, ethyl, propyl, butyl, pentyl, hexyl, heptyl, octyl, nonyl, decyl, diphenylamino, naphthylphenylamino, dinaphthylamino, dianthranylamino, diphenanthrenylamino, and dipyrenylamino. Preferred examples include cyano, methyl, ethyl, propyl, butyl, pentyl, hexyl, heptyl, octyl, diphenylamino, naphthylphenylamino, or dinaphthylamino.

It is understood that hydrogen may be deuterium in the present specification. Accordingly, when a skeleton such as an indolocarbazole ring or a carbazole ring, or a group such as $R^1$, $L^{11}$ or $Ar^{11}$ in the general formulas (1) to (5) has hydrogen, such hydrogen may be partially or fully deuterium.

$L^1$ and $L^{11}$ independently represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group. It is preferred that at least one of $L^1$ and $L^{11}$ represents a substituted or unsubstituted nitrogen-containing 6-membered ring, or a substituted or unsubstituted ring-fused aromatic heterocyclic group containing a nitrogen-containing 6-membered ring.

Specific examples of $L^1$ and $L^{11}$ being each an unsubstituted aromatic group or an unsubstituted aromatic heterocyclic group are the same as in the case of $Ar^1$ and $Ar^{11}$ except that the group is (c+1)-valent or (d+1)-valent. Preferred is a group generated from pyridine, pyrimidine, triazine, quinoline, isoquinoline, quinoxaline, naphthyridine, phenazine, dibenzofuran, dibenzothiophene, carbazole, benzene, or naphthalene.

Specific examples of the unsubstituted nitrogen-containing 6-membered ring group or the unsubstituted ring-fused aromatic heterocyclic group containing a nitrogen-containing 6-membered ring include pyridine, pyrimidine, triazine, quinoline, isoquinoline, quinoxaline, naphthyridine, or phenazine.

Preferred aspects of the general formula (1) include formula (11), and preferred aspects of the formula (11) include formula (12) or formula (13).

In the formula (11) to formula (13), the same symbols as in the general formula (1) have the same meaning.

In other words, $R^1$, a ring A, $Ar^1$, a, and b are as defined for the general formula (1).

In the formula (12), Y represents O, S, $NAr^{14}$, $CAr^{15}$, or $Ar^{16}$, preferably O, S, or $NAr^{14}$, and further preferably O or S.

$Ar^{13}$, $Ar^{11}$, $Ar^{15}$, and $Ar^{16}$ each independently represent an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other. Preferred is a substituted or unsubstituted aromatic hydrocarbon group having 6 to 24 carbon atoms, a substituted or unsubstituted aromatic heterocyclic group having 3 to 17 carbon atoms, or a substituted or unsubstituted linked aromatic group in which two to five of these aromatic rings are linked to each other, and more preferred is a substituted or unsubstituted aromatic hydrocarbon group having 6 to 18 carbon atoms, a substituted or unsubstituted aromatic heterocyclic group having 3 to 12 carbon atoms, or a substituted or unsubstituted linked aromatic group in which two to five of these aromatic rings are linked to each other.

In the case of $Ar^{13}$, $Ar^{14}$, $Ar^{15}$, and $Ar^{16}$ being each an unsubstituted aromatic hydrocarbon group, an unsubstituted aromatic heterocyclic group, or an unsubstituted linked aromatic group, specific examples thereof are the same as in the case of $Ar^1$ and $Ar^{11}$, provided that two to five aromatic rings are linked to each other in the case of the linked aromatic group. In the case of an aliphatic hydrocarbon group, specific examples thereof are the same as in the case where $R^1$ is an aliphatic hydrocarbon group.

m represents an integer of 0 to 4, n represents an integer of 0 to 3, m and n are each preferably 0 to 2 and further preferably 0 to 1.

In the formula (13), $L^{12}$ represents a substituted or unsubstituted aromatic hydrocarbon group having 6 to 30 carbon atoms, preferably represents a substituted or unsubstituted aromatic hydrocarbon group having 6 to 10 carbon atoms, and further preferably represents a phenylene group represented by any of formula (1b) or formula (1c).

[C 9]

(1b)

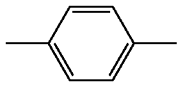

(1c)

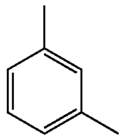

$L^{13}$ represents a nitrogen-containing 6-membered ring group, preferably represents a pyridine group or a triazine group, and further preferably represents a triazine group.

$Ar^{12}$ independently represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other. Preferred is a substituted or unsubstituted aromatic hydrocarbon group having 6 to 10 carbon atoms, a substituted or unsubstituted aromatic heterocyclic group having 3 to 12 carbon atoms, or a substituted or unsubstituted linked aromatic group in which two to five of these aromatic rings are linked to each other.

In the case of $Ar^{12}$ being an unsubstituted aromatic hydrocarbon group, an unsubstituted aromatic heterocyclic group, or an unsubstituted linked aromatic group, specific examples thereof are the same as in the case of $Ar^1$ and $Ar^{11}$ except that two to five of the aromatic rings in the linked aromatic group are linked to each other.

l represents an integer of 0 to 4, preferably 0 to 2.

Specific examples of the compounds represented by the general formula (1) are described below, but the compounds are not limited to these exemplified compounds.

[C 10]
1-1
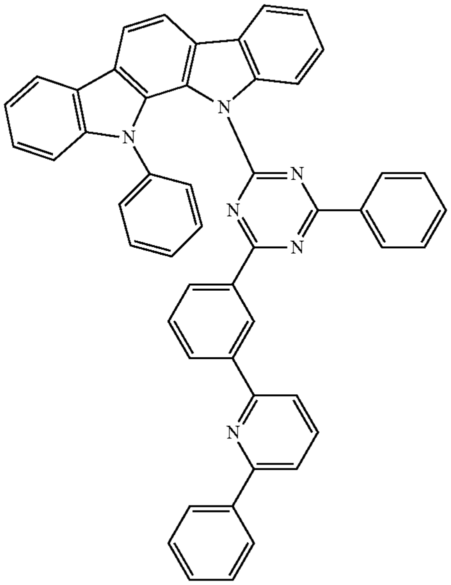
1-2
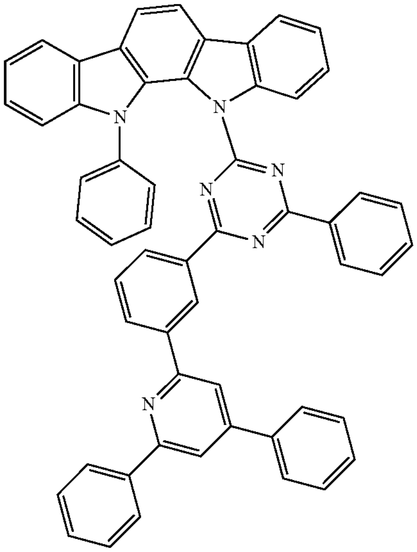
-continued
1-3
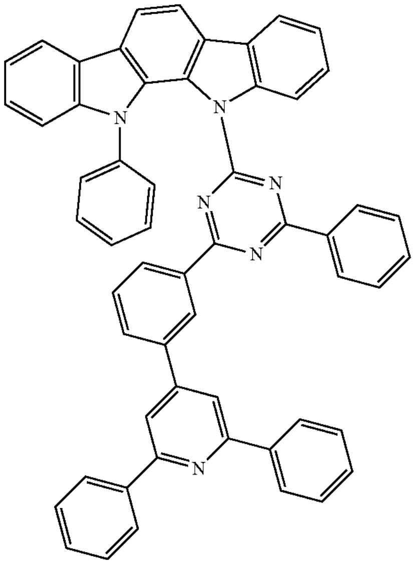
1-4
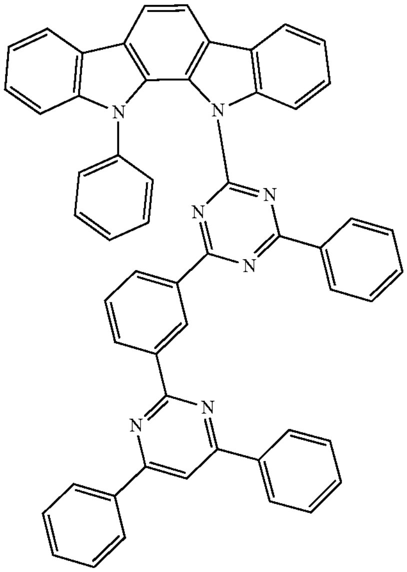

1-5
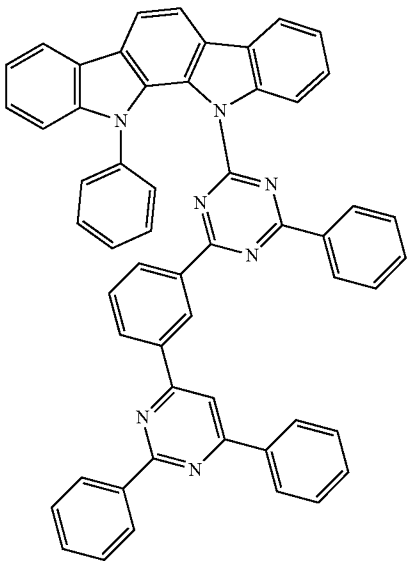
1-6
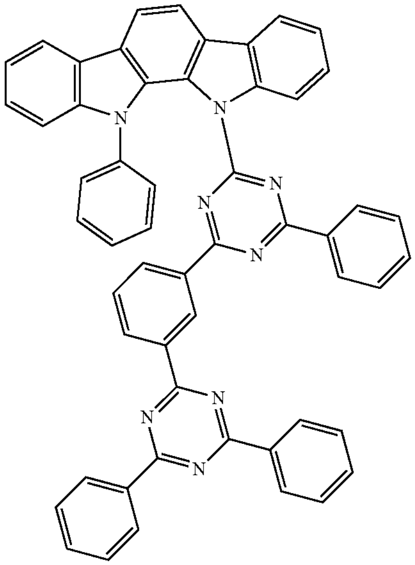
1-7
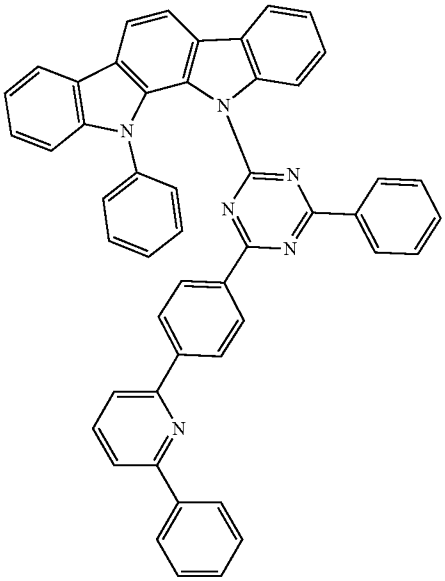
1-8
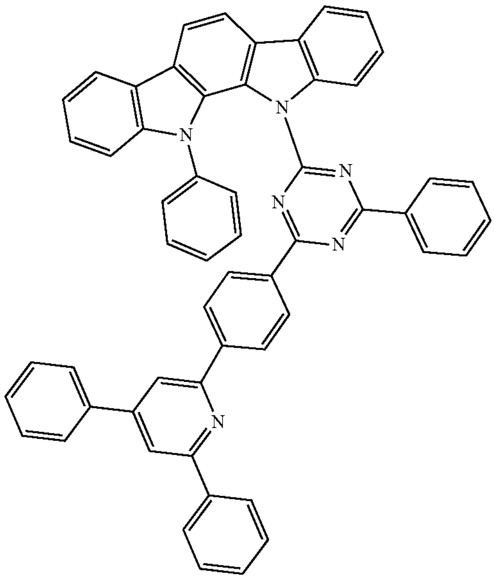

-continued
1-9
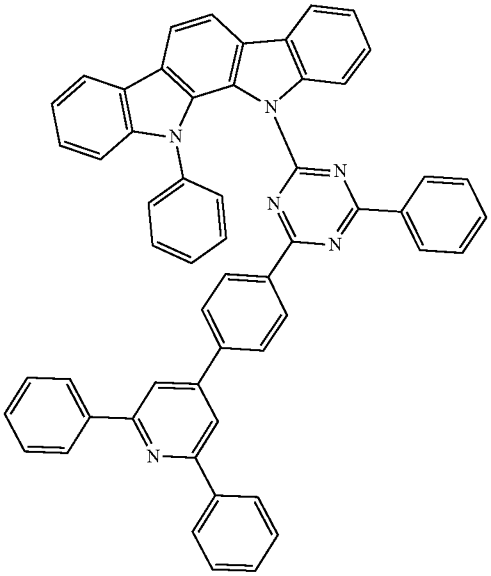
1-10
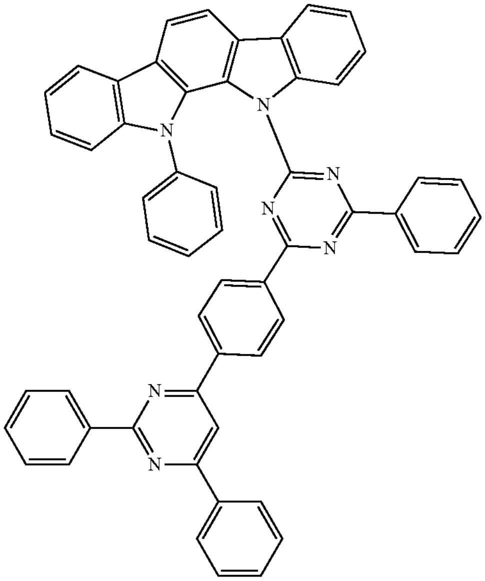
-continued
1-11
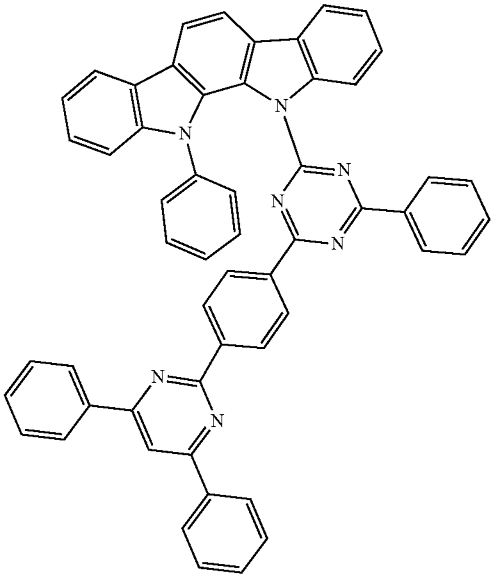
1-12
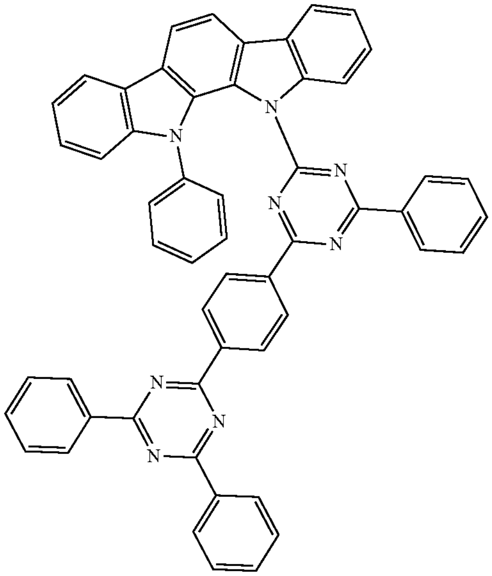
1-13
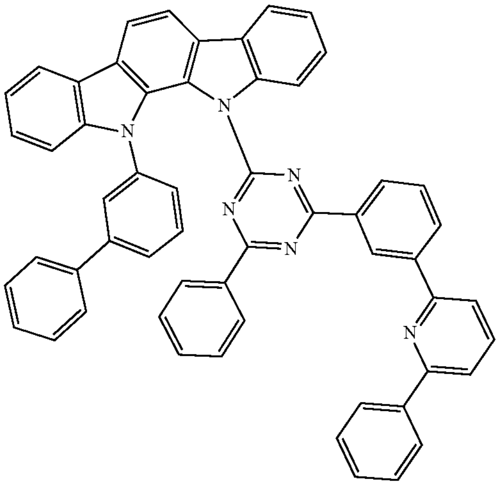

-continued
1-14
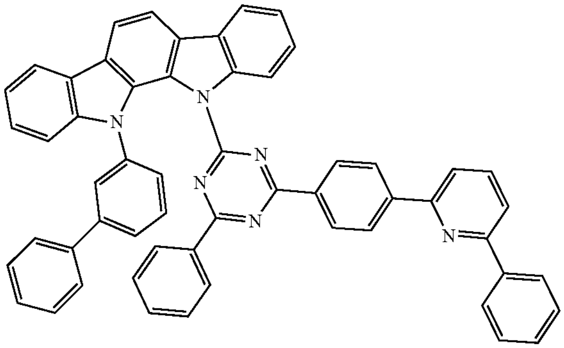
1-15
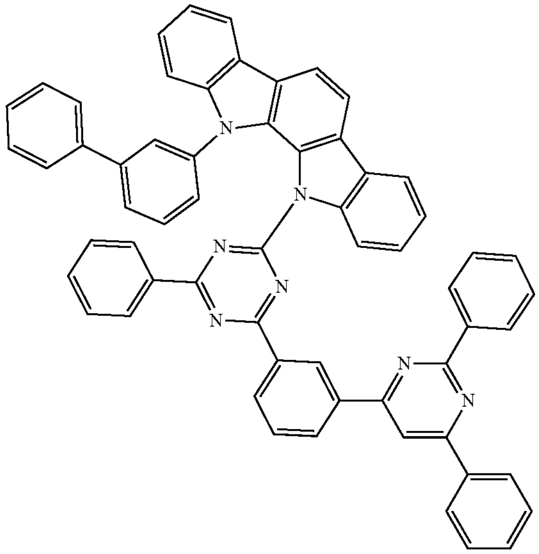
1-16
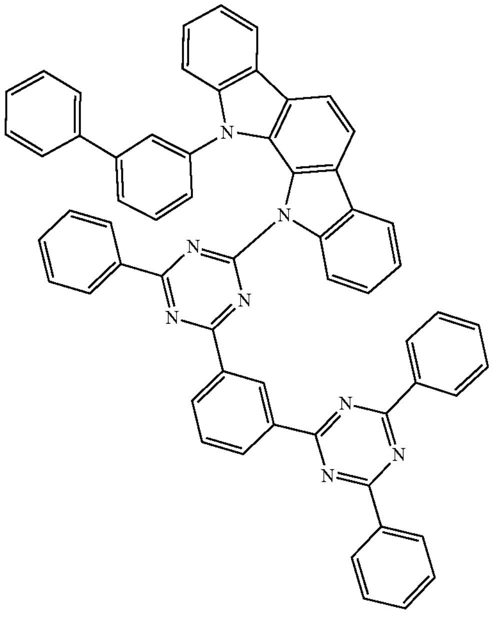
-continued
1-17
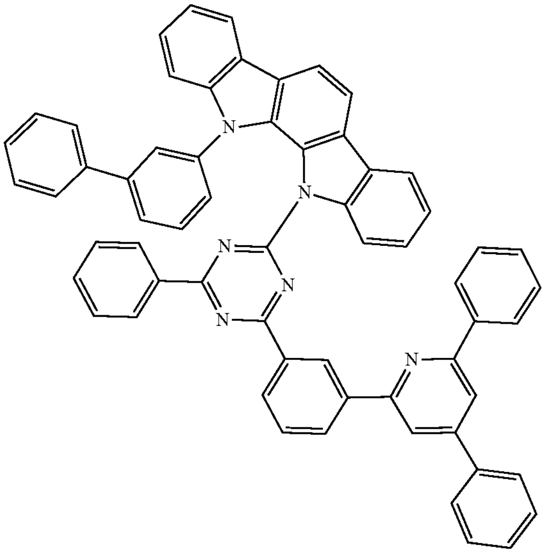
1-18
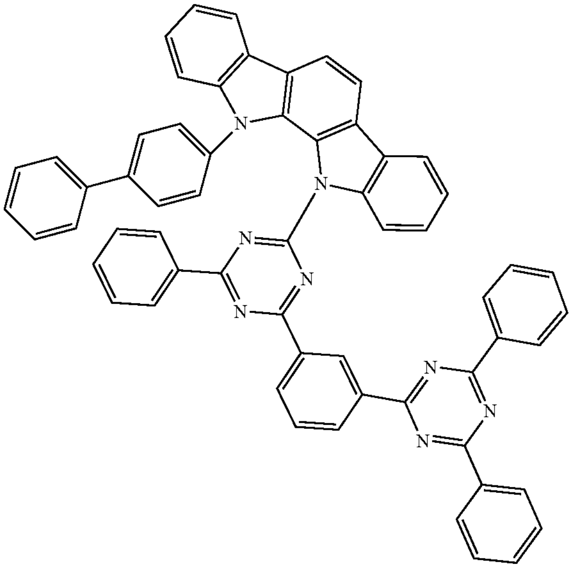

-continued
1-19
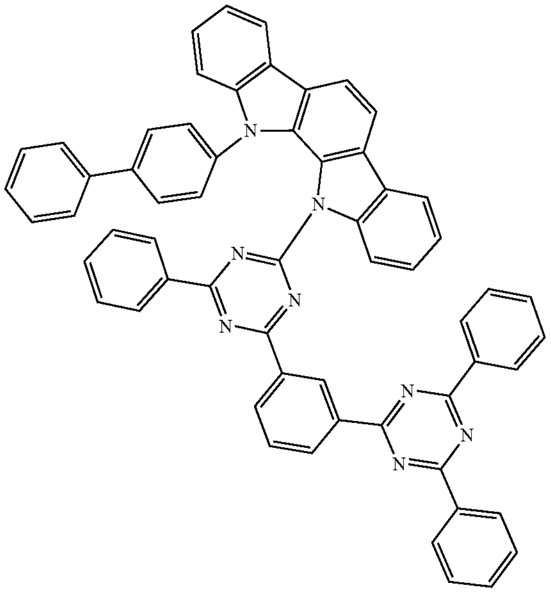
1-20
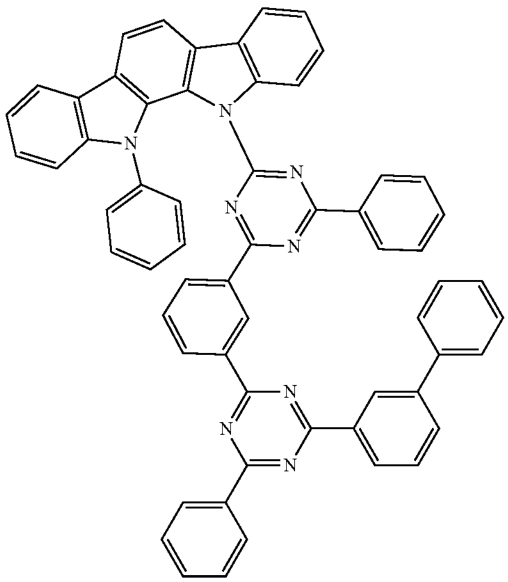
-continued
[C 11]
1-22
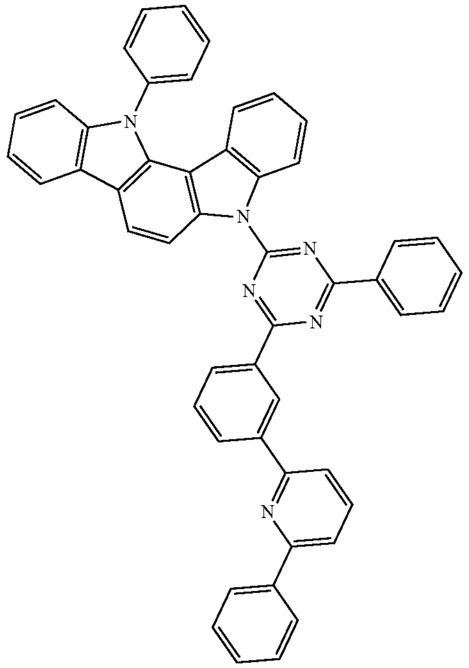
1-23
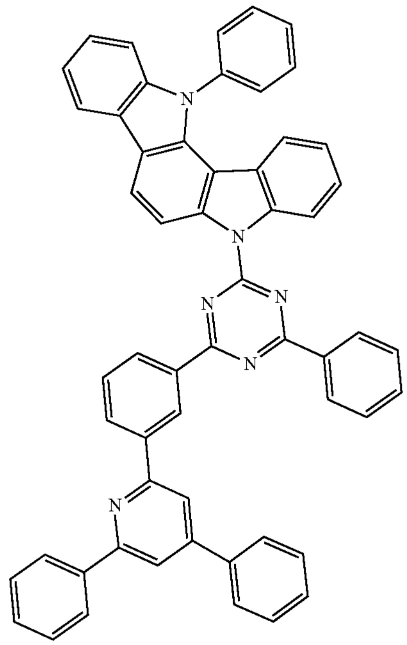

-continued
1-24
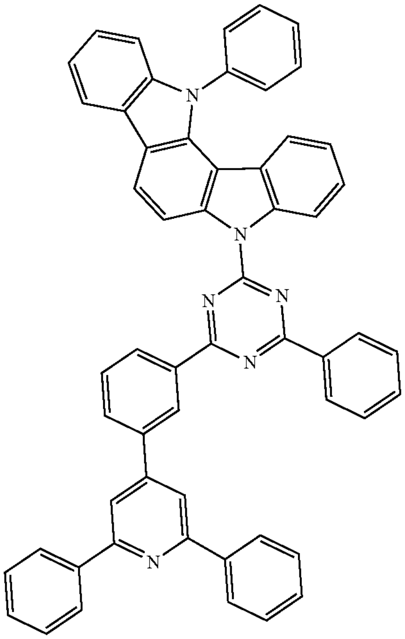
-continued
1-26
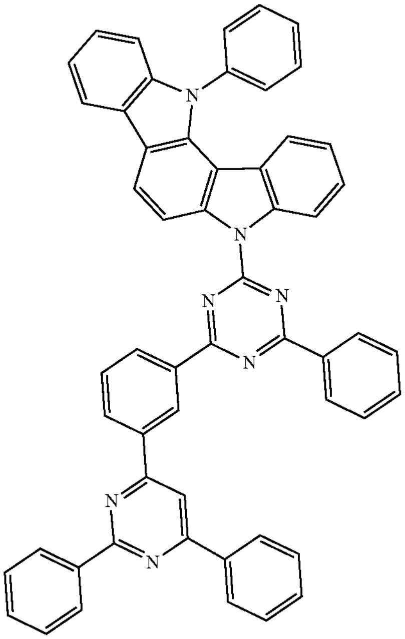
1-25
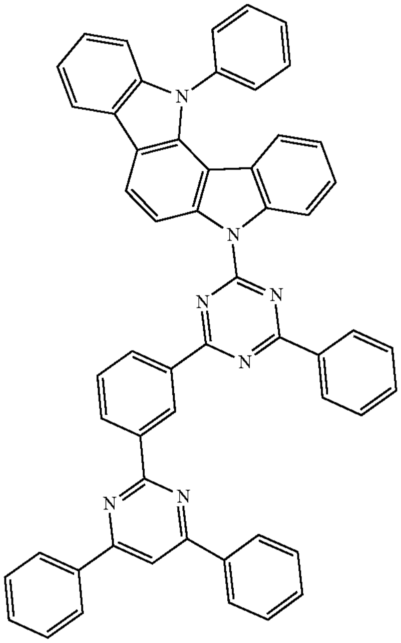
1-27
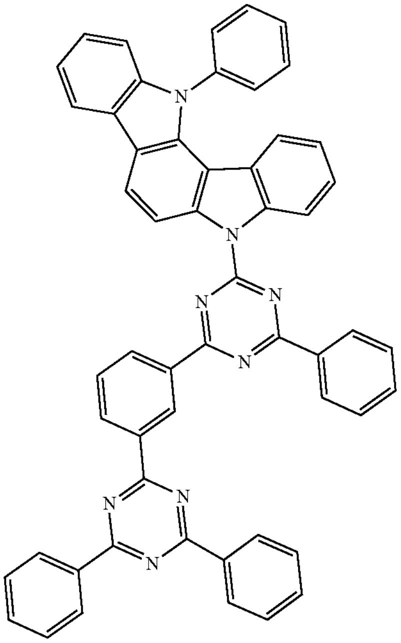

-continued
1-28
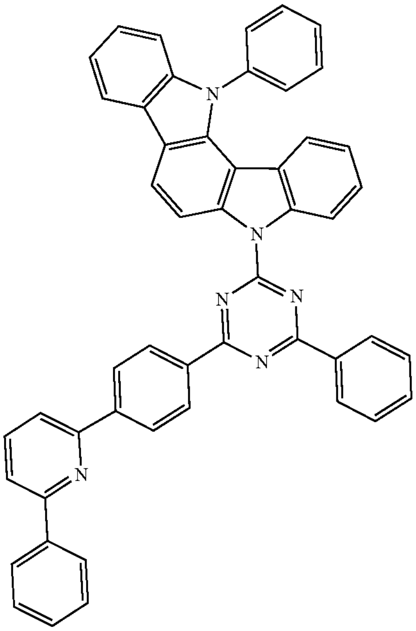
1-29
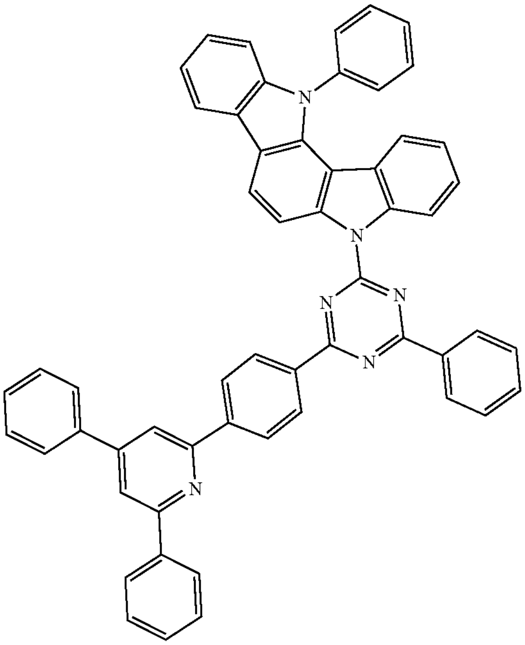
-continued
1-30
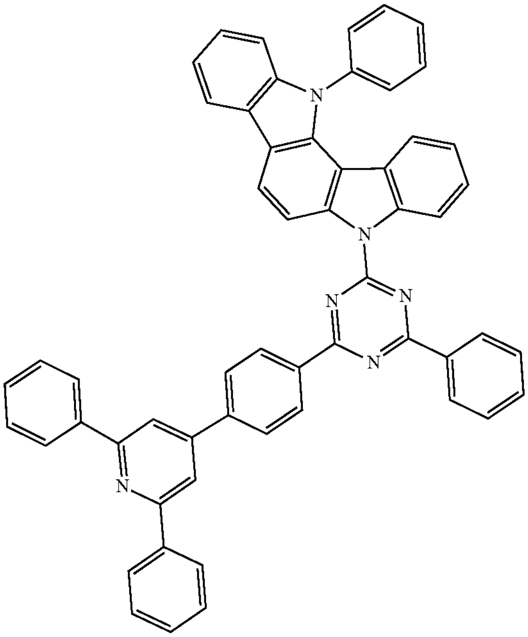
1-31
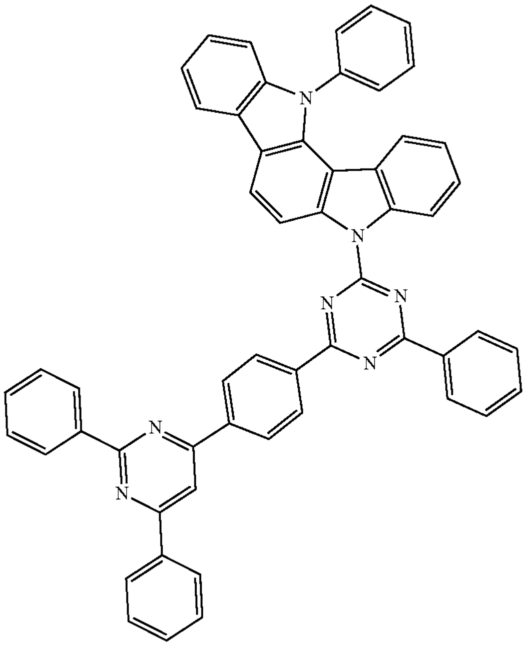

-continued
1-32
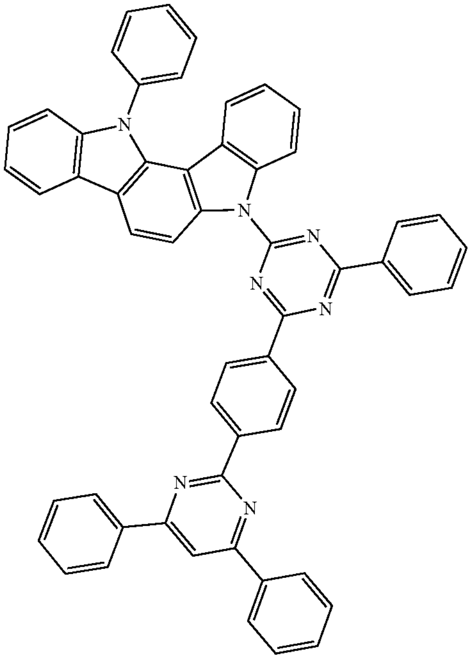
1-33
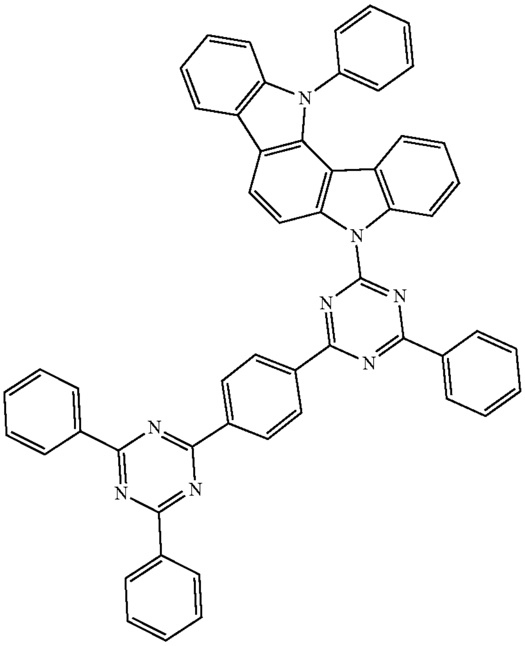
-continued
1-34
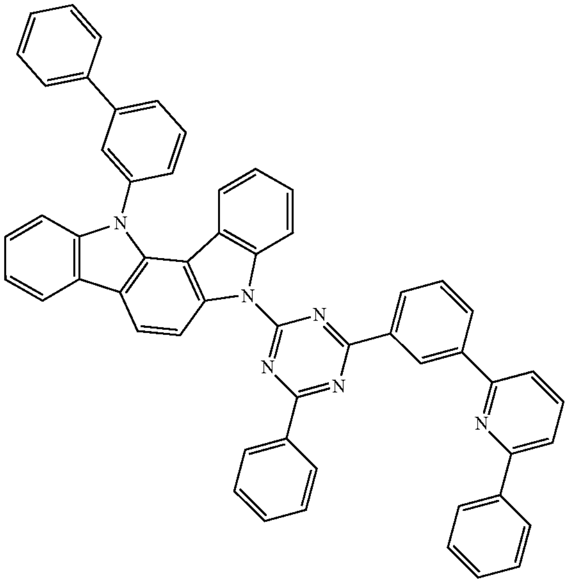
1-35
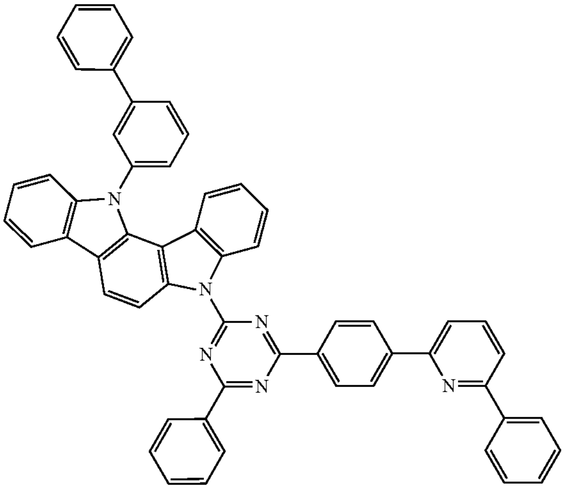

-continued
1-36
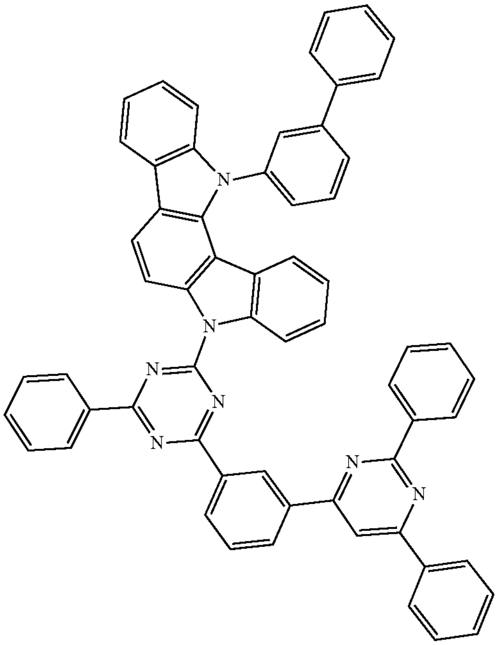
1-37
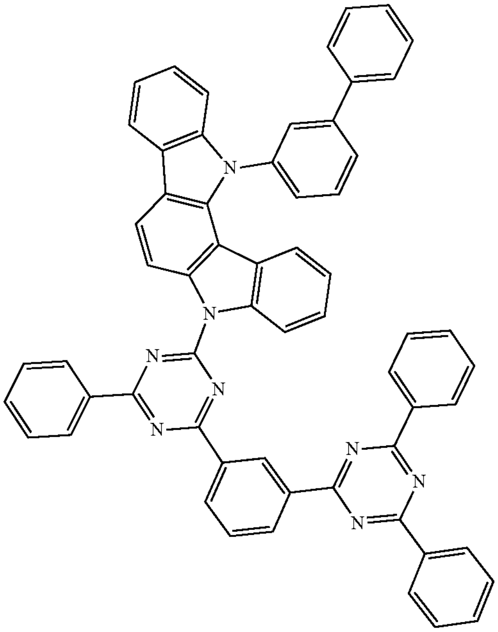
-continued
1-38
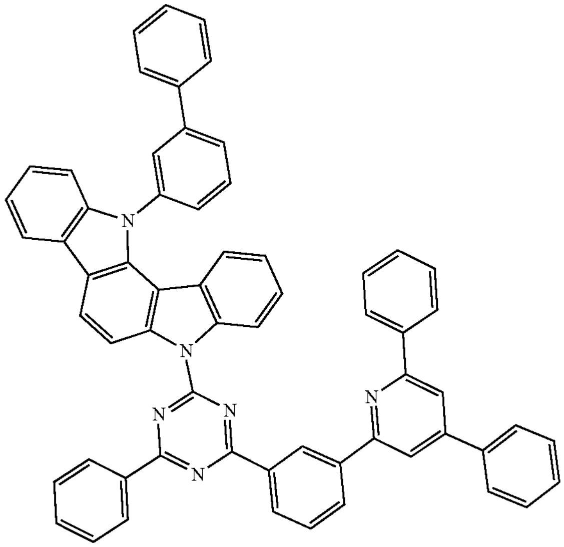
1-39
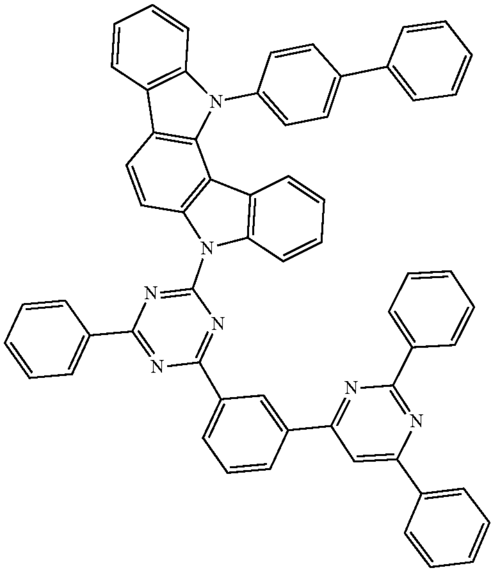

-continued
1-40
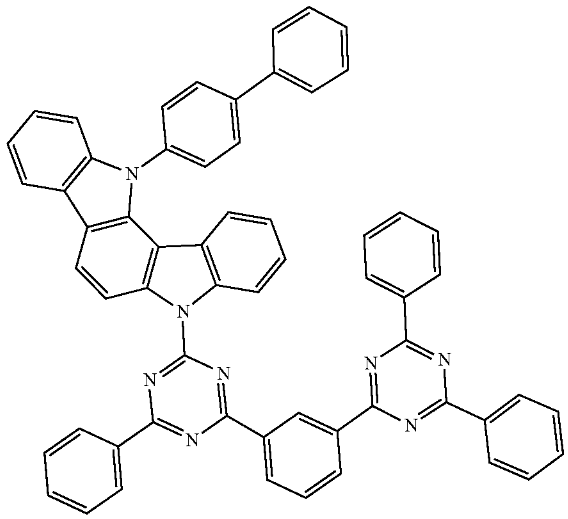
1-41
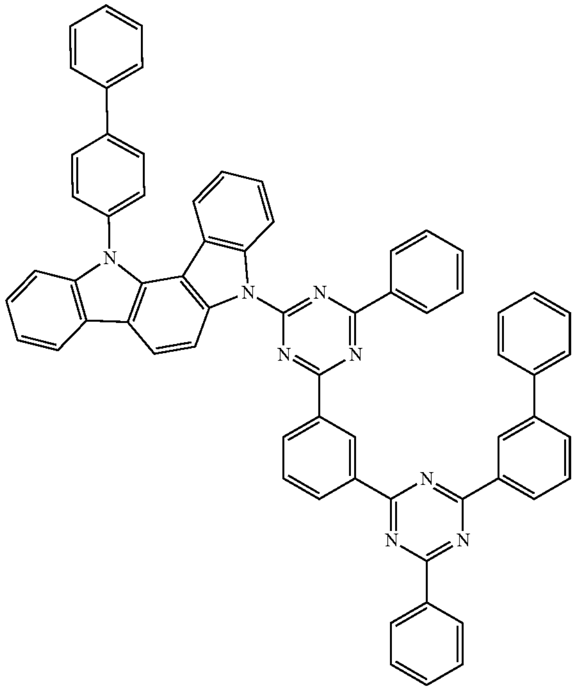
-continued
[C 12]
1-42
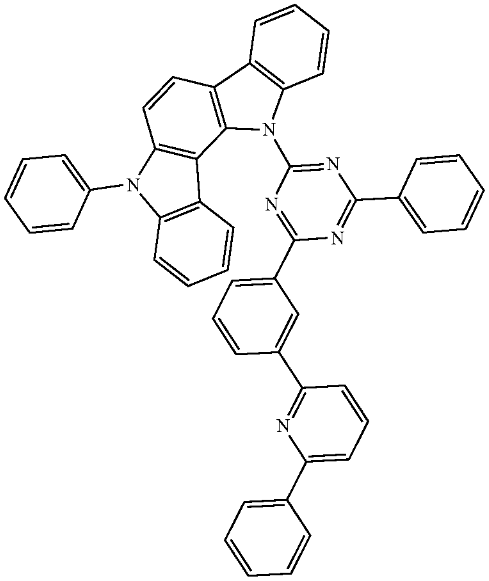
1-43
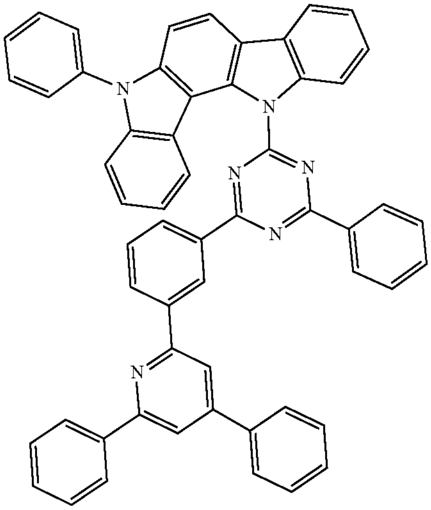
1-44
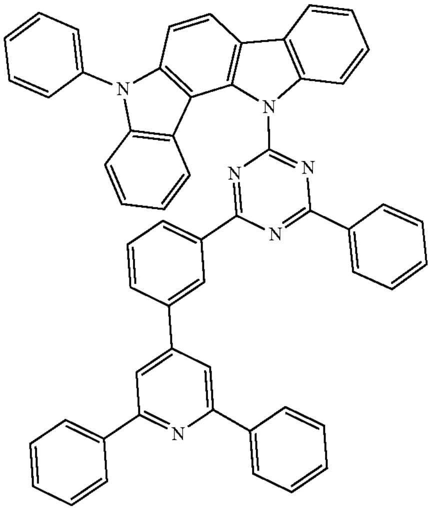

-continued
1-45
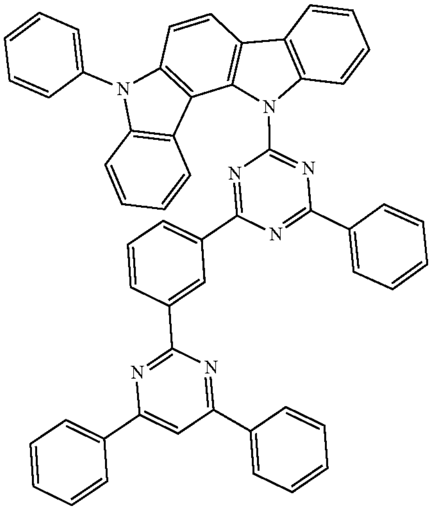
1-46
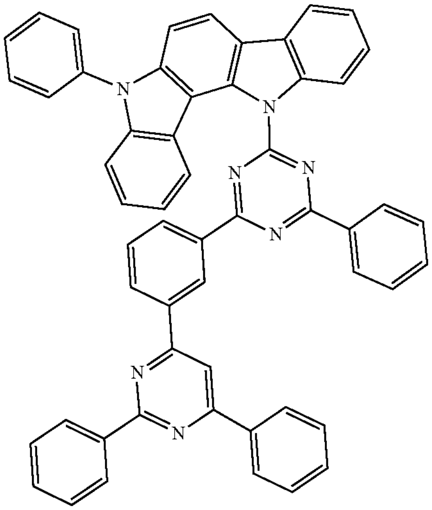
1-47
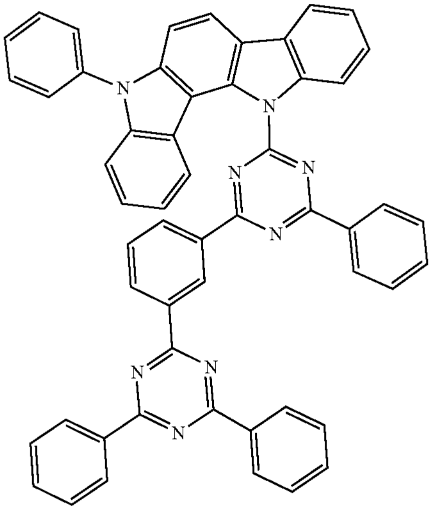
-continued
1-48
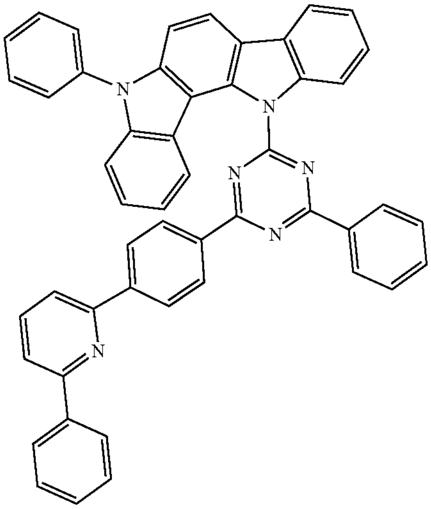
1-49
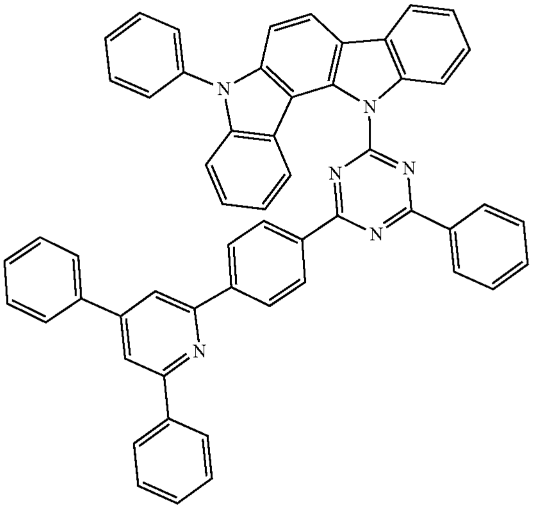
1-50
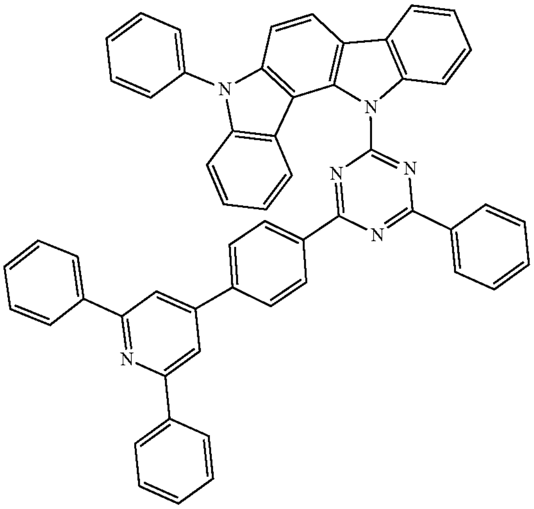

-continued
1-51
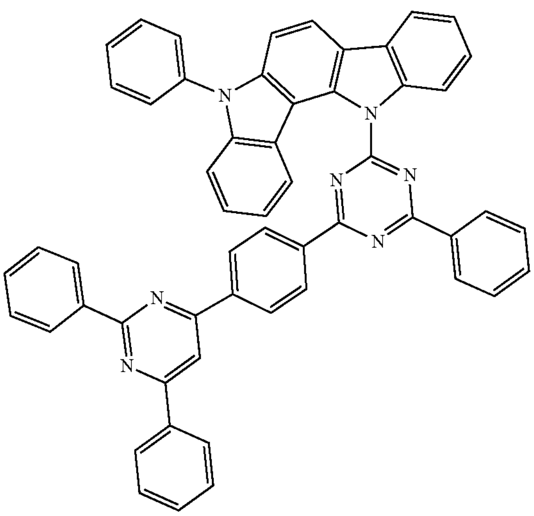
1-52
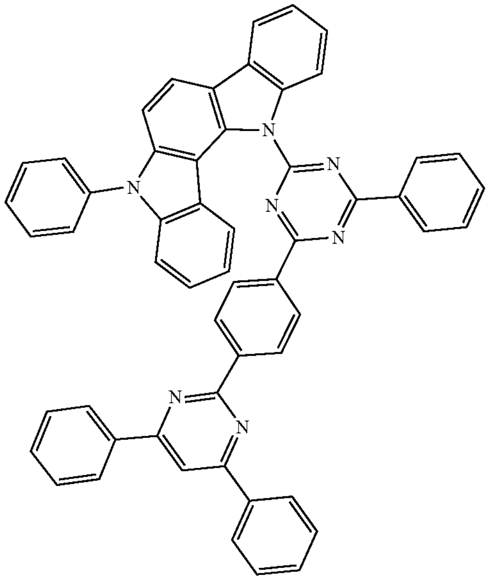
1-53
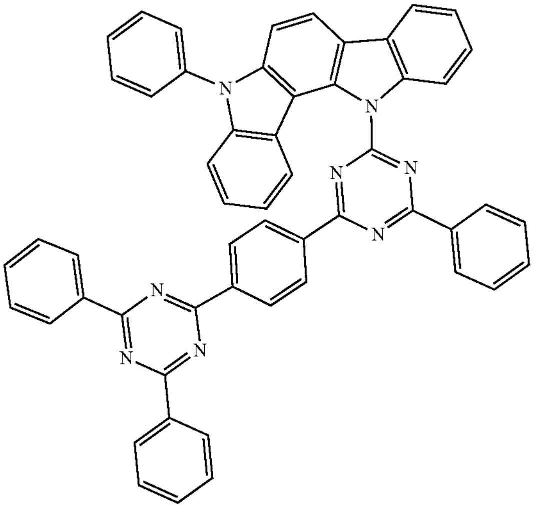
-continued
1-54
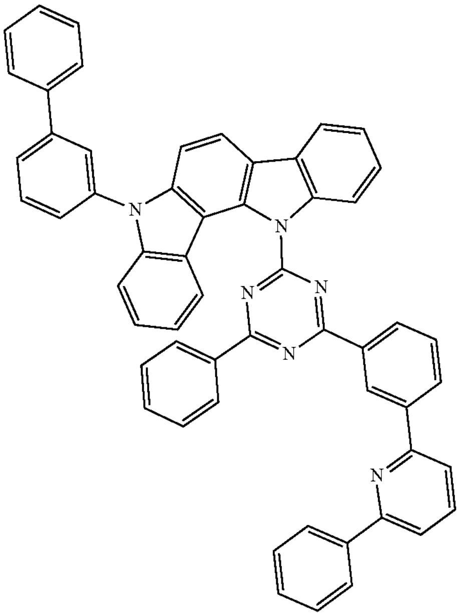
1-55
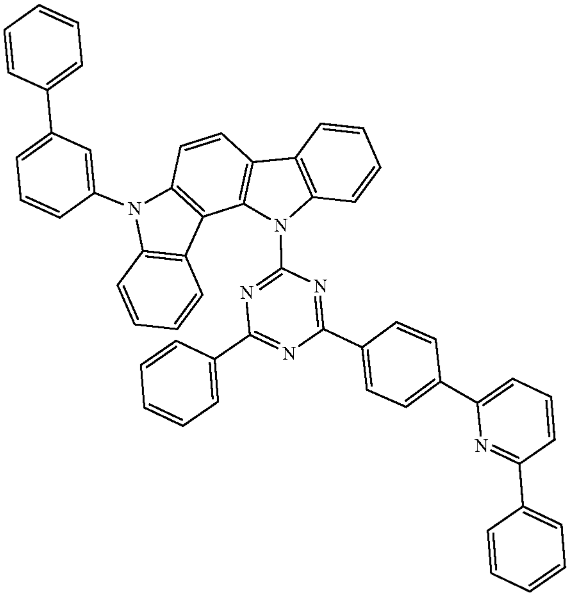

-continued
1-56
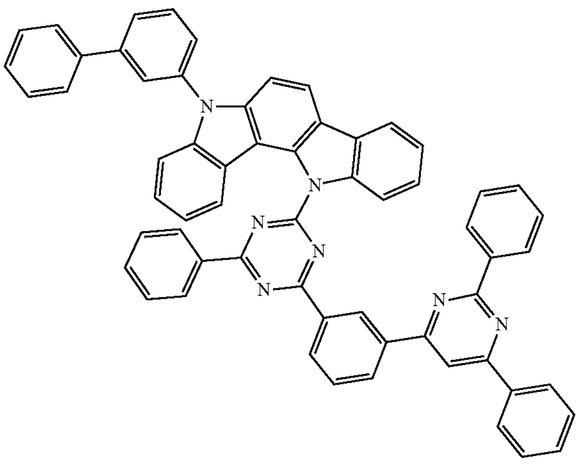
I-57
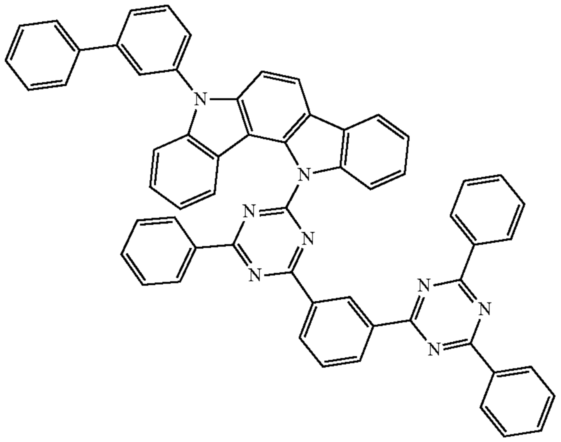
1-58
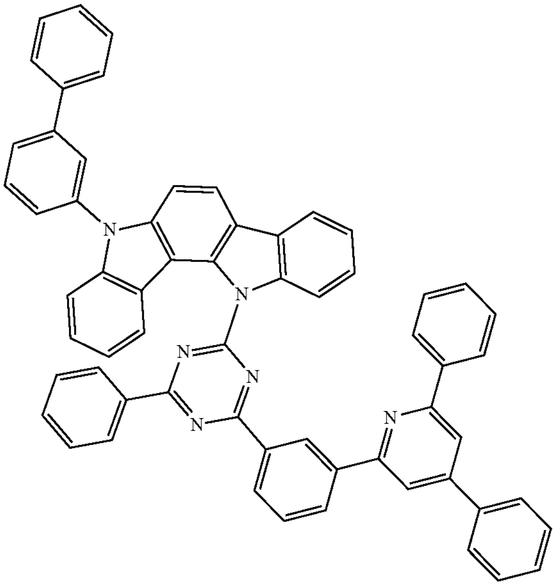
-continued
1-59
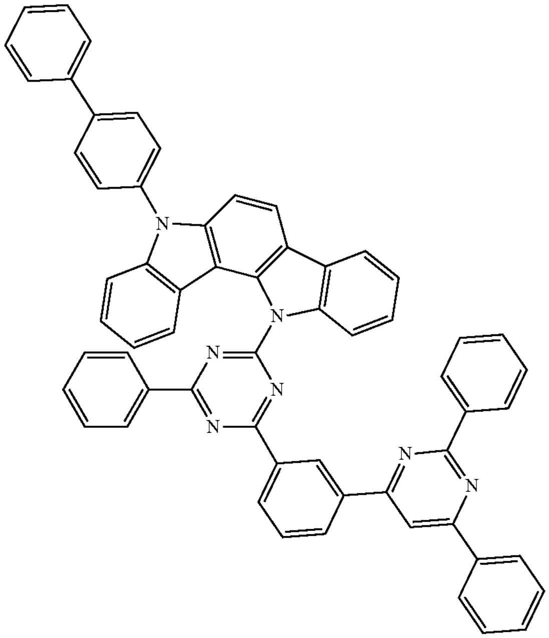
1-60
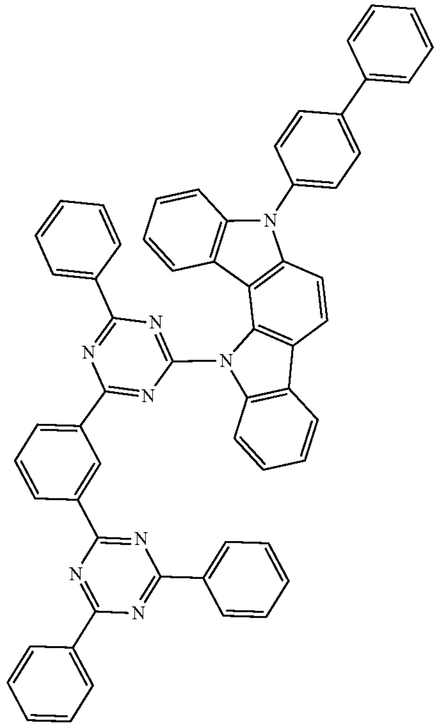

-continued
1-61
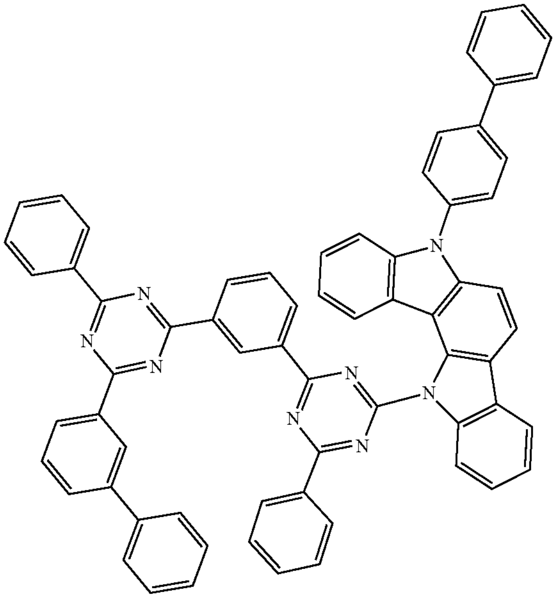
[C 13]
1-62
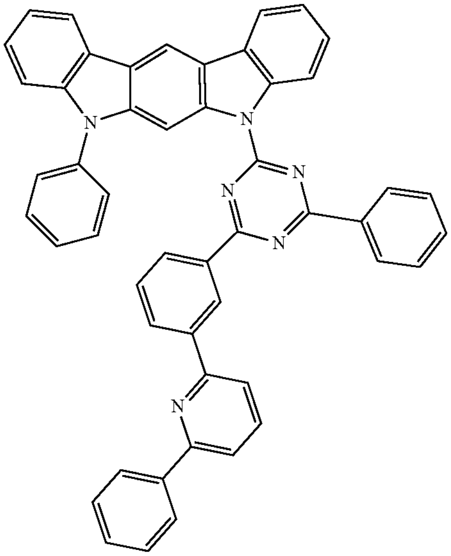
-continued
1-63
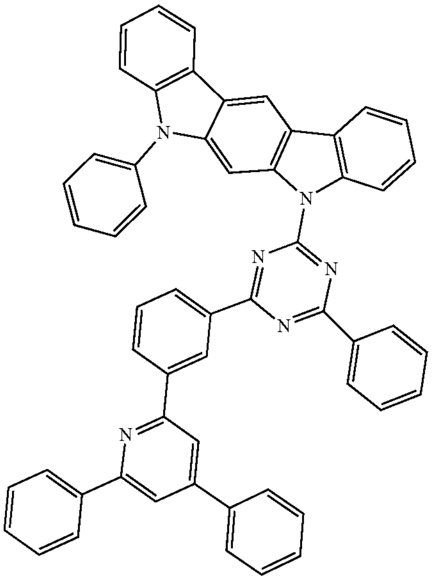
1-64
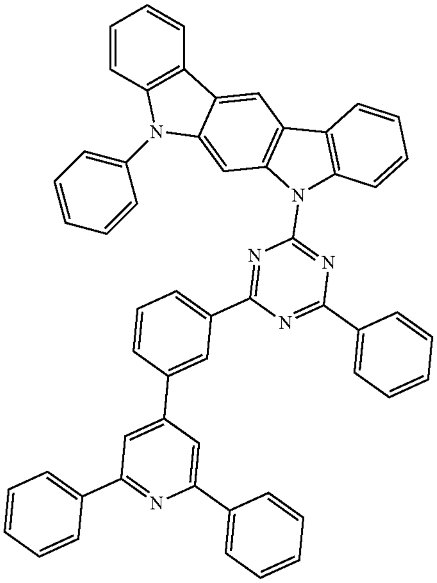

-continued
1-65
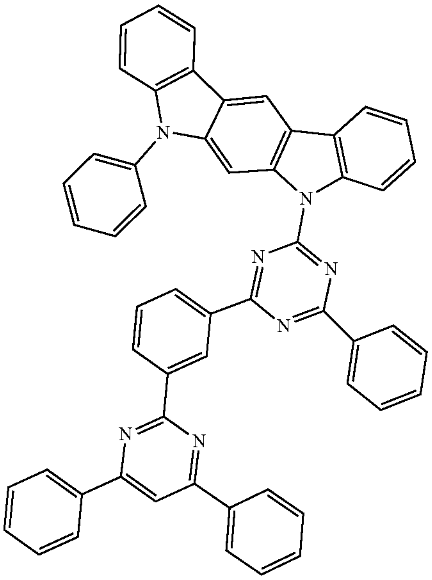
1-66
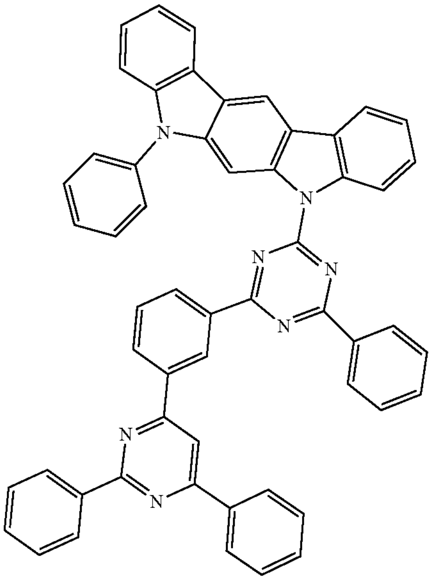
-continued
1-67
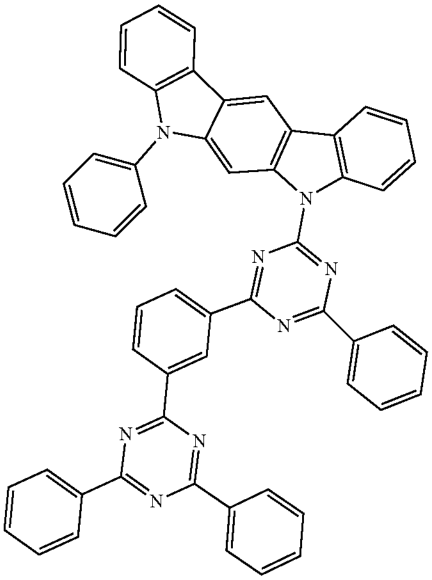
1-68
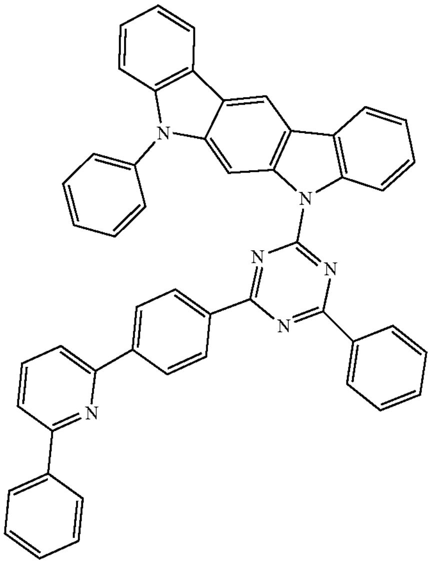

-continued
1-69
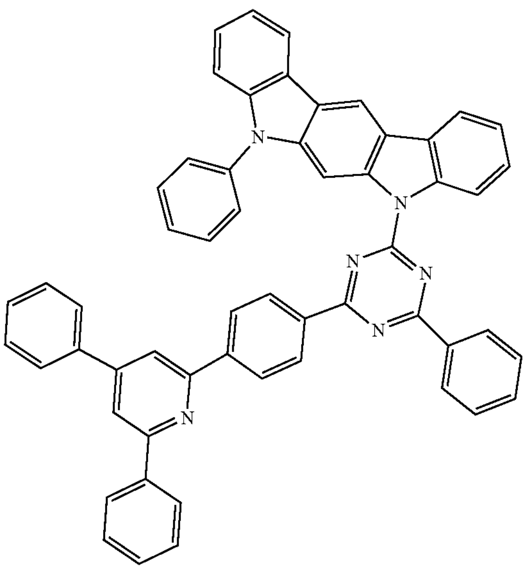
1-70
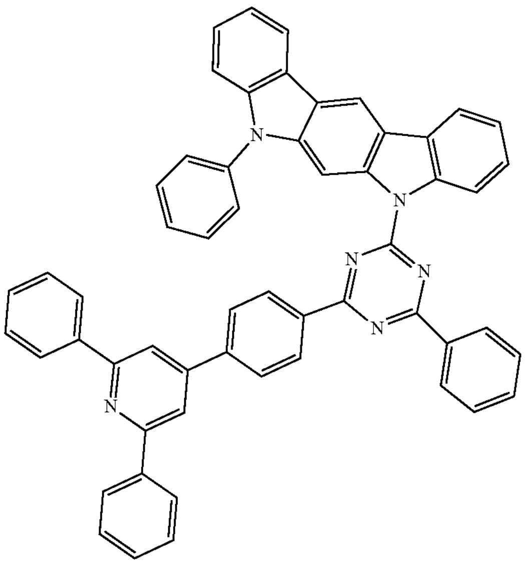
-continued
1-71
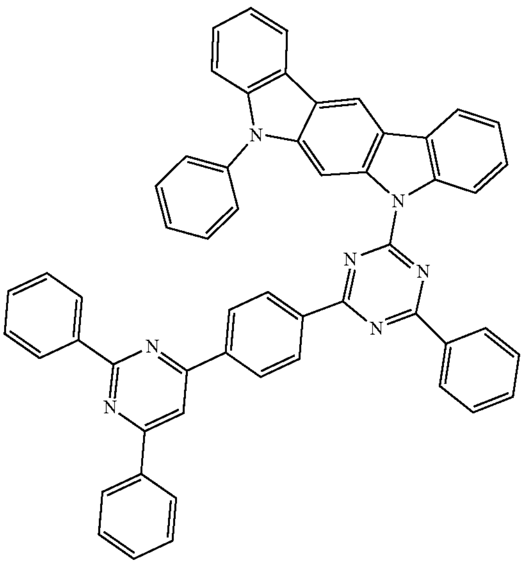
1-72
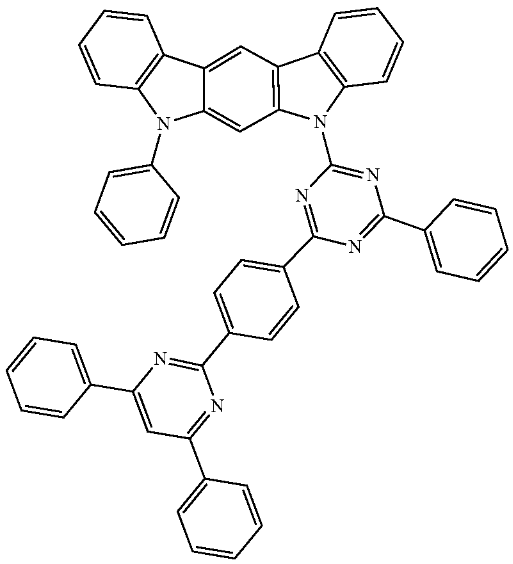

-continued
1-73
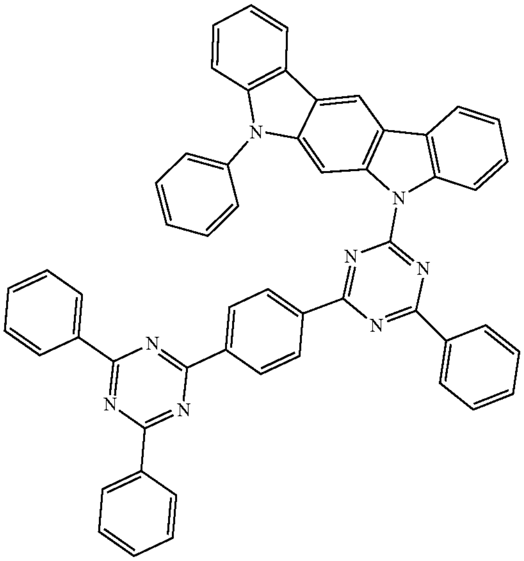
1-74
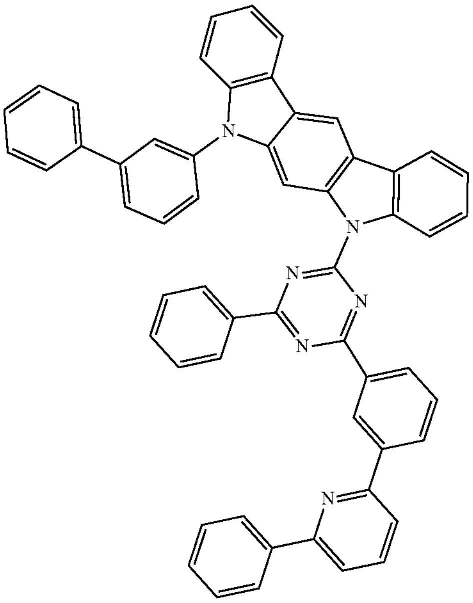
-continued
1-75
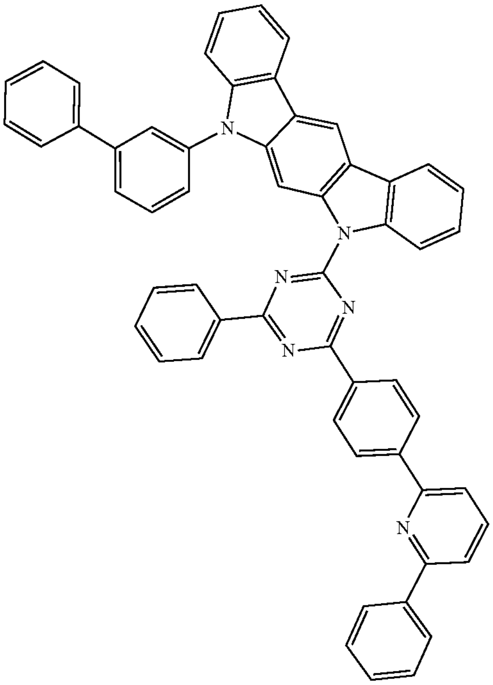
1-76
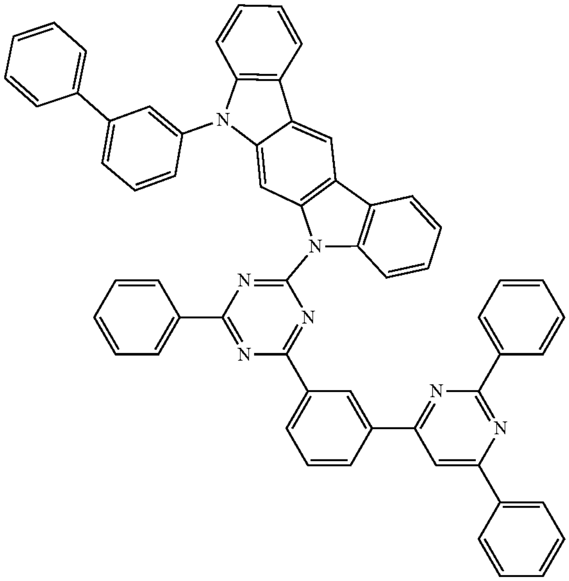

-continued
1-77
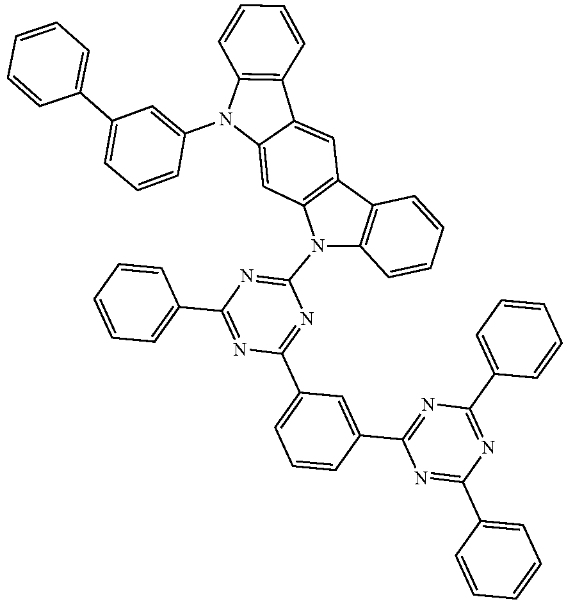
1-78
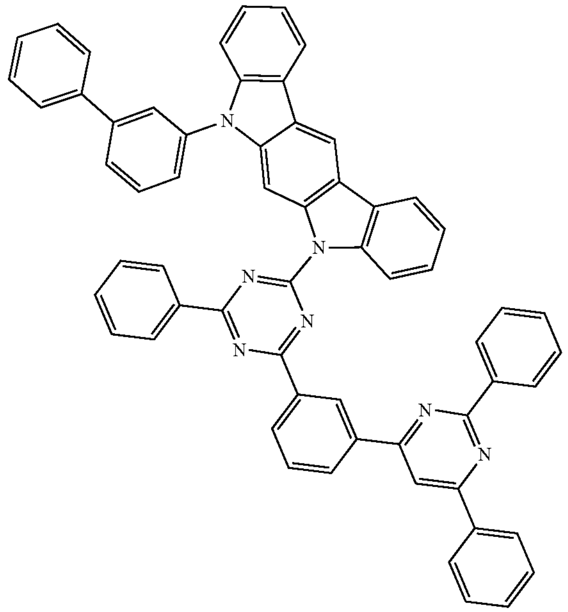
-continued
1-79
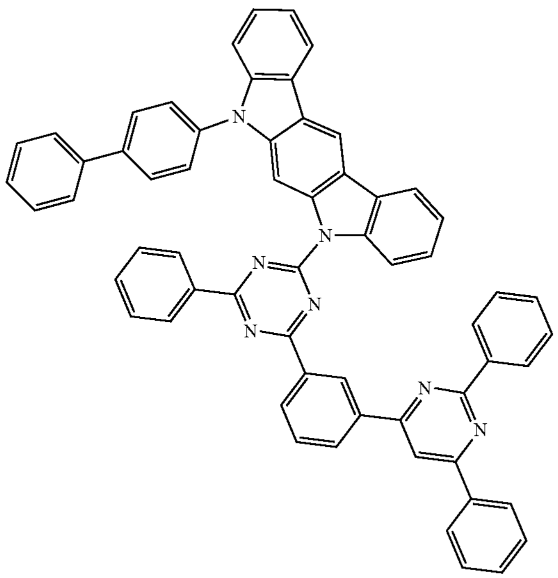
1-80
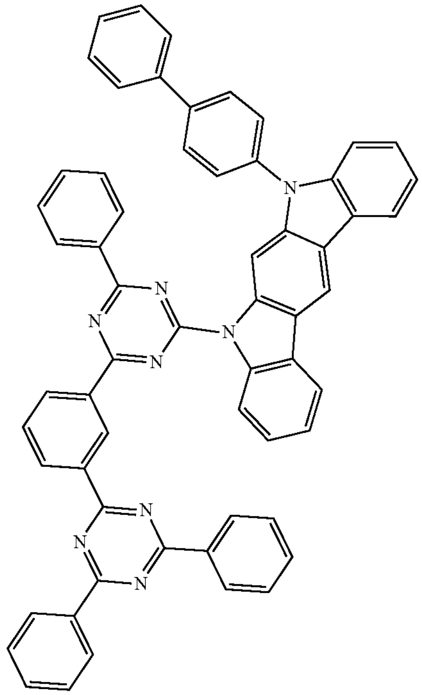

-continued
1-81
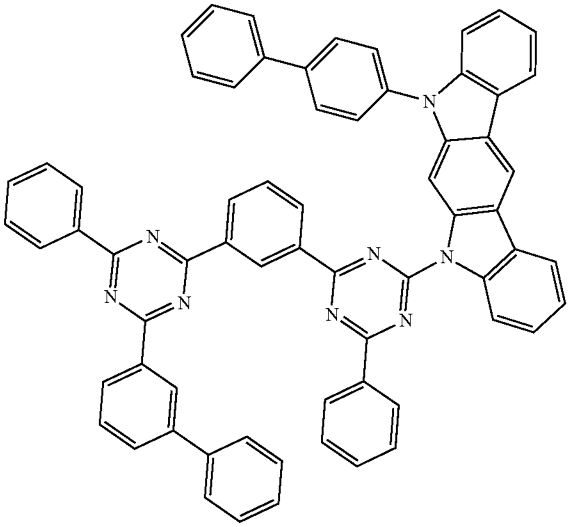
[C 14]
1-82
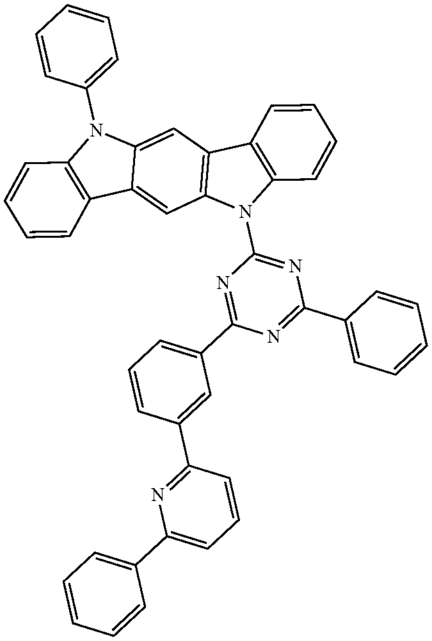
-continued
1-83
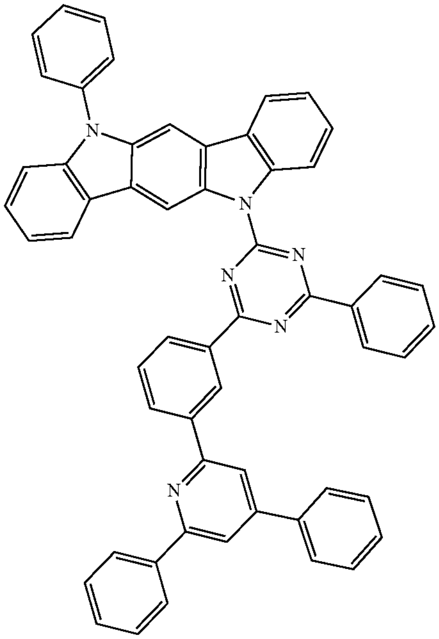
1-84
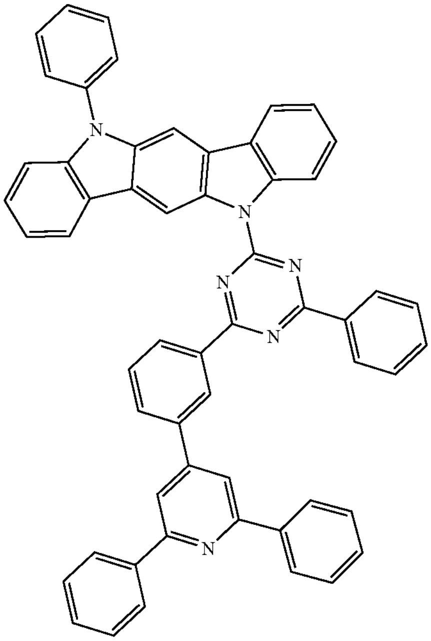

-continued
1-85
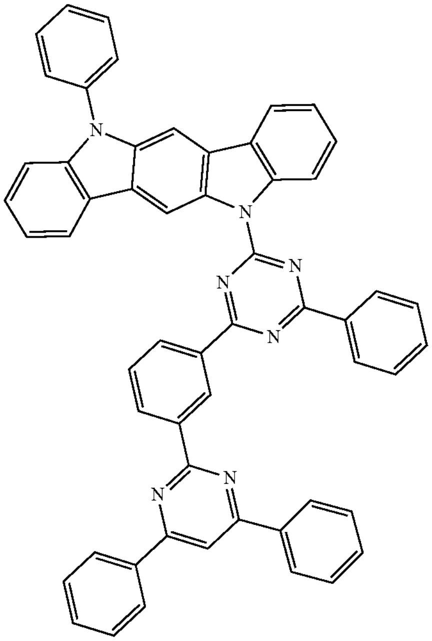
1-86
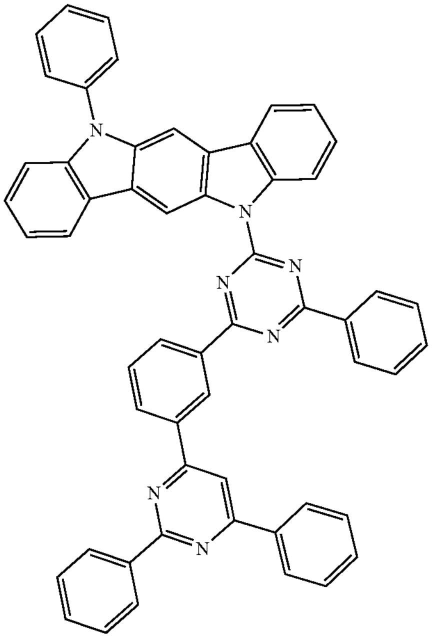
-continued
1-87
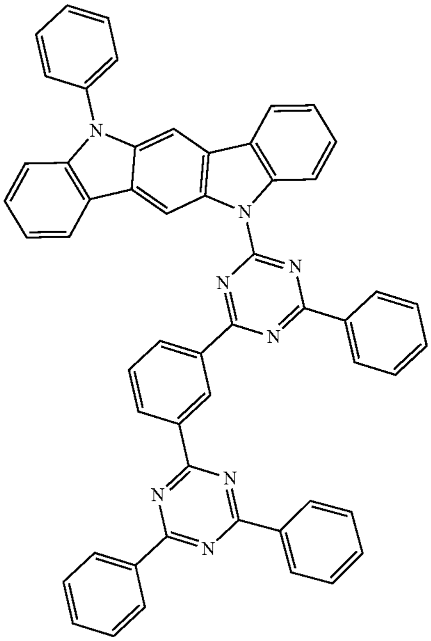
1-88
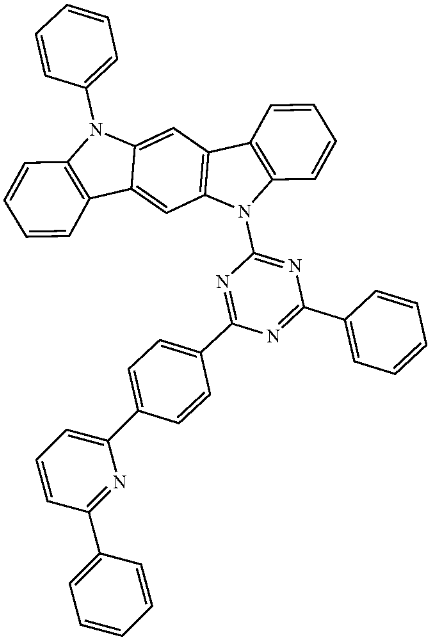

-continued
1-89
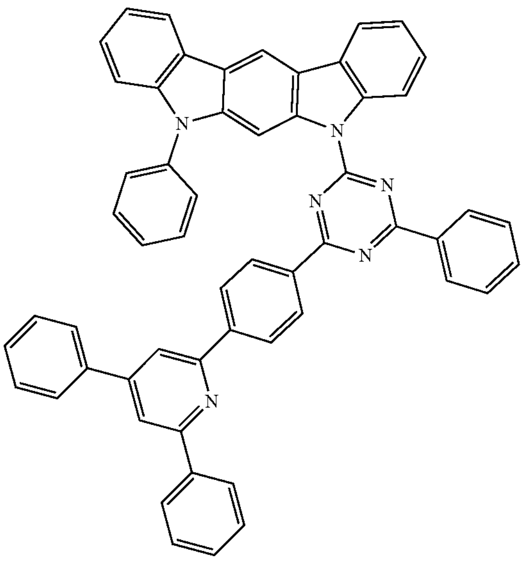
1-90
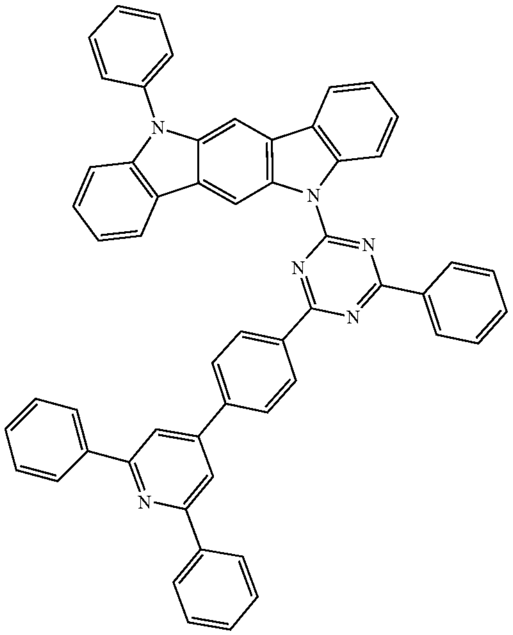
-continued
1-91
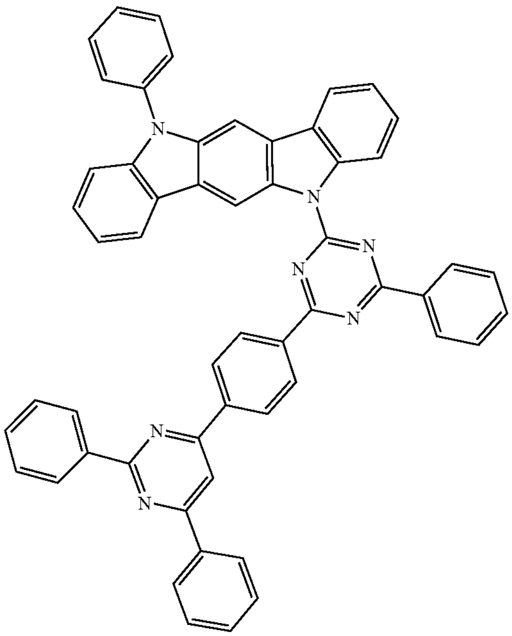
1-92
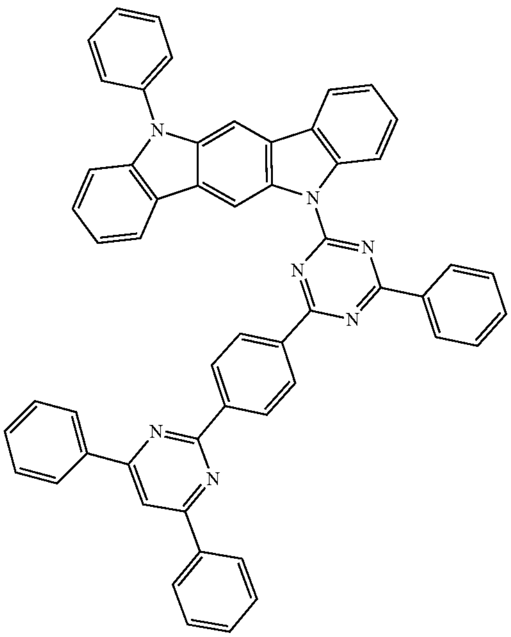

-continued
1-93
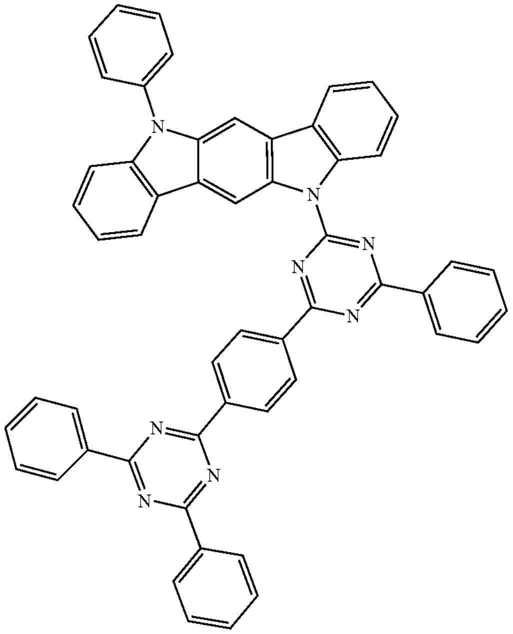
1-94
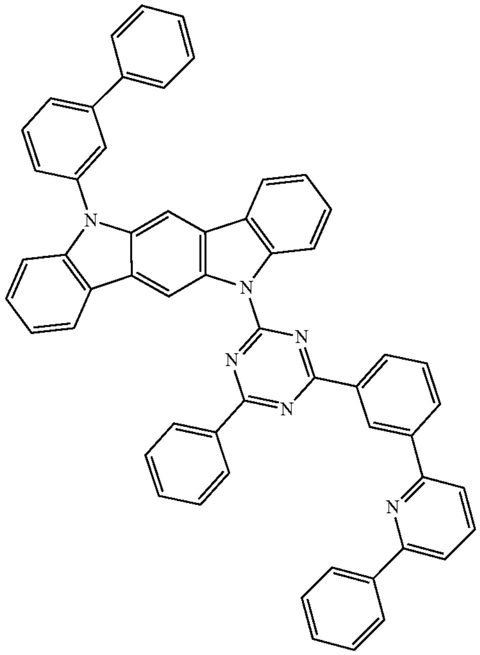
-continued
1-95
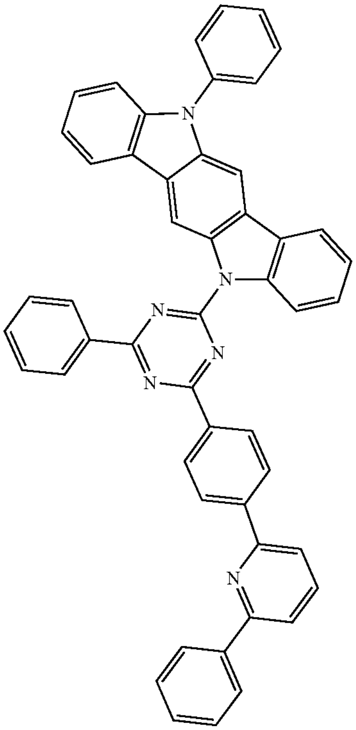
1-96
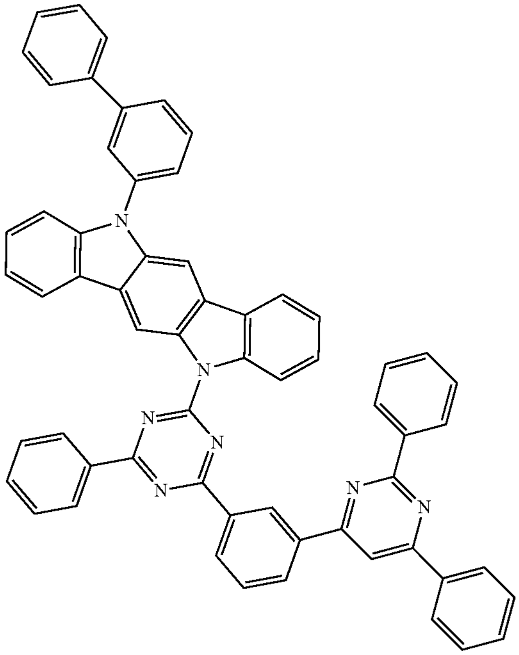

-continued
1-97
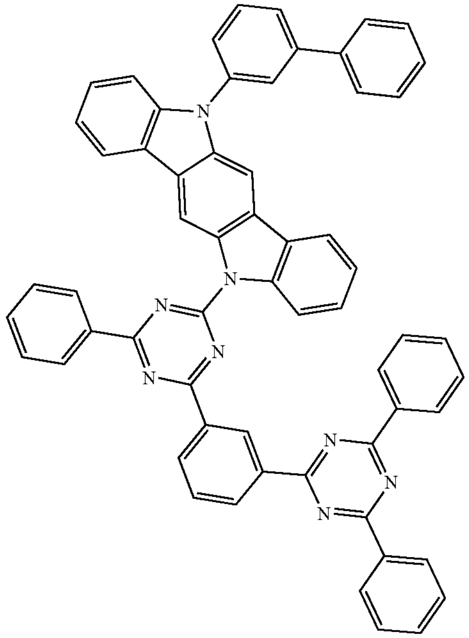
1-98
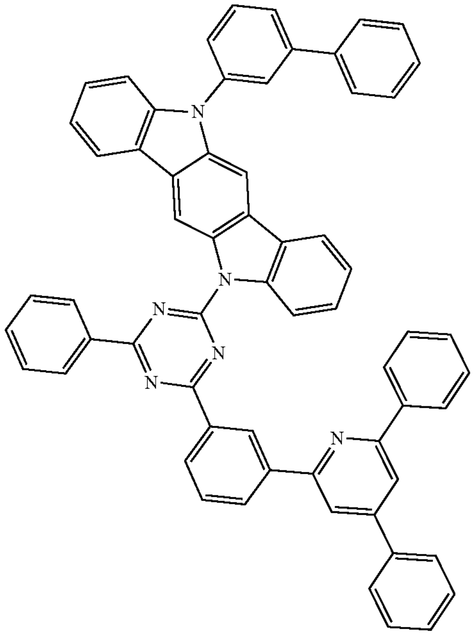
-continued
1-99
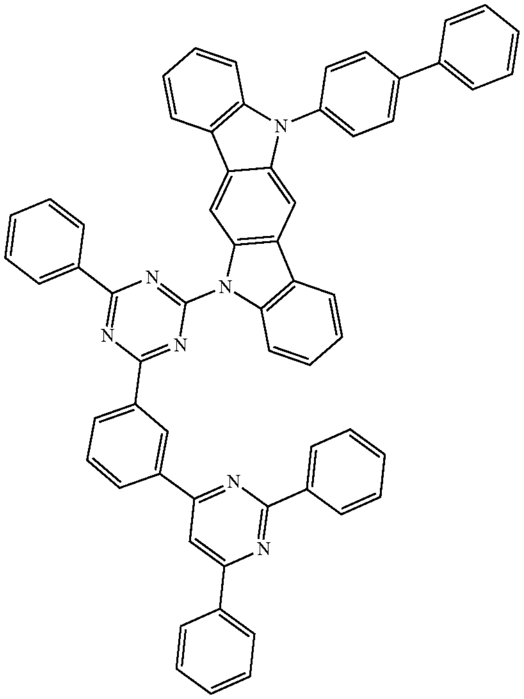
1-100
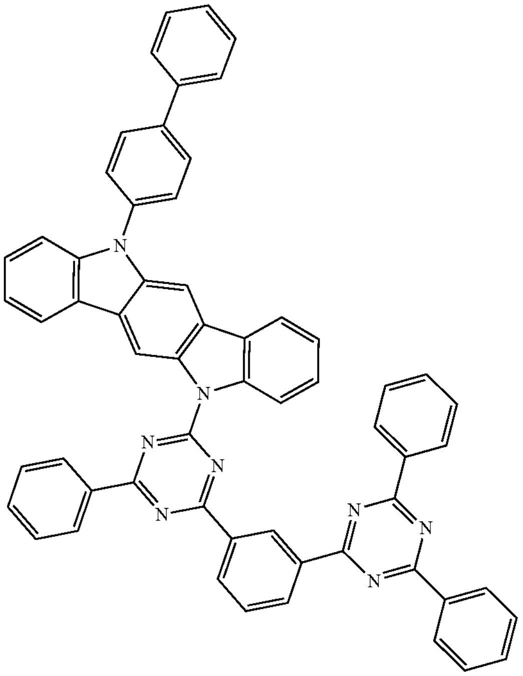

-continued
1-101
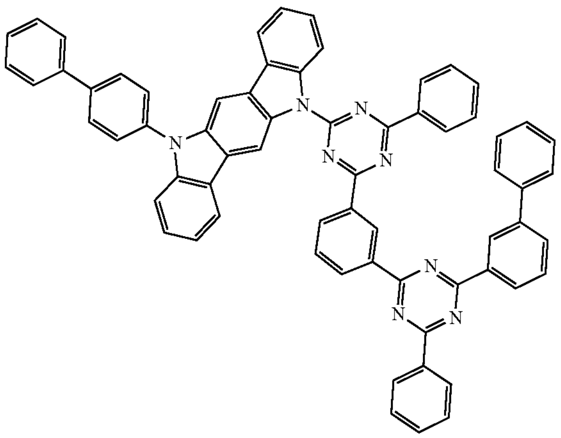
[C 15]
1-102
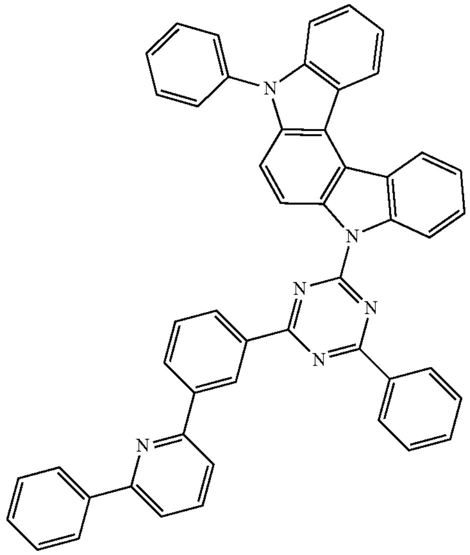
1-103
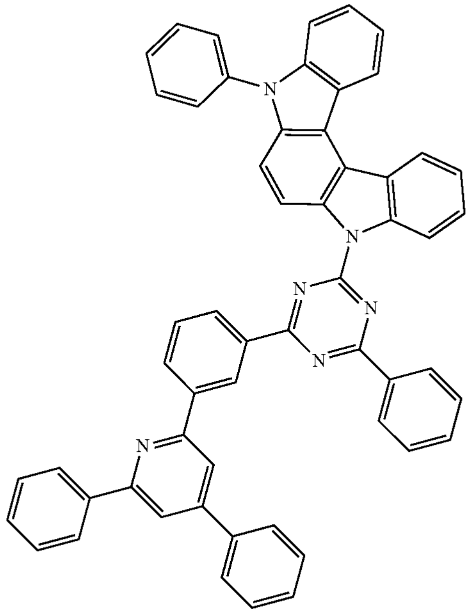
-continued
1-104
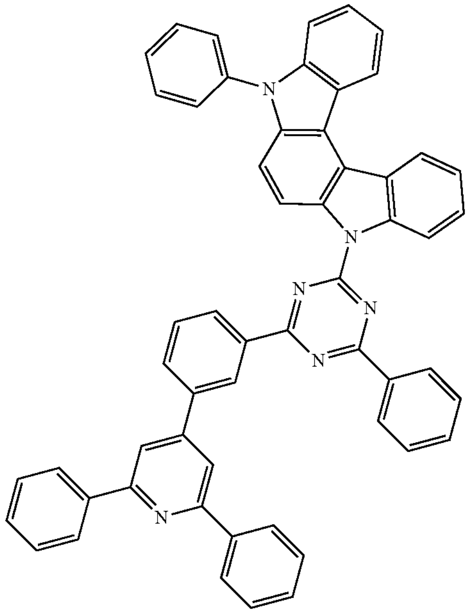
1-105
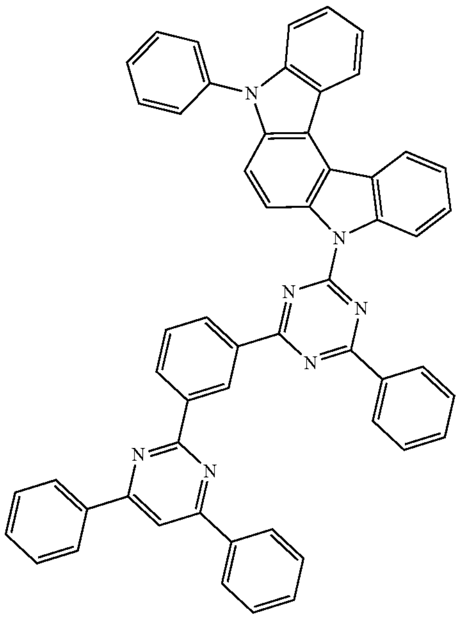

1-106
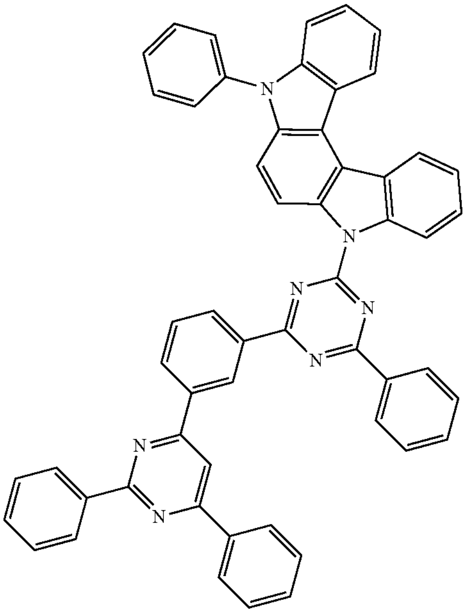
1-107
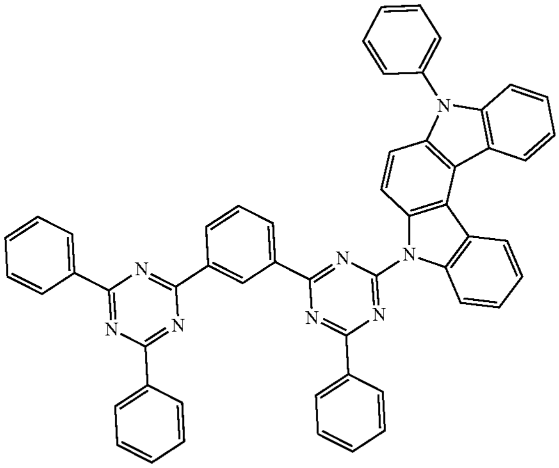
1-108
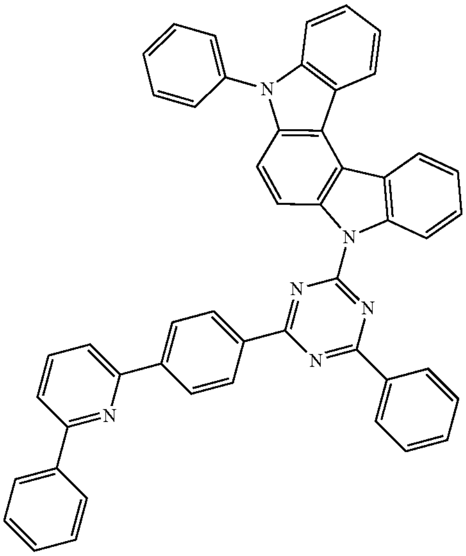
1-109
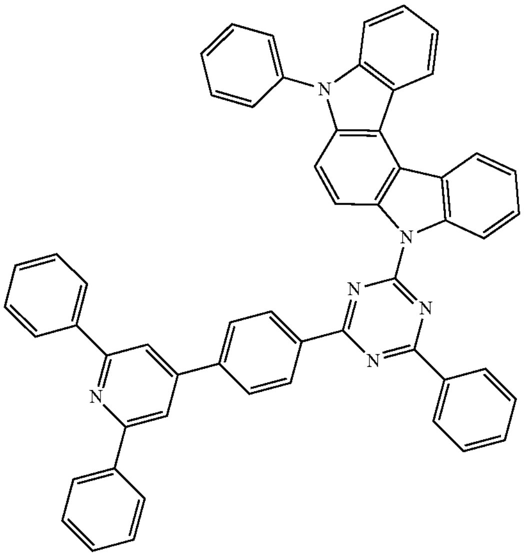
1-110
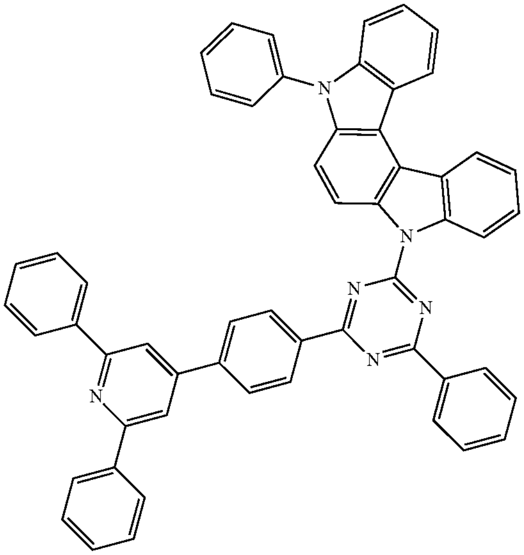

-continued
1-111
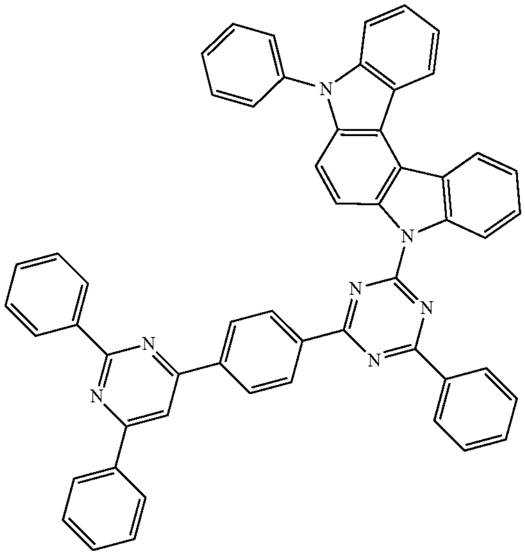
1-112
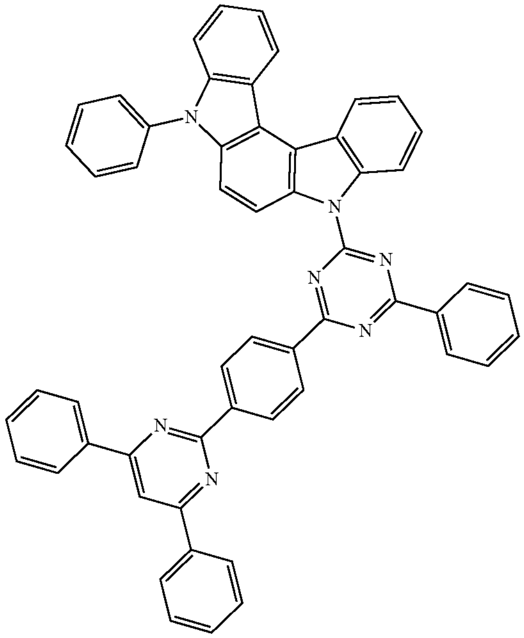
-continued
1-113
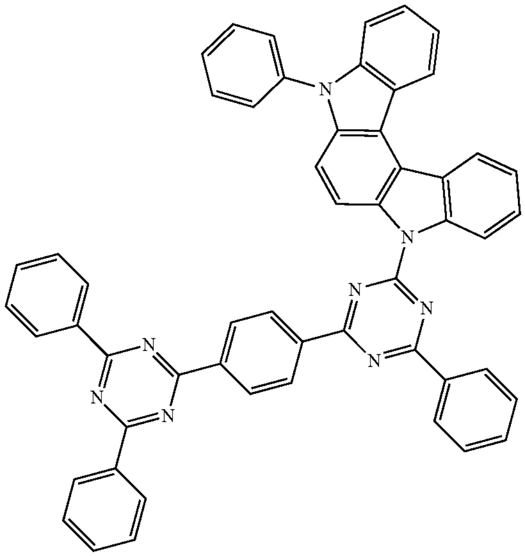
1-114
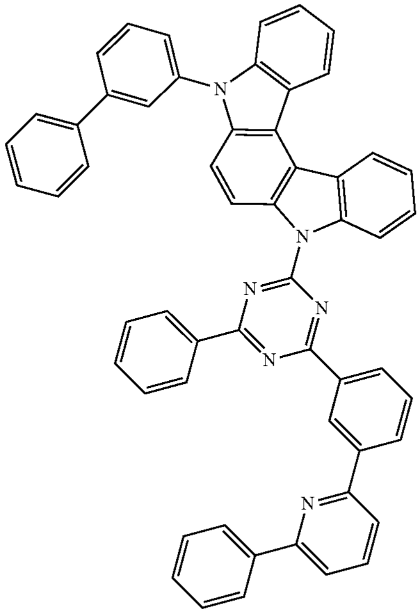

-continued
1-115
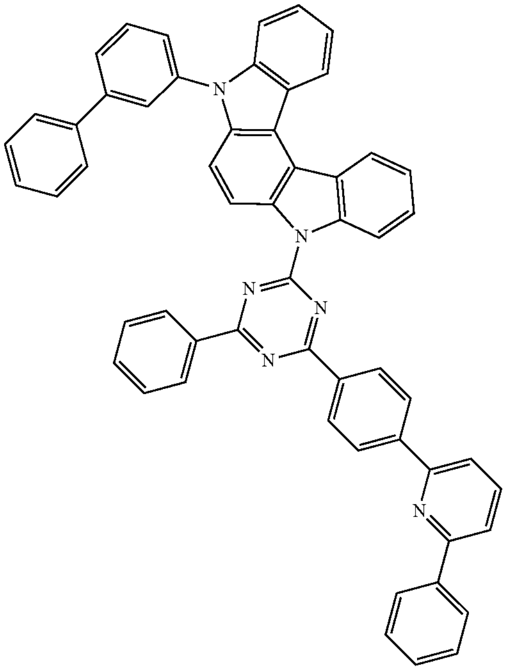
1-116
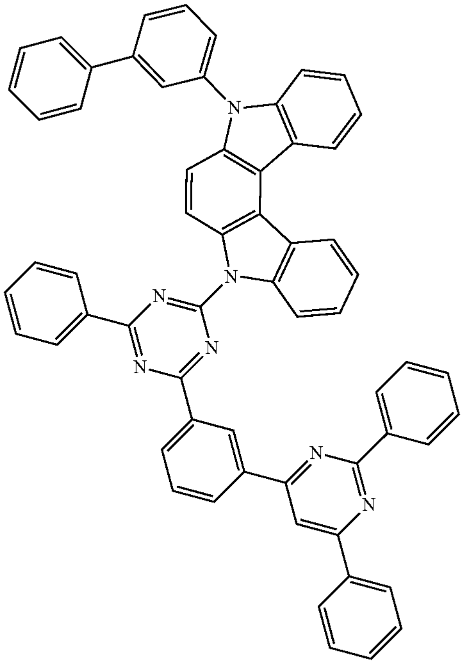
-continued
1-117
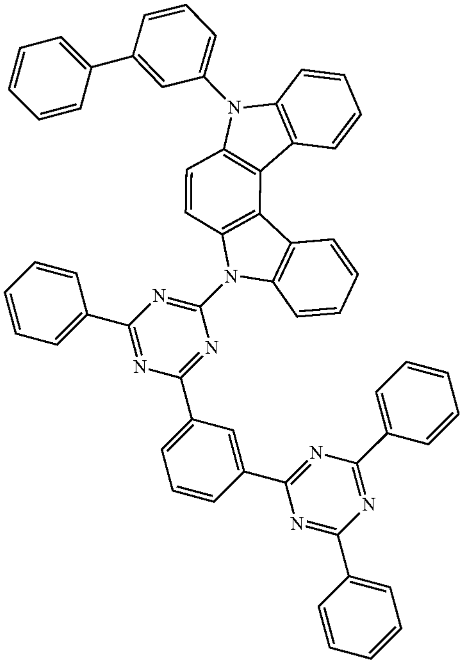
1-118
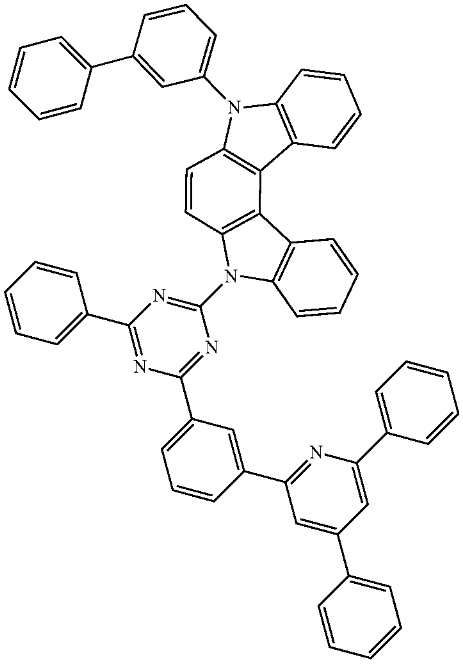

-continued
1-119
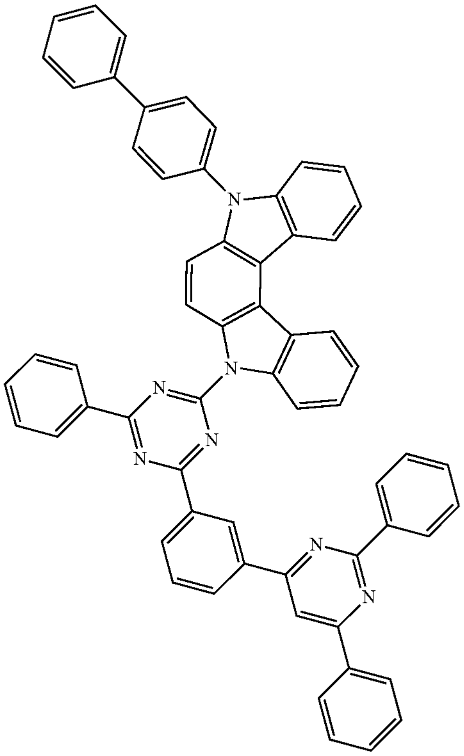
1-120
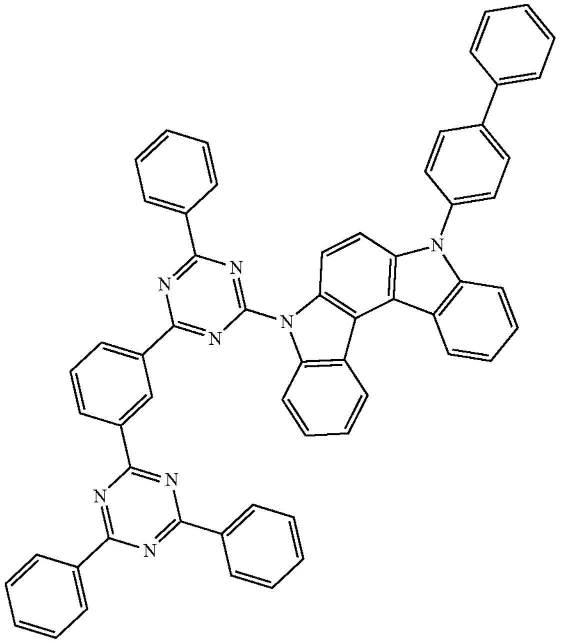
-continued
1-121
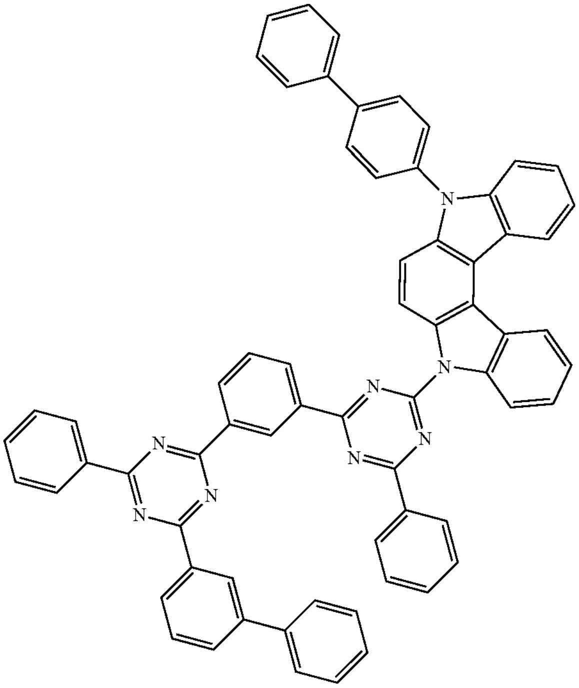
[C 16]
1-122
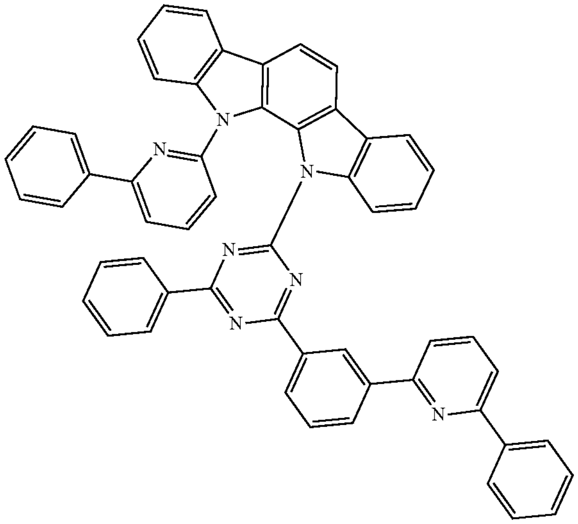

-continued
1-123
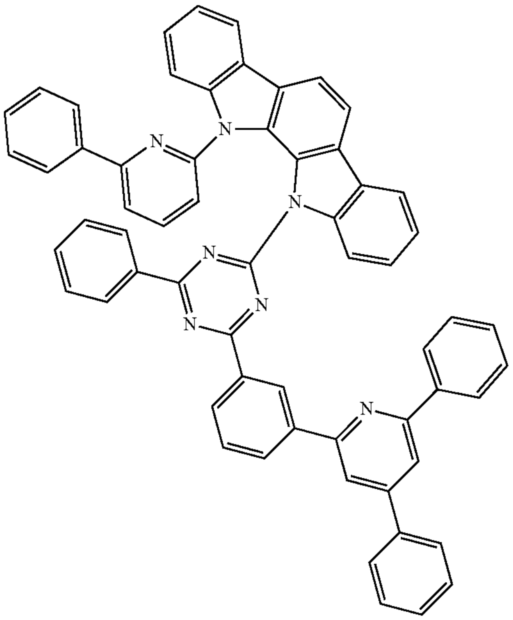
1-124
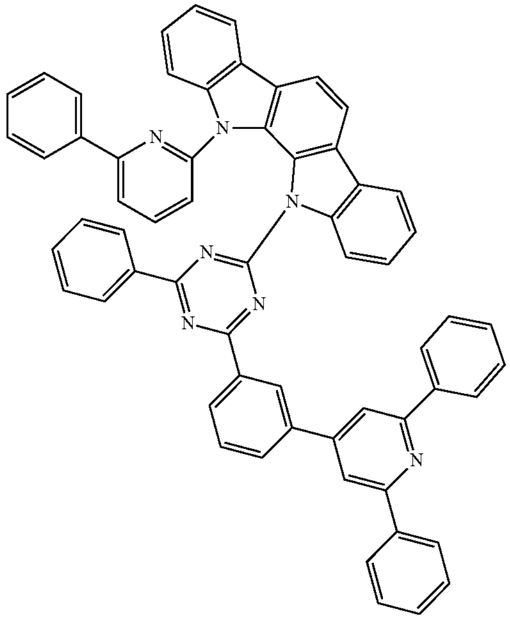
-continued
1-125
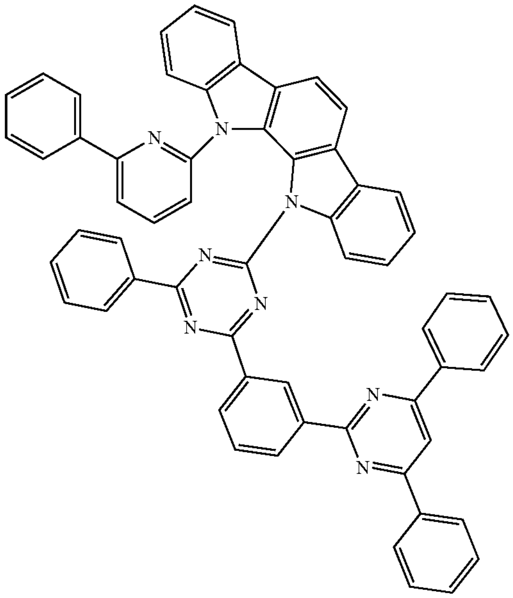
1-126
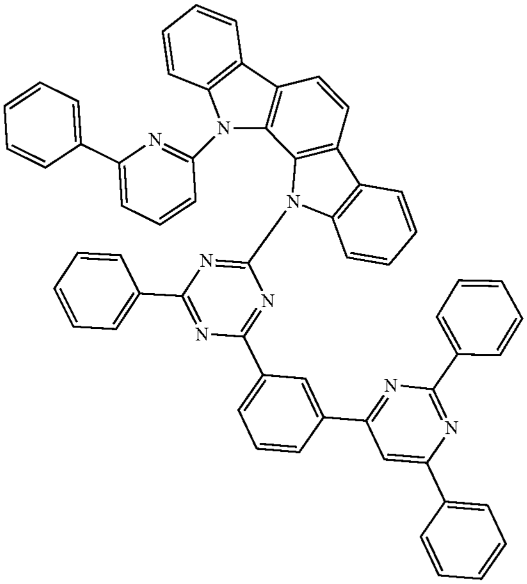

-continued
1-127
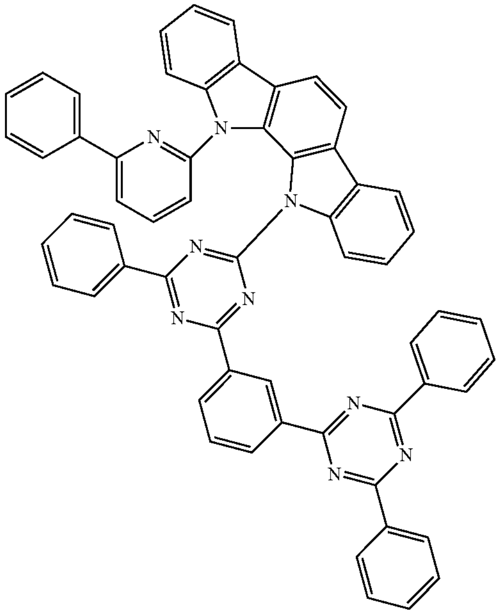
1-128
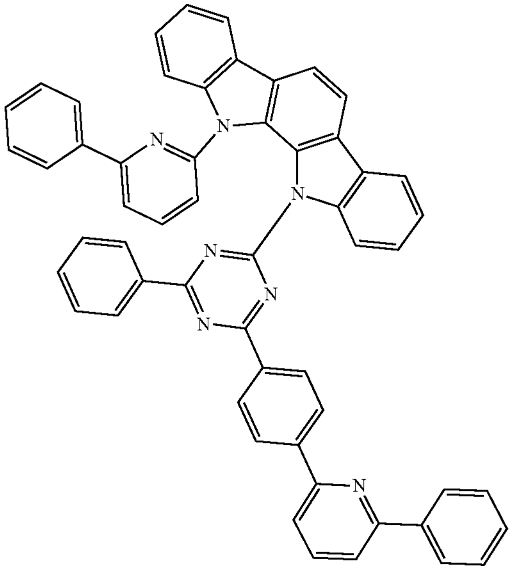
-continued
1-129
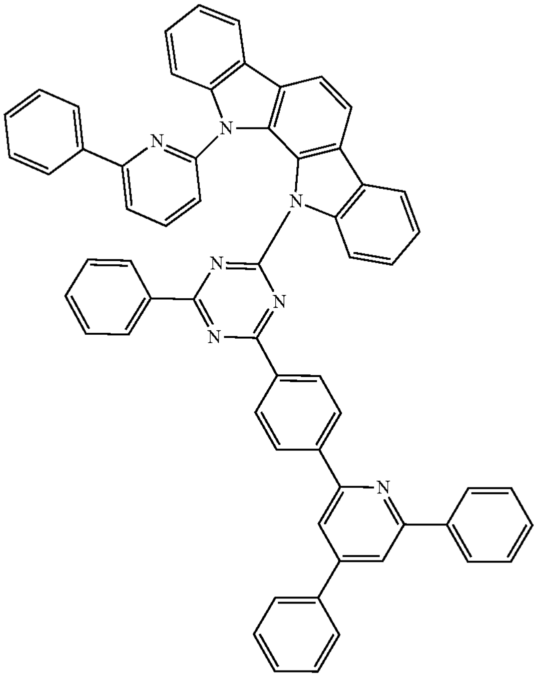
1-130
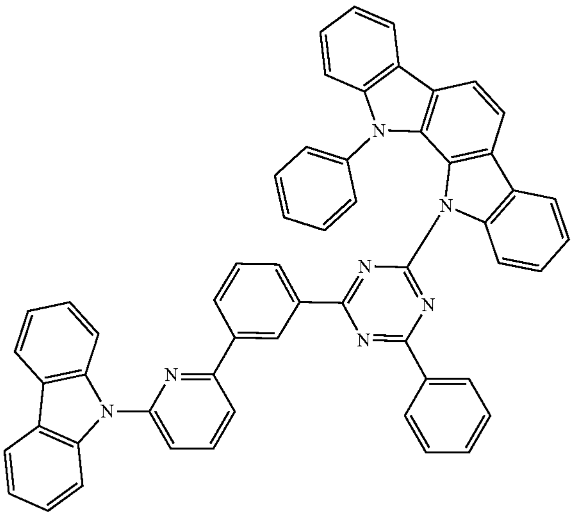

-continued
1-131
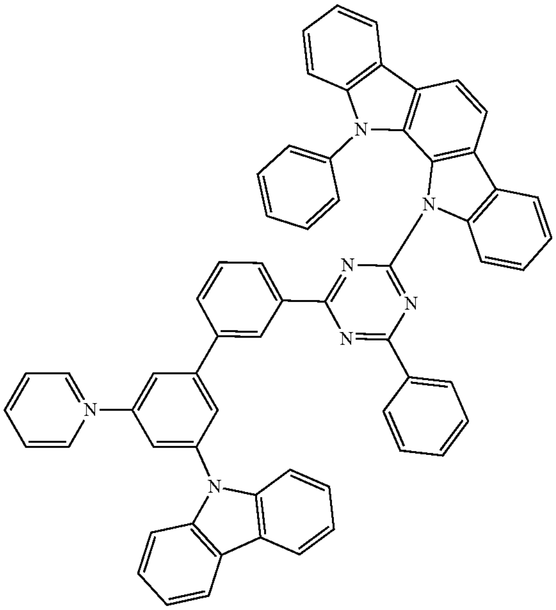
1-132
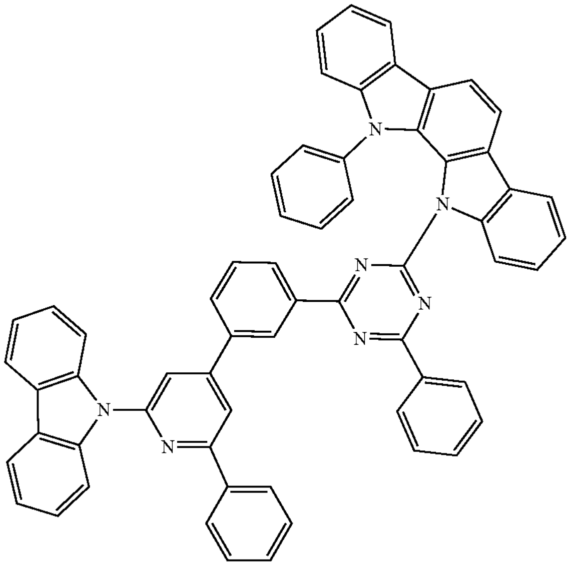
-continued
1-133
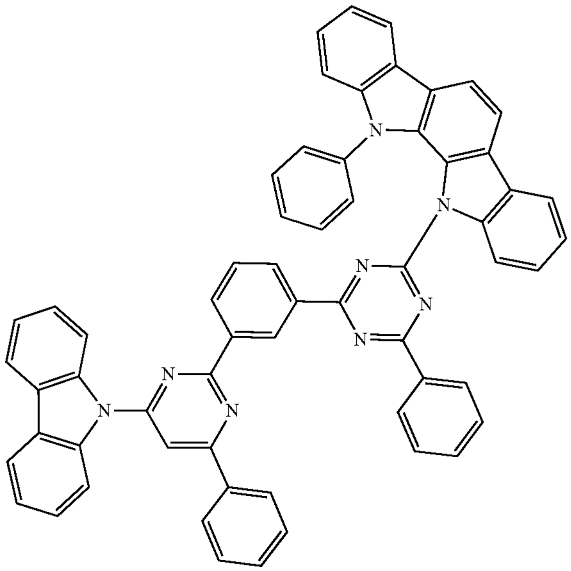
1-134
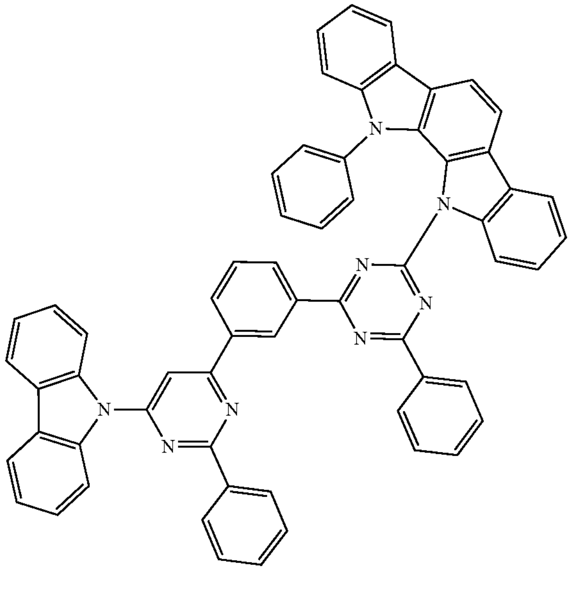

-continued
1-135
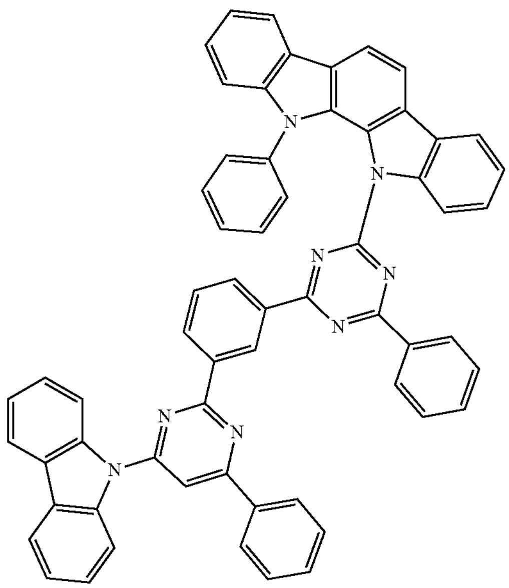
1-137
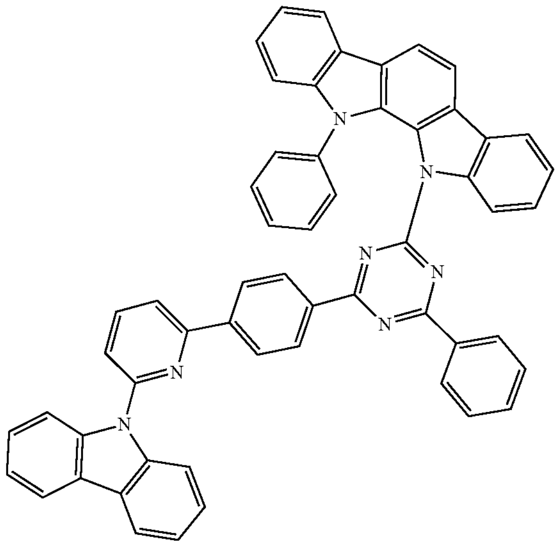
-continued
1-138
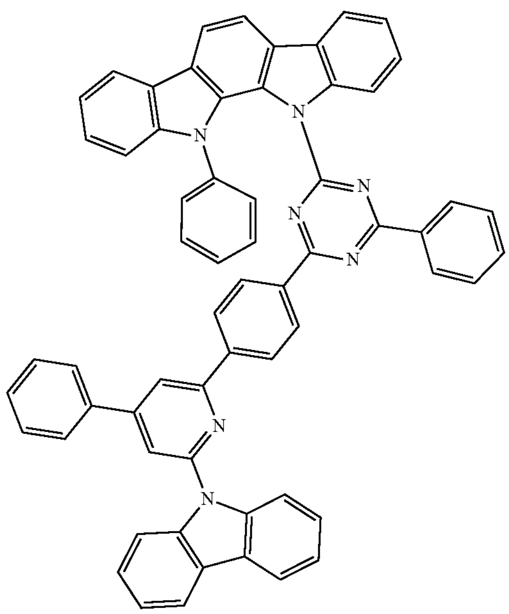
1-139
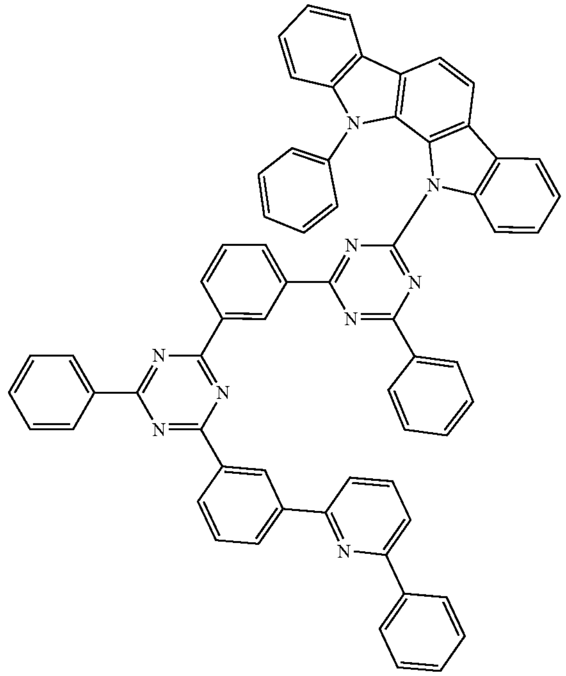

-continued
1-140
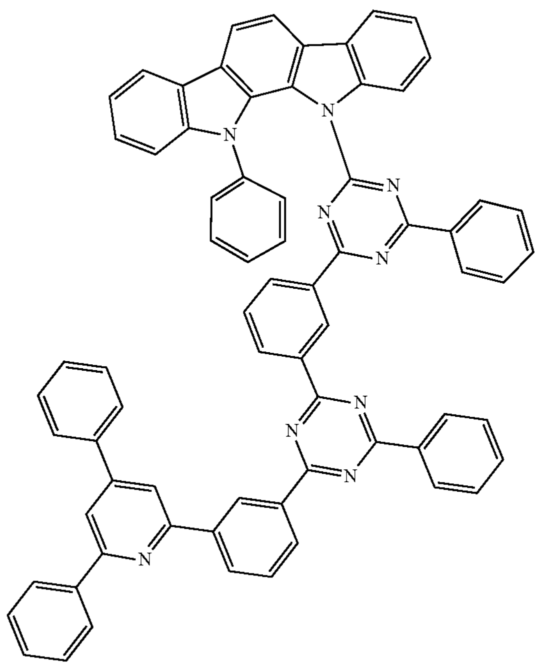
1-141
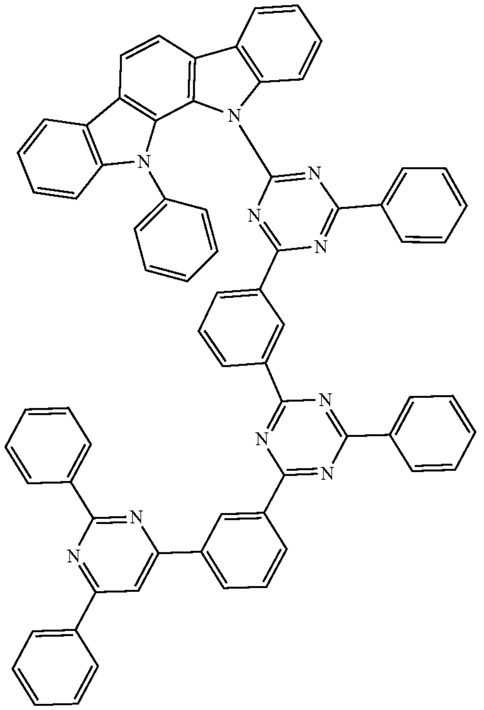
-continued
1-142
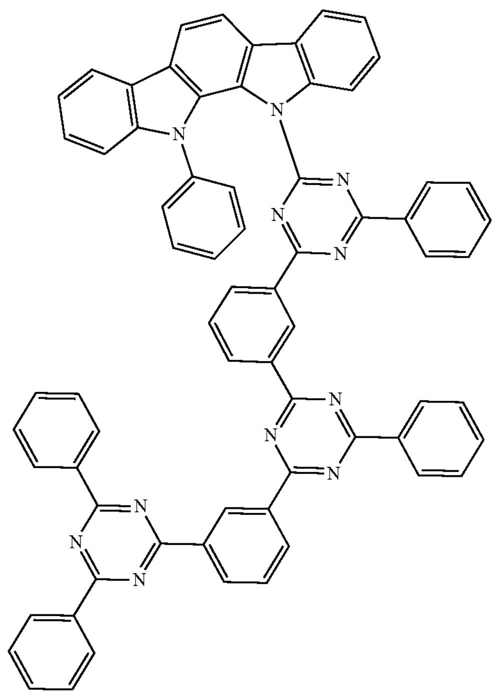
[C 17]
1-143
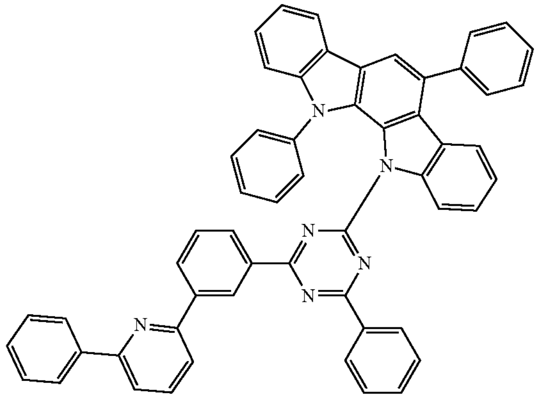
1-144
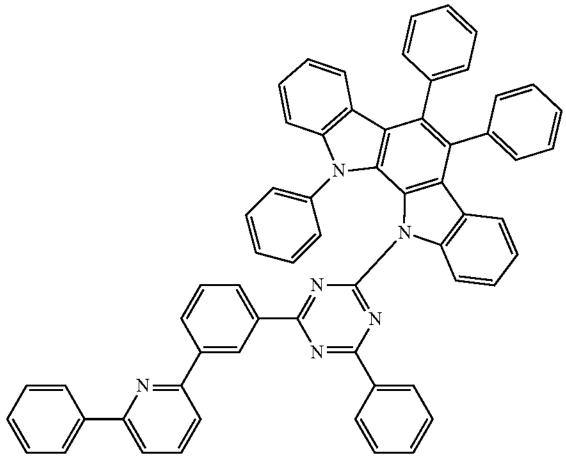

-continued
1-145
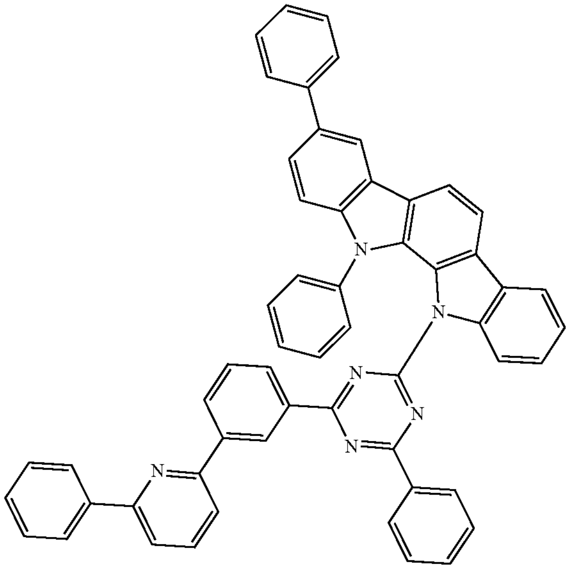
1-146
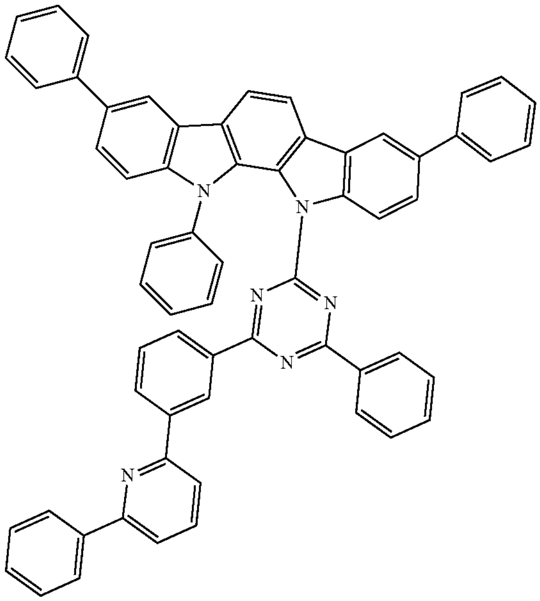
1-147
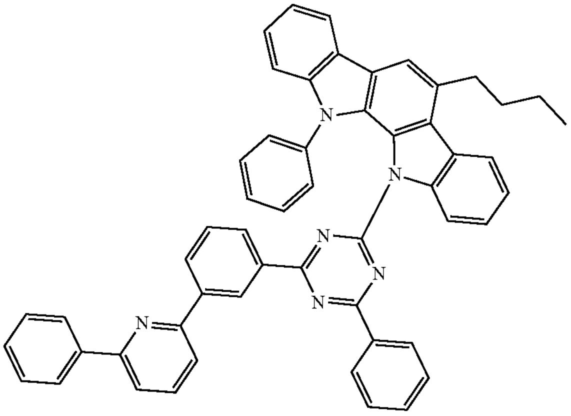
-continued
1-148
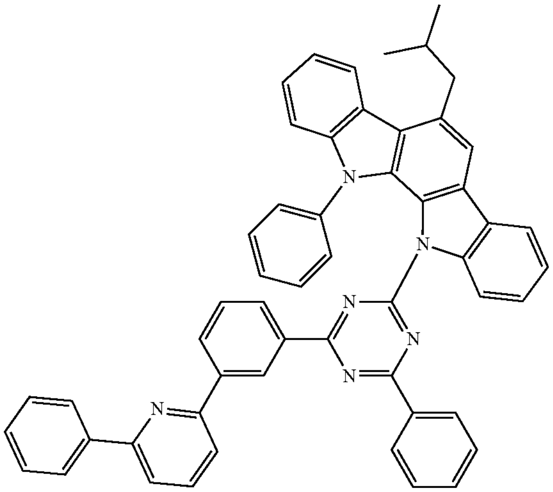
1-149
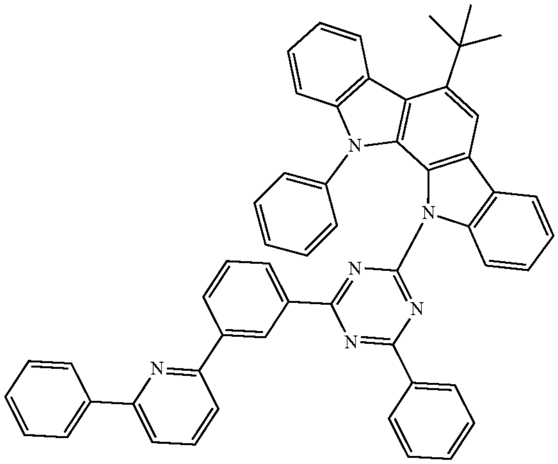
1-150
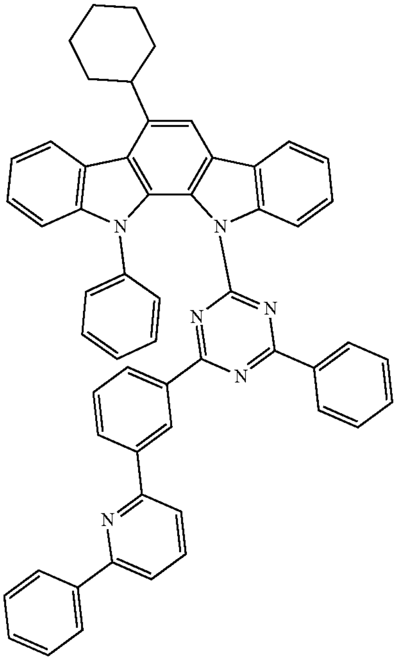

-continued
1-151
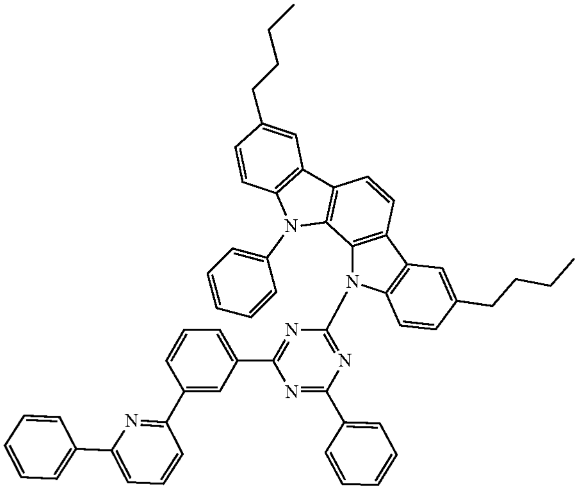
1-152
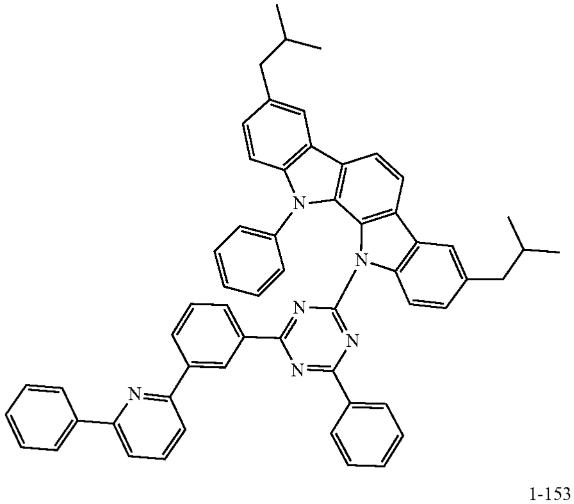
1-153
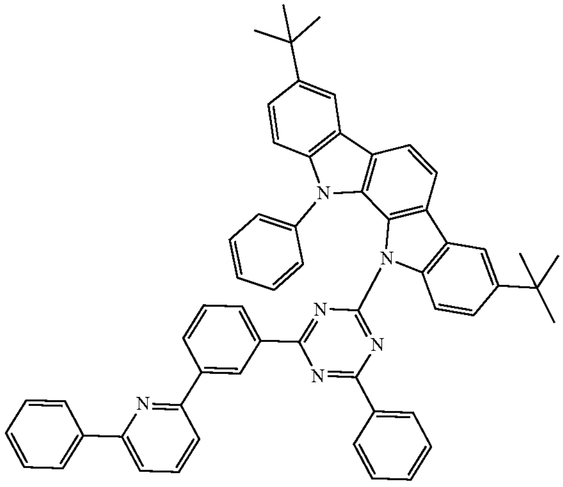
-continued
1-154
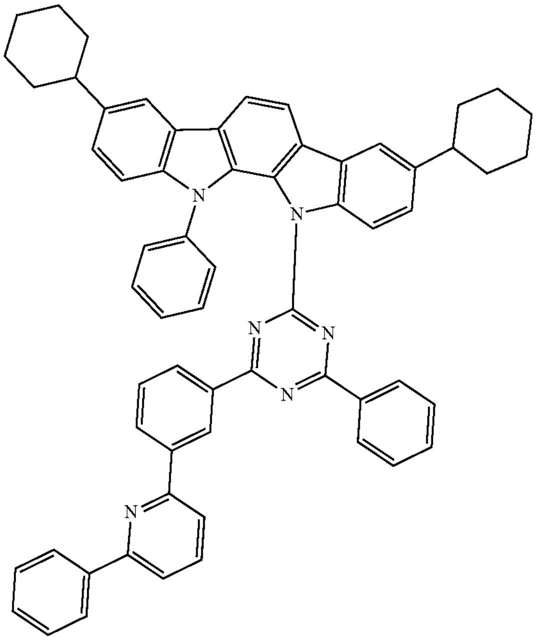
1-155
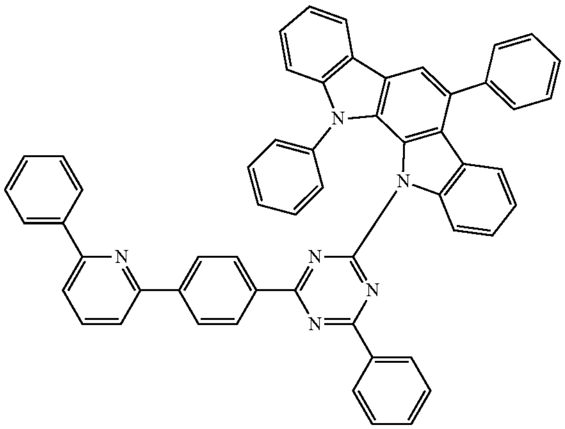
1-156
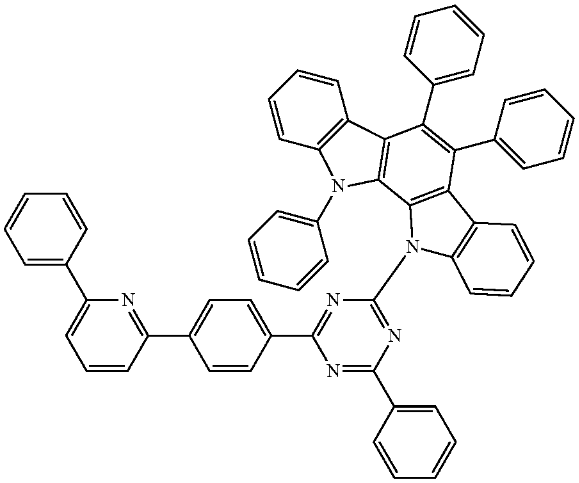

-continued
1-157
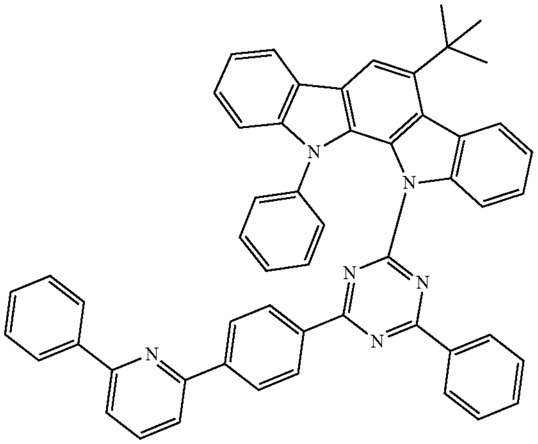
1-158
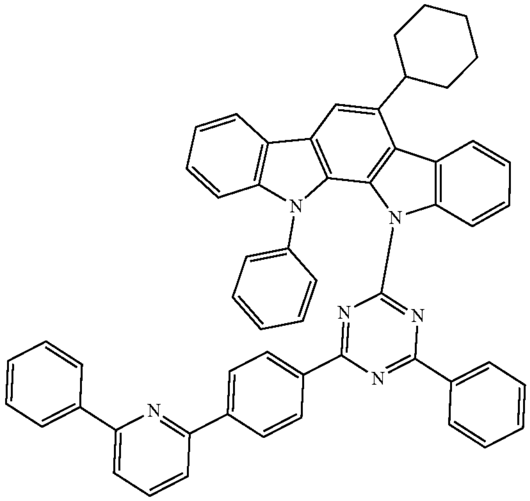
1-159
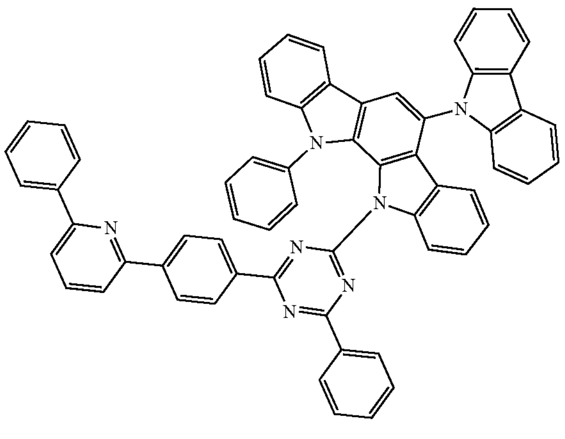
-continued
1-160
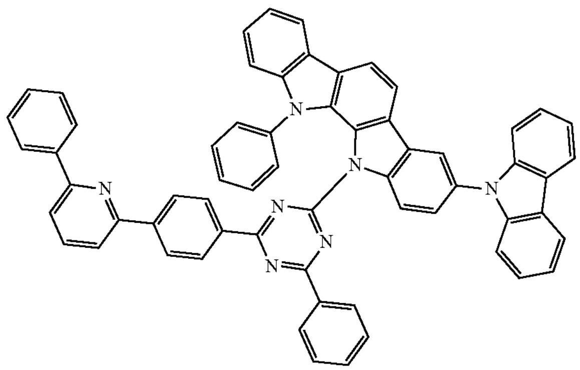
1-161
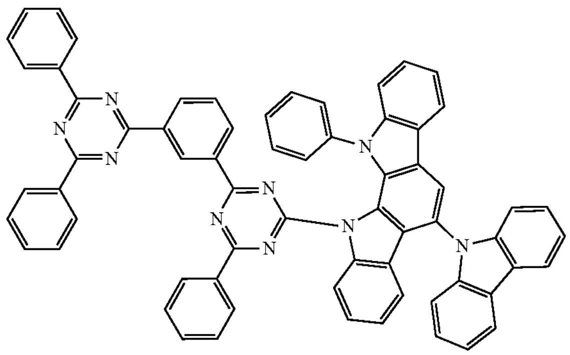
1-162
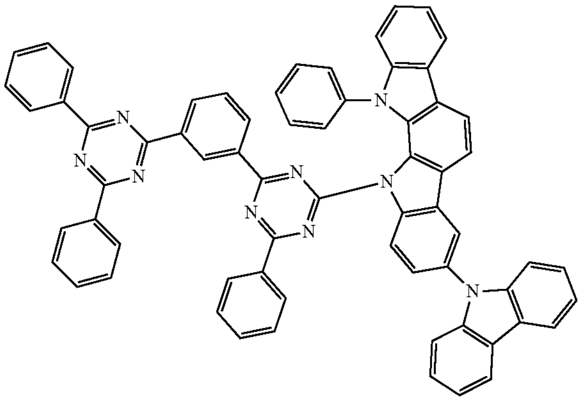
1-163
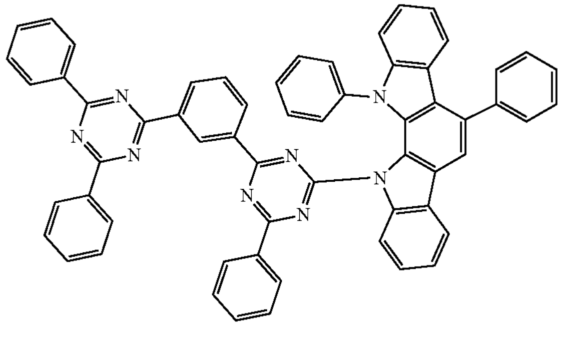

-continued
1-164
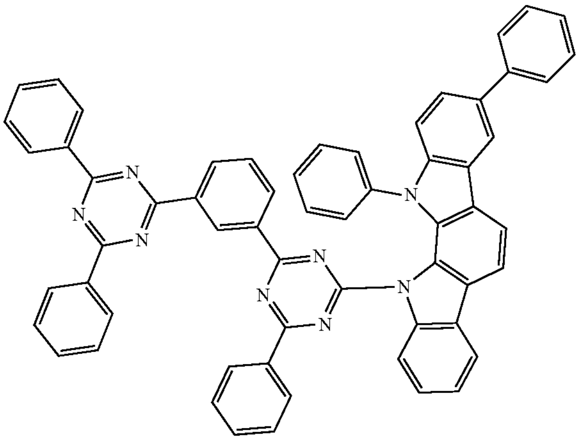
[C 18]
1-165
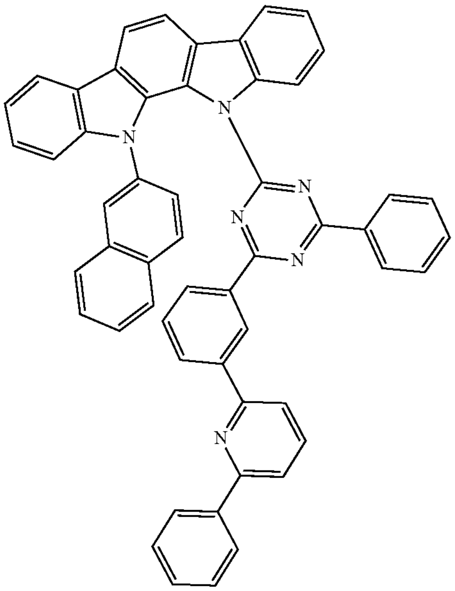
1-166
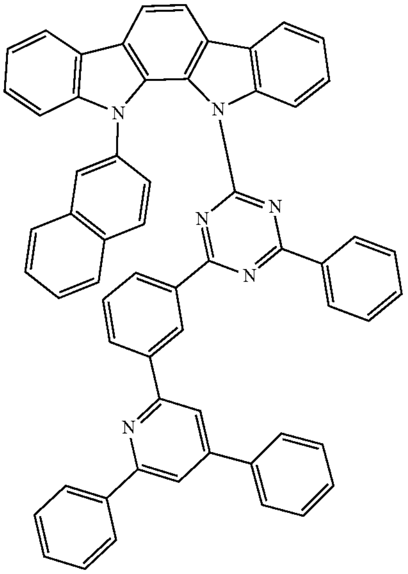
-continued
1-167
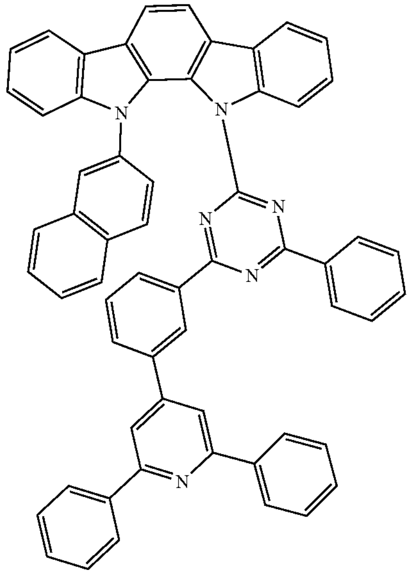
1-168
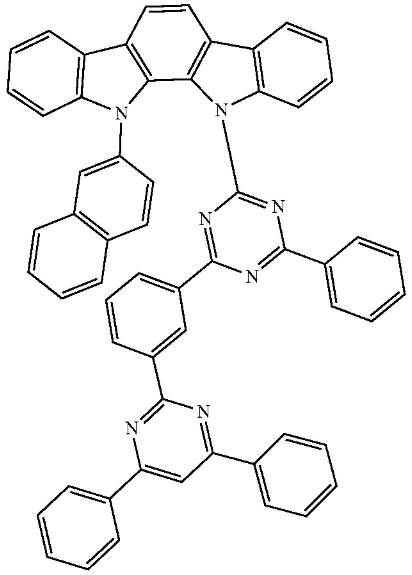
1-169
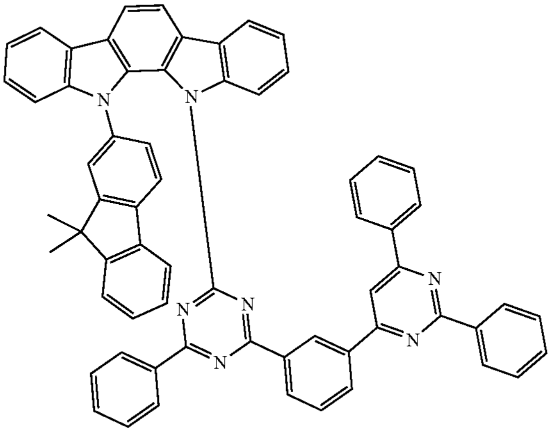

-continued
1-170
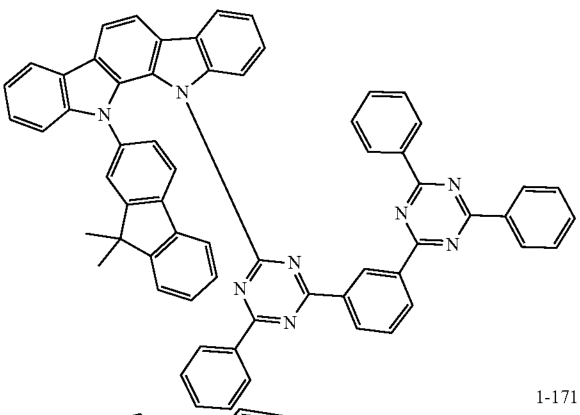
1-171
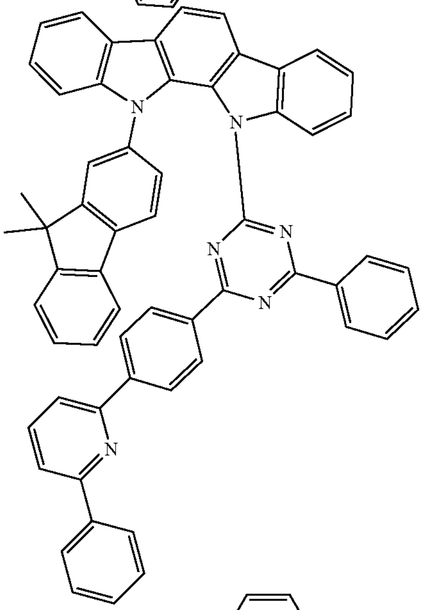
1-172
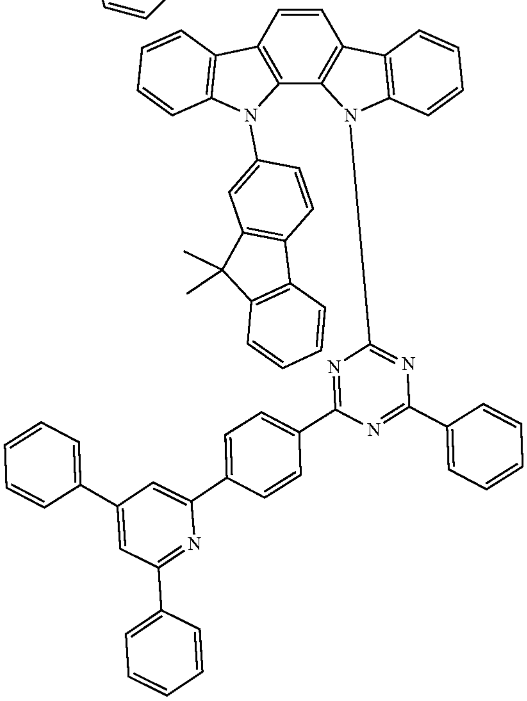
-continued
1-173
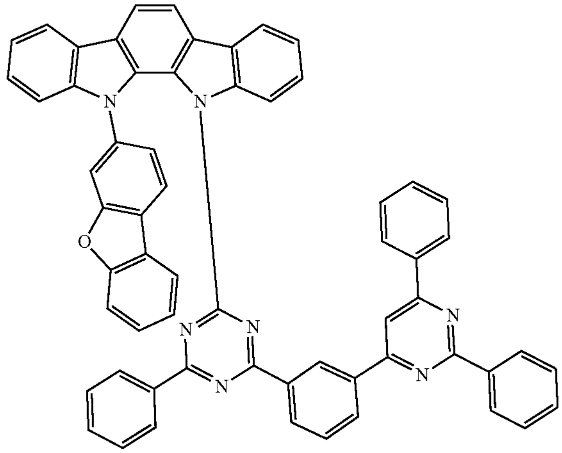
1-174
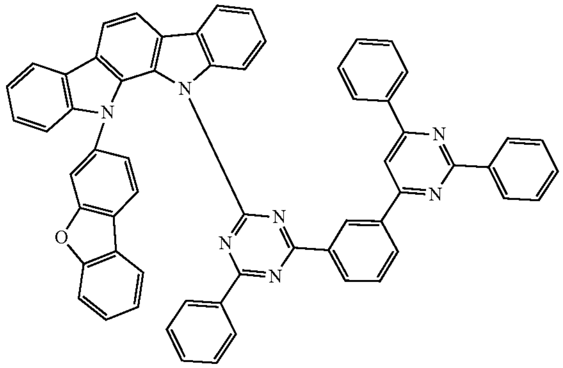
1-175
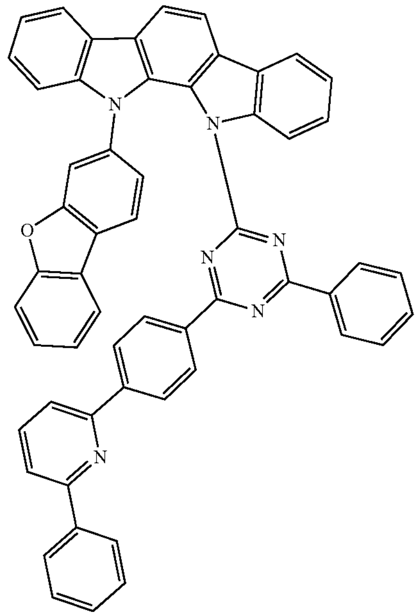

-continued
1-176
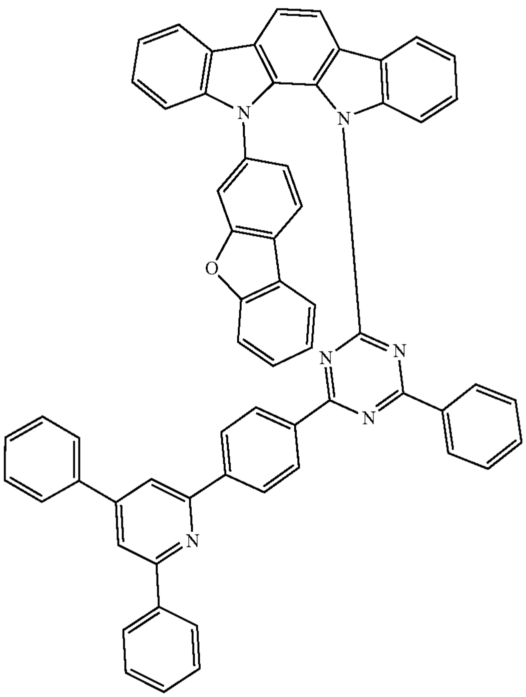
1-177
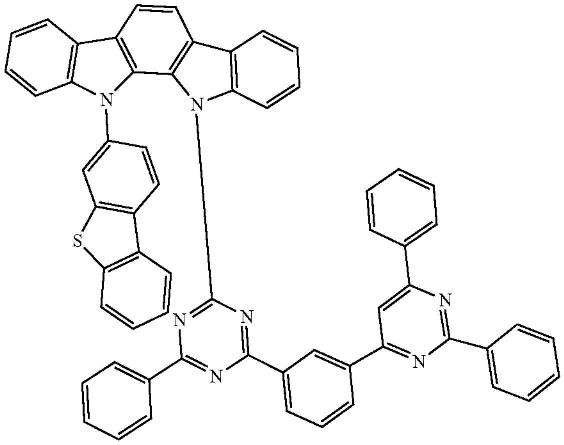
1-178
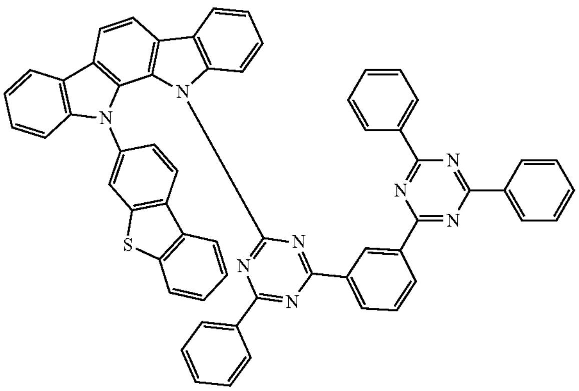
-continued
1-179
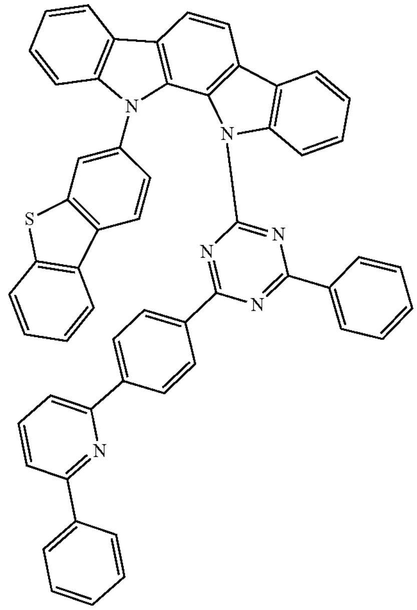
1-180
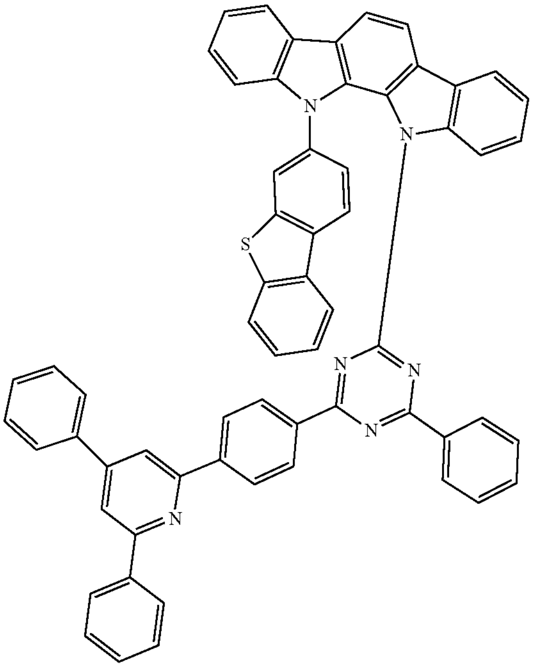

-continued
1-181
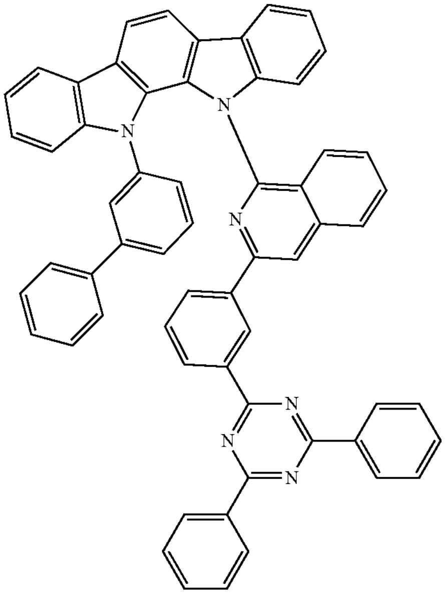
1-182
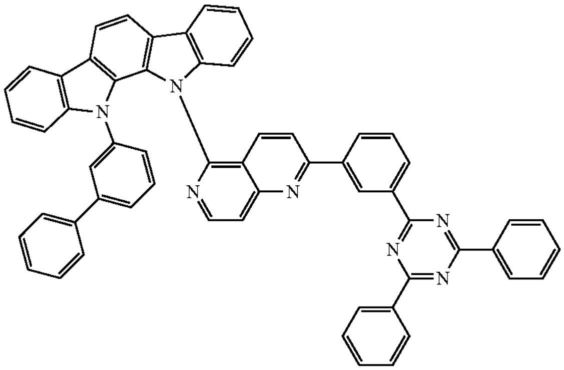
[C 19]
1-183
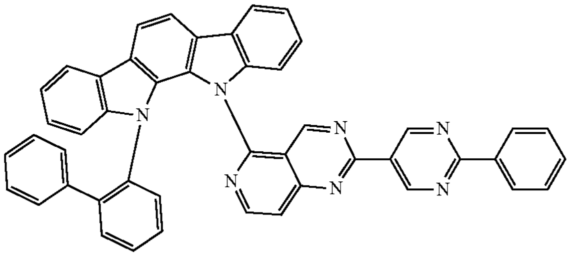
-continued
1-184
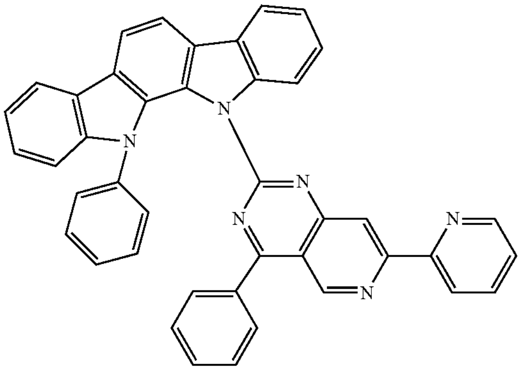
1-185
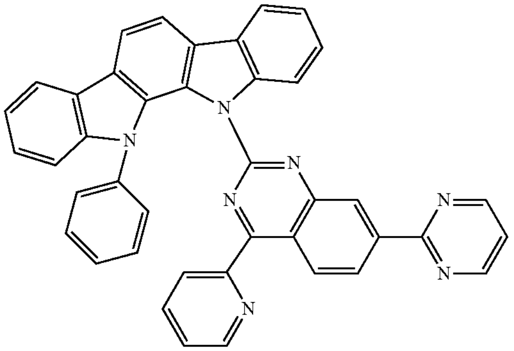
1-186
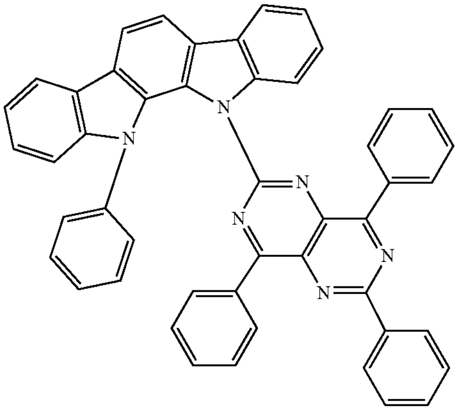

-continued
1-187
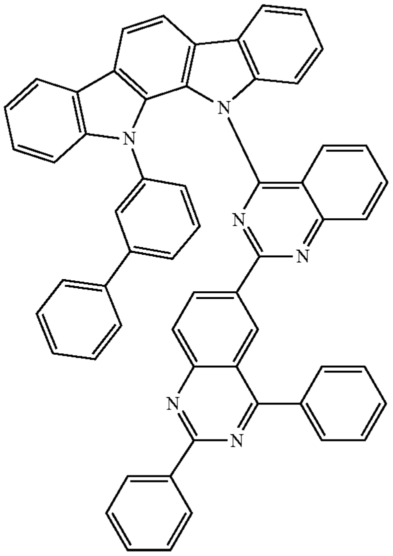
1-188
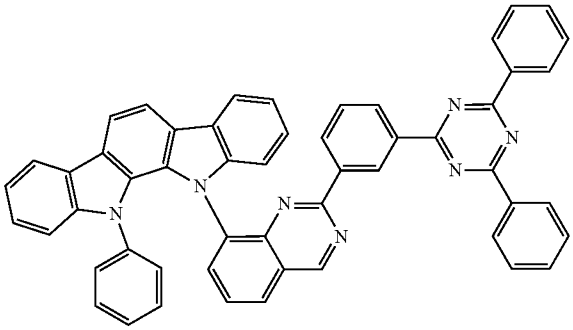
1-189
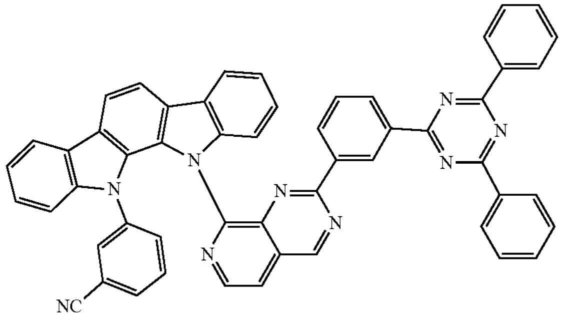
-continued
1-190
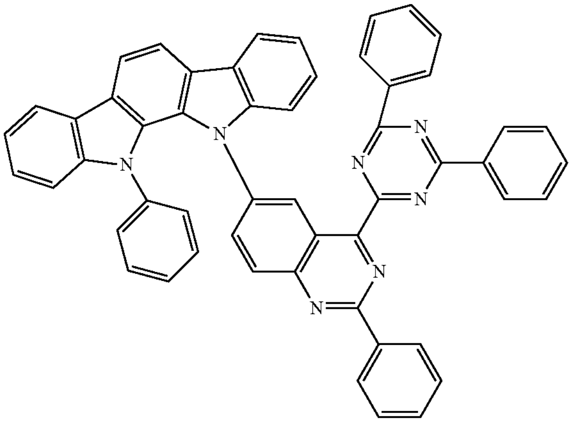
1-191
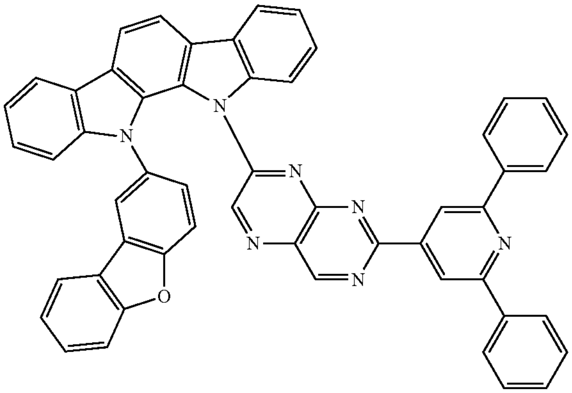
1-192
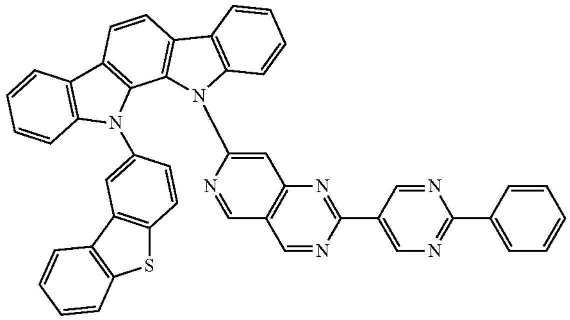
1-193
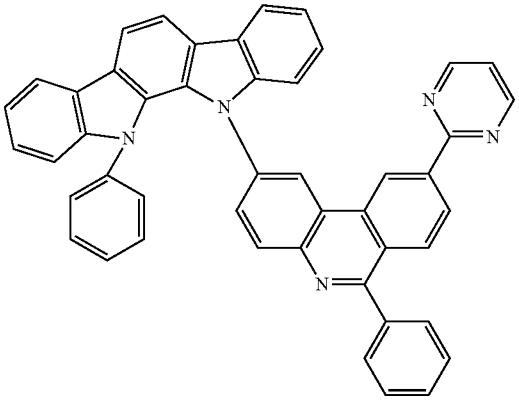

-continued
[C 20]
1-194
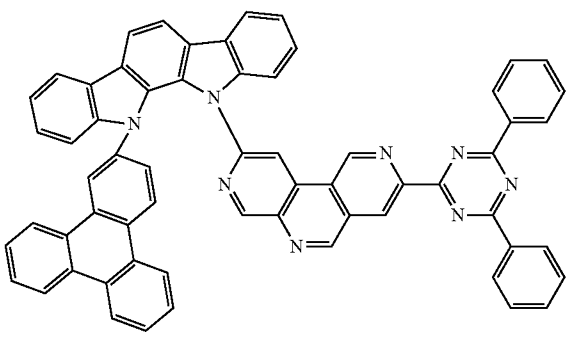
1-195
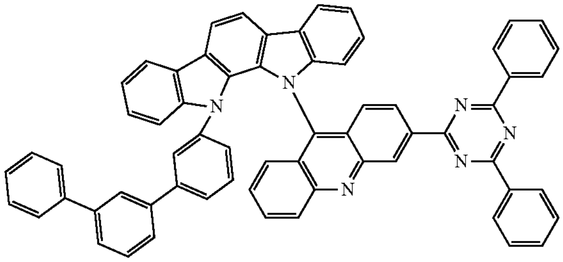
1-196
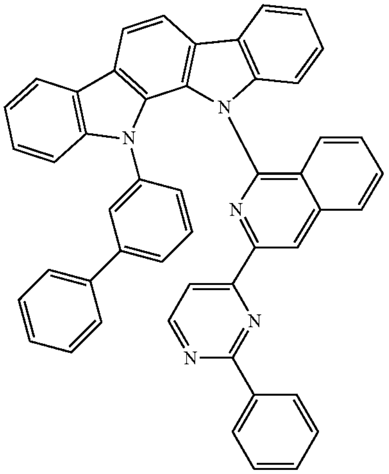
1-197
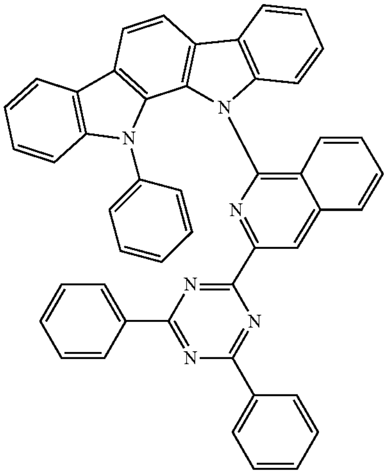
-continued
1-198
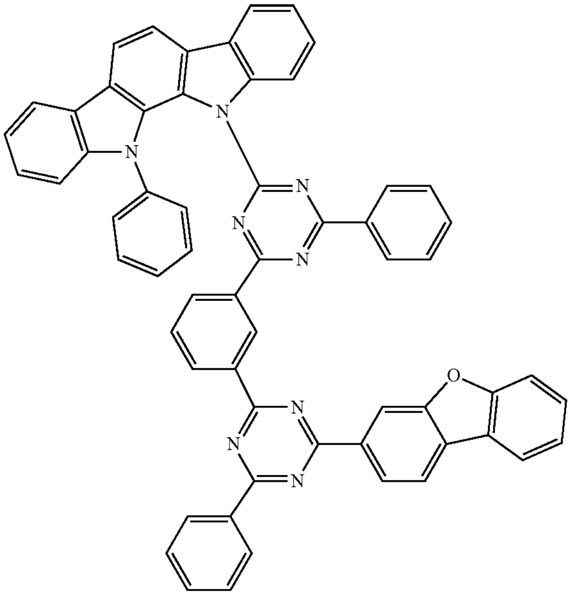
1-199
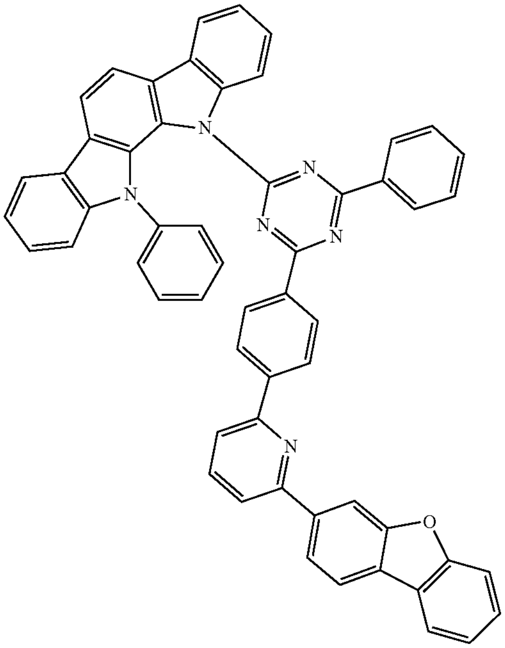

-continued
1-200
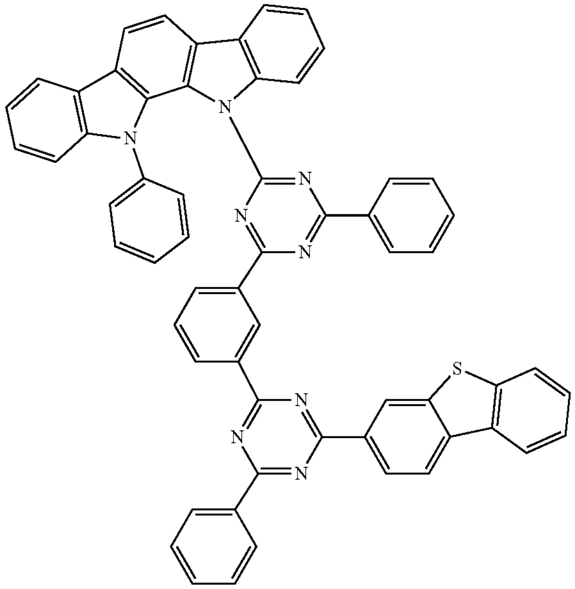
1-201
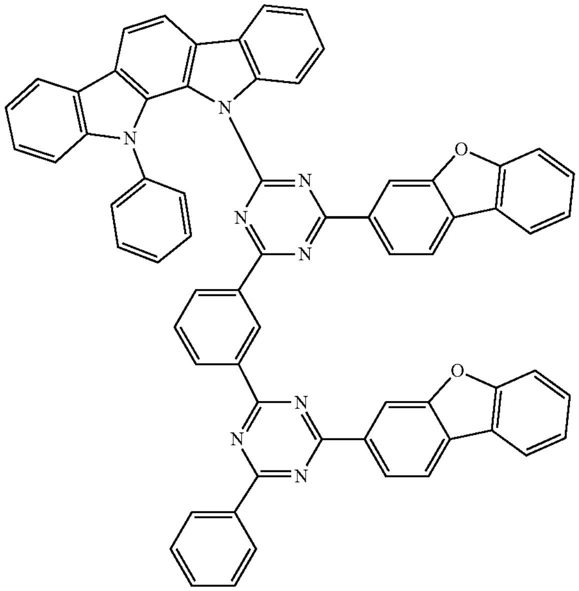
-continued
[C 21]
1-202
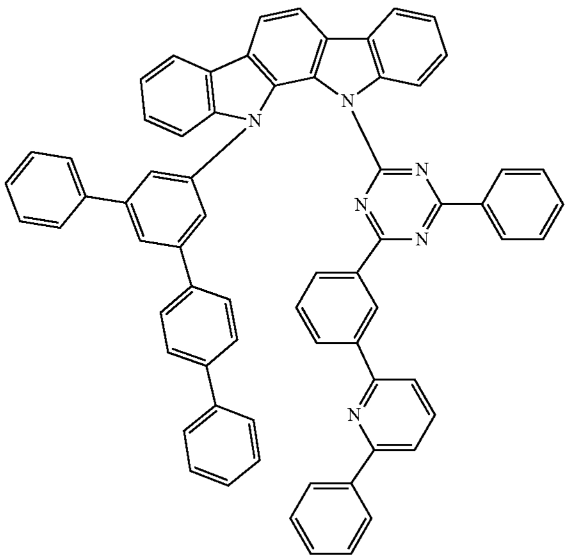
1-203
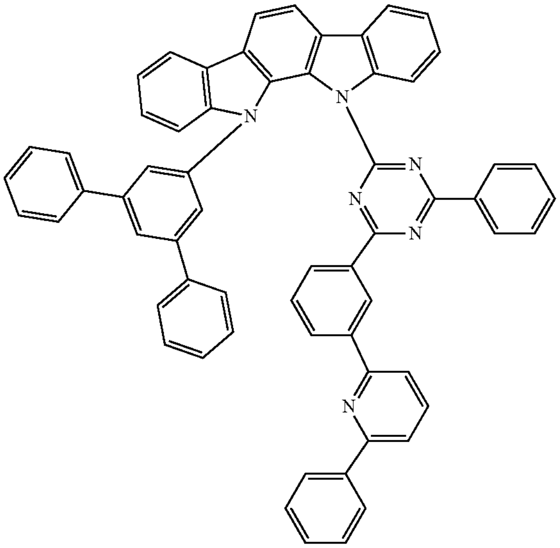

-continued
1-204
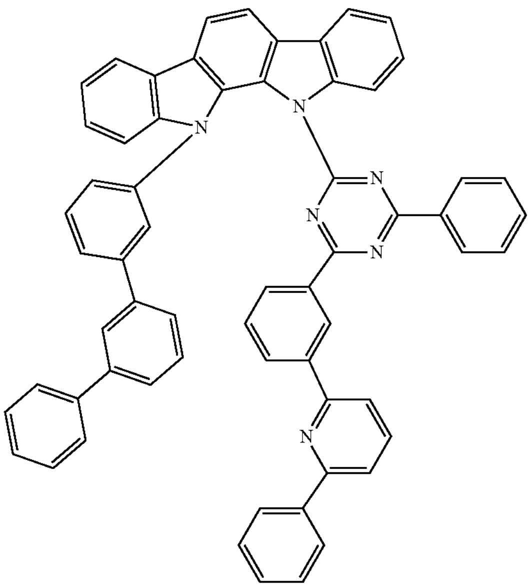
1-205
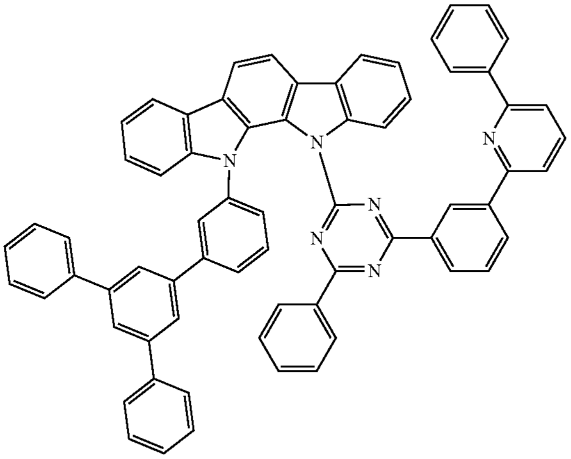
1-206
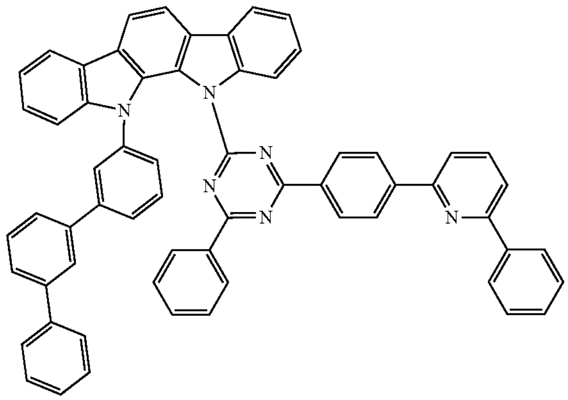
-continued
1-207
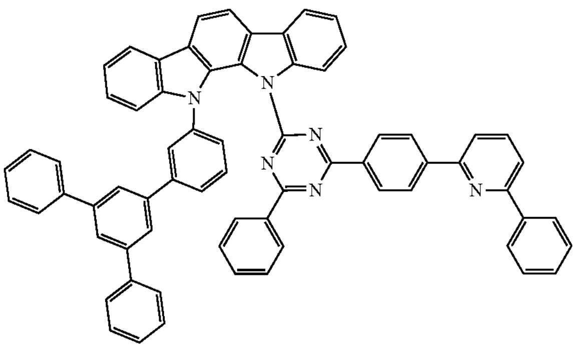
1-208
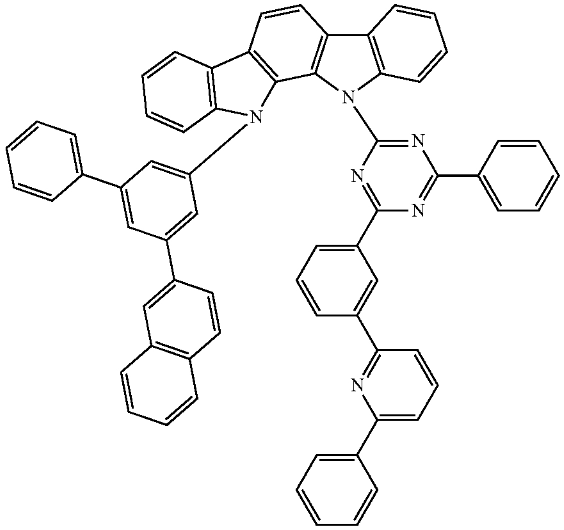
1-209
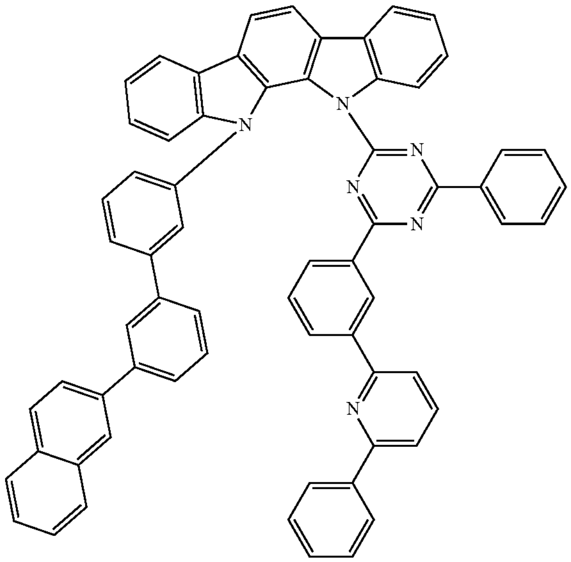

-continued
1-210
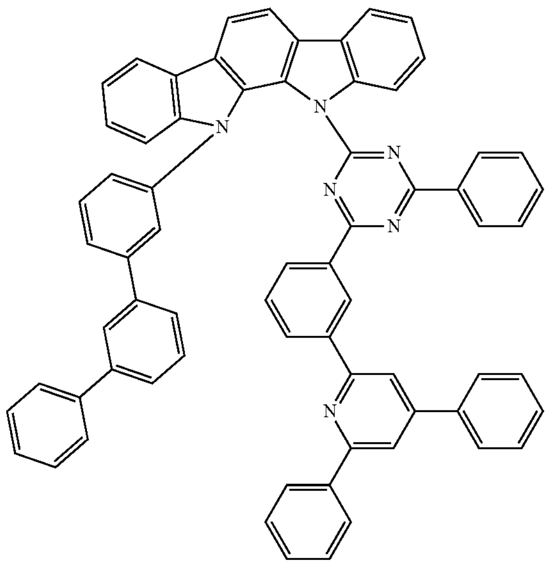
1-211
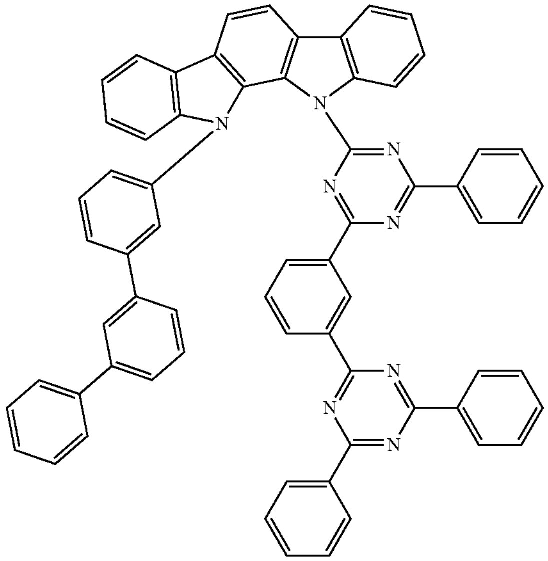
-continued
1-212
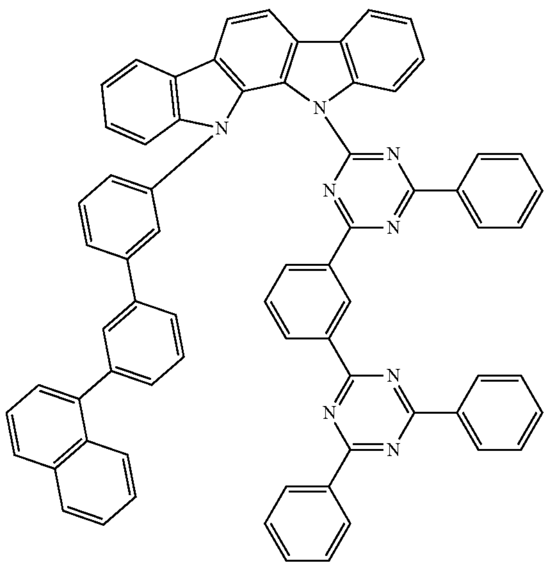
1-213
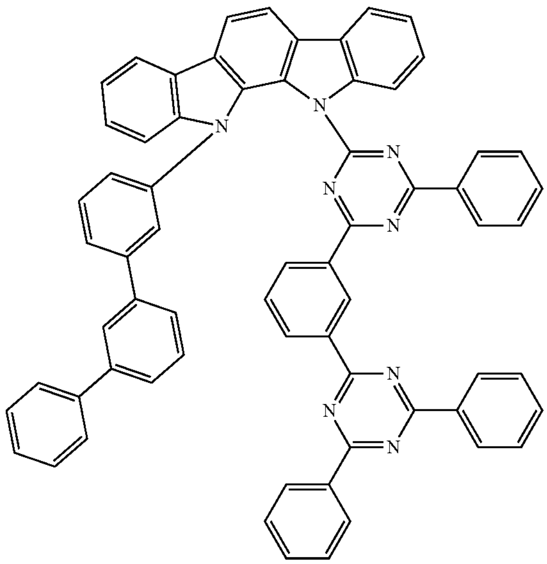
1-214
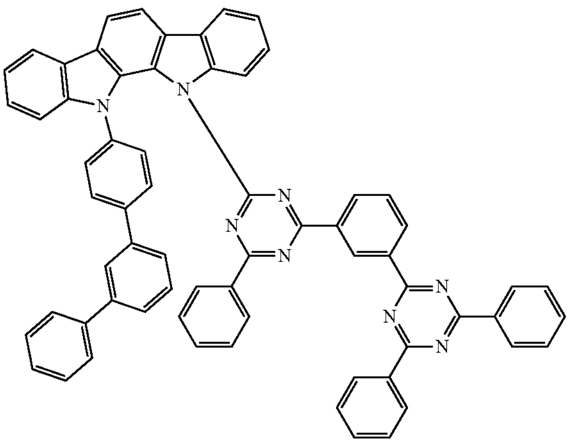

-continued
1-215
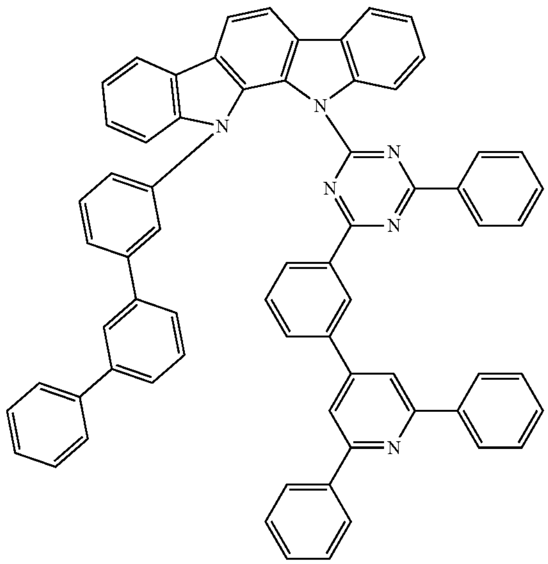
1-216
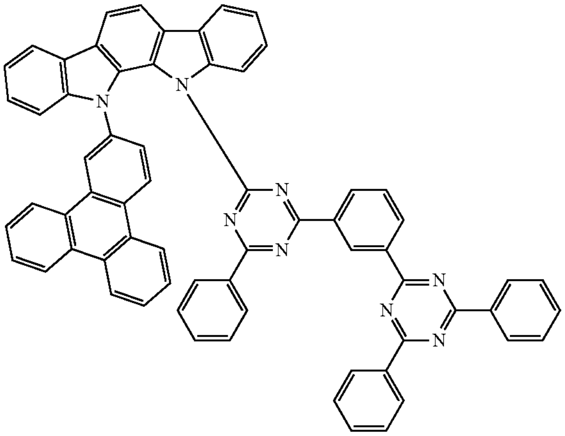
[C 22]
1-217
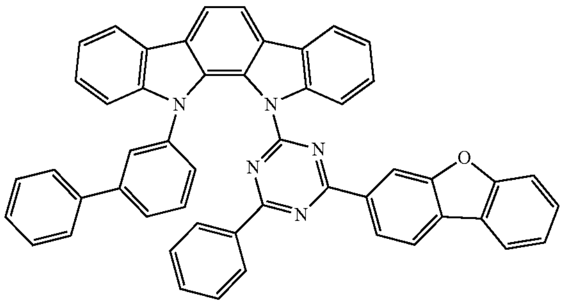
-continued
1-219
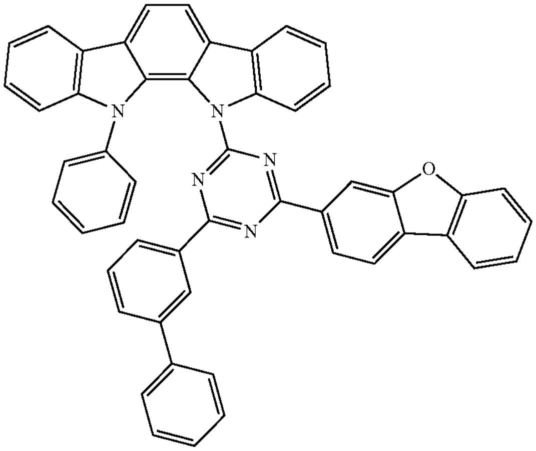
1-220
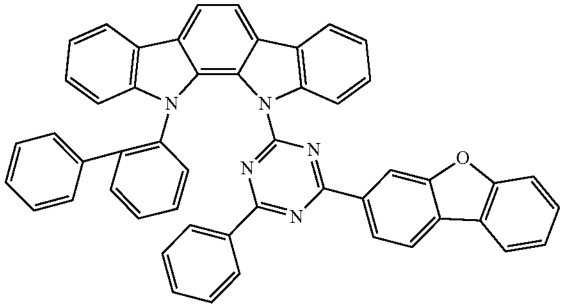
1-221
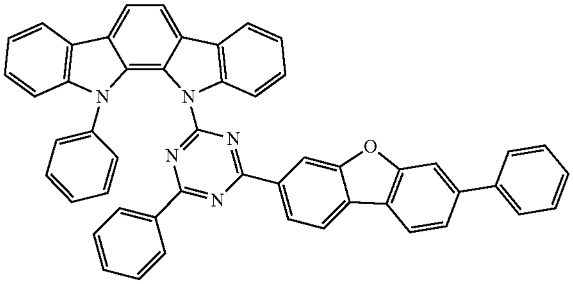
1-222
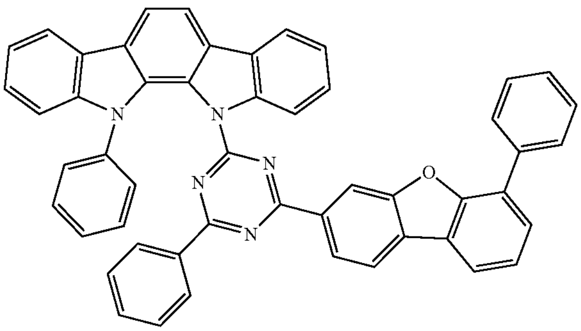

-continued
1-223
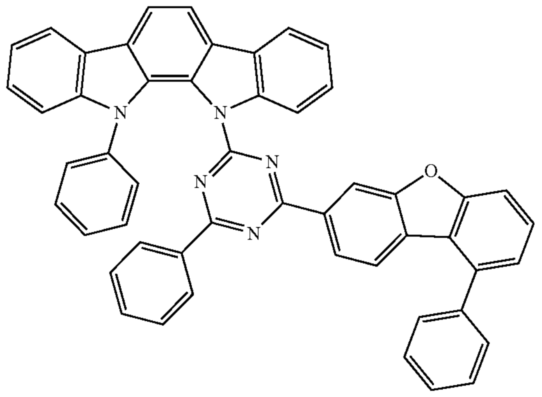
1-224
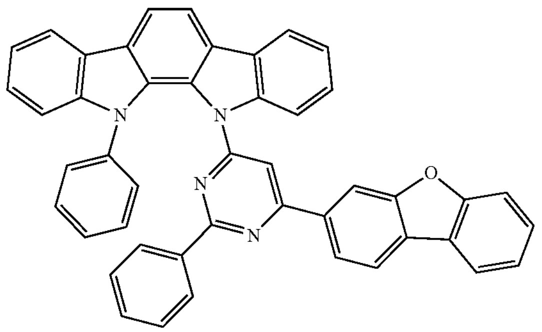
1-225
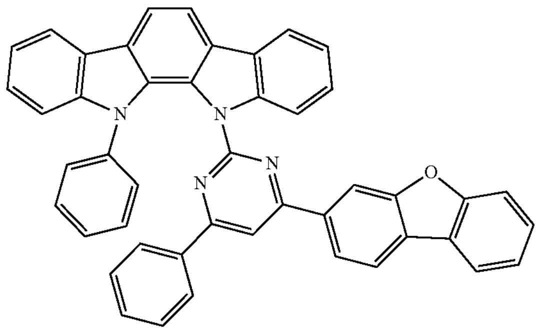
1-226
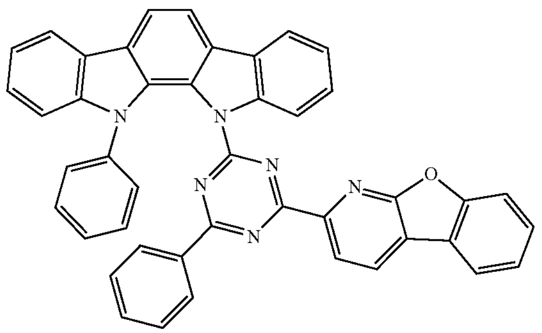
-continued
1-227
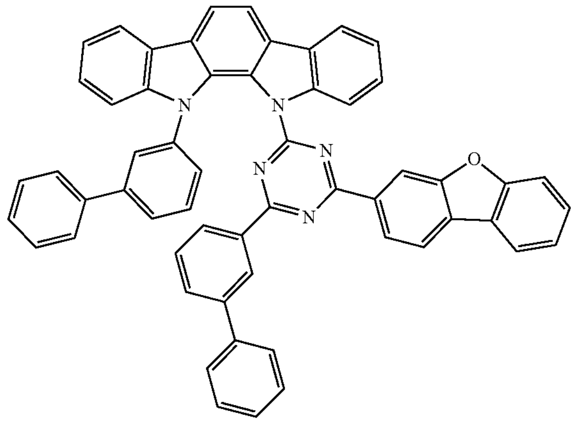
1-228
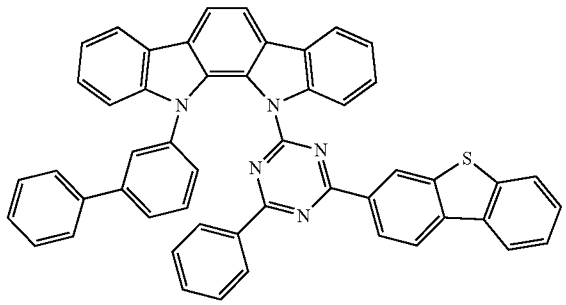
1-229
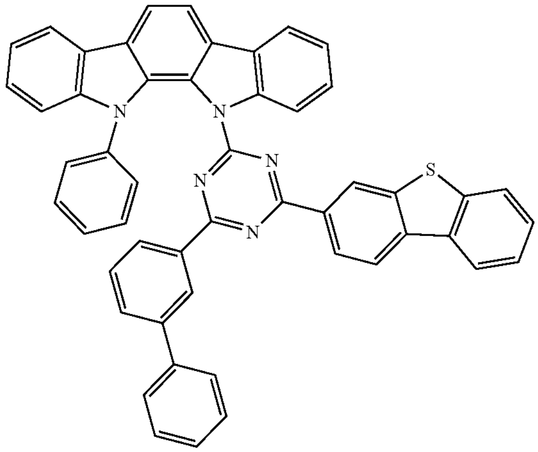
[C 23]
1-230
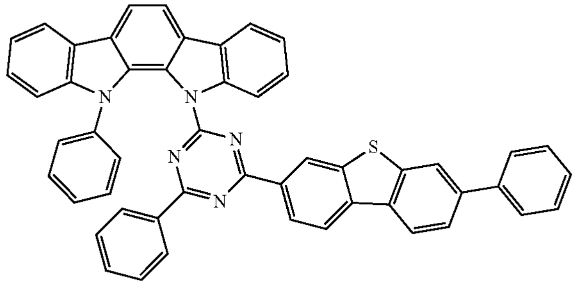

-continued
1-231
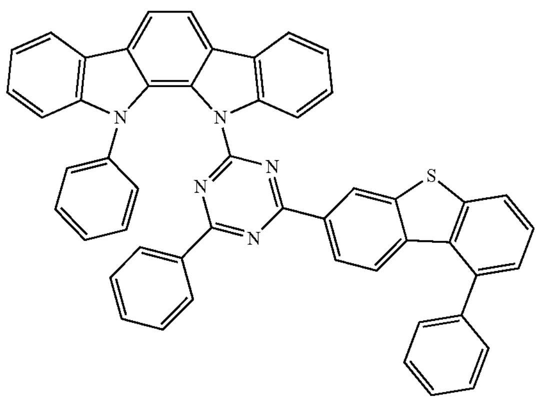
1-232
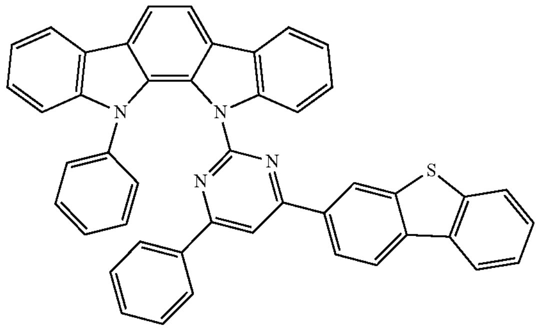
[C 24]
1-248
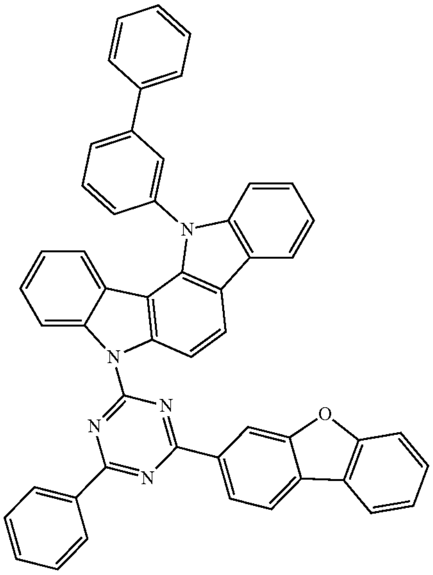
-continued
1-249
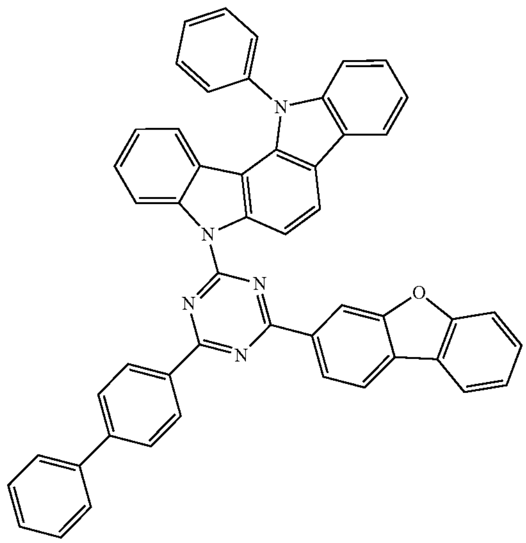
[C 25]
1-250
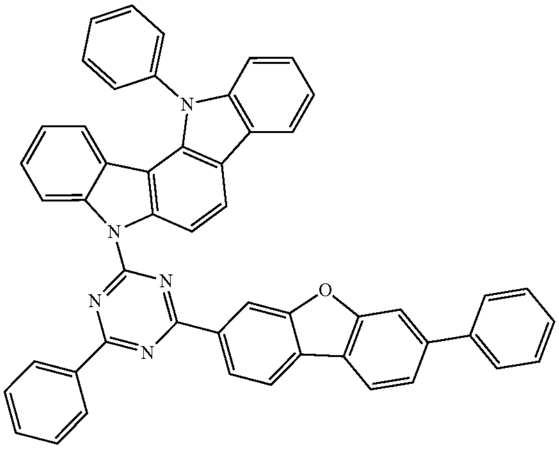
1-251
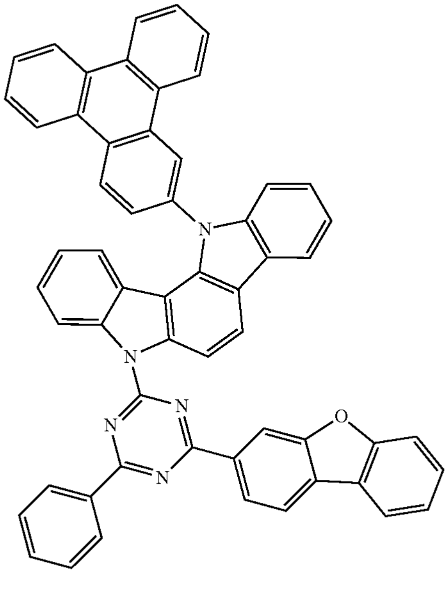

-continued
1-252
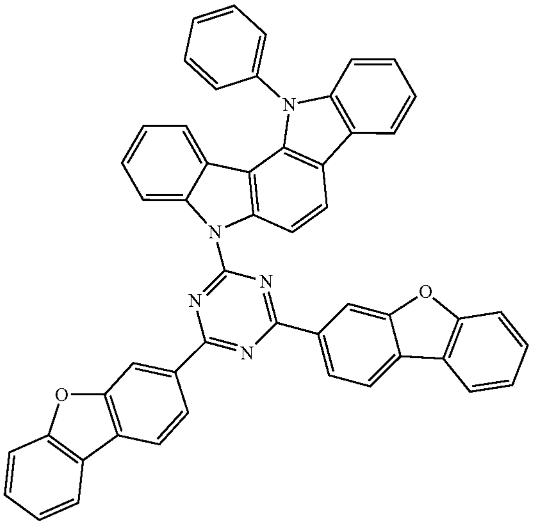
1-253
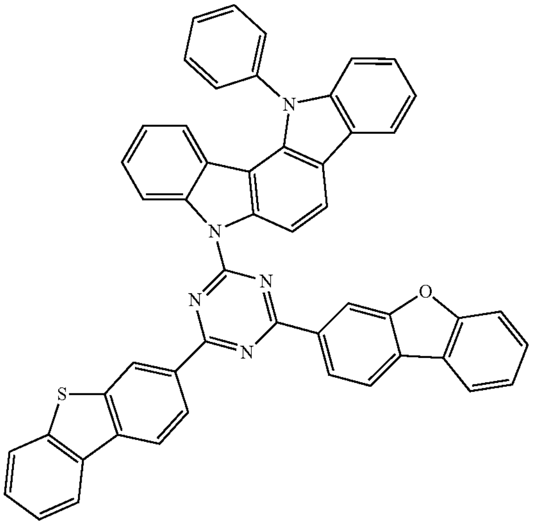
1-254
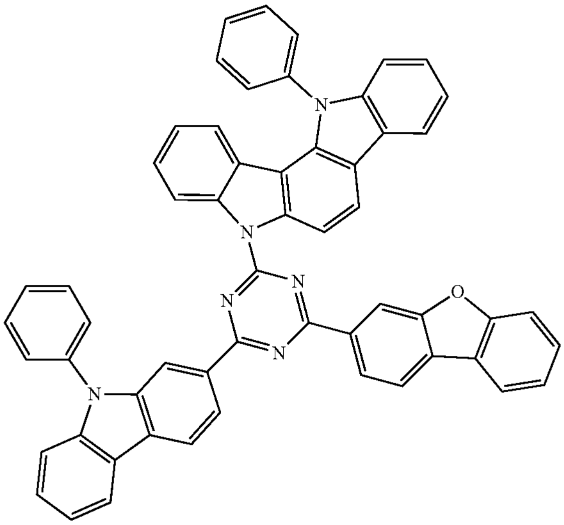
-continued
1-255
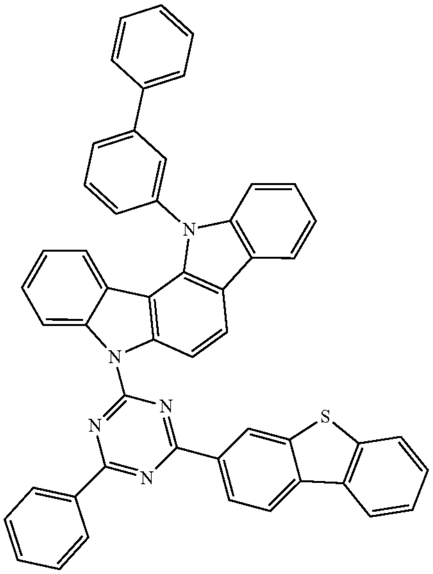
[C 26]
1-256
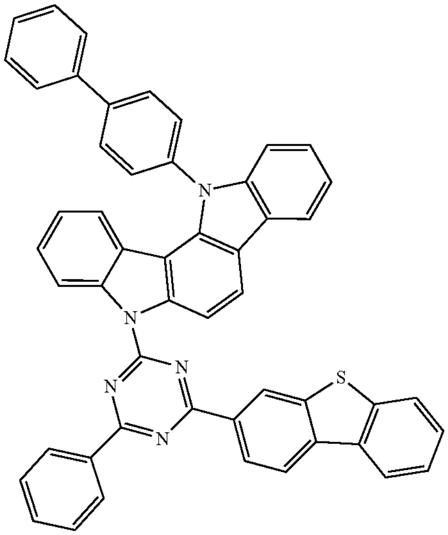

-continued
1-257
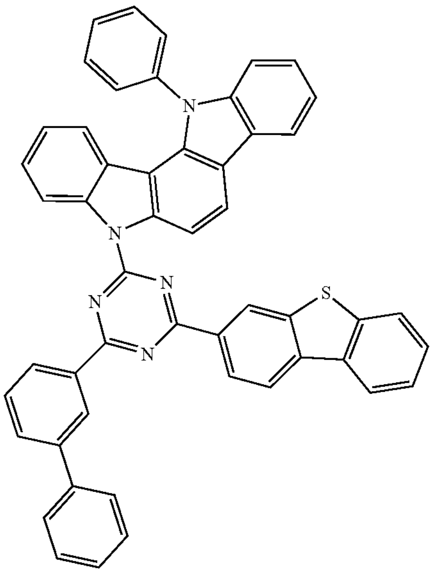
[C 27]
1-258
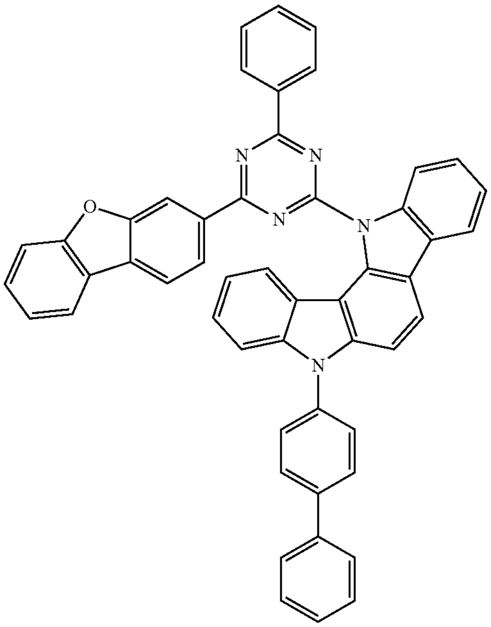
-continued
1-259
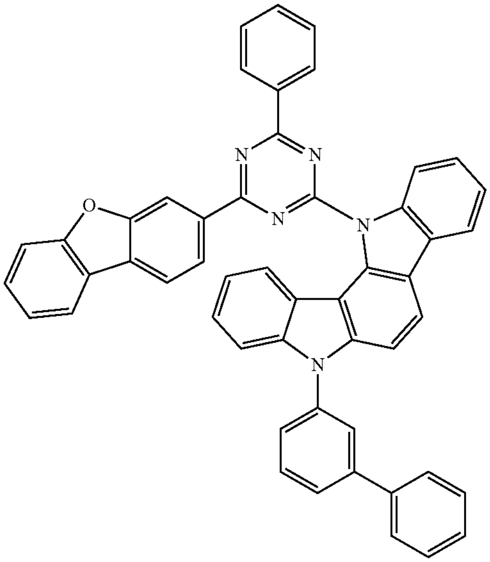
1-260
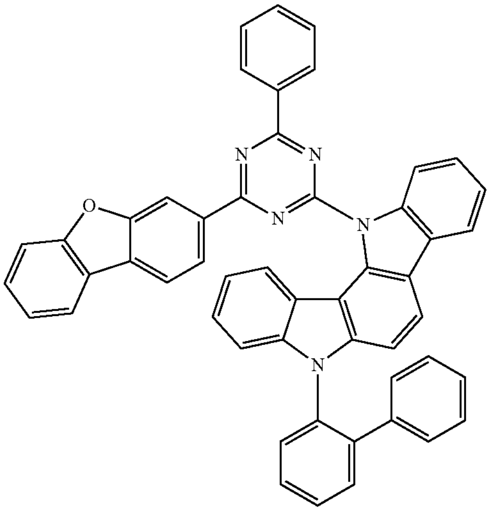
1-261
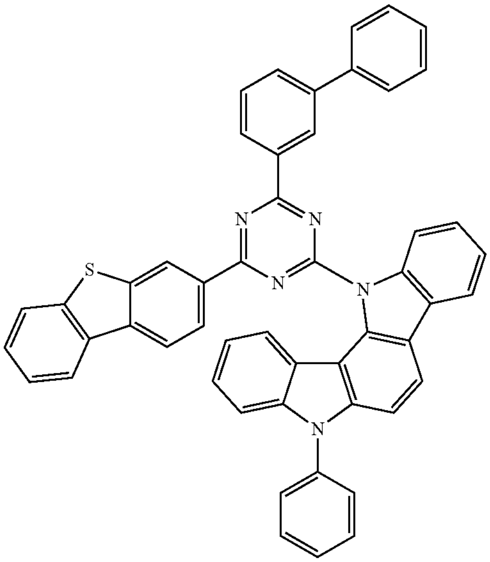

-continued
1-270
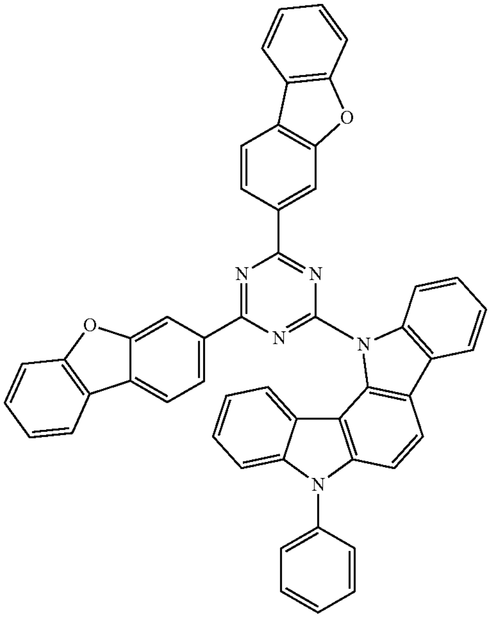
1-271
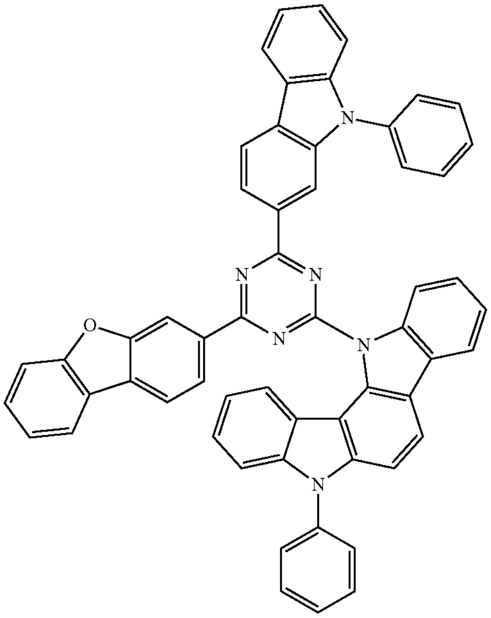
-continued
[C 28]
1-274
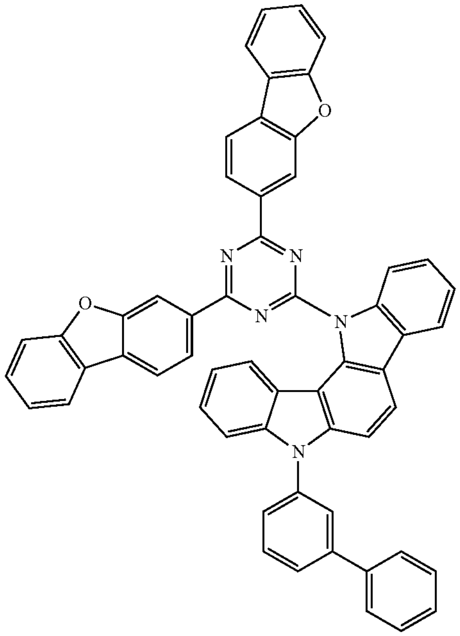
1-275
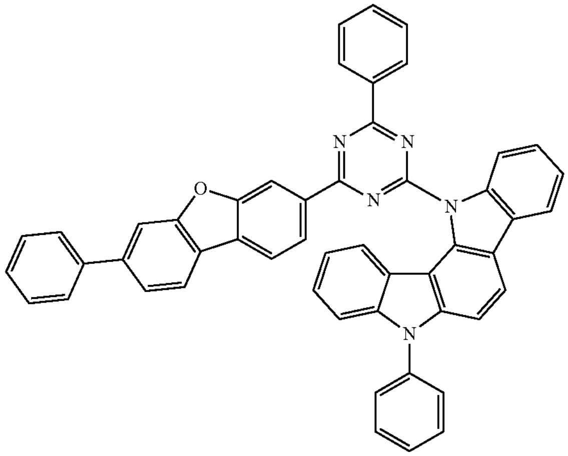
1-276
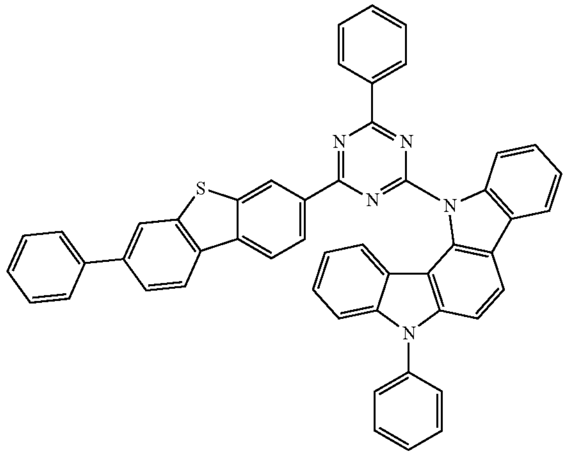

-continued
1-277
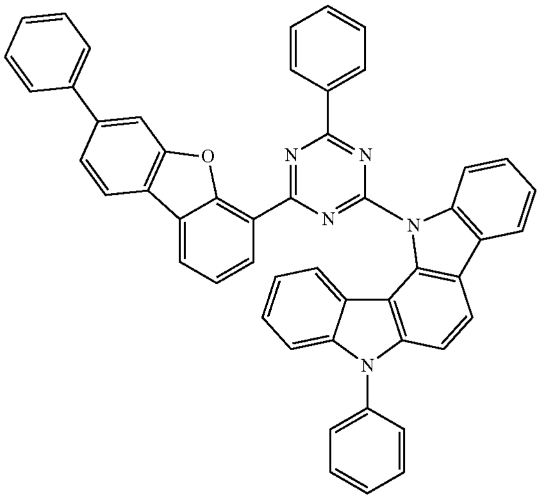
1-278
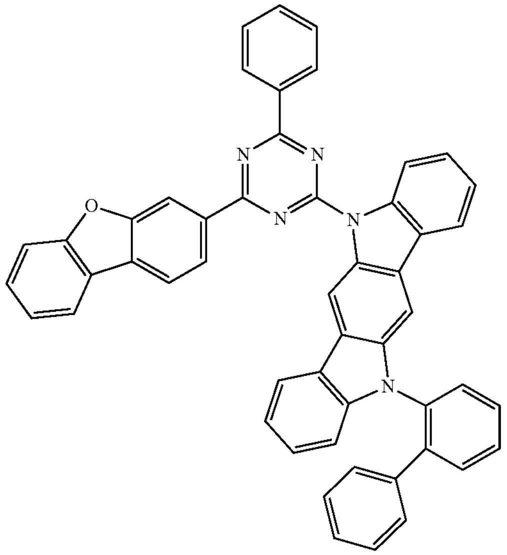
1-279
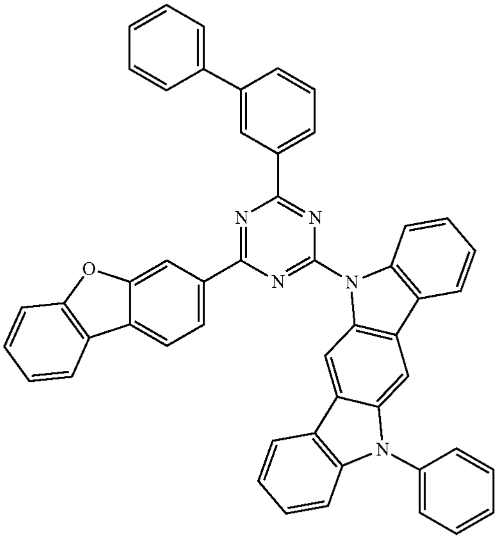
-continued
1-280
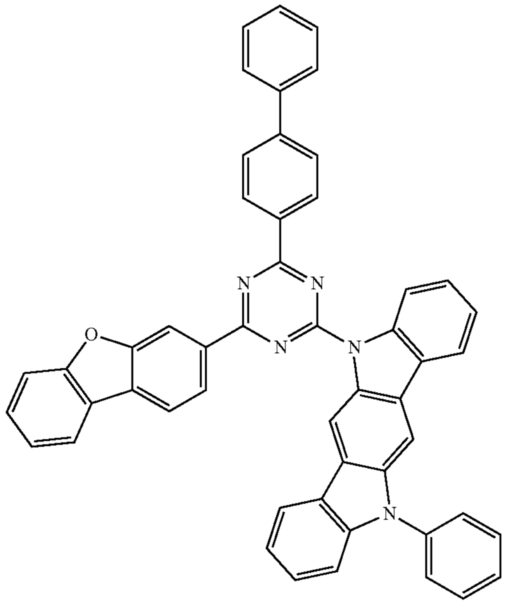
1-281
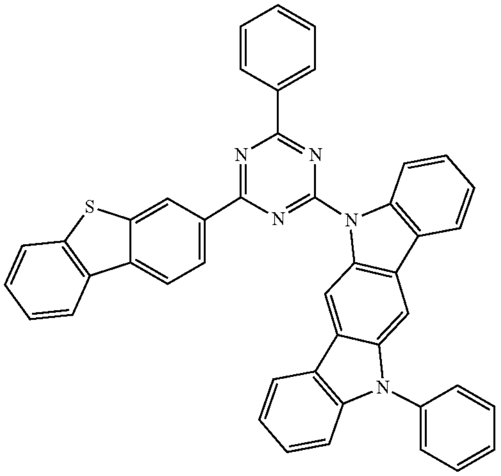
[C 29]
1-282
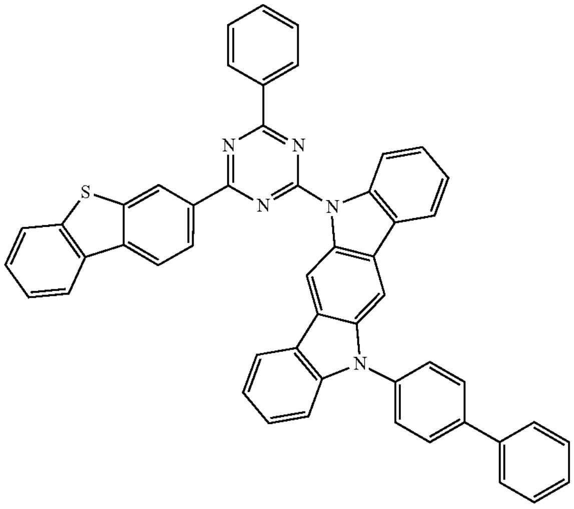

-continued
[C 30]
1-290
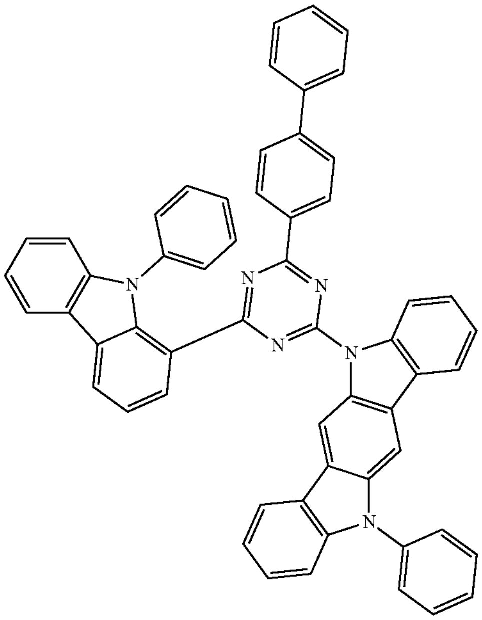
1-291
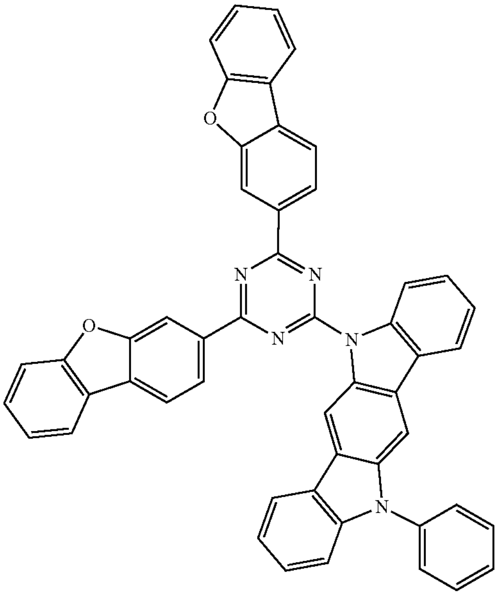
-continued
1-292
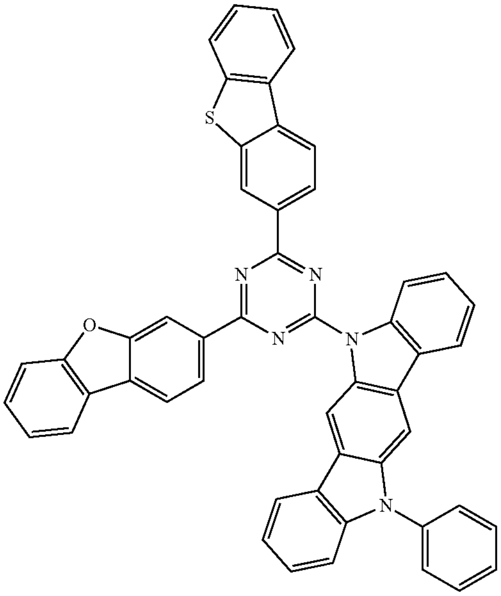
1-293
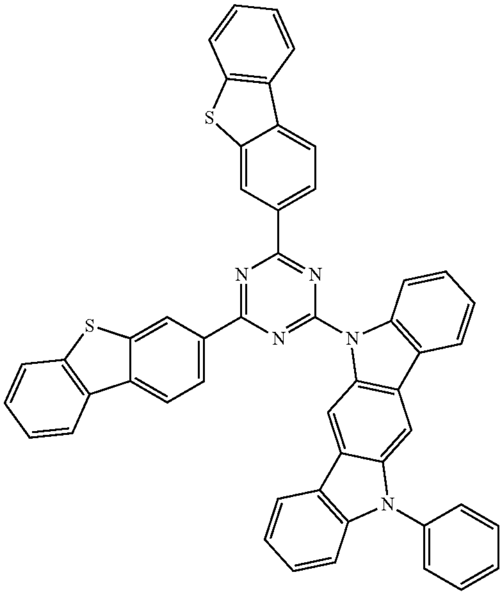

-continued
[C 31]
1-298
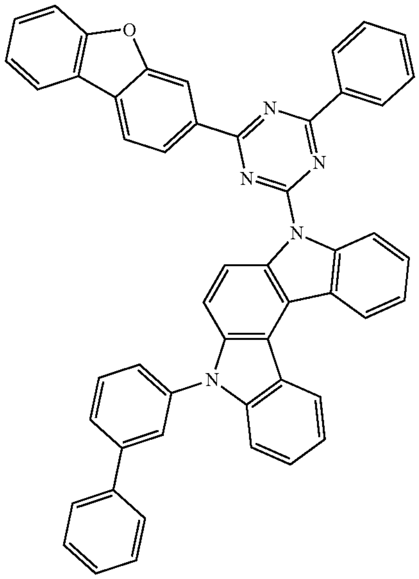
1-299
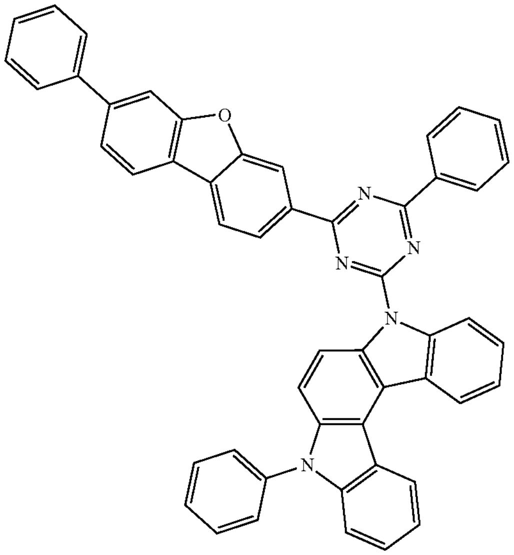
-continued
1-300
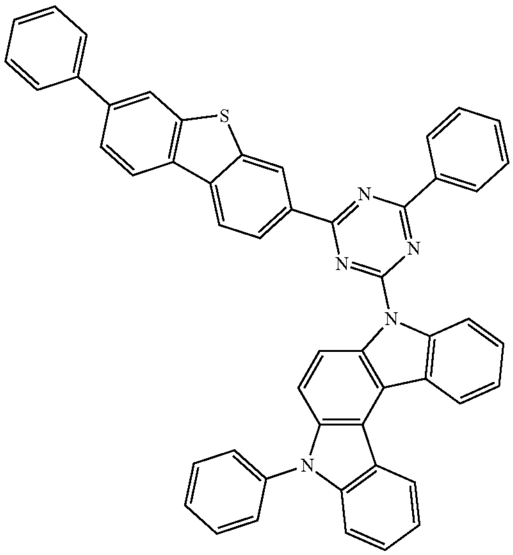
1-301
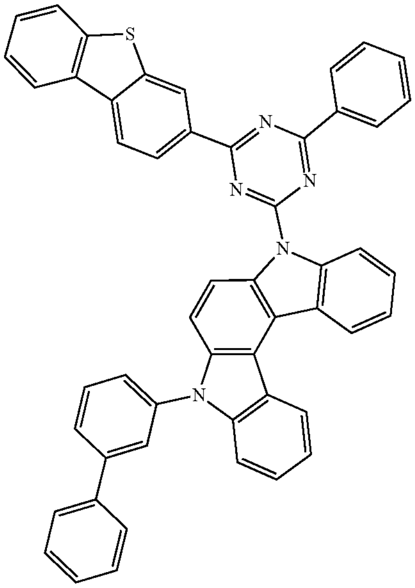
1-306
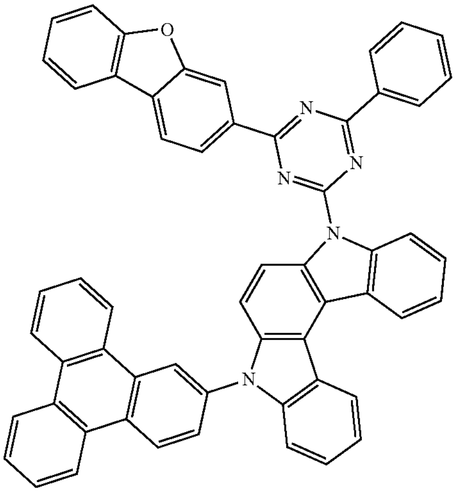

-continued
1-307
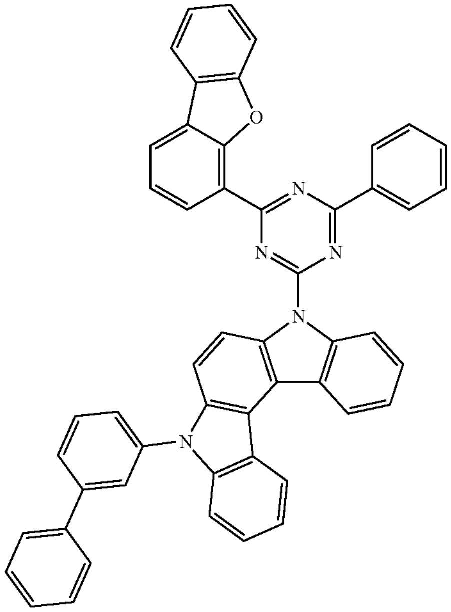
-continued
1-309
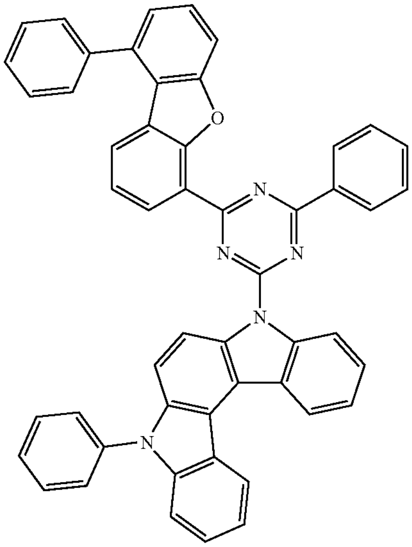
[C 32]
1-308
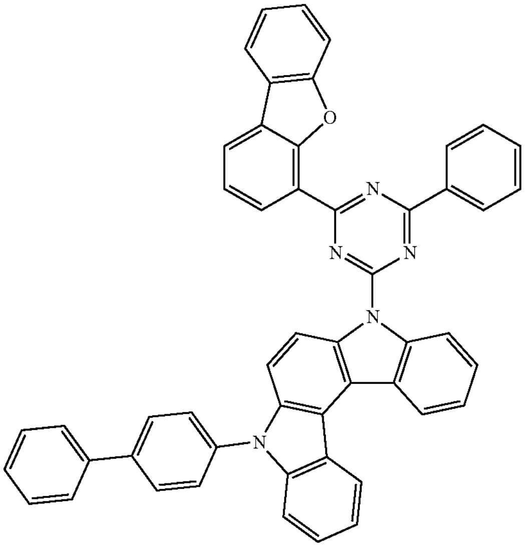
1-310
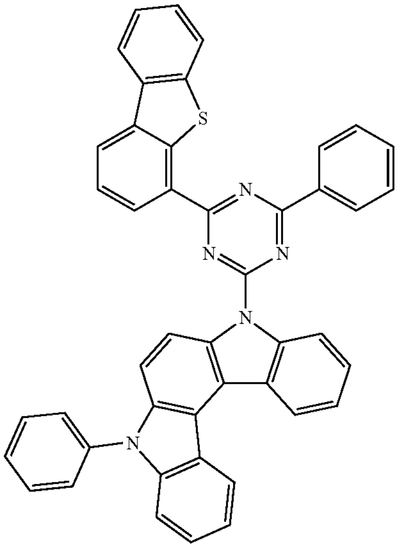

-continued
1-311
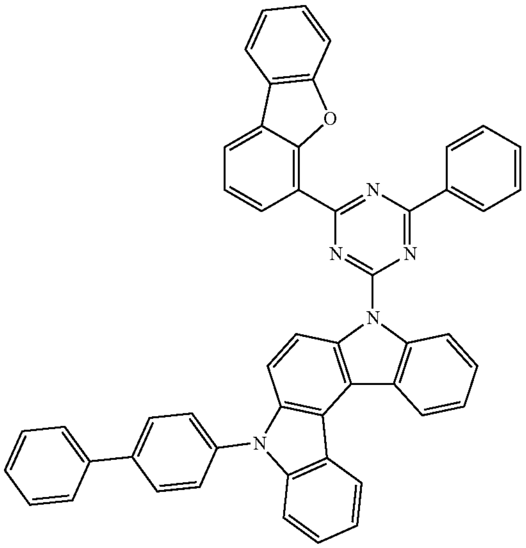
[C 33]
1-312
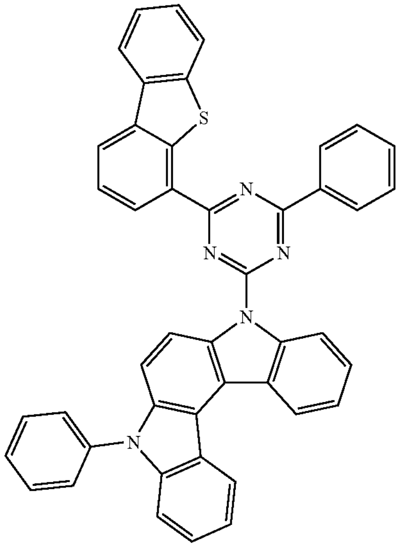
-continued
1-313
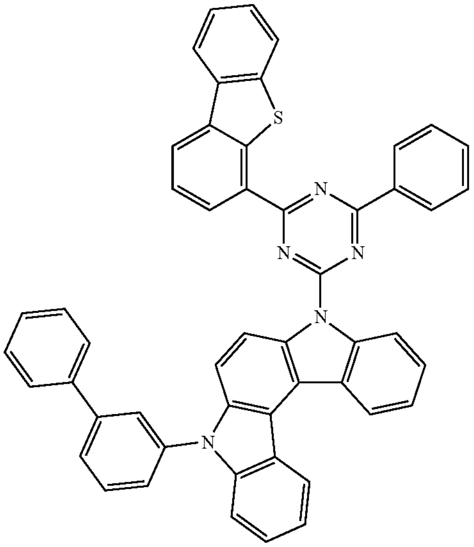
1-314
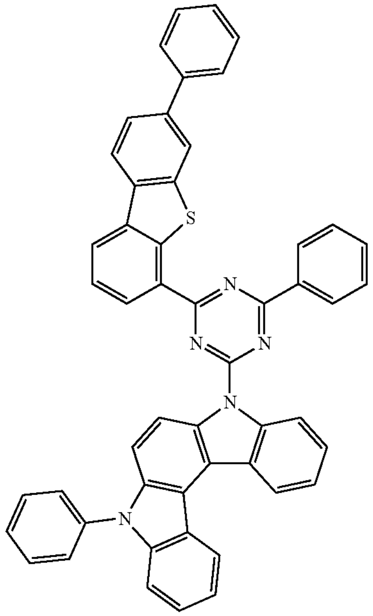

-continued
1-315
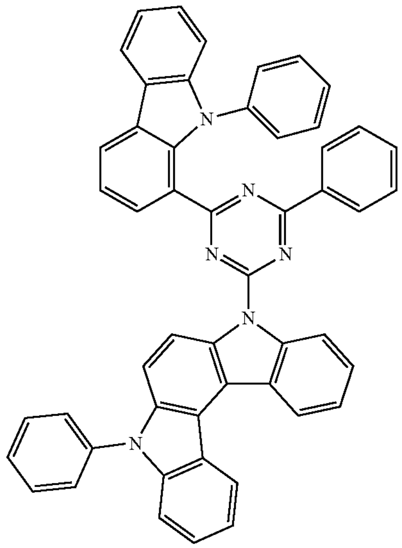
[C 34]
1-316
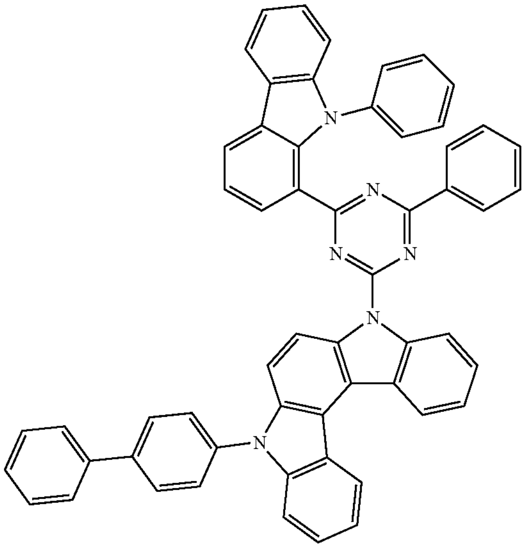
-continued
1-317
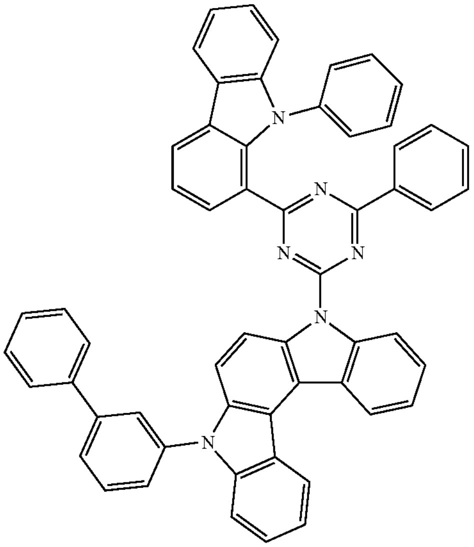
1-318
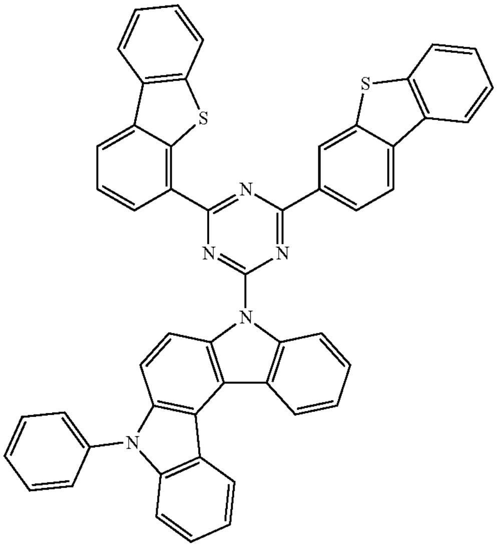
1-319
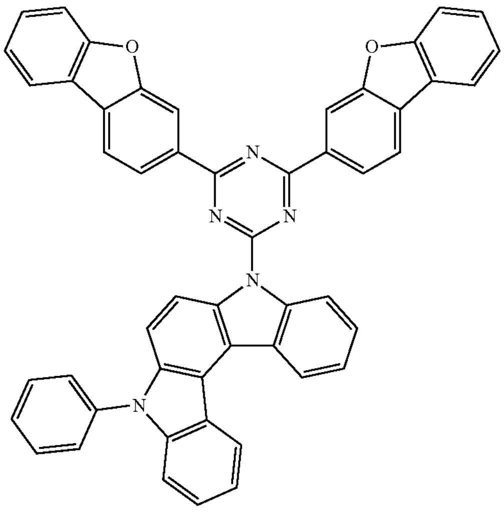

-continued
1-320
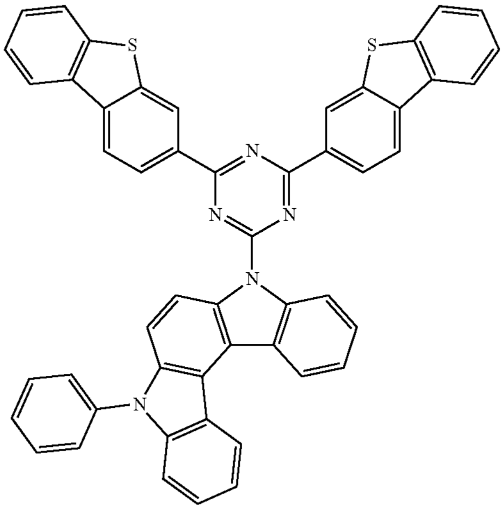
1-321
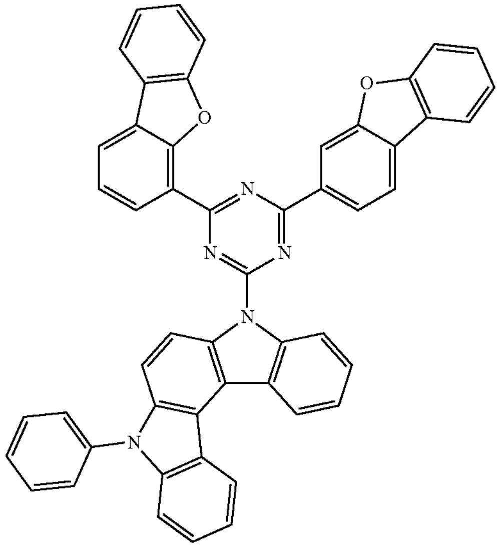
1-326
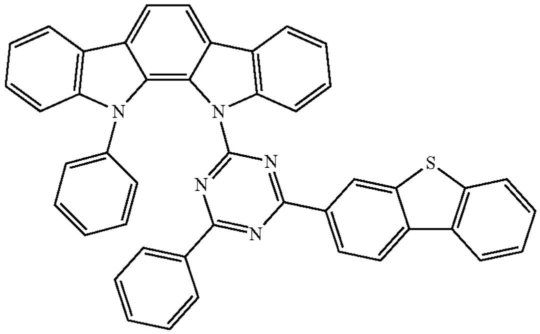
-continued
1-327
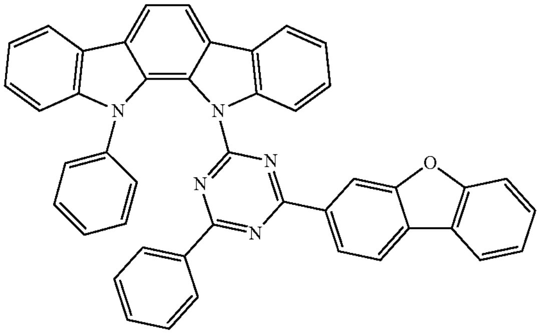
[C 35]
1-328
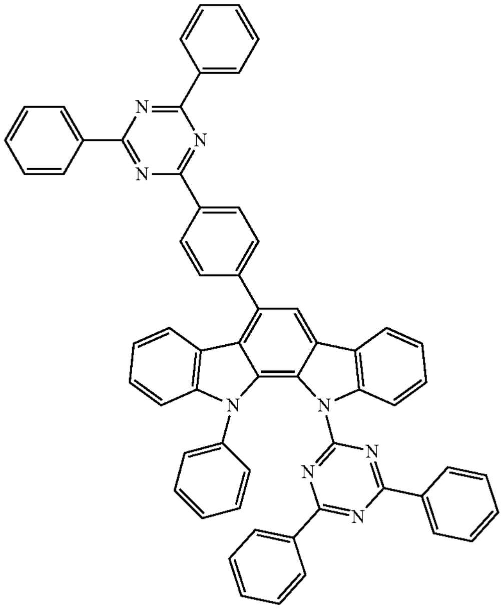
1-329
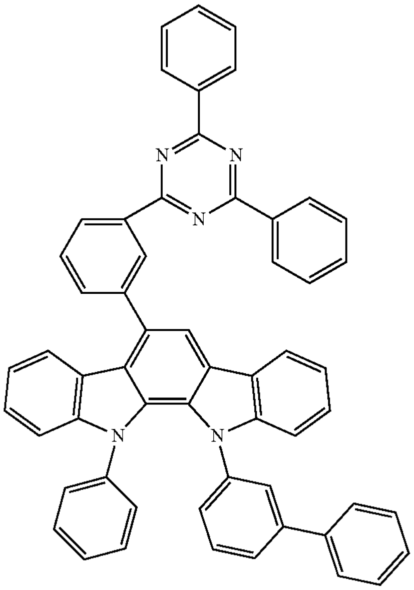

-continued 1-330

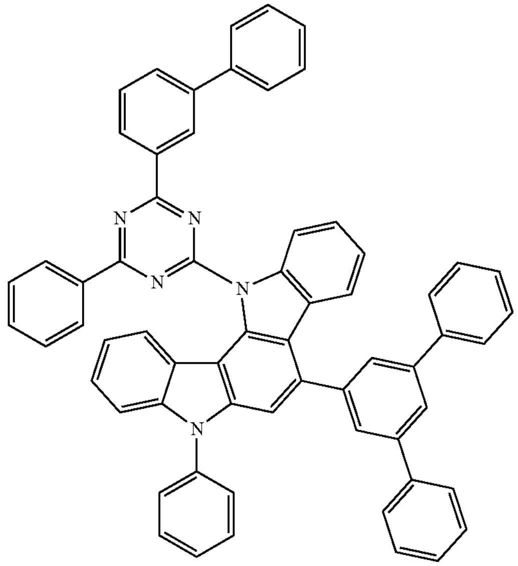

The second host material is preferably a compound represented by general formula (2), general formula (3) or general formula (4).

In the general formula (2), $Ar^{21}$, and $Ar^{22}$ independently represent hydrogen, deuterium, a substituted or unsubstituted aromatic hydrocarbon group having 6 to 14 carbon atoms, a substituted or unsubstituted aromatic heterocyclic group having 3 to 17 carbon atoms, or a substituted or unsubstituted linked aromatic group in which two of the aromatic rings are linked to each other. Preferred is hydrogen, a substituted or unsubstituted aromatic hydrocarbon group having 6 to 12 carbon atoms, a substituted or unsubstituted aromatic heterocyclic group having 3 to 17 carbon atoms, or a substituted or unsubstituted linked aromatic group in which two of the aromatic rings are linked to each other, and more preferred is hydrogen, a substituted or unsubstituted aromatic hydrocarbon group having 6 to 10 carbon atoms, or a substituted or unsubstituted linked aromatic group in which two of these are linked to each other.

In the case of $Ar^{21}$ and $Ar^{22}$ being each an unsubstituted aromatic hydrocarbon group, an unsubstituted aromatic heterocyclic group, or an unsubstituted linked aromatic group, specific examples thereof include a linked aromatic group generated by removing one H atom from benzene, naphthalene, anthracene, phenanthrene, fluorene, dibenzofuran, dibenzothiophene, carbazole, pyridine, or a compound in which two of these aromatic rings are linked. Preferred examples include an aromatic group generated from benzene, naphthalene, pyridine, dibenzofuran, dibenzothiophene or carbazole, or a linked aromatic group in which two of these aromatic groups are linked to each other, and more preferred is an aromatic group generated from benzene or naphthalene. $Ar^{21}$ or $Ar^{22}$ may be hydrogen, and in this case, other thereof is preferably the aromatic group (which means the aromatic hydrocarbon group or the aromatic heterocyclic group.) or the linked aromatic group.

$L^{21}$ and $L^{22}$ are each a direct bond or a phenylene group, and the phenylene group may be any of an o-phenylene group, a m-phenylene group and a p-phenylene group. Preferred is a p-phenylene group or a m-phenylene group.

When $L^{21}$ and $L^{22}$ are direct bonds, it is preferred that $Ar^{21}$ and $Ar^{22}$ are not hydrogen or deuterium.

Specific examples of the compounds represented by the general formula (2) are described below, but the compounds are not limited to these exemplified compounds.

[C 36]

2-1

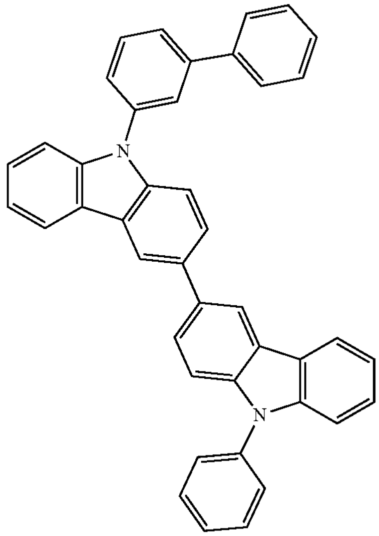

2-2

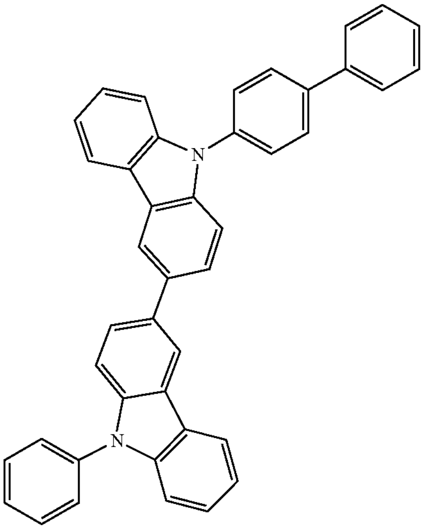

-continued
2-3
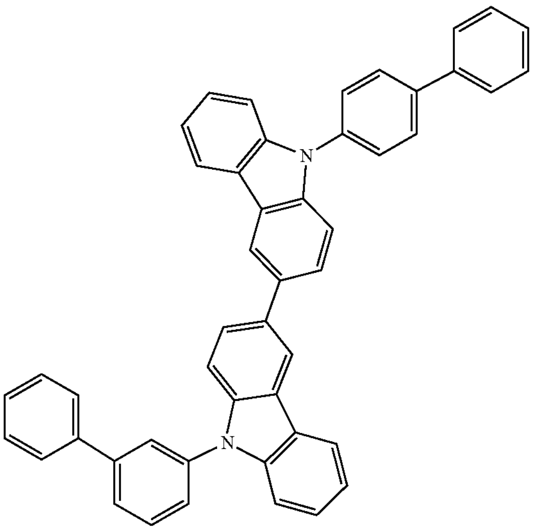
2-4
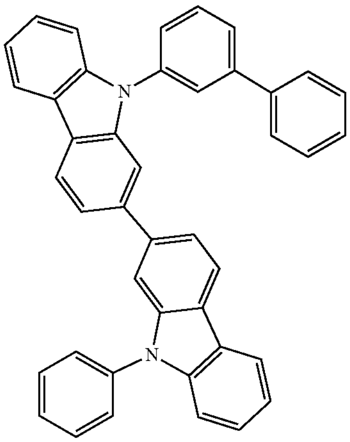
2-5
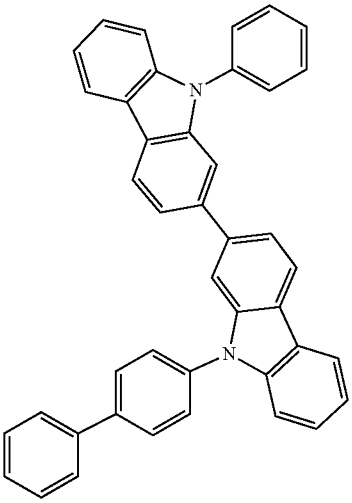
-continued
2-6
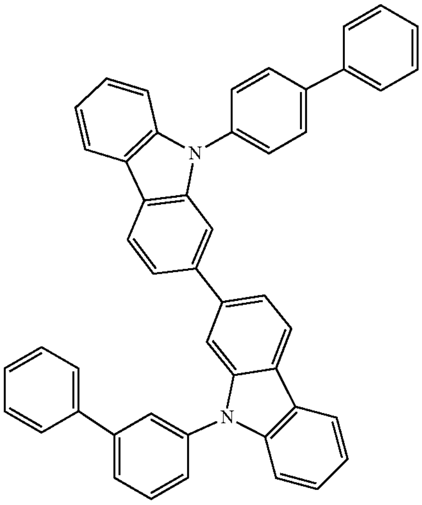
2-7
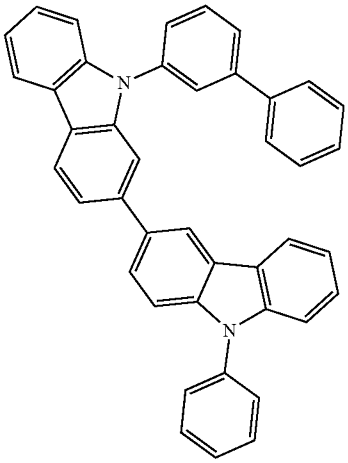
2-8
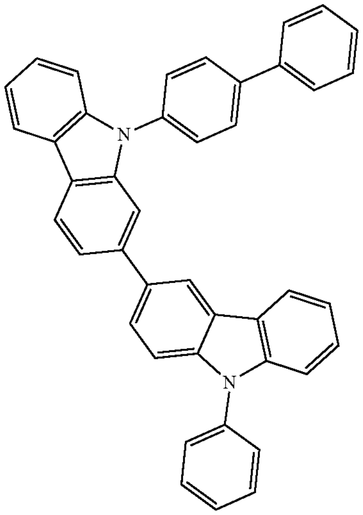

-continued
2-9
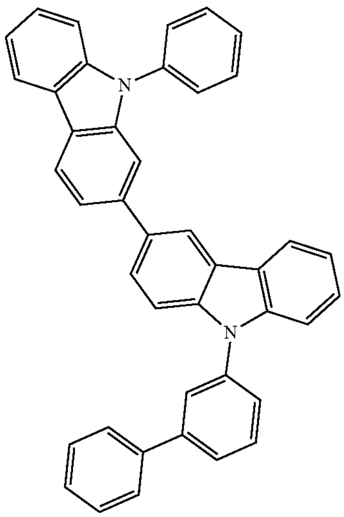
2-10
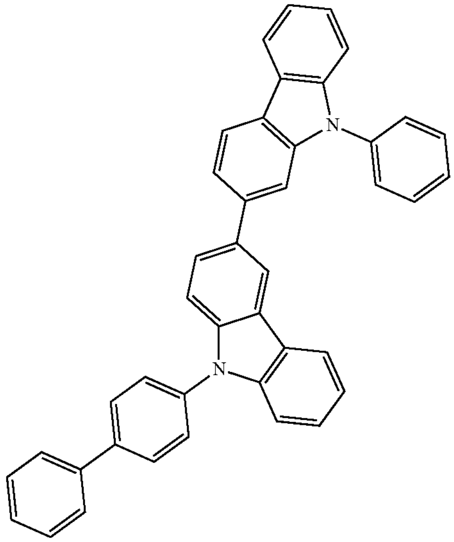
2-11
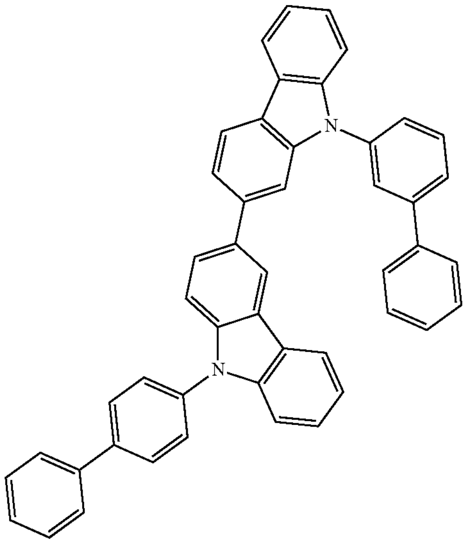
-continued
2-12
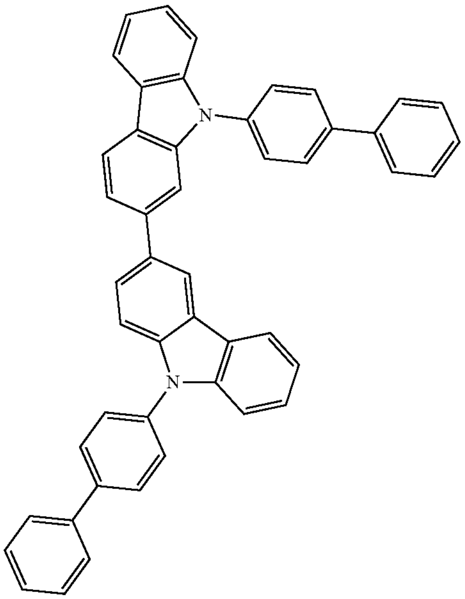
2-13
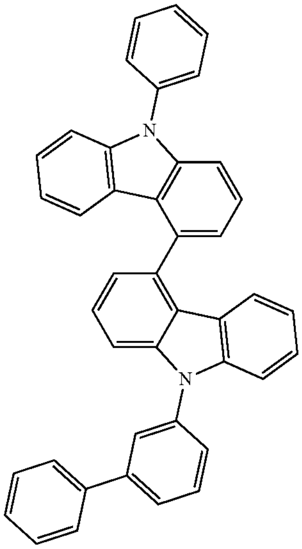

-continued
2-14
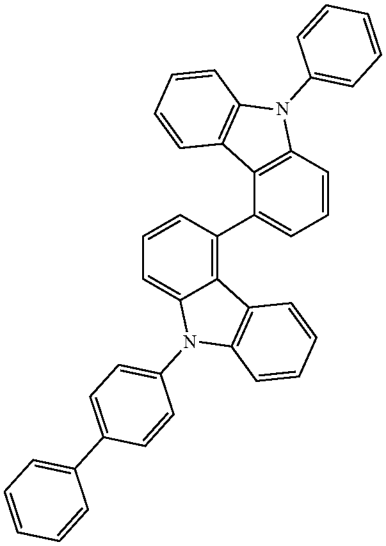
2-15
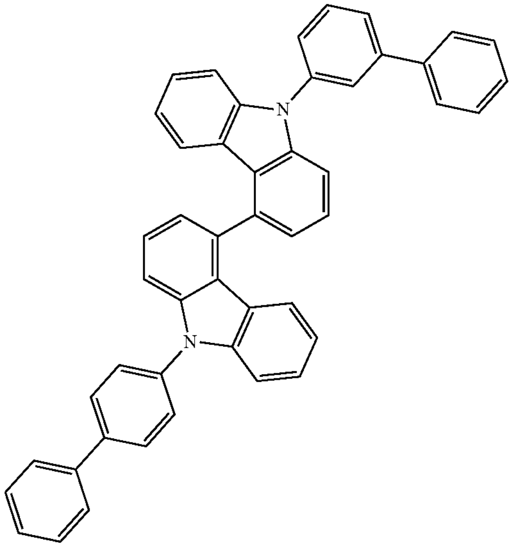
2-16
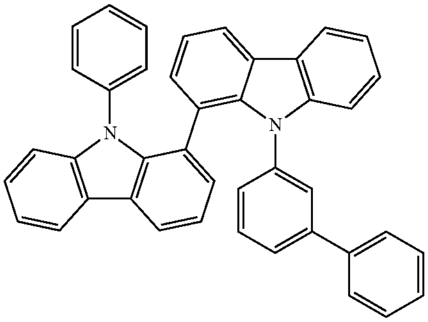
-continued
2-17
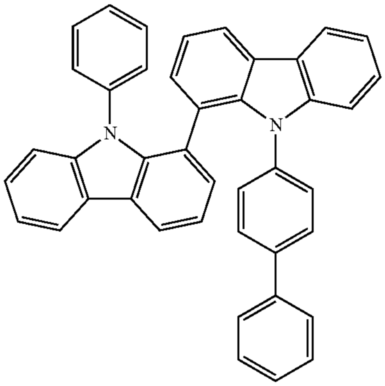
2-18
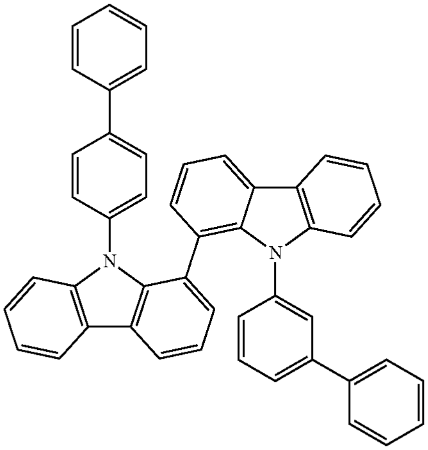
2-19
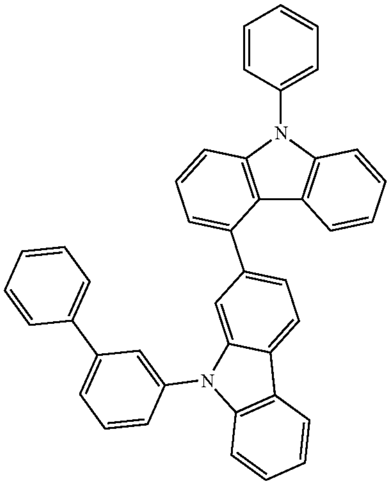

-continued
2-20
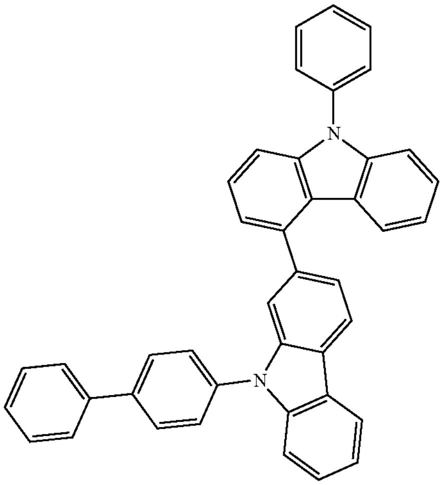
[C 37]
2-21
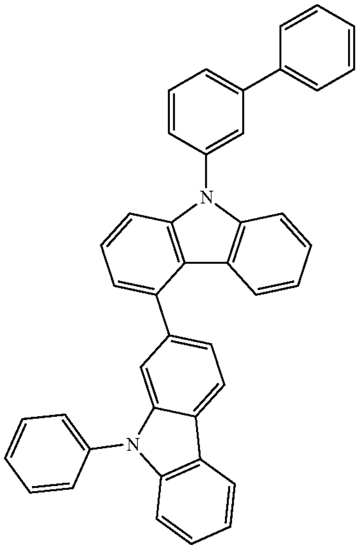
-continued
2-22
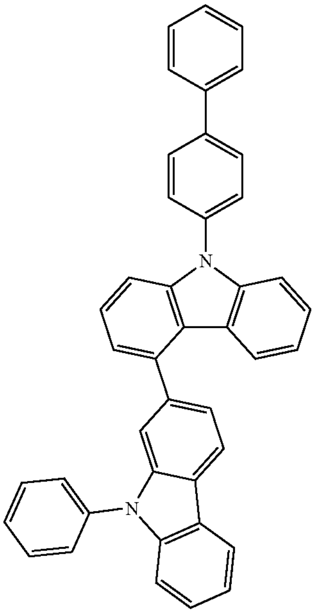
2-23
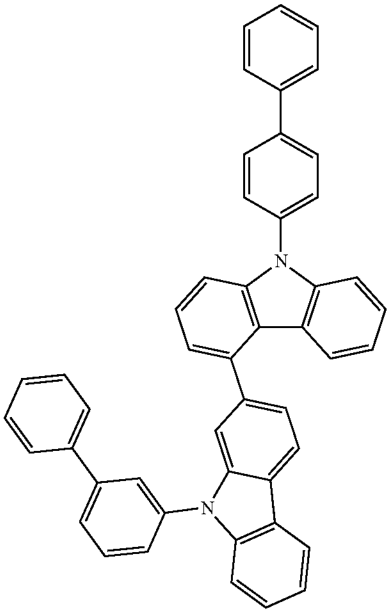

-continued
2-24
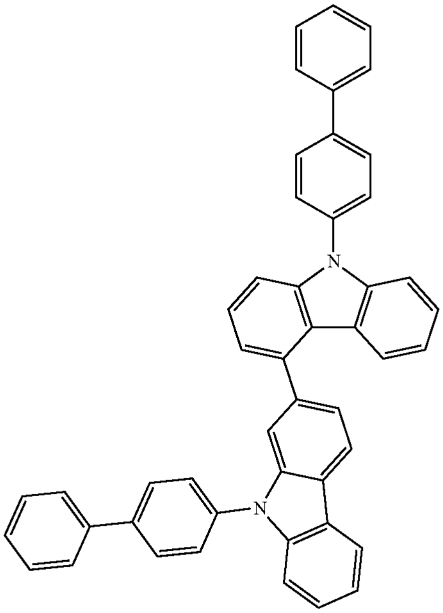
2-25
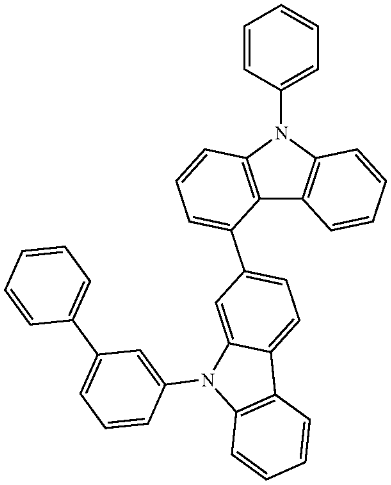
2-26
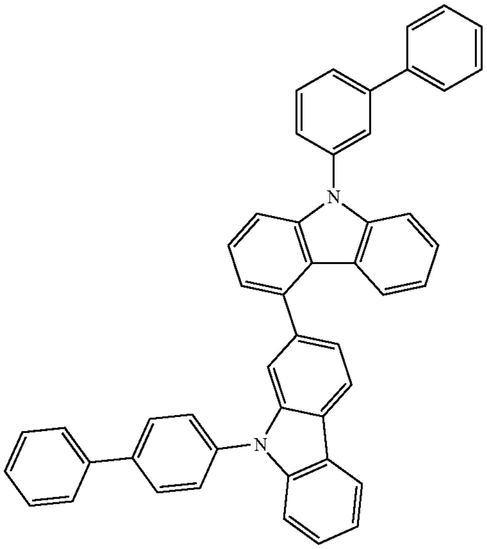
-continued
2-27
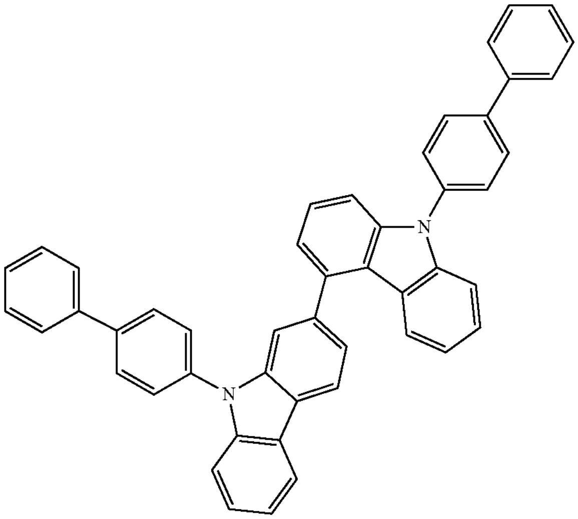
2-28
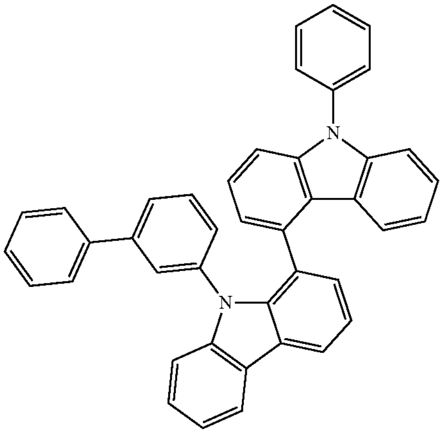
2-29
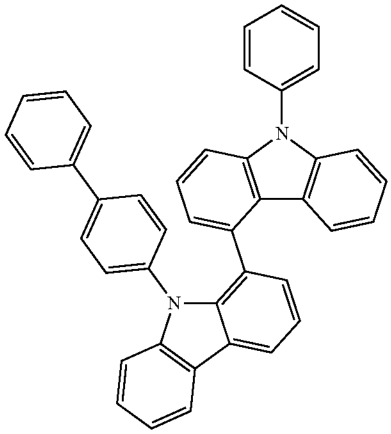

-continued
2-30
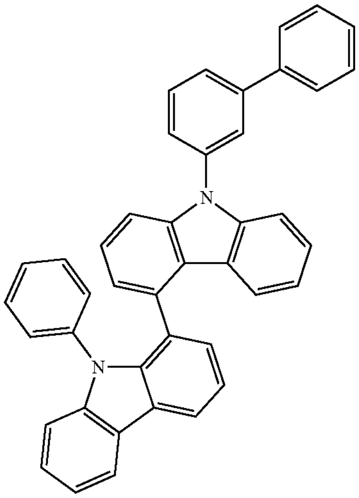
2-31
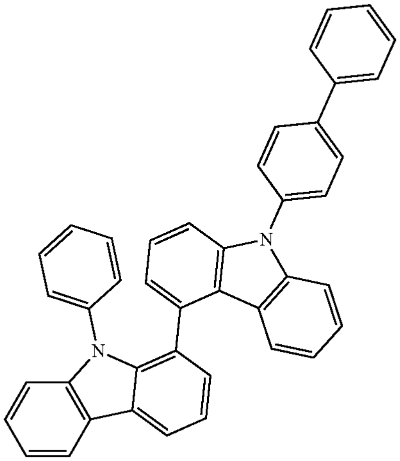
2-32
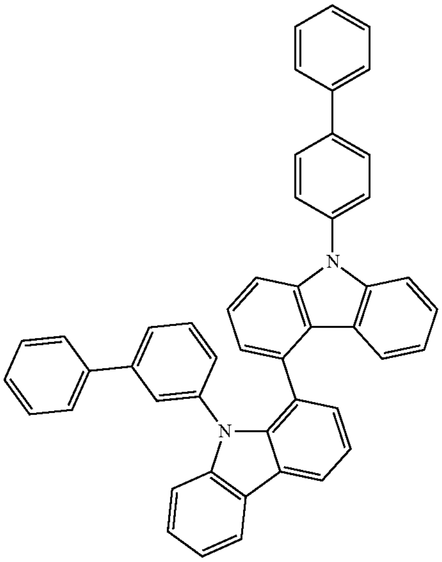
-continued
2-33
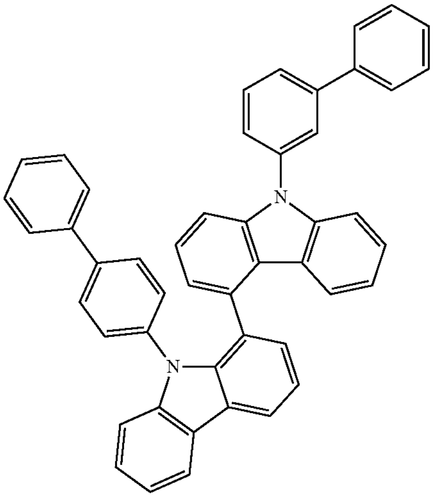
2-34
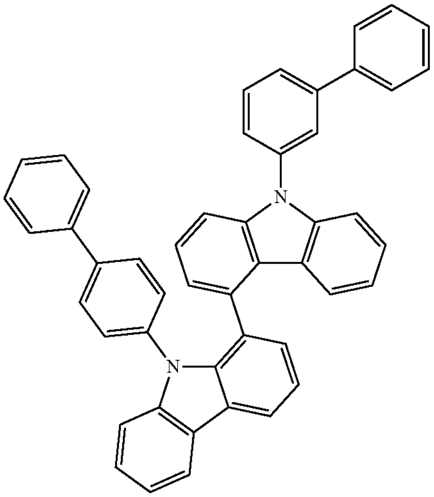
2-35
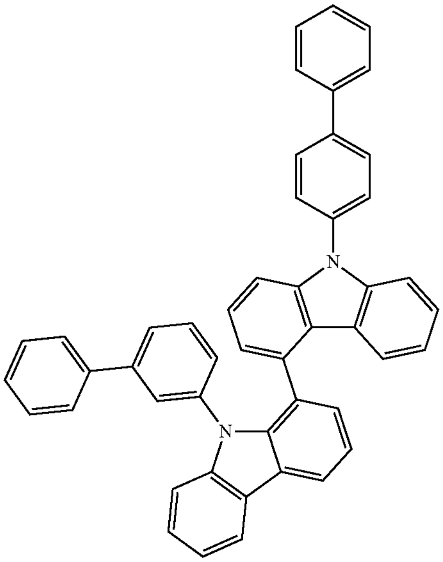

-continued
2-36
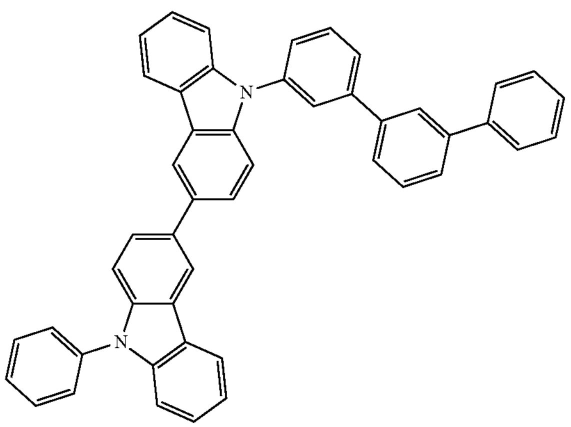
2-37
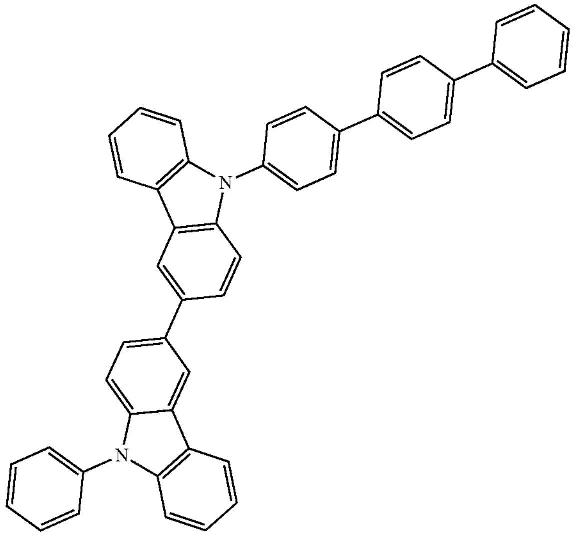
2-38
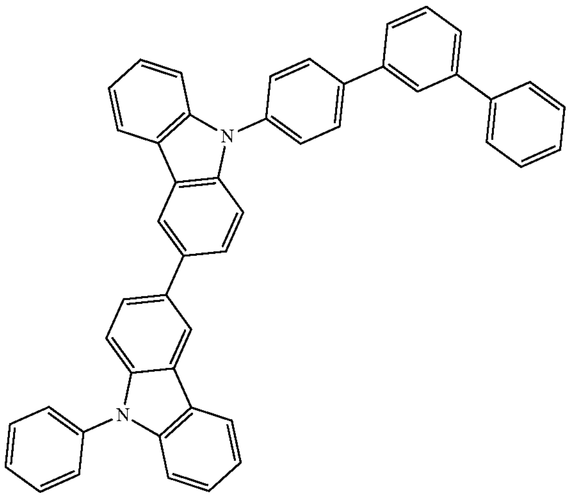
-continued
2-39
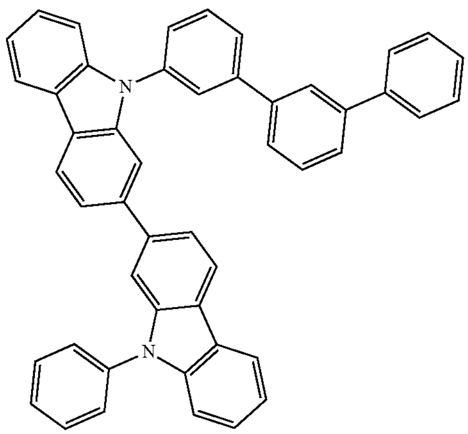
2-40
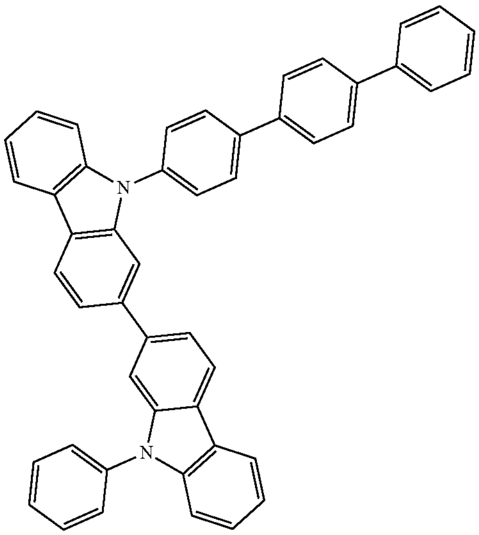
2-41
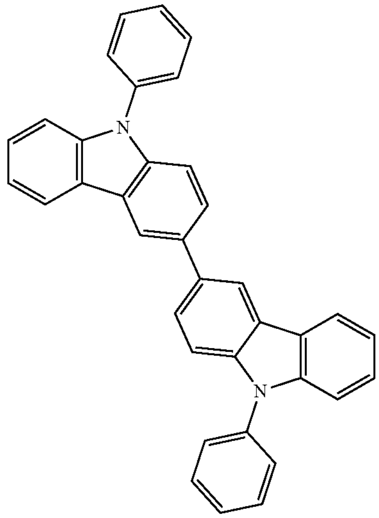

-continued
2-42
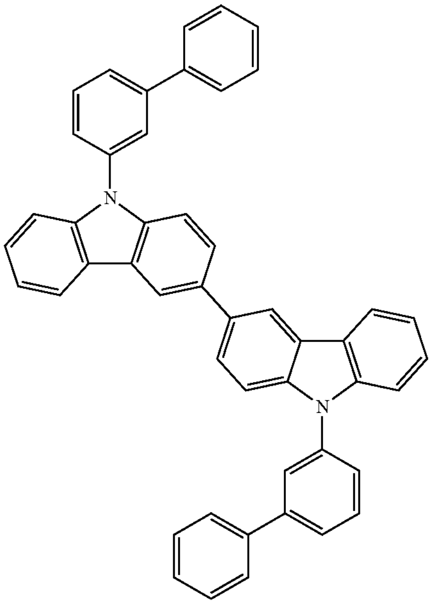
2-43
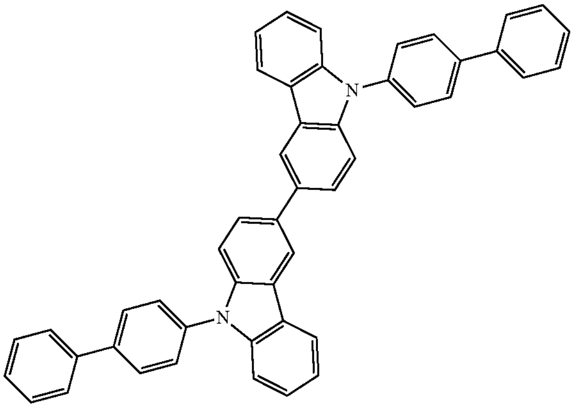
2-44
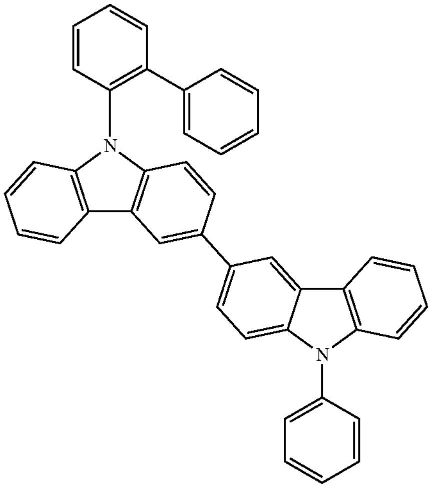
-continued
[C 38]
2-45
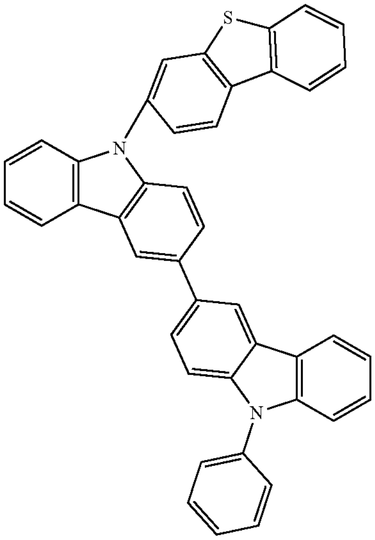
2-46
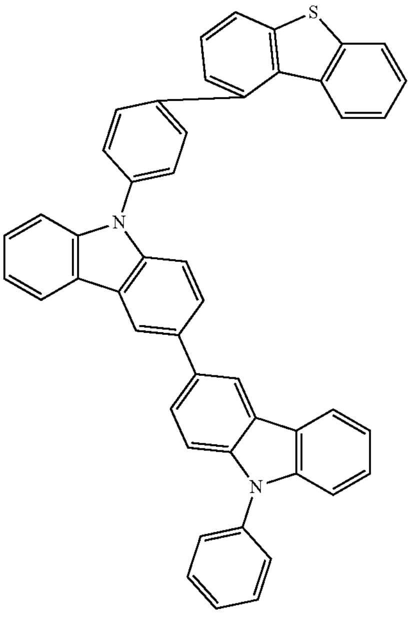

-continued
2-47
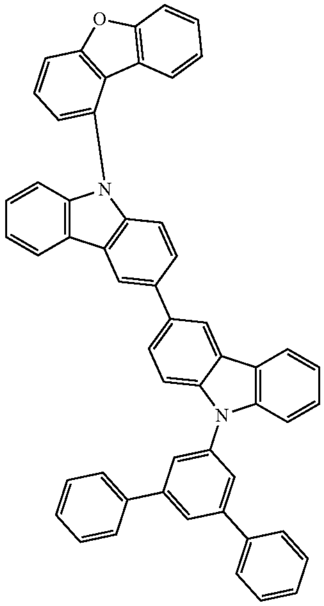
2-48
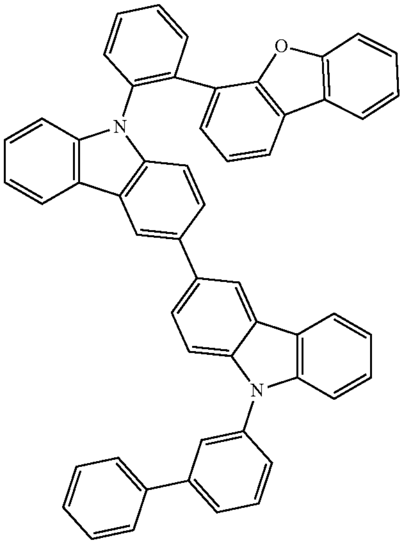
-continued
2-49
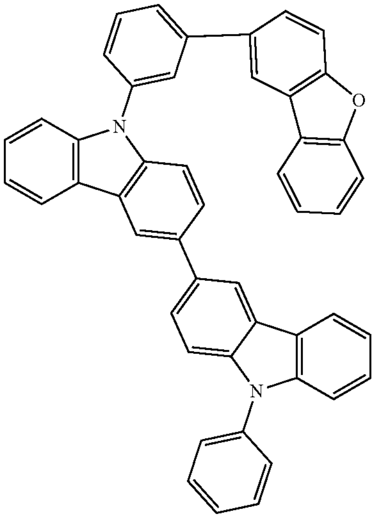
2-50
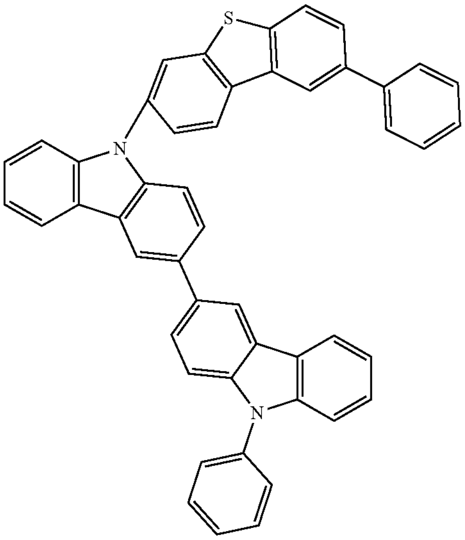
2-51
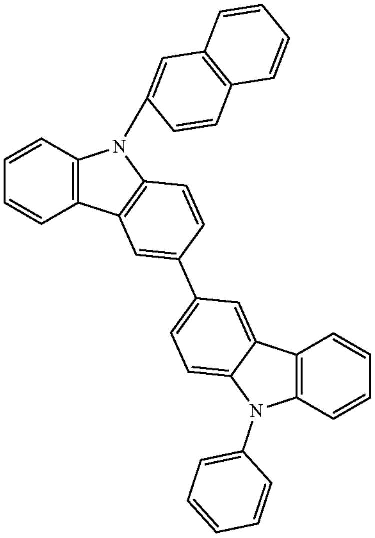

-continued 2-52

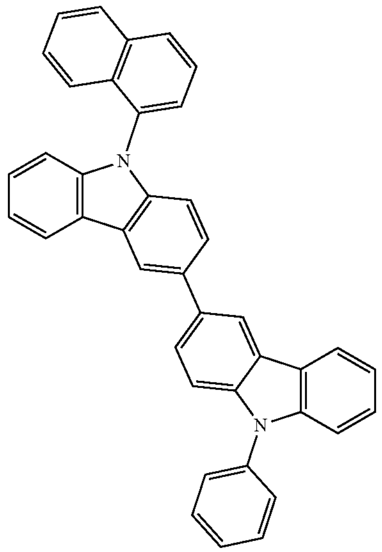

In the general formula (3), a ring B is a heterocycle represented by formula (3a) and the ring B is fused to an adjacent ring at any position.

$R^3$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other. Preferred is an aliphatic hydrocarbon group having 1 to 8 carbon atoms, a substituted or unsubstituted aromatic hydrocarbon group having 6 to 10 carbon atoms, or a substituted or unsubstituted aromatic heterocyclic group having 3 to 12 carbon atoms. More preferred is an aliphatic hydrocarbon group having 1 to 6 carbon atoms, a substituted or unsubstituted phenyl group, or a substituted or unsubstituted aromatic heterocyclic group having 3 to 6 carbon atoms.

In the case of $R^3$ being an aliphatic hydrocarbon group, an aromatic hydrocarbon group, an aromatic heterocyclic group, or a linked aromatic group, specific examples thereof are the same as in the case of $R^1$ described above.

$L^{31}$ independently represents a substituted or unsubstituted aromatic hydrocarbon group having 6 to 30 carbon atoms, or a substituted or unsubstituted aromatic heterocyclic group having 3 to 17 carbon atoms. Preferred is a substituted or unsubstituted aromatic hydrocarbon group having 6 to 10 carbon atoms, or a substituted or unsubstituted aromatic heterocyclic group having 3 to 12 carbon atoms.

$L^{32}$ independently represents a substituted or unsubstituted aromatic hydrocarbon group having 6 to 10 carbon atoms, preferably represents a group generated from benzene.

$Ar^{31}$ represents a substituted or unsubstituted aromatic hydrocarbon group having 6 to 10 carbon atoms, a substituted or unsubstituted carbazolyl group, or a substituted or unsubstituted linked aromatic group in which two to five of these aromatic rings are linked to each other. The aromatic ring is here selected from an aromatic hydrocarbon ring and a carbazole ring.

Preferred is a substituted or unsubstituted aromatic hydrocarbon group having 6 to 10 carbon atoms, a carbazolyl group, or a substituted or unsubstituted linked aromatic group in which two to three of these aromatic rings are linked to each other.

Specific examples of the unsubstituted aromatic hydrocarbon group include a phenyl group and a naphthyl group.

$Ar^{32}$ represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other. Preferred is a substituted or unsubstituted aromatic hydrocarbon group having 6 to 10 carbon atoms, a substituted or unsubstituted aromatic heterocyclic group having 3 to 12 carbon atoms, or a substituted or unsubstituted linked aromatic group in which two to five of these aromatic rings are linked to each other.

In the case of $R^3$, $L^{31}$, and $Ar^{32}$ being each an unsubstituted aromatic hydrocarbon group or an aromatic heterocyclic group, specific examples thereof are the same as in the case of $Ar^1$ and $Ar^{11}$ except that $L^{31}$ is a divalent or (h+1)-valent group. In the case of $Ar^{32}$ and $R^3$ being an unsubstituted linked aromatic group, specific examples thereof are the same as in the case of $Ar^1$ and $Ar^{11}$ except that two to five aromatic rings are linked to each other.

f is the number of repetitions, and represents an integer of 1 to 3, g is the number of repetitions and represents an integer of 0 to 3, and h represents the number of substitutions and each independently represents an integer of 0 to 7. Preferably, f is 1, g is 0 to 1, and h is 0 to 2. i represents an integer of 0 to 4, and j represents an integer of 0 to 2, and preferably, i is 0 or 1 and j is 0 or 1.

Preferred examples of the compound represented by the general formula (3) include a compound represented by the following formula (31) or formula (32).

[C 39]

(31)

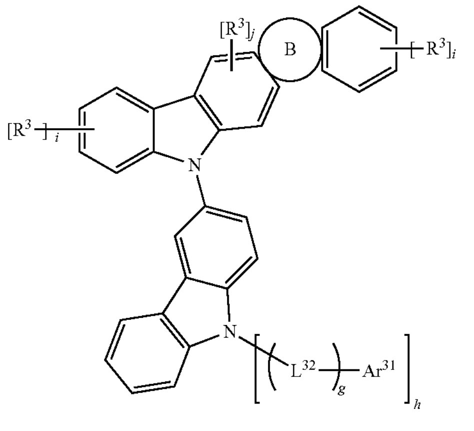

-continued
(32)
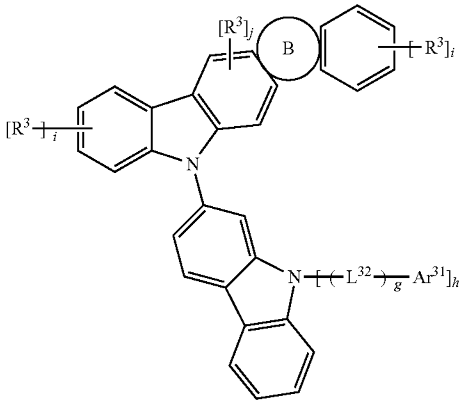
In the formula (31) or formula (32), a ring B, $R^3$, $L^{32}$, $Ar^{31}$, g, h, i and j are as defined for the general formula (3).
Specific examples of the compounds represented by the general formula (3) are described below, but the compounds are not limited to these exemplified compounds.
[C 40]
3-1
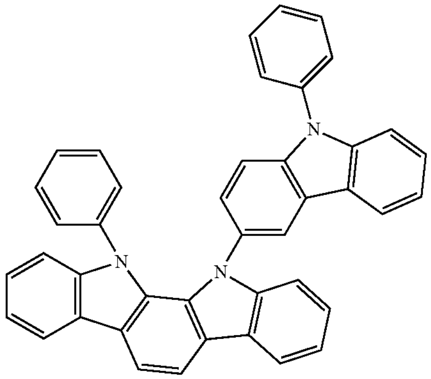
3-2
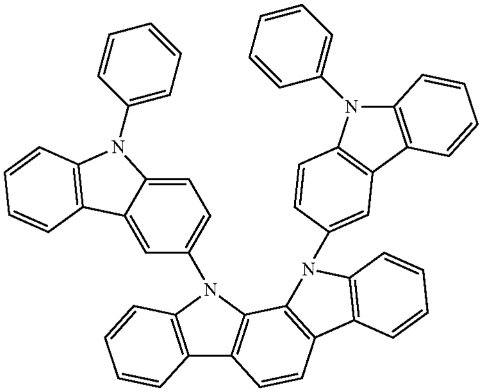
-continued
3-3
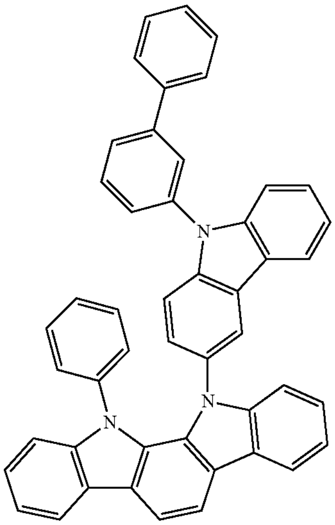
3-4
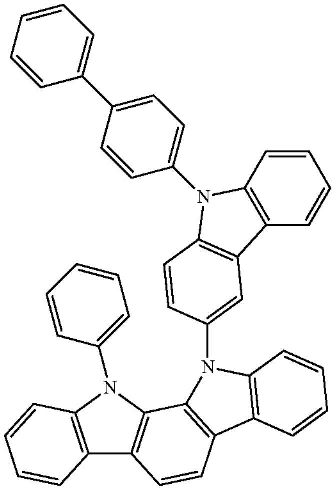
3-5
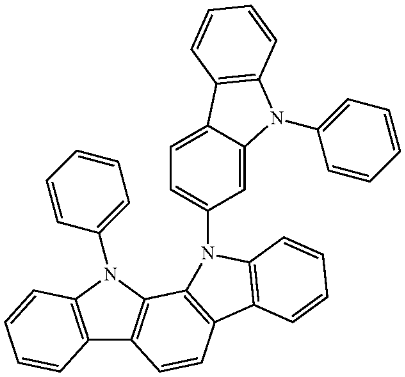

-continued
3-6
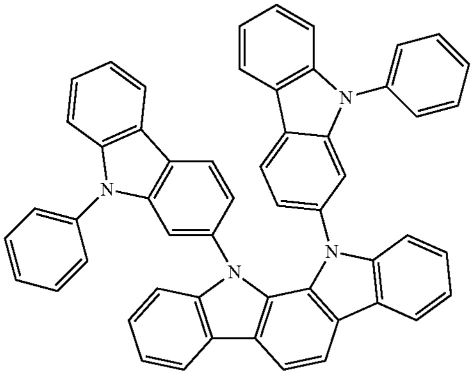
3-7
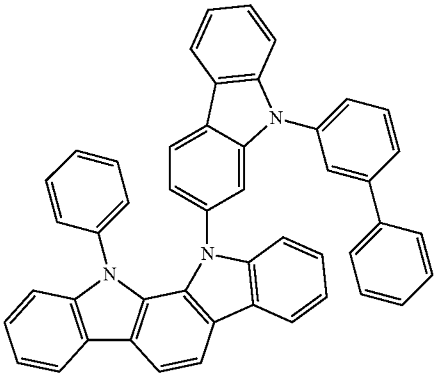
3-8
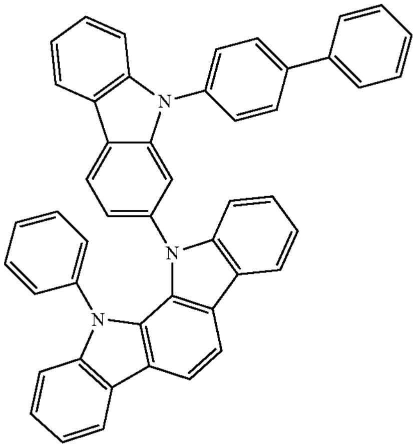
3-9
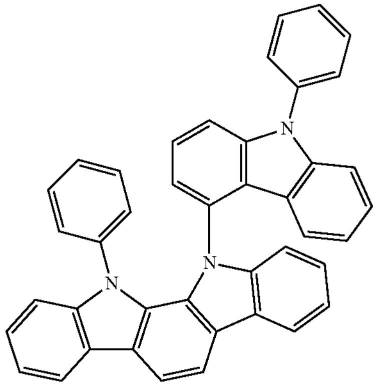
-continued
3-10
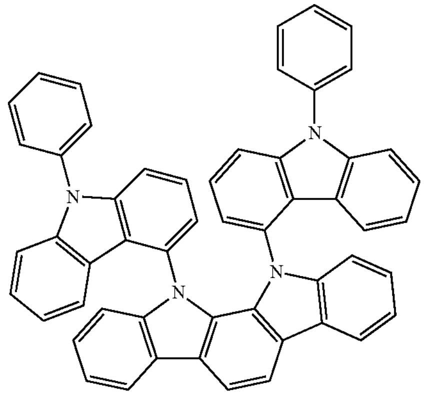
3-11
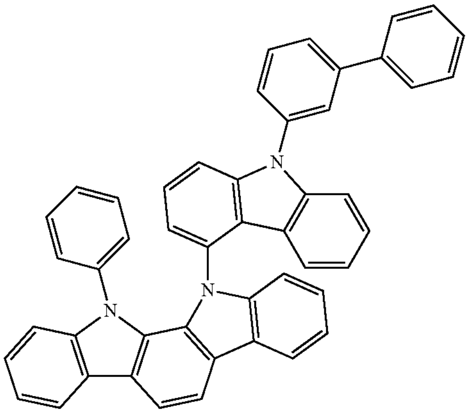
3-12
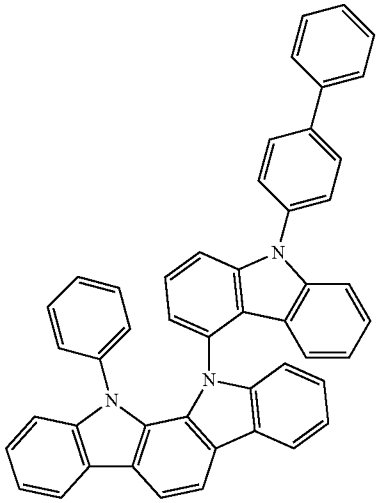

-continued
3-13
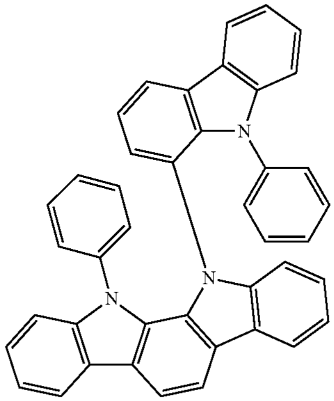
3-14
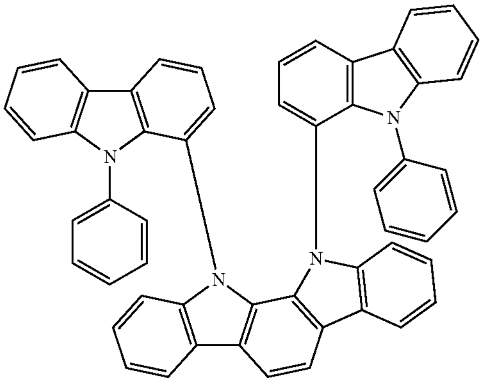
3-15
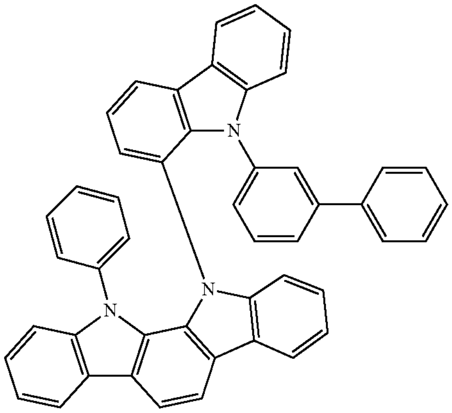
3-16
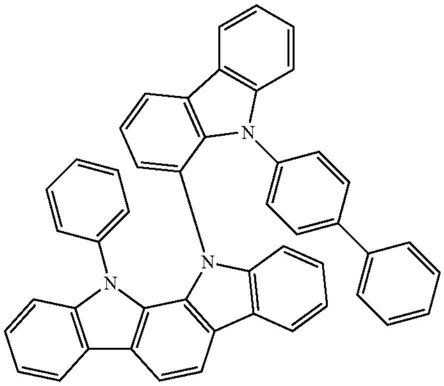
-continued
3-17
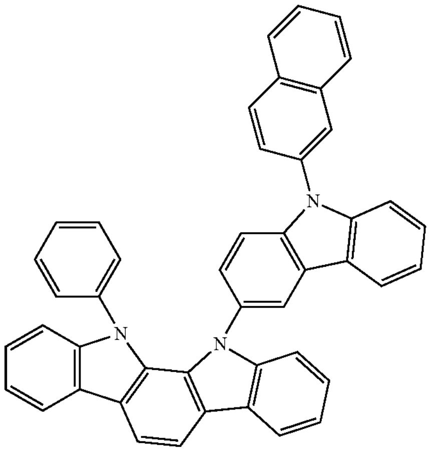
3-18
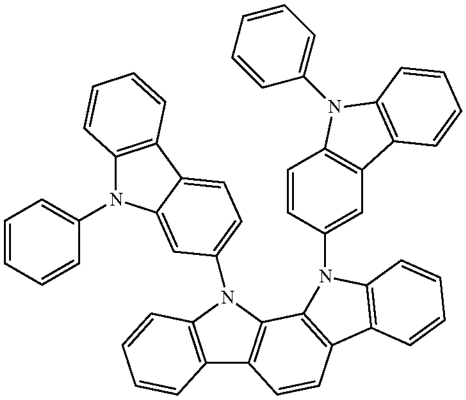
3-19
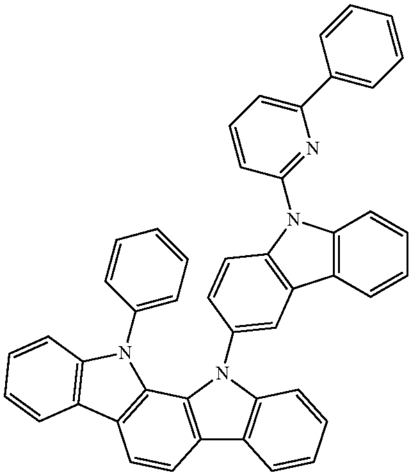

-continued
3-20
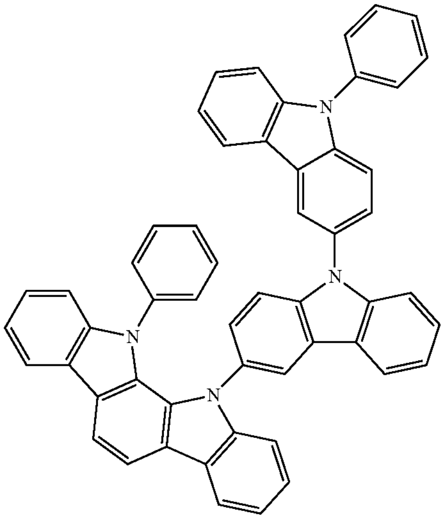
[C 41]
3-21
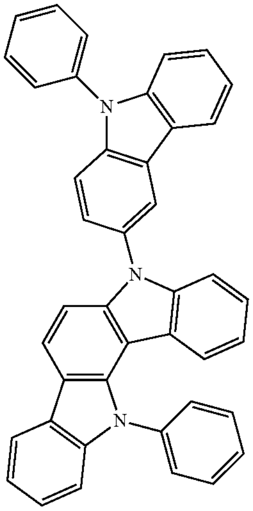
3-22
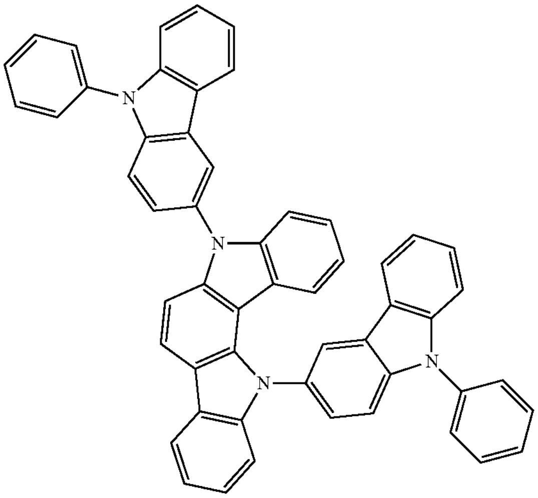
-continued
3-23
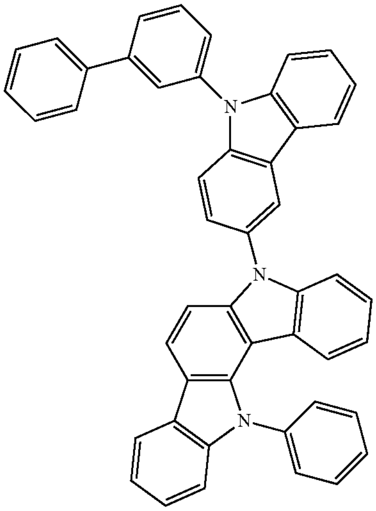
3-24
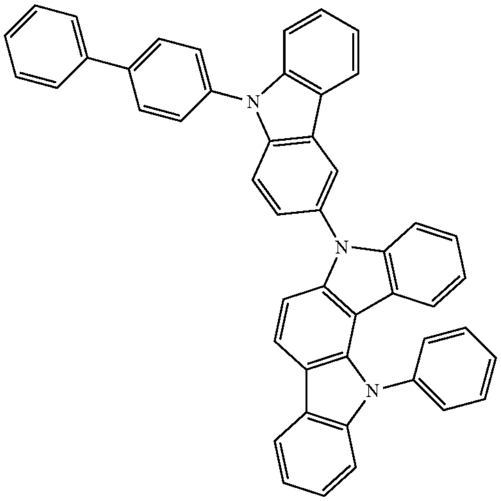
3-25
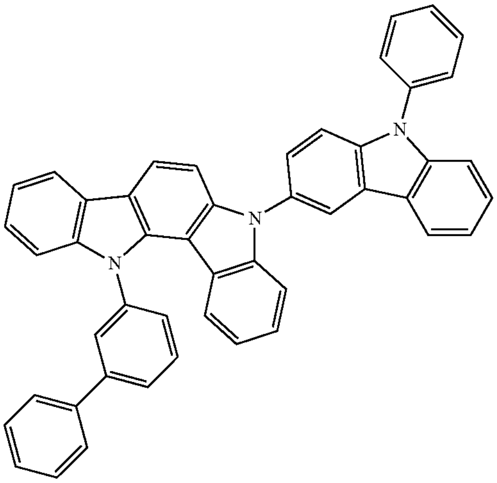

-continued
3-26
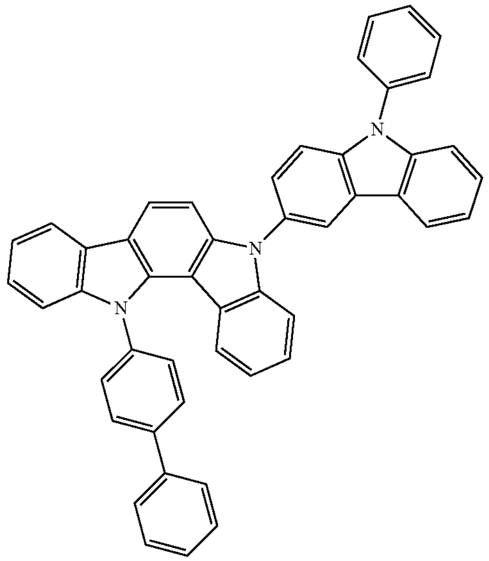
3-27
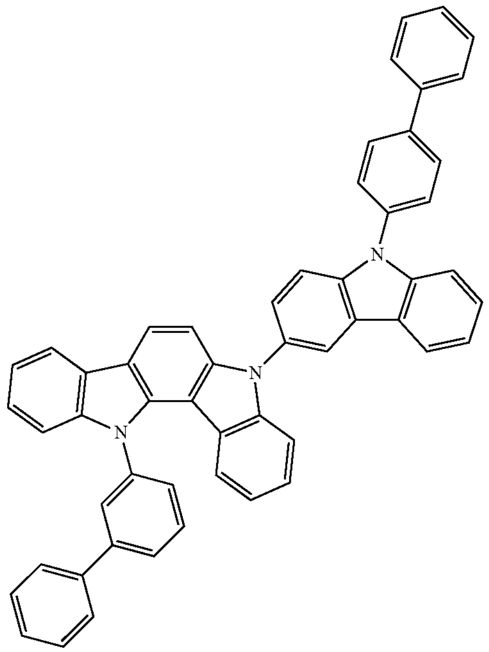
-continued
3-28
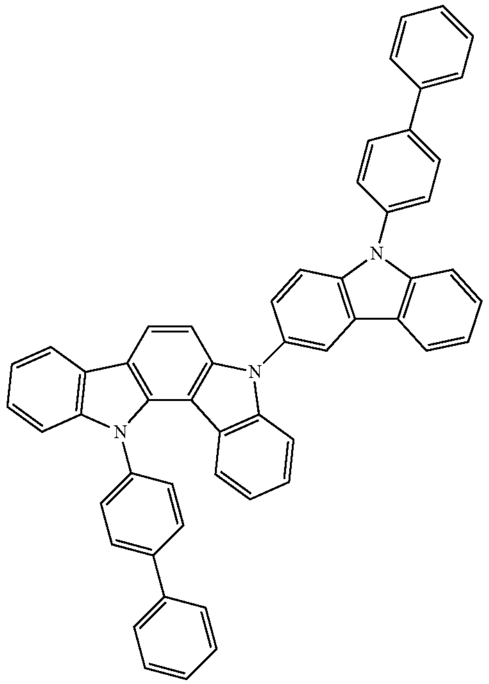
3-29
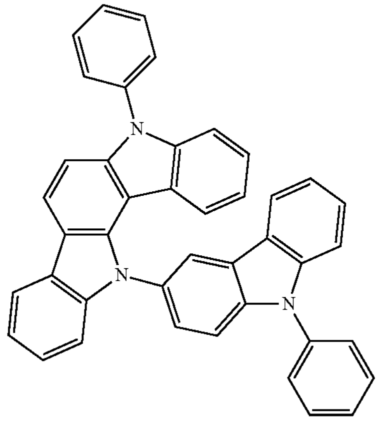
3-30
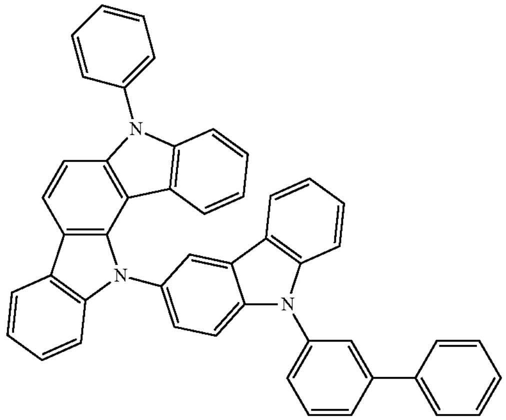

-continued
3-31
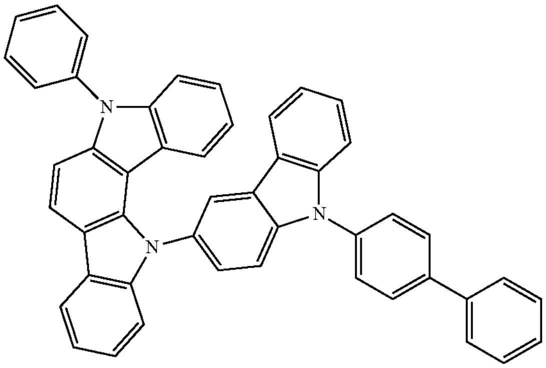
3-32
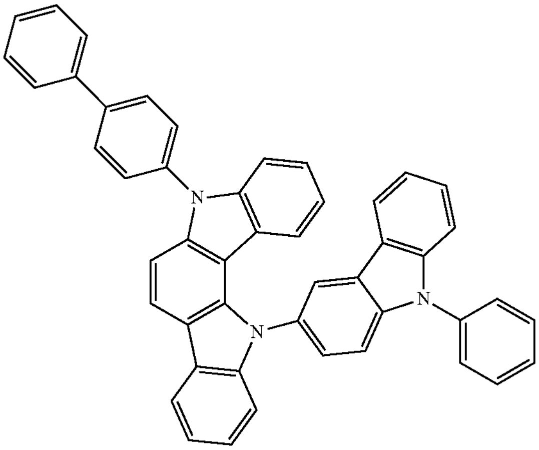
3-33
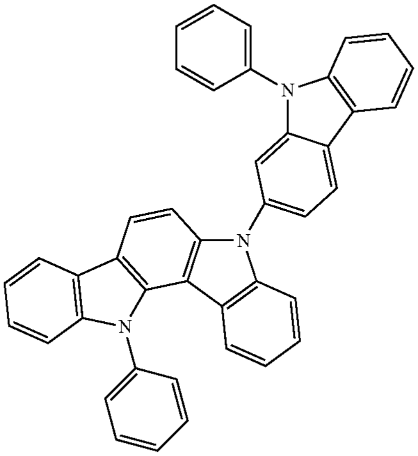
-continued
3-34
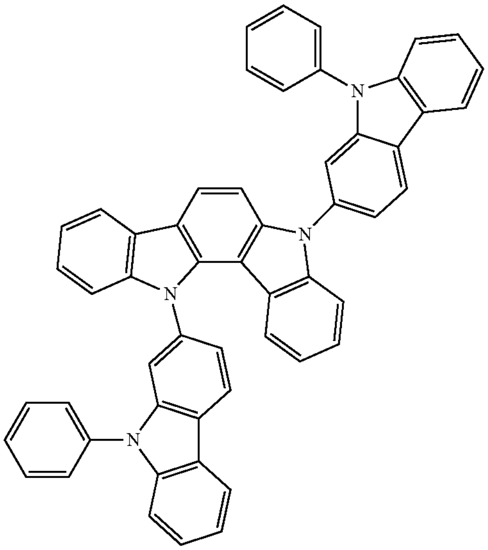
3-35
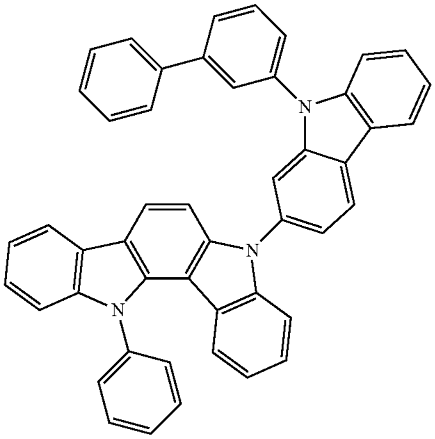
3-36
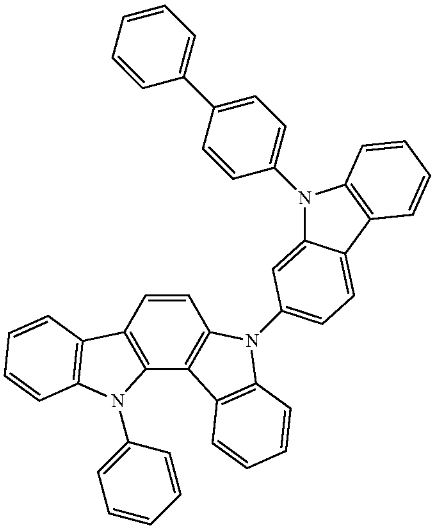

-continued
3-37
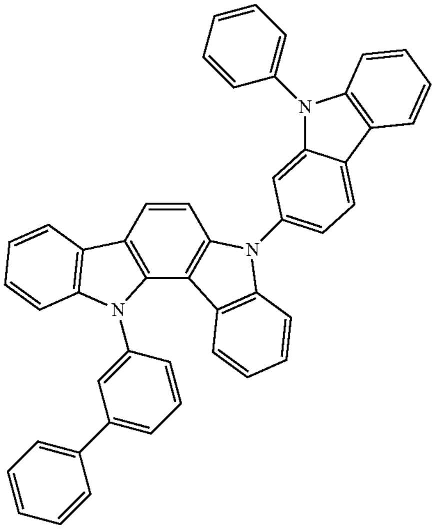
3-38
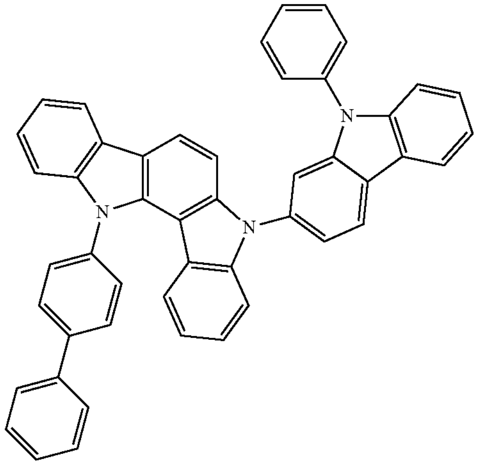
3-39
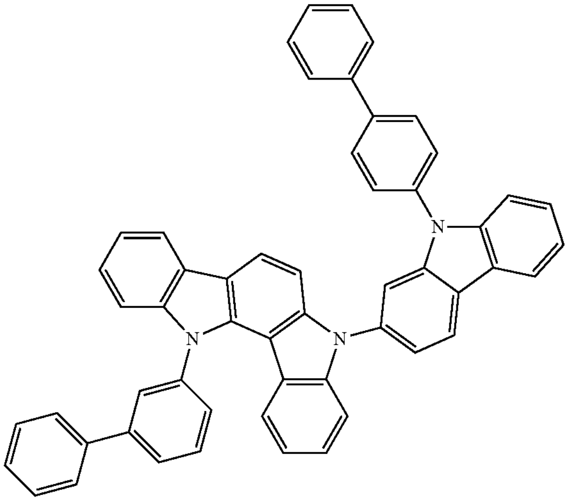
-continued
3-40
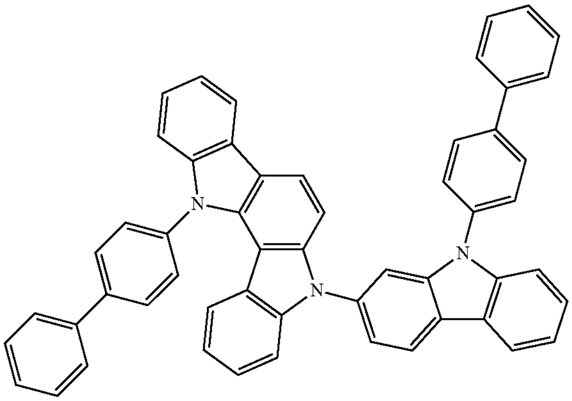
[C 42]
3-41
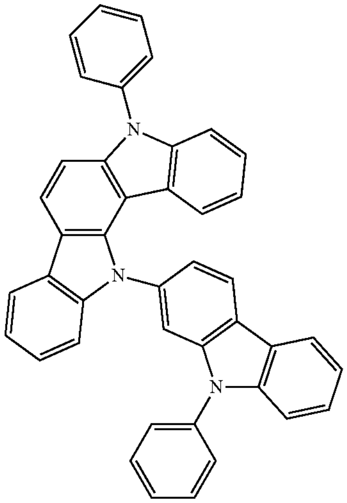
3-42
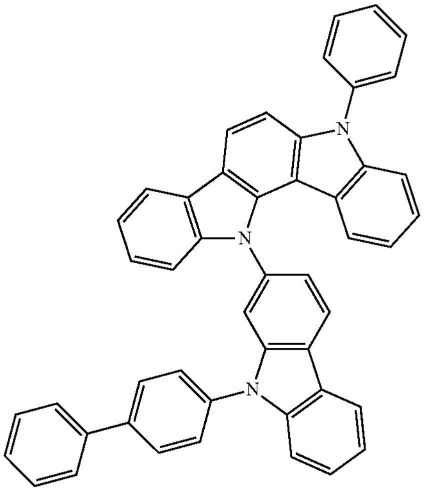

-continued
3-43
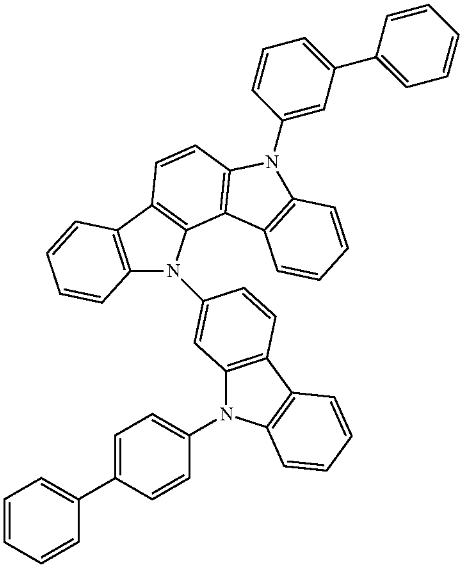
3-44
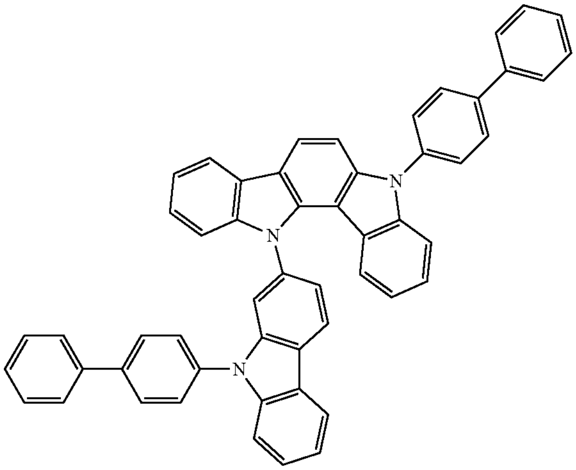
3-45
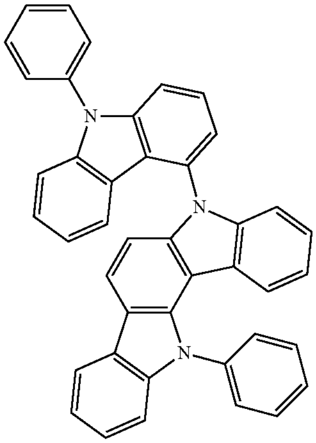
-continued
3-46
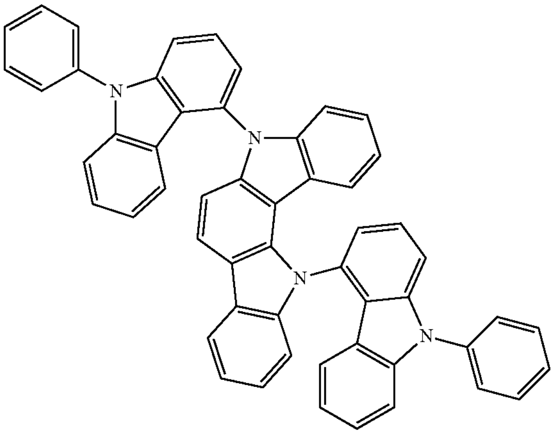
3-47
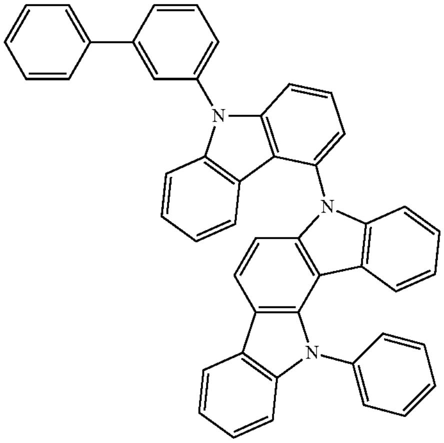
3-48
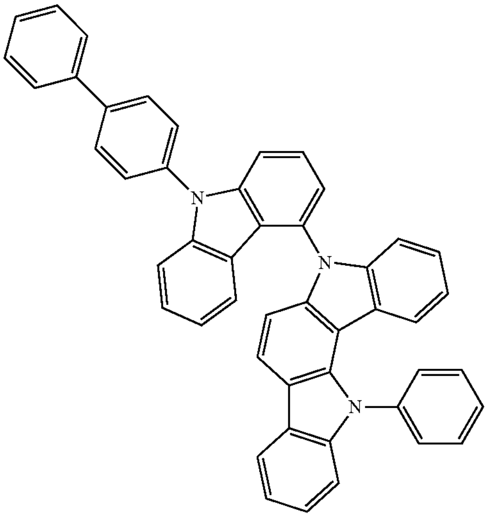

-continued
3-49
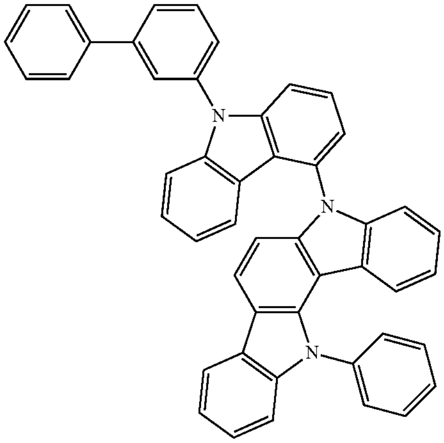
3-50
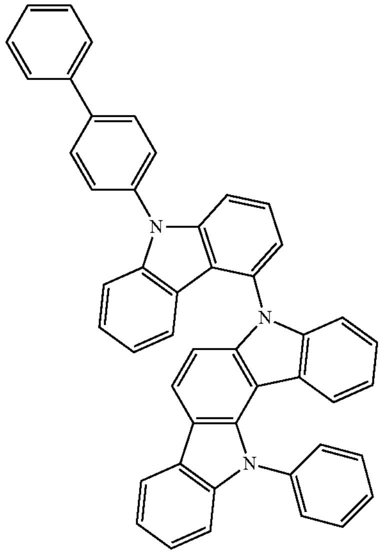
3-51
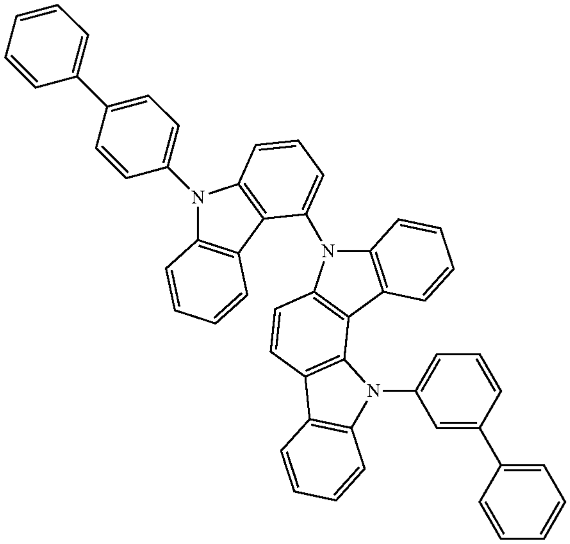
-continued
3-52
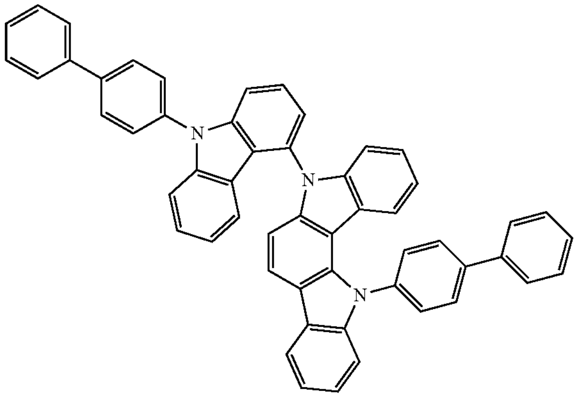
3-53
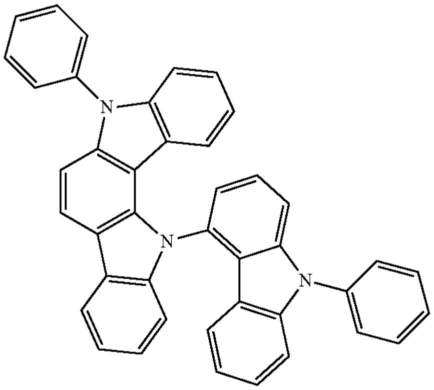
3-54
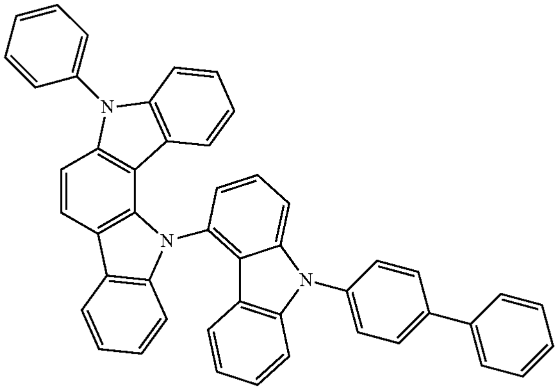

-continued
3-55
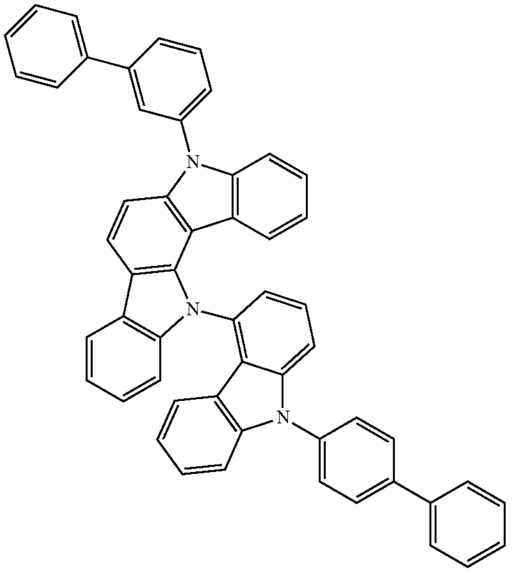
3-56
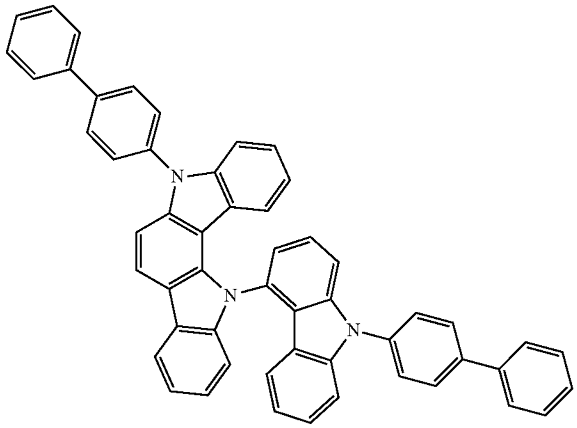
3-57
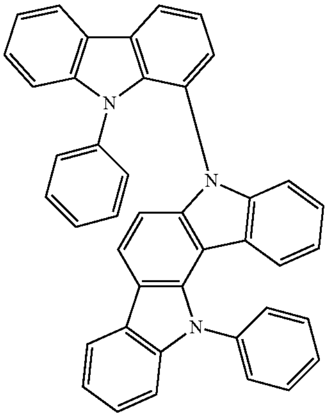
-continued
3-58
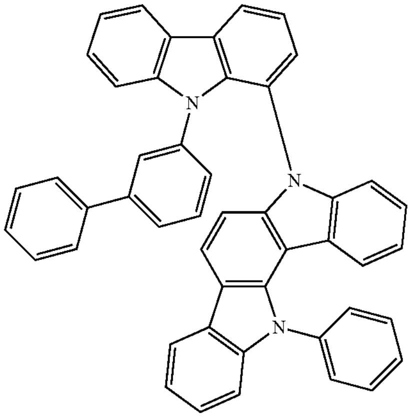
3-59
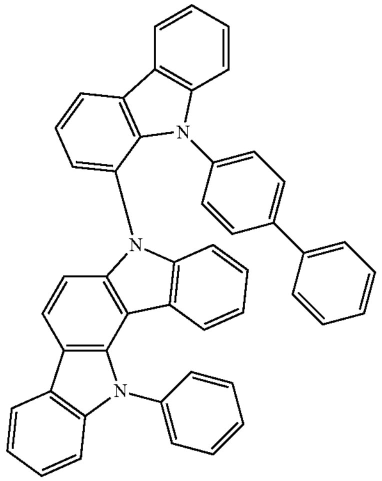
3-60
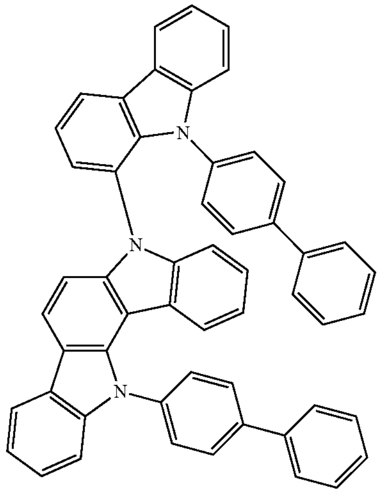

-continued
[C 43]
3-61
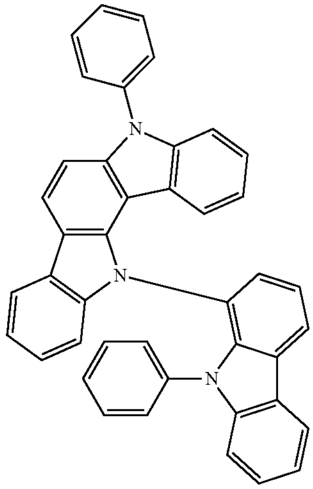
3-62
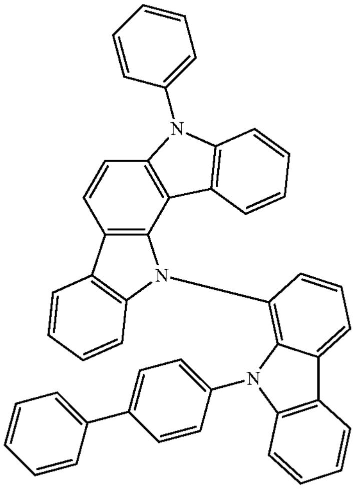
3-63
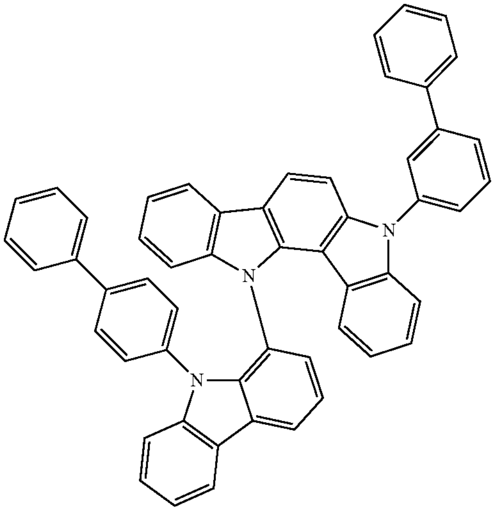
-continued
3-64
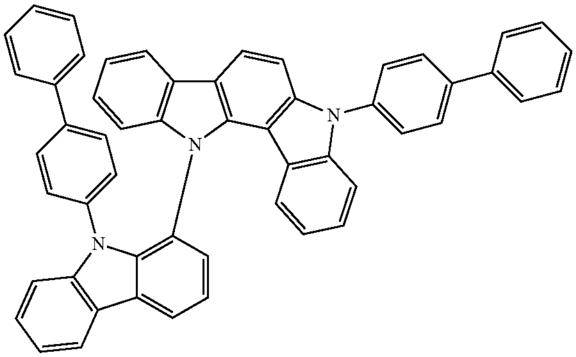
3-65
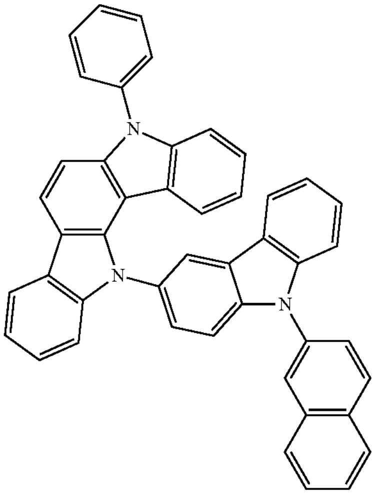
3-66
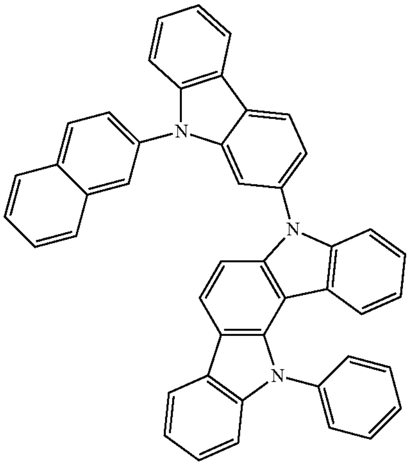

-continued
3-67
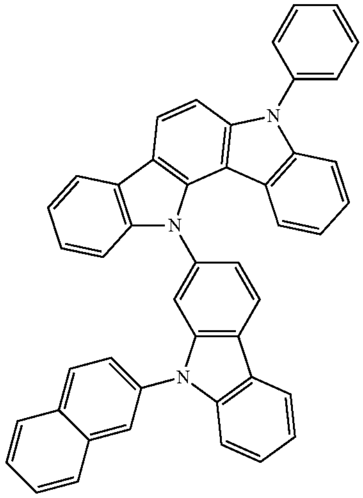
3-68
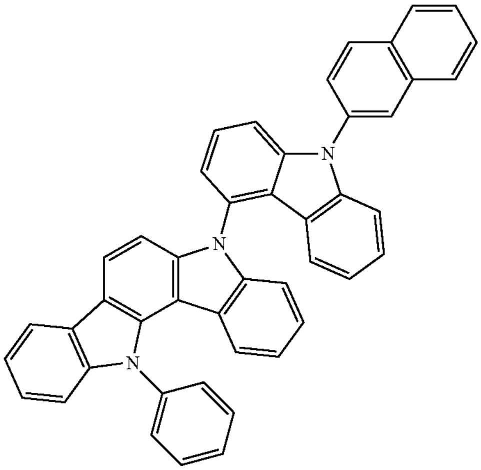
3-69
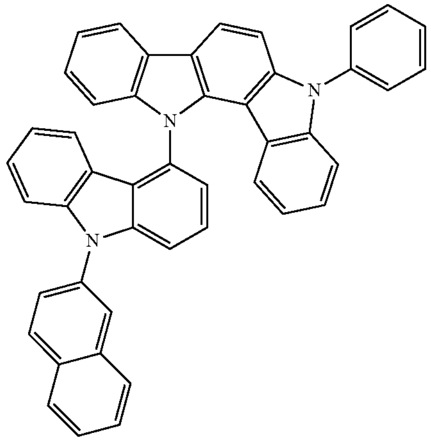
-continued
3-70
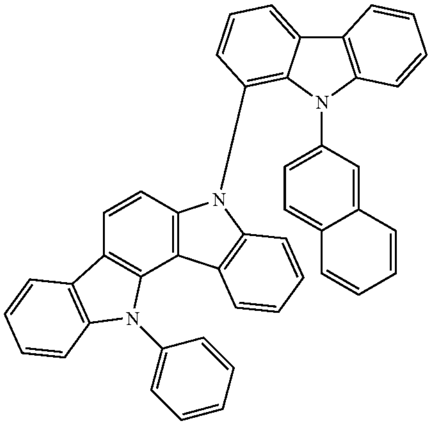
3-71
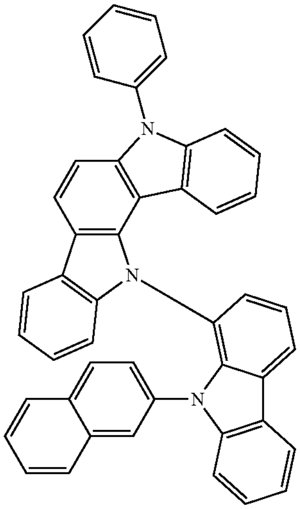
3-72
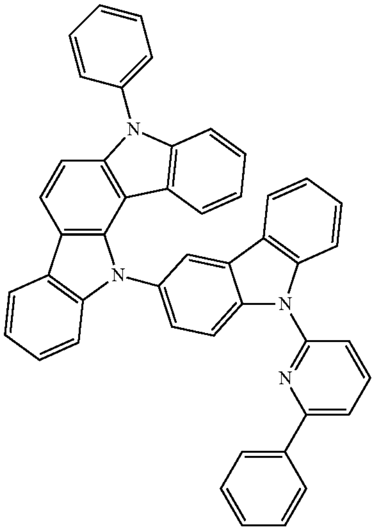

-continued
3-73
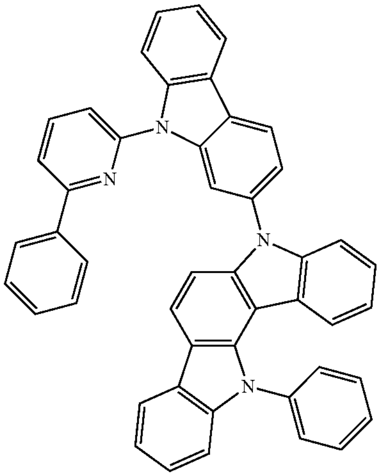
3-74
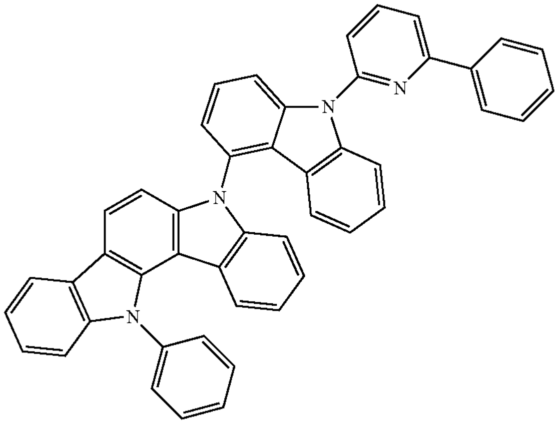
3-75
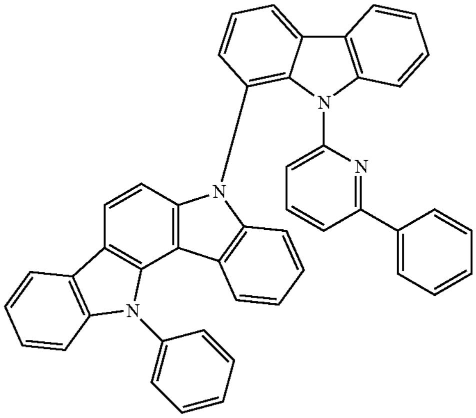
-continued
3-76
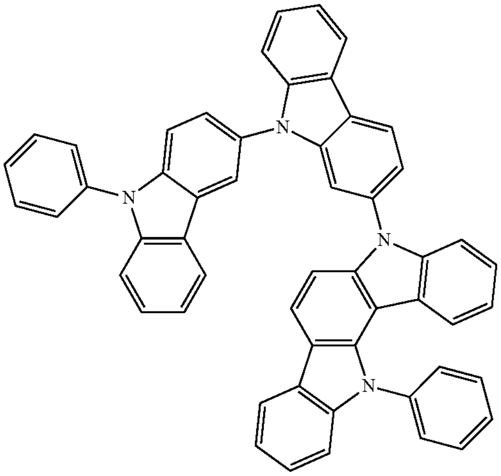
3-77
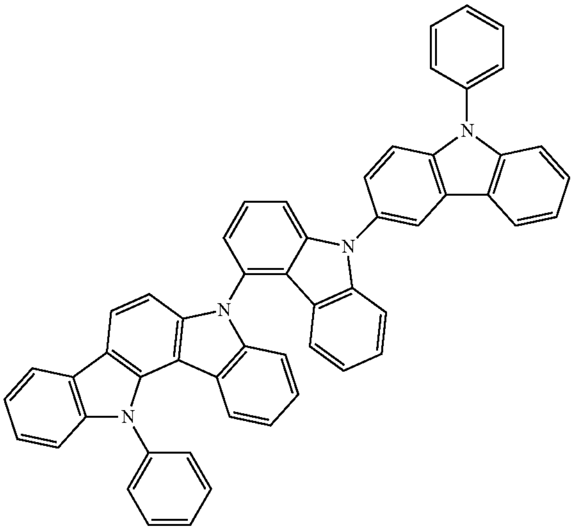
3-78
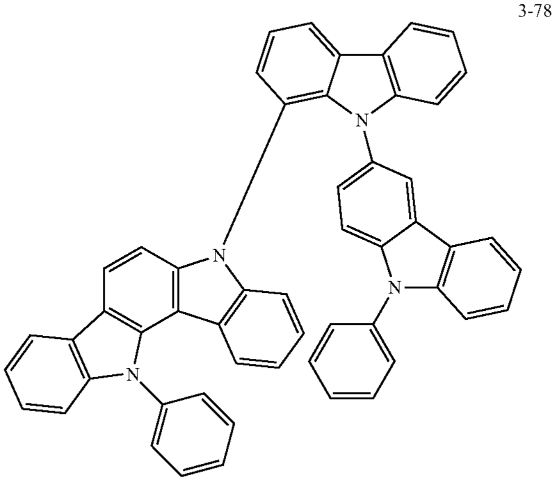

-continued
3-79
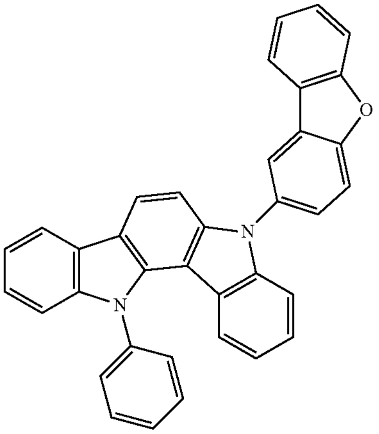
3-80
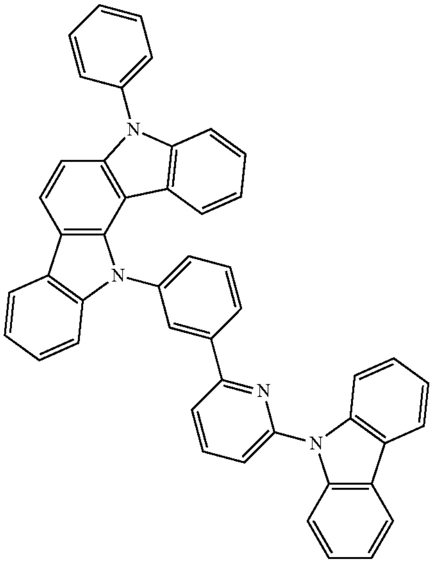
[C 44]
3-81
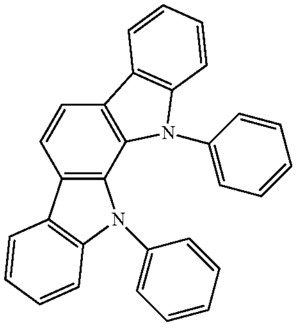
-continued
3-82
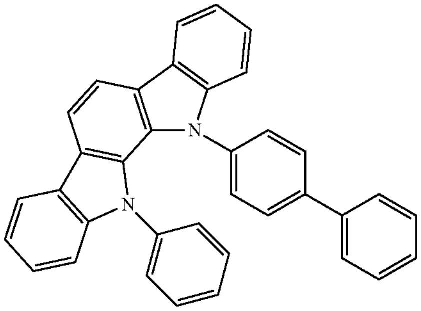
3-83
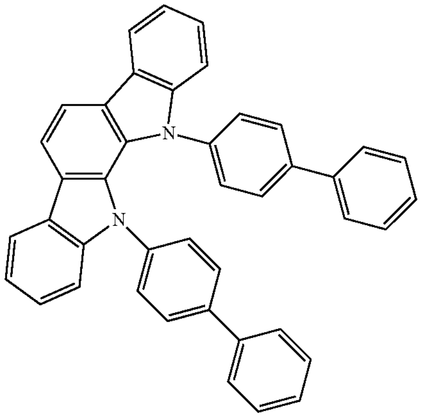
3-84
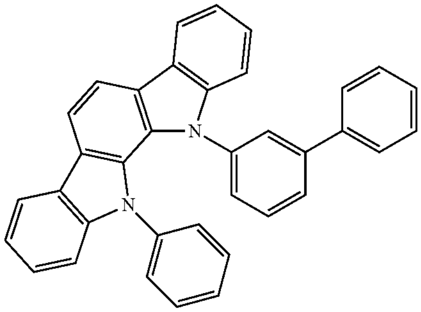
3-85
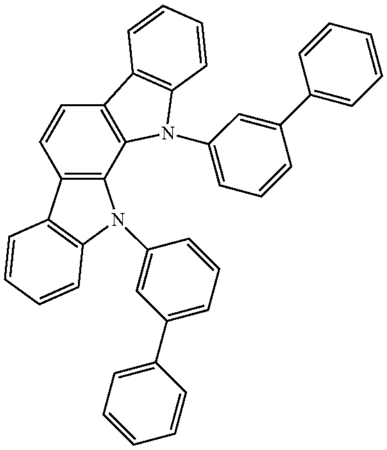

-continued
3-86
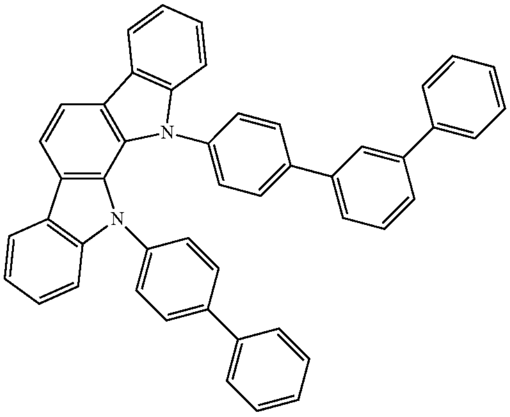
3-87
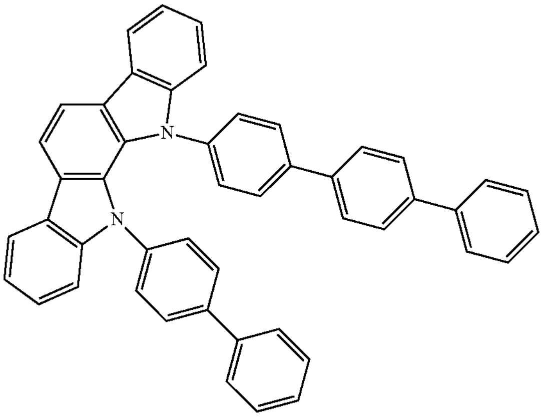
3-88
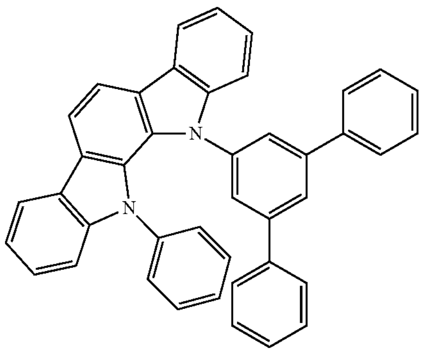
-continued
3-89
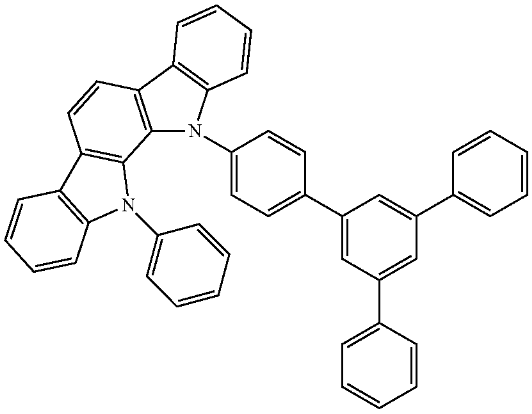
3-90
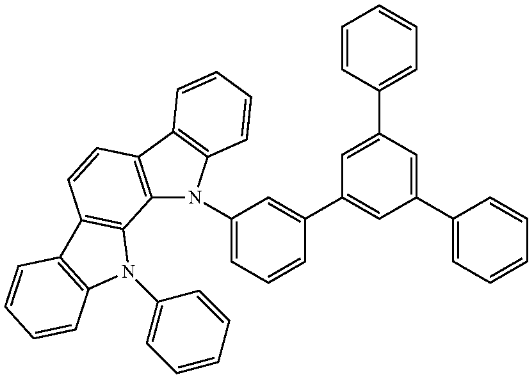
3-91
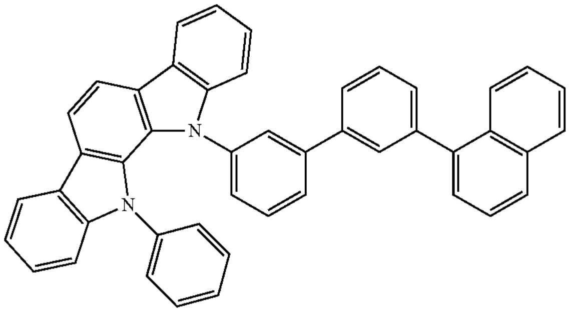
3-92
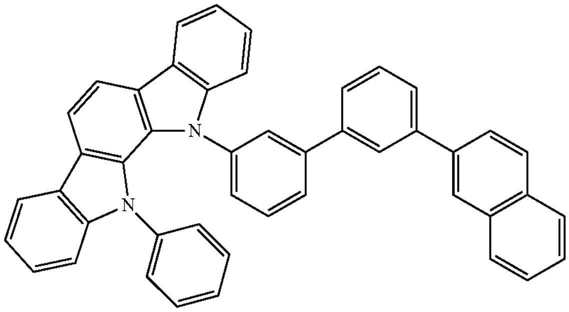

-continued
3-93
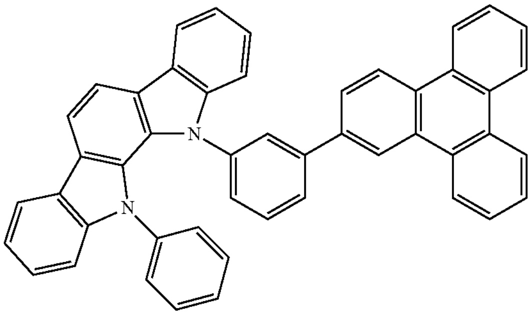
3-94
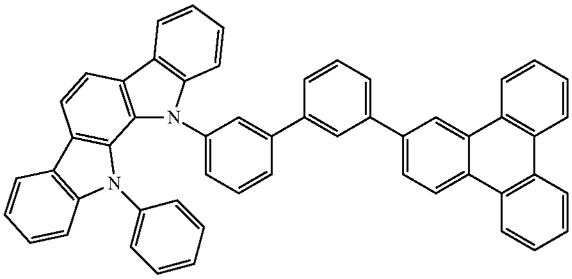
3-95
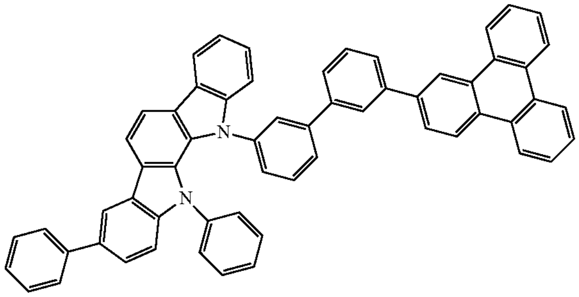
3-96
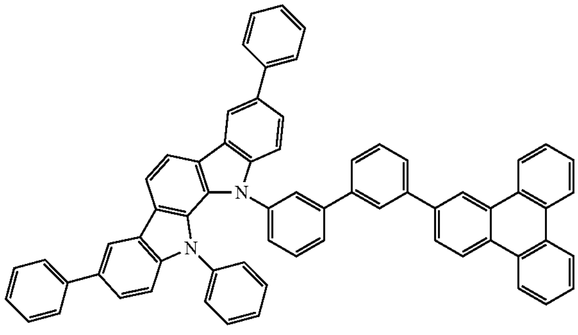
-continued
3-97
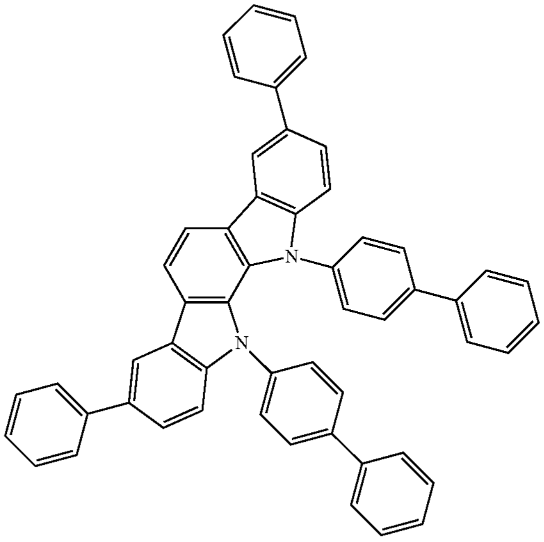
3-98
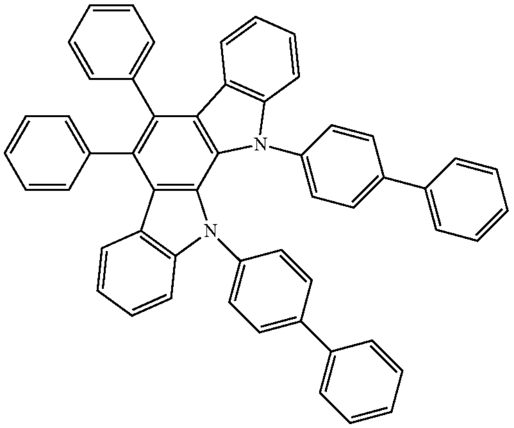
3-99
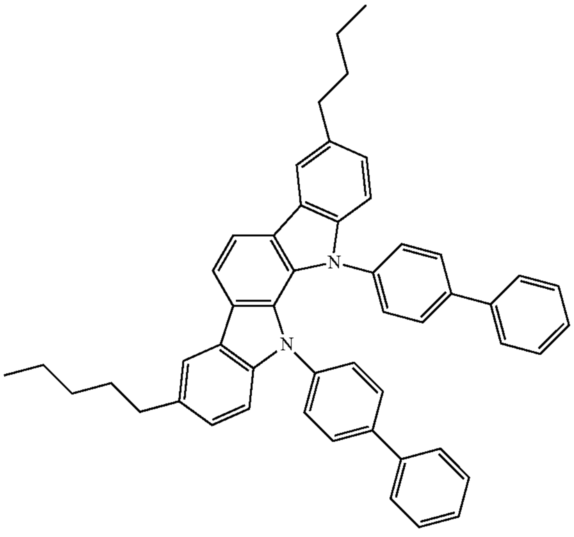

-continued
3-100
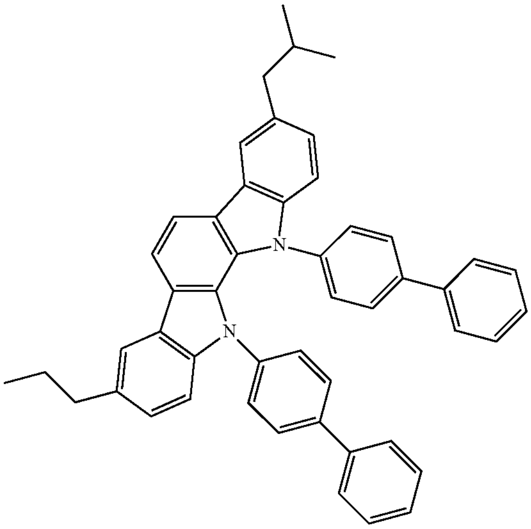
3-101
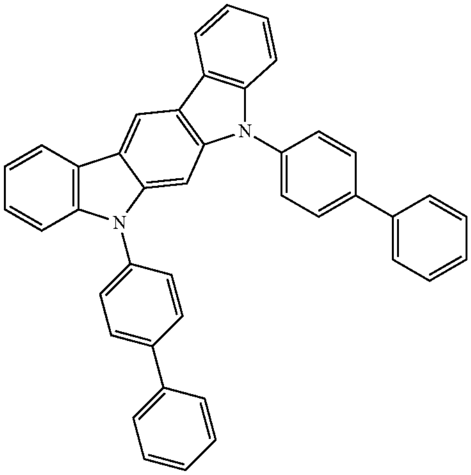
3-102
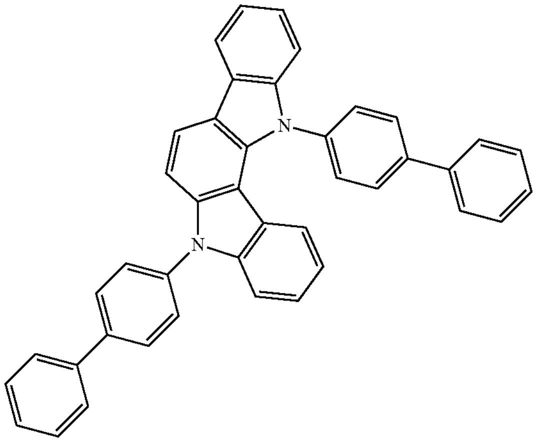
-continued
3-103
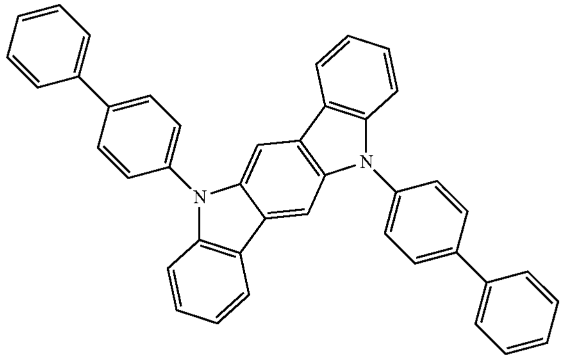
3-104
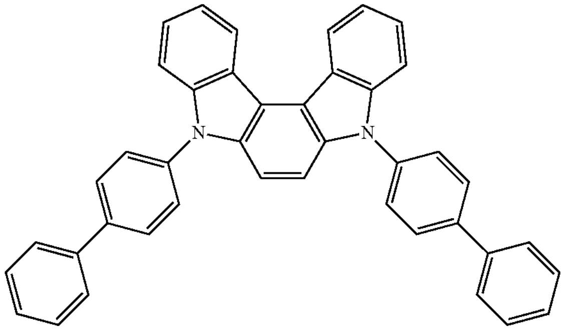
3-105
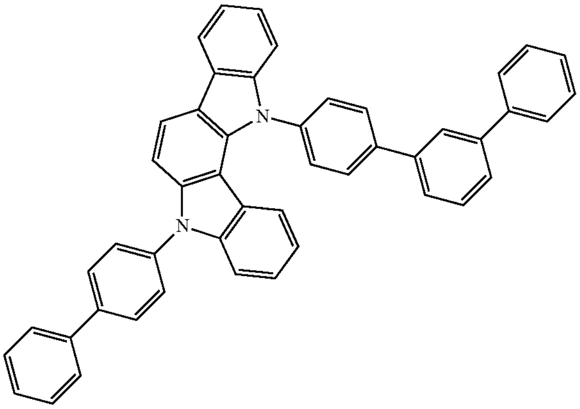

3-106
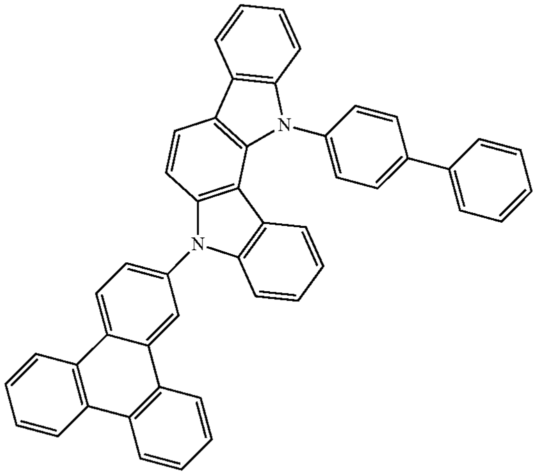
3-107
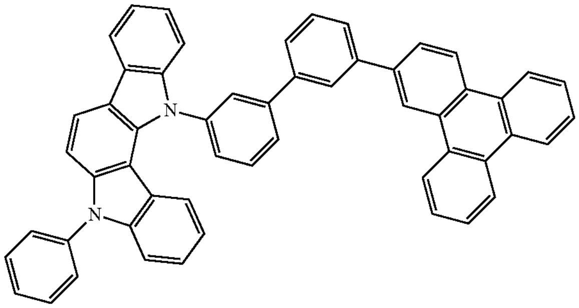
3-108
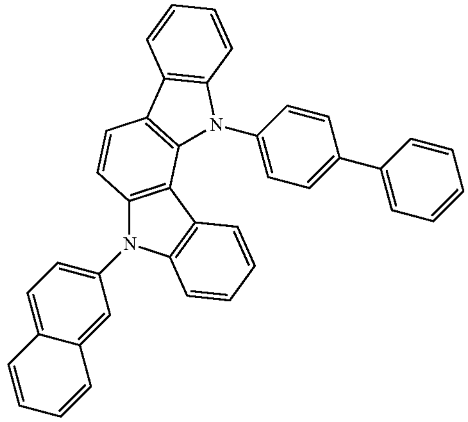
[C 45]
3-109
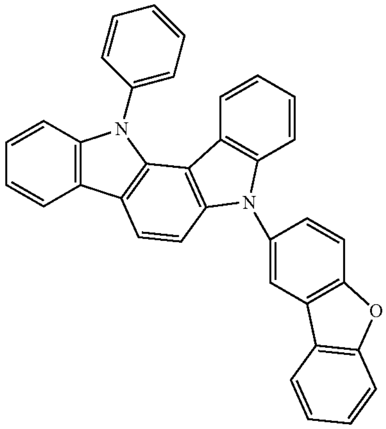
3-110
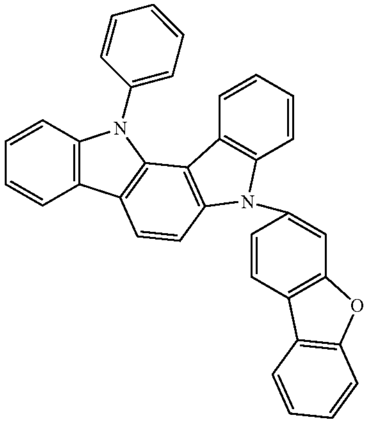
3-111
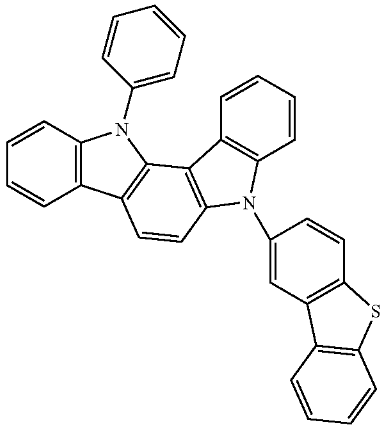

-continued
3-112
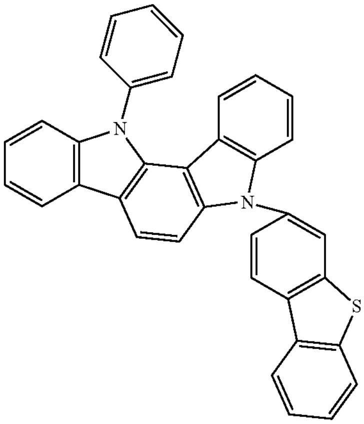
3-113
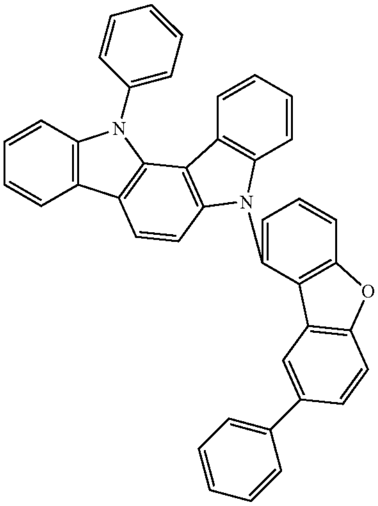
3-114
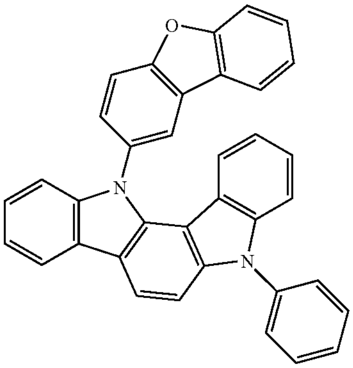
-continued
3-115
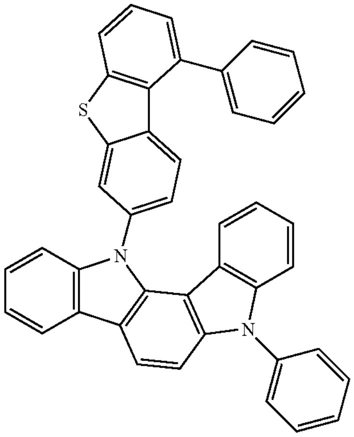
3-116
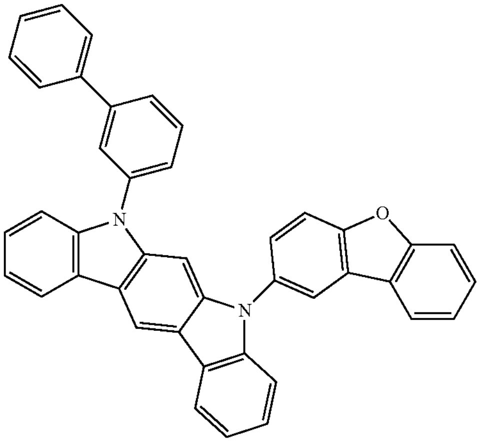
3-117
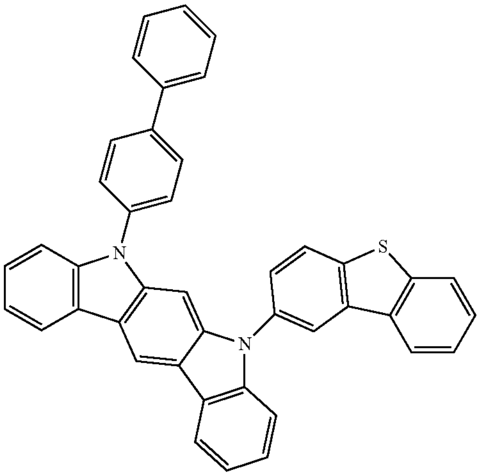

-continued 3-118

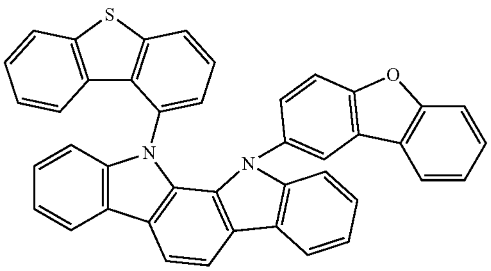

3-119

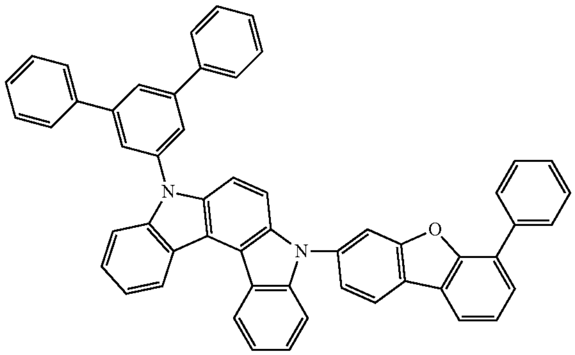

3-120

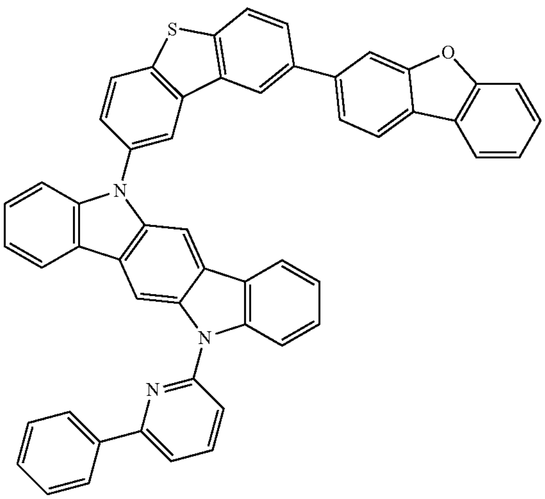

-continued 3-121

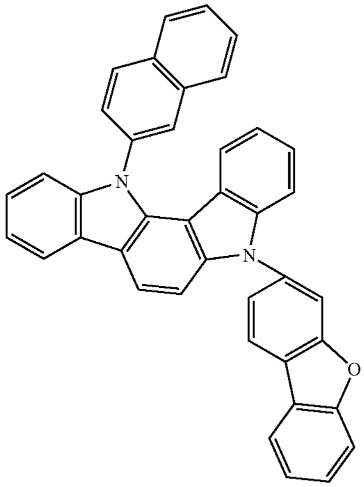

Next, the general formula (4) will be described.

In the general formula (4), $Ar^{41}$ represents a substituted or unsubstituted aromatic hydrocarbon group having 6 to 30 carbon atoms, a substituted or unsubstituted aromatic heterocyclic group having 3 to 17 carbon atoms, or a linked aromatic group in which two to five of these aromatic rings are linked. Preferred is a substituted or unsubstituted aromatic hydrocarbon group having 6 to 10 carbon atoms, a substituted or unsubstituted aromatic heterocyclic group having 3 to 12 carbon atoms, or a substituted or unsubstituted linked aromatic group in which two to five of these aromatic rings are linked to each other.

In the case of $Ar^{41}$ being an unsubstituted aromatic hydrocarbon group, an unsubstituted aromatic heterocyclic group, or an unsubstituted linked aromatic group, specific examples thereof are the same as in the case of $Ar^1$ and $Ar^{11}$ except that the group is y-valent and that, in the case of the linked aromatic group, two to five aromatic rings are linked to each other. Preferred is a group generated from pyridine, pyrimidine, triazine, dibenzofuran, dibenzothiophene, benzene, naphthalene, or a compound formed by linking two to five of these to each other.

$R^{41}$ each independently represents deuterium, an aliphatic hydrocarbon group having 1 to 10 carbon atoms, a substituted or unsubstituted aromatic hydrocarbon group having 6 to 30 carbon atoms, or a substituted or unsubstituted aromatic heterocyclic group having 3 to 17 carbon atoms, provided that $R^{41}$ is not a carbazole group and advantageously $R^{41}$ is not a group containing a carbazole ring. Preferred is an aliphatic hydrocarbon group having 1 to 6 carbon atoms, a substituted or unsubstituted aromatic hydrocarbon group having 6 to 12 carbon atoms, or a substituted or unsubstituted aromatic heterocyclic group having 3 to 17 carbon atoms.

In the case of $R^{41}$ being an aliphatic hydrocarbon group, specific examples thereof are the same as in the case of $R^1$.

In the case of $R^{41}$ being an unsubstituted aromatic hydrocarbon group or aromatic heterocyclic group, specific examples thereof are the same as in the case of $Ar^1$ and $Ar^{11}$ except that no carbazole is included.

y represents the number of substitutions, and represents an integer of 1 to 4. Preferably, y is 1 or 2, and more preferably 1.

x is the number of repetitions, and each independently represents an integer of 1 to 4. Preferably, x is 1 to 3.

However, at least one x is an integer of 2 to 4. z is an integer of 0 to 3, and preferably 0 or 1.

The sum of x (total number of carbazolyl groups) can be an integer of 2 to 12, and is preferably 2 to 9 and more preferably 2 to 6.

The general formula (4) preferably has at least one binding structure represented by the following formula (4a) or formula (4b) therein. It is more preferred that all of the binding structures among carbazolyl groups should be a binding structure represented by formula (4a) or formula (4b).

[C 46]

(4a)

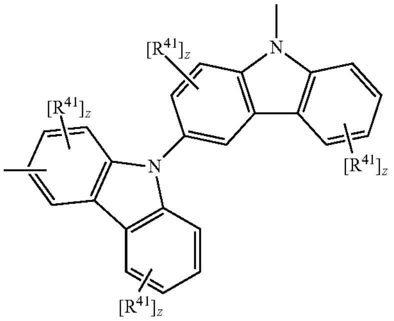

-continued (4b)

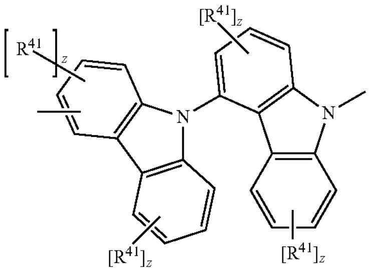

In the formulas, $R^{41}$ and z are as defined for the general formula (4).

Specific examples of the compounds represented by the general formula (4) are described below, but the compounds are not limited to these exemplified compounds.

[C 47]

4-1

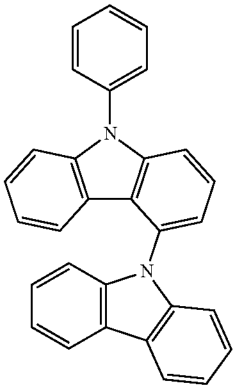

4-2

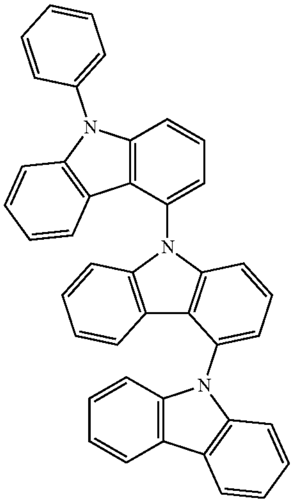

-continued
4-3
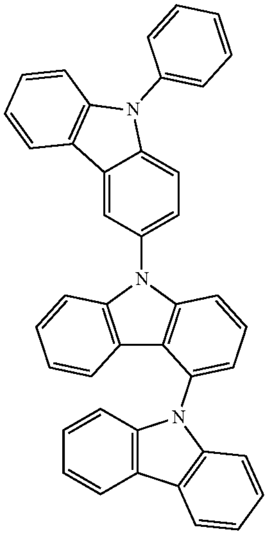
4-4
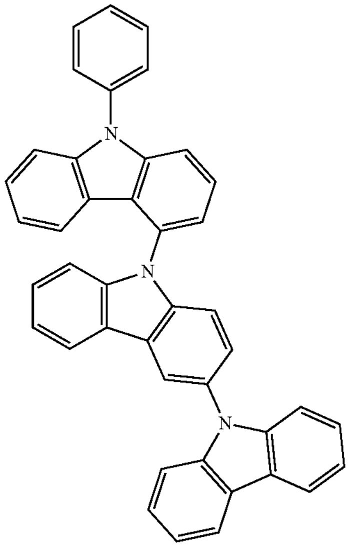
4-5
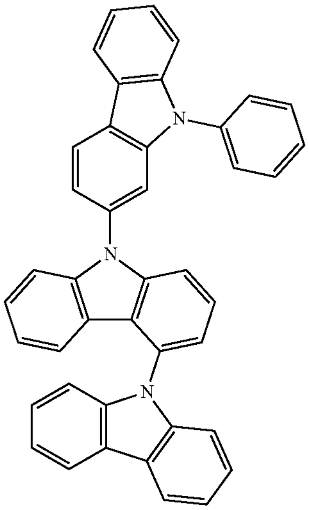
4-6
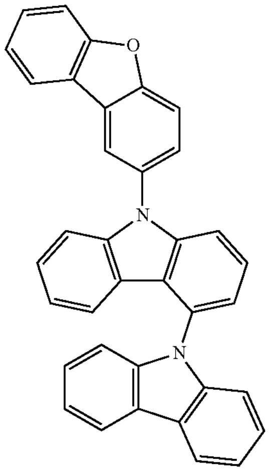
4-7
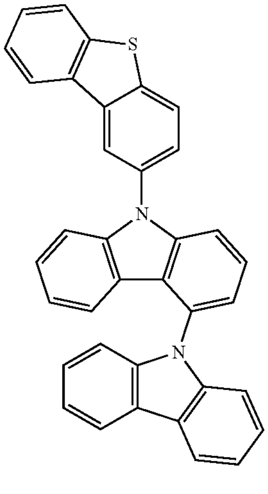
4-8
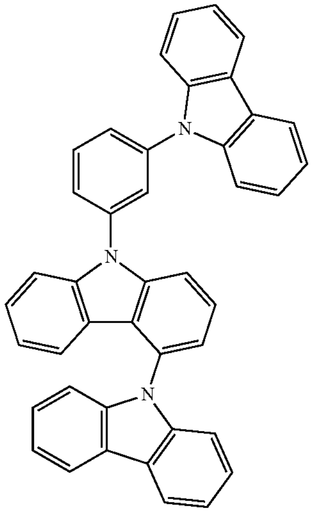

-continued
4-9
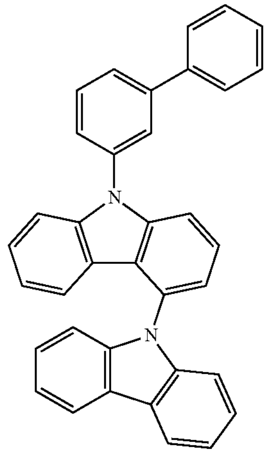
4-10
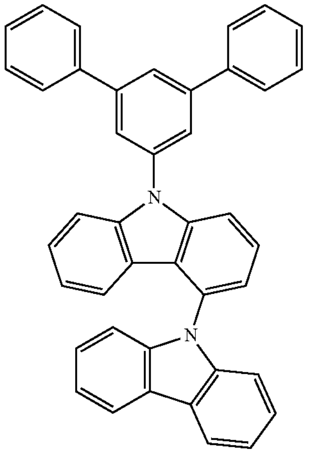
4-11
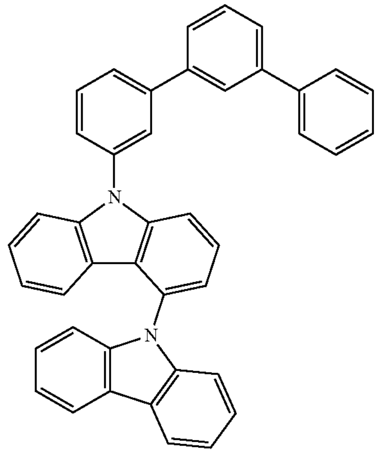
4-12
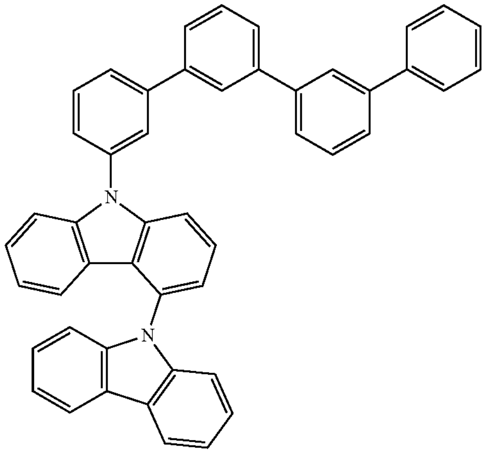
4-13
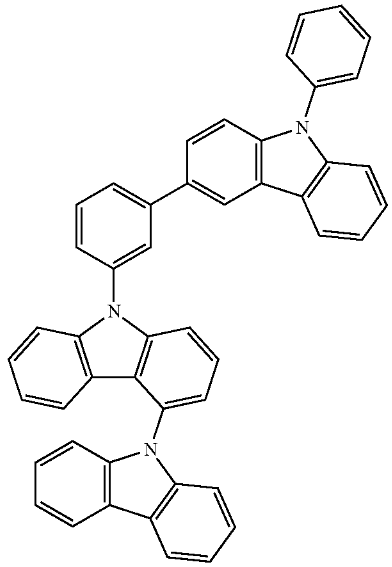
4-14
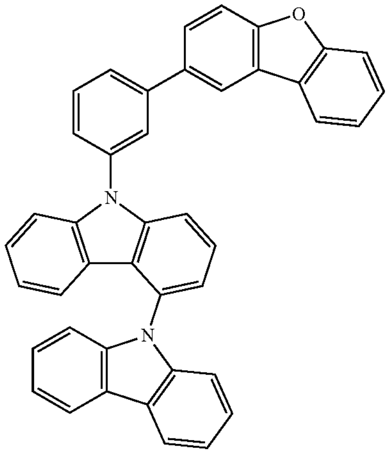

-continued
4-15
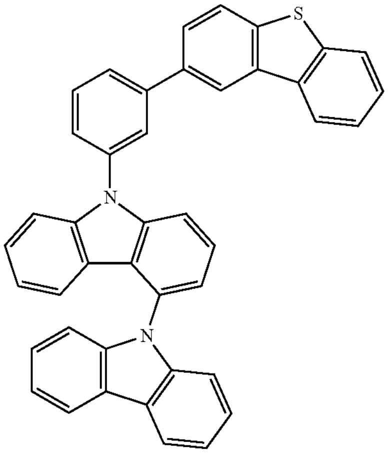
4-16
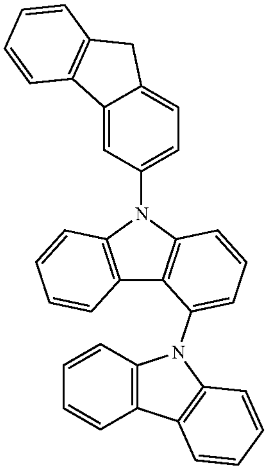
4-17
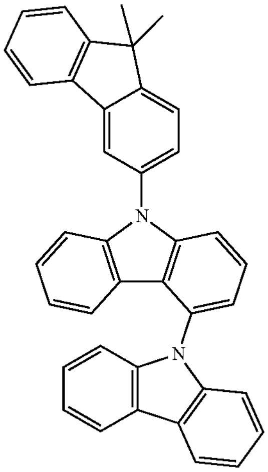
4-18
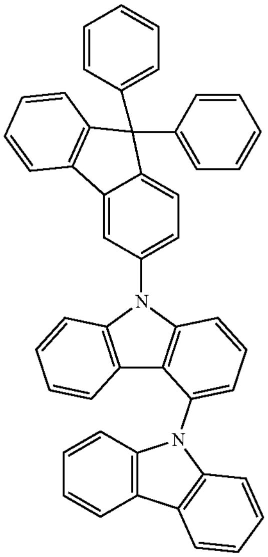
4-19ka
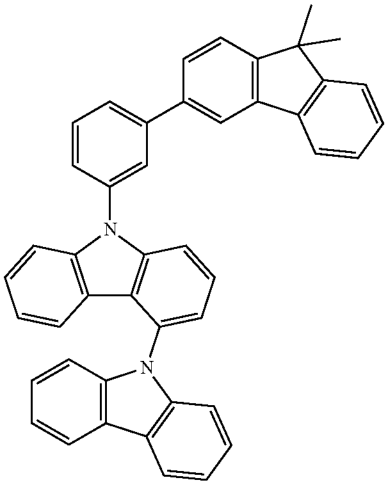

-continued
[C 48]
4-19
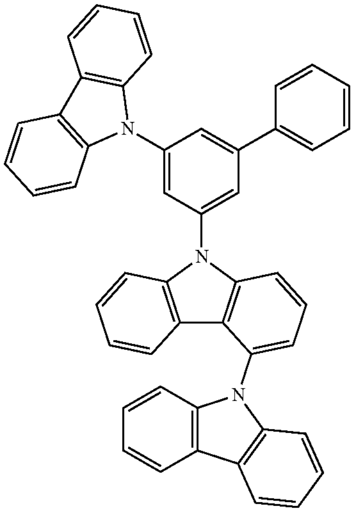
4-20
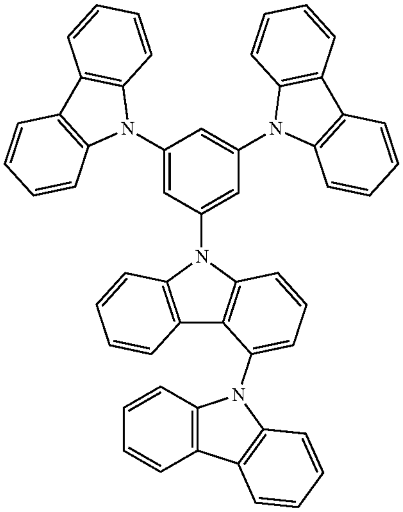
4-21
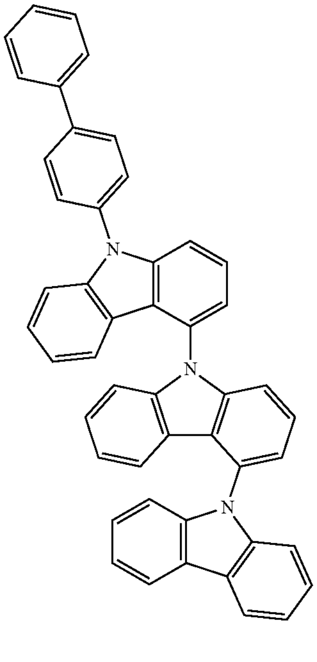
4-22
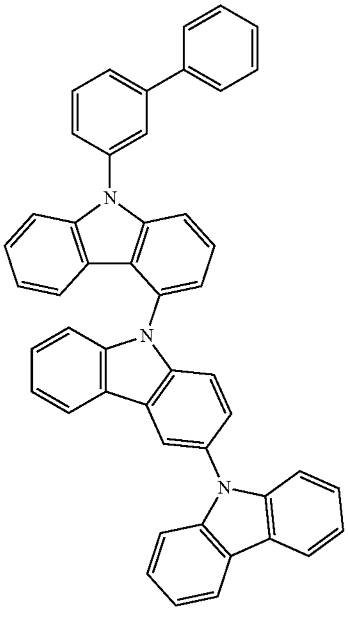

-continued
4-23
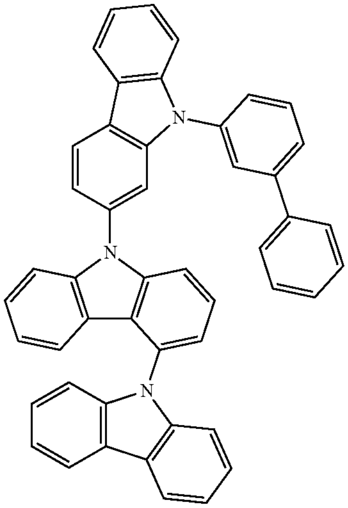
4-24
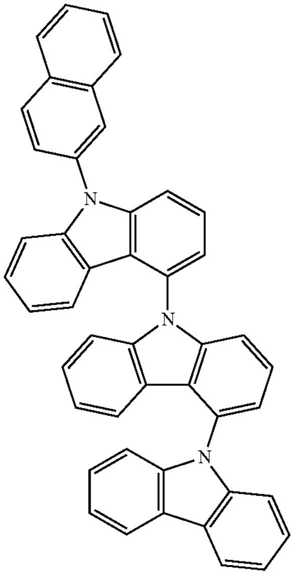
4-25
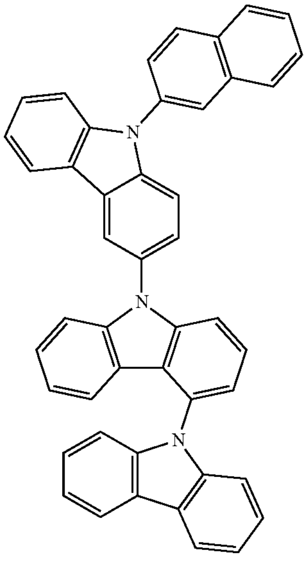
4-26
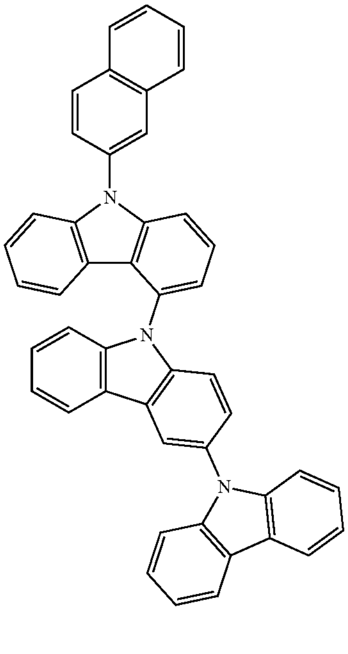

-continued
4-27
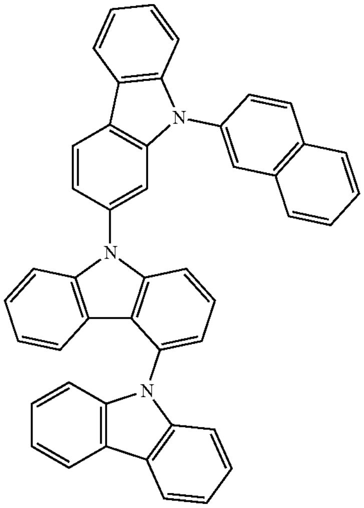
4-28
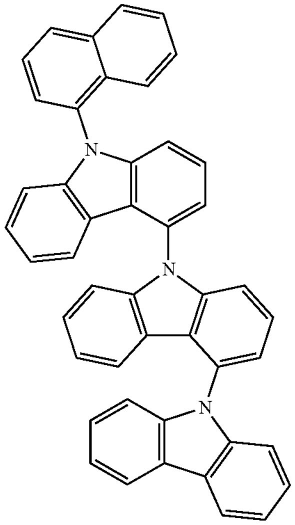
4-29
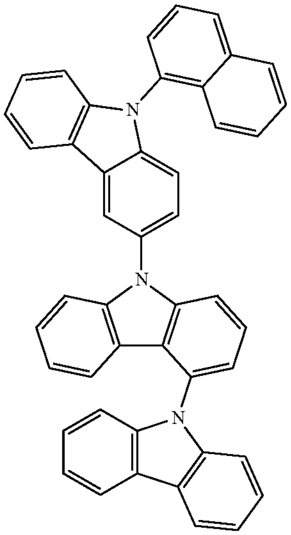
4-30
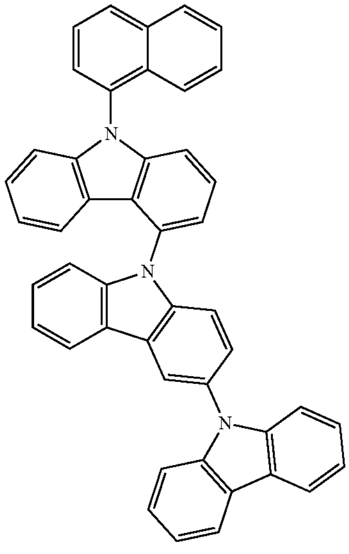

-continued
4-31
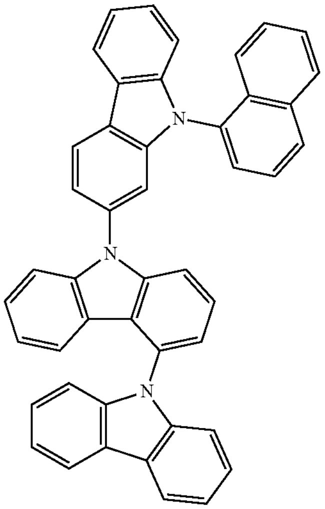
4-32
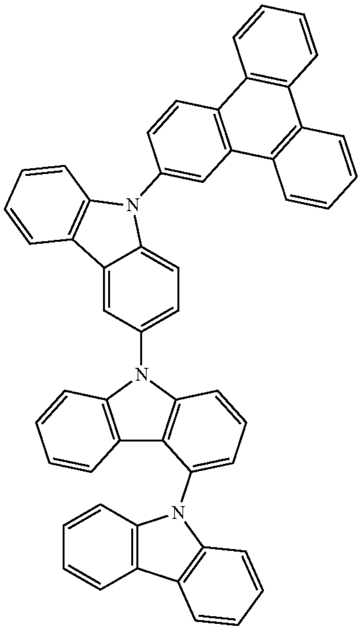
[C 49]
4-33
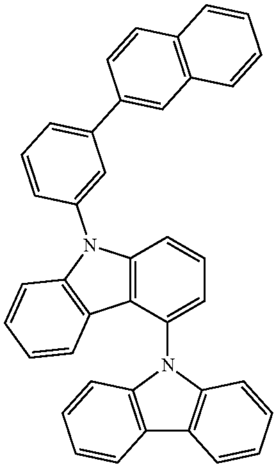
4-34
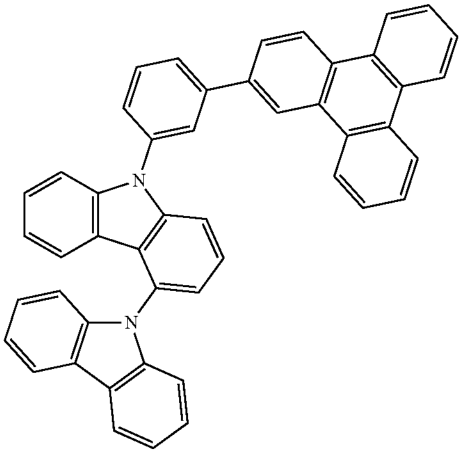
4-35
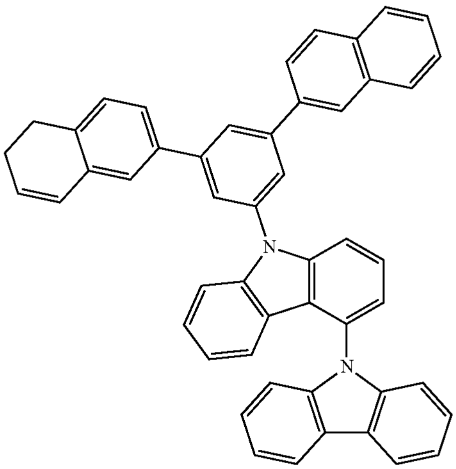
4-36
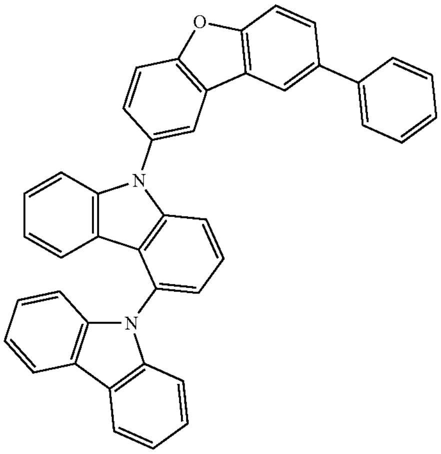

-continued
4-37
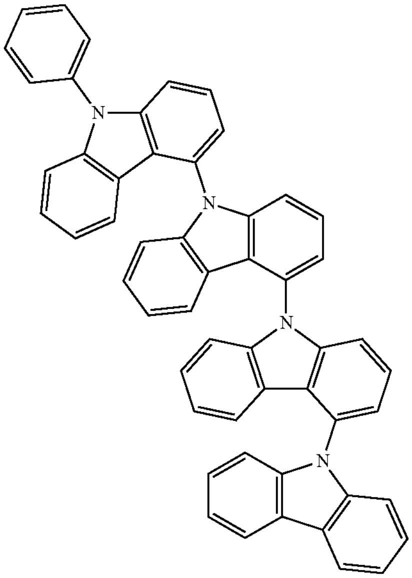
4-38
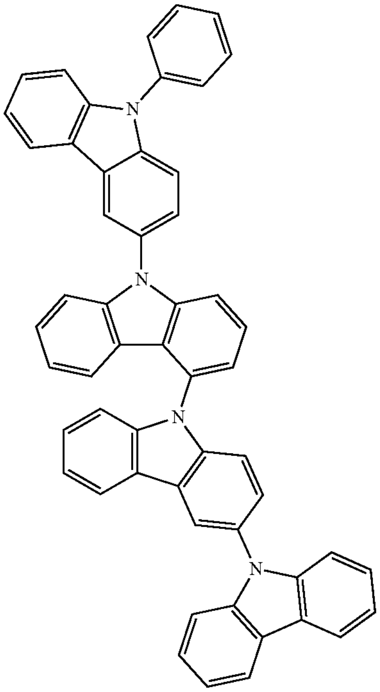
4-39
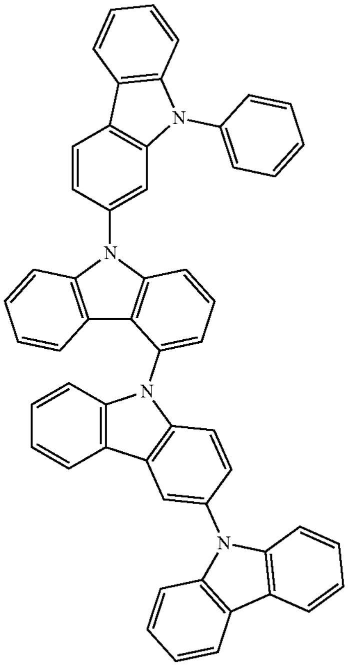
4-40
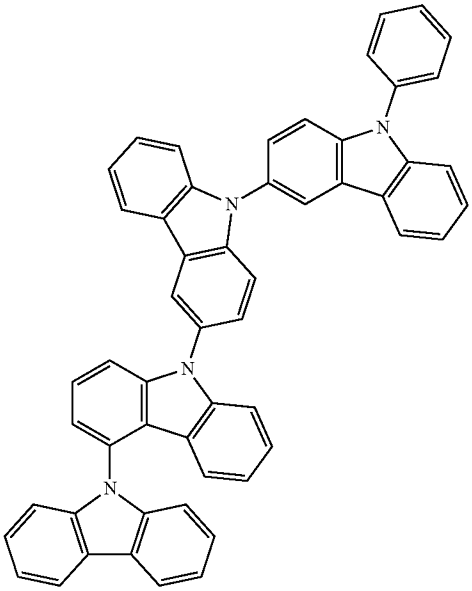

-continued
4-41
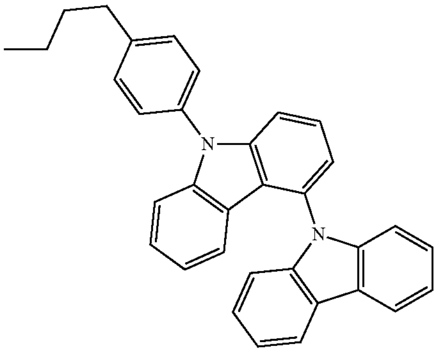
4-42
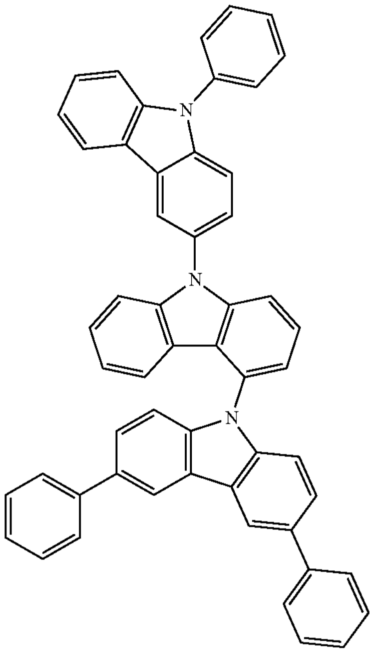
4-43
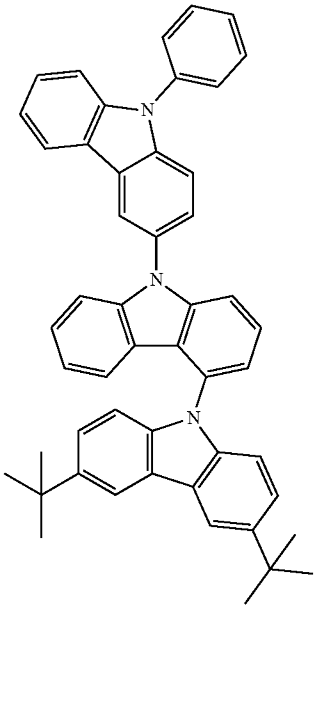
4-44
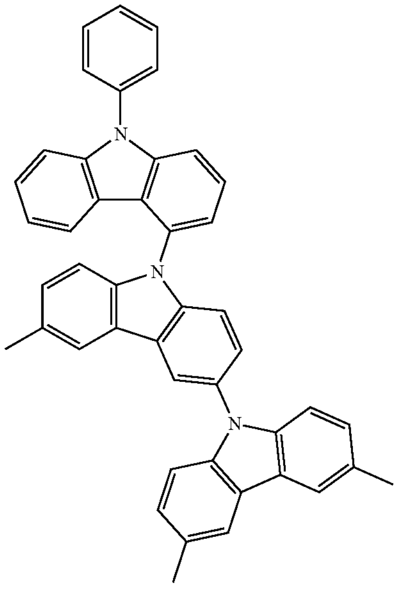

-continued
[C 50]
4-45
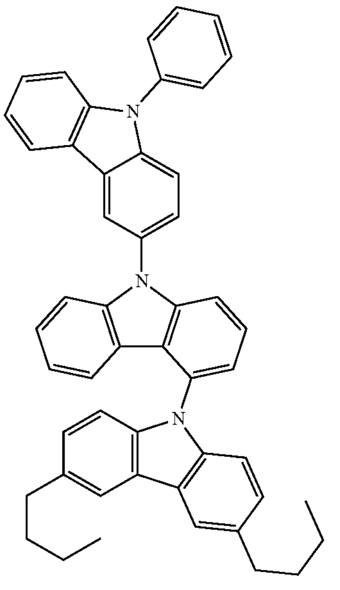
4-46
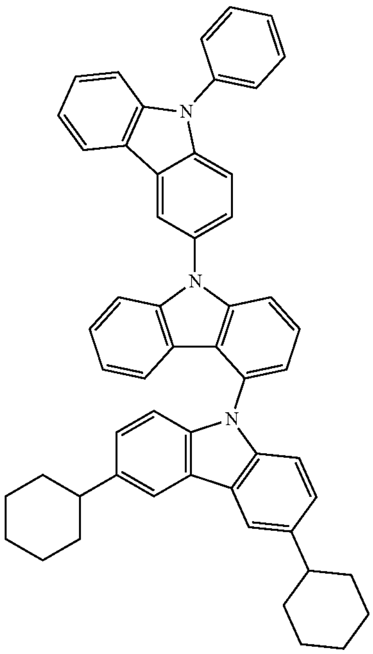
4-47
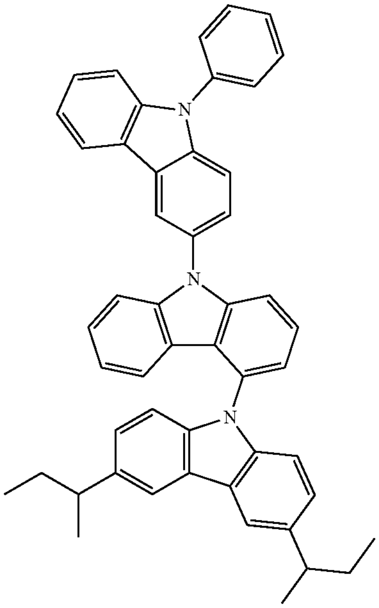
4-48
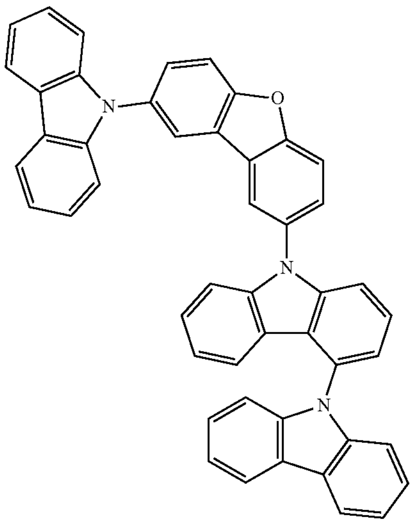

-continued
4-49
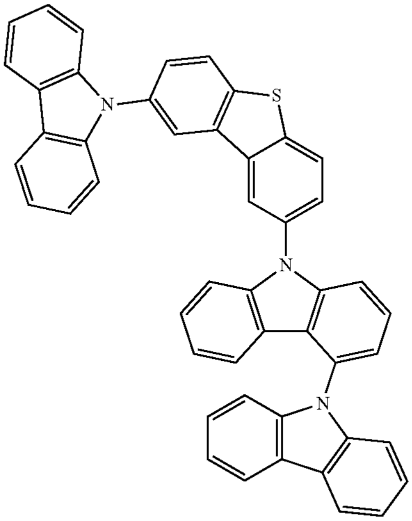
4-50
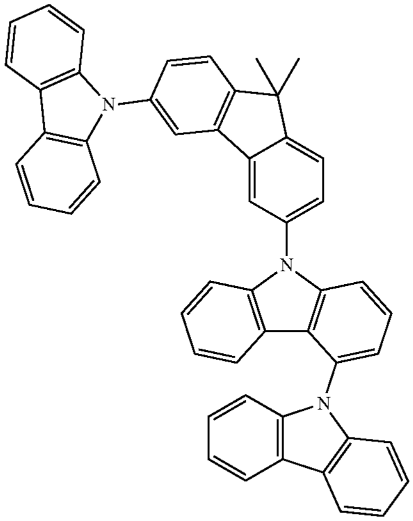
4-51
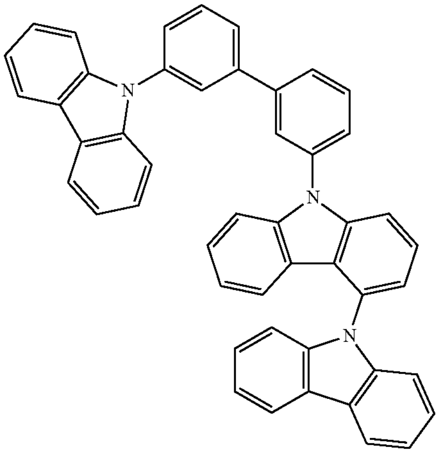
4-52
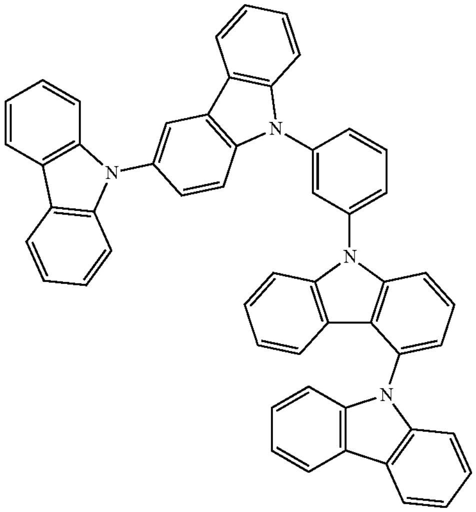
4-53
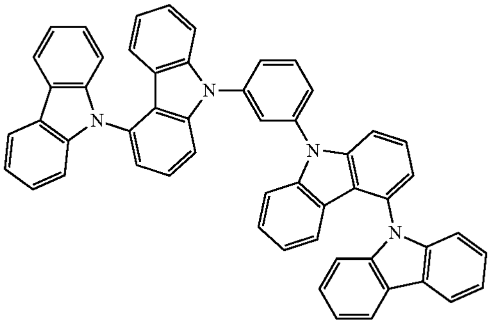
4-54
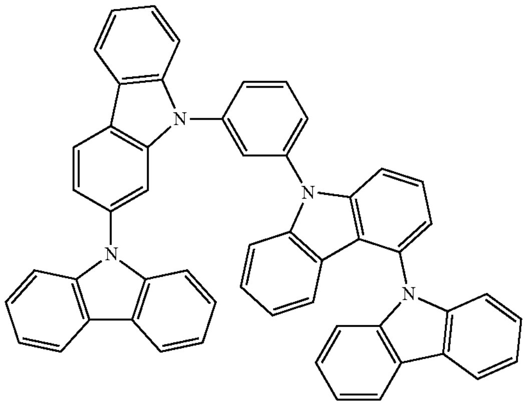

-continued
4-55
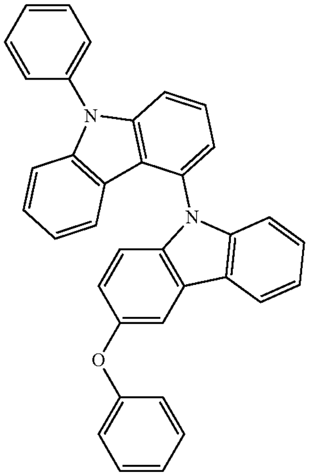
4-56
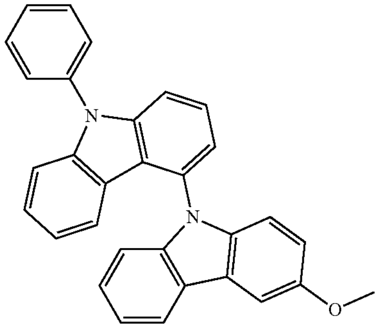
4-57
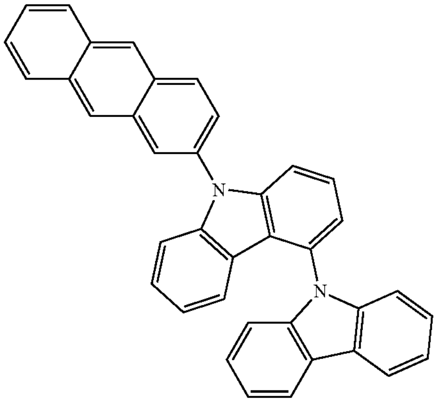
4-58
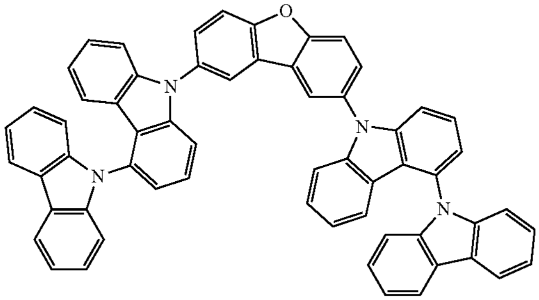
4-59
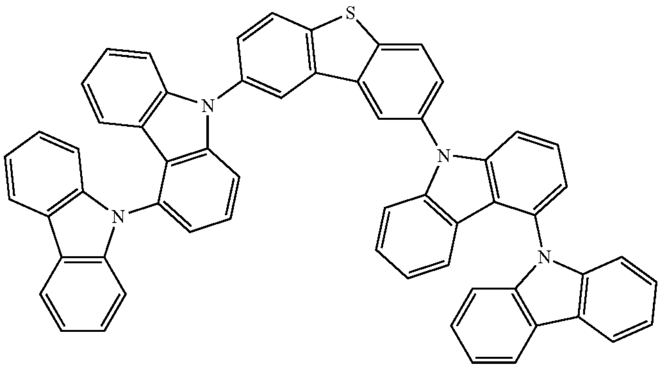
[C 52]
4-60
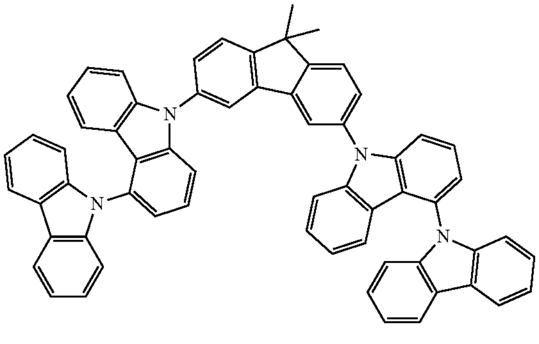
4-61
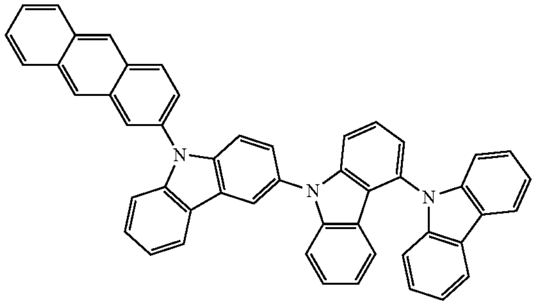

-continued
4-62
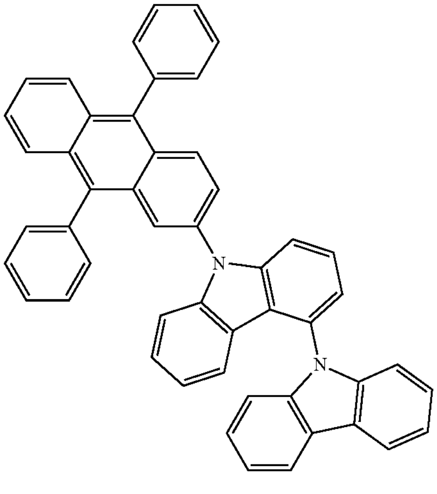
4-63
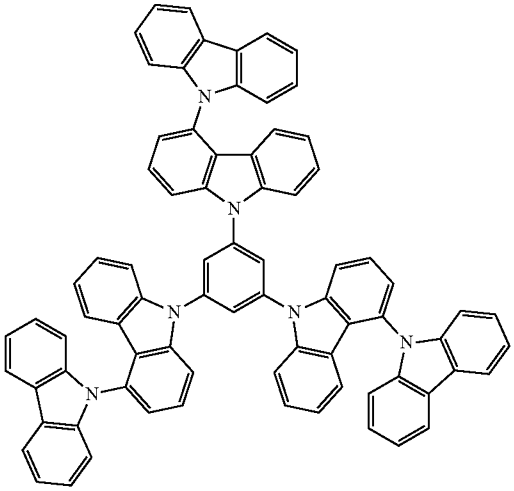
4-64
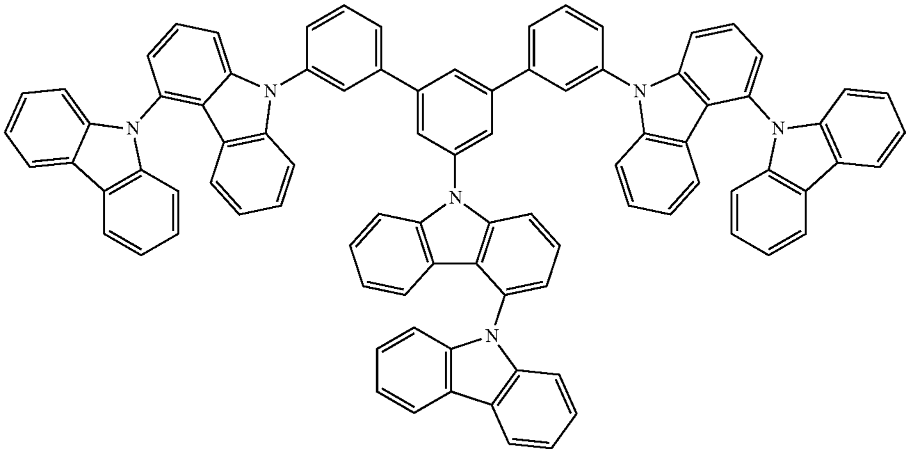
4-65
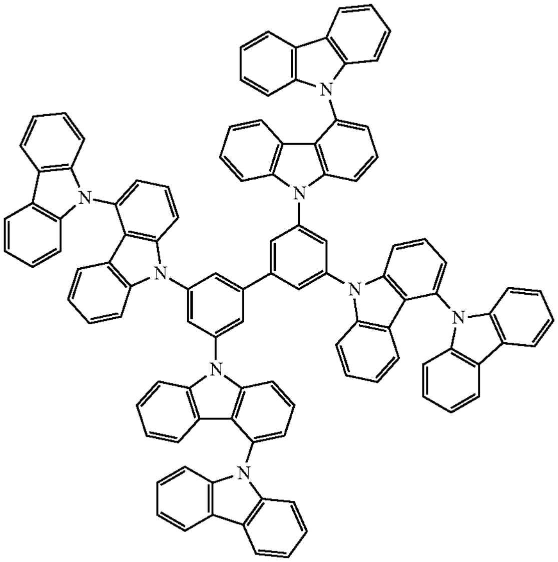
4-66
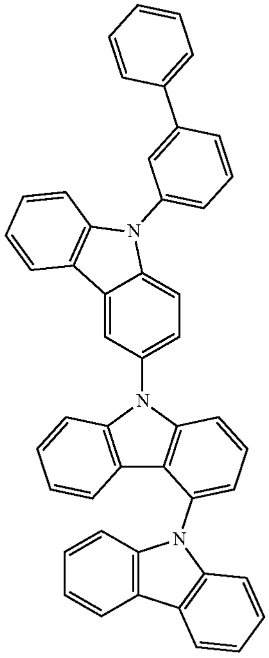

-continued
4-67
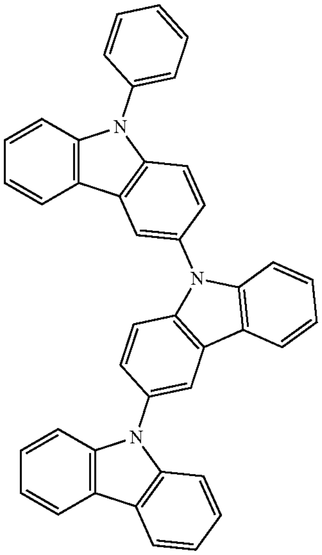
4-68
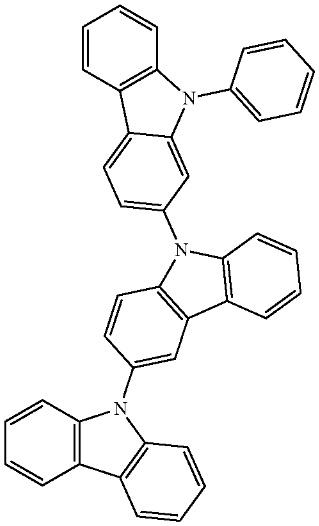
4-69
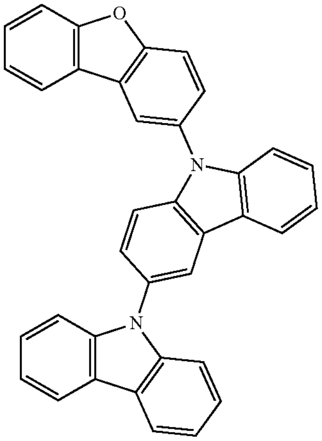
4-70
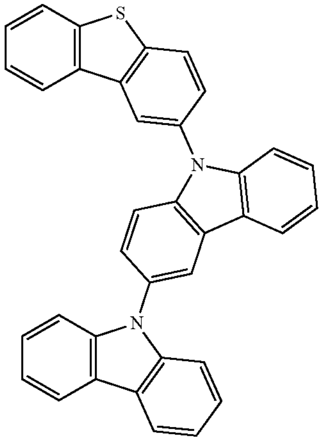
4-71
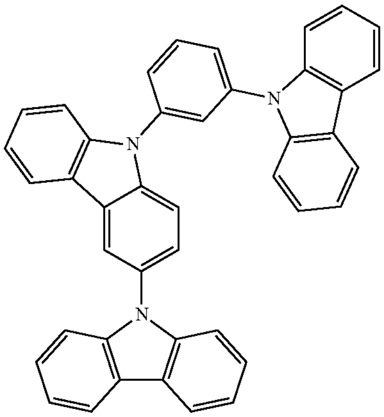
4-72
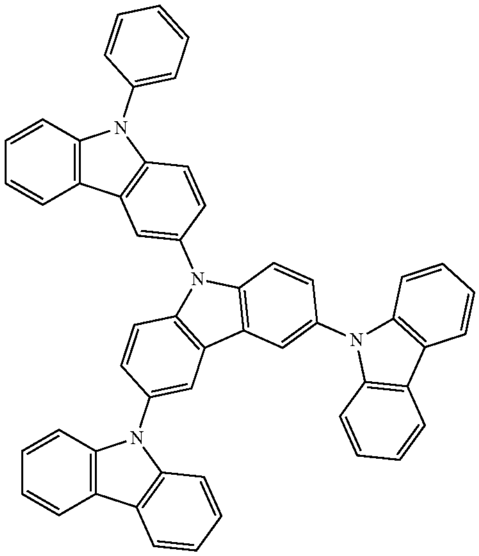

-continued
4-73
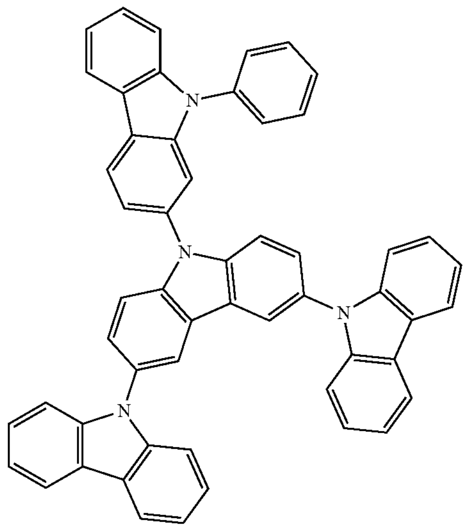
4-74
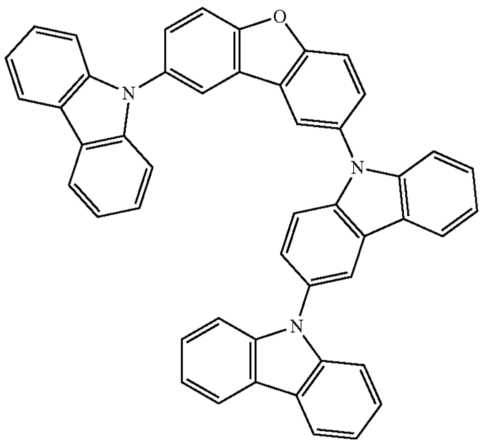
[C 53]
4-75
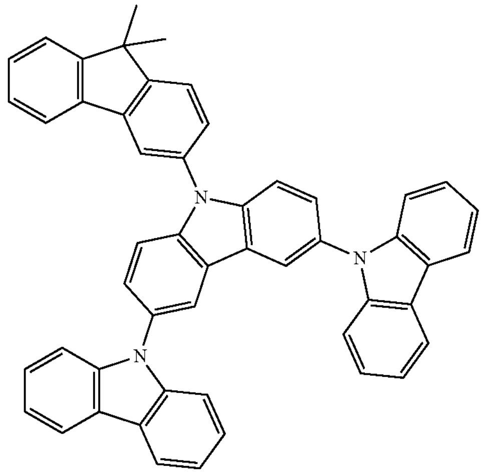
4-76
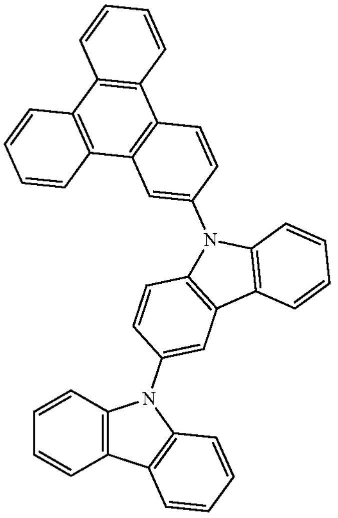
4-79
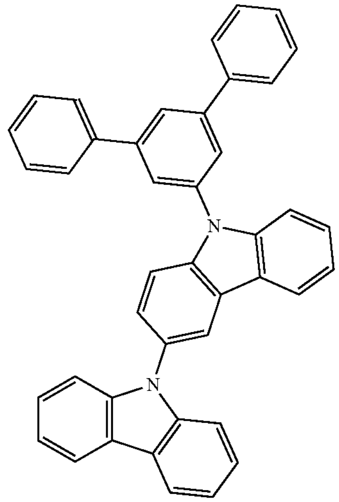

The second host material is preferably the compound represented by the general formula (2) or the general formula (3).

The third host material is suitably the compound represented by the general formula (5). Preferred is the compound represented by the formula (51).

In the general formula (5) and the formula (51), the same symbols have the same meaning.

A ring D is a heterocycle represented by formula (5a) and the ring D is fused to an adjacent ring at any position.

$R^5$ independently represents deuterium, an aliphatic hydrocarbon group having 1 to 10 carbon atoms, a substituted or unsubstituted aromatic hydrocarbon group having 6 to 30 carbon atoms, or a substituted or unsubstituted aromatic heterocyclic group having 3 to 17 carbon atoms. Preferred is hydrogen, an aliphatic hydrocarbon group having 1 to 6 carbon atoms, a substituted or unsubstituted aromatic hydrocarbon group having 6 to 10 carbon atoms, or a substituted or unsubstituted aromatic heterocyclic group having 3 to 10 carbon atoms.

In the case of $R^5$ being an aliphatic hydrocarbon group, specific examples thereof are the same as in the case of $R^1$.

In the case of $R^5$ being an unsubstituted aromatic hydrocarbon group having 6 to 30 carbon atoms, an aromatic heterocyclic group having 3 to 17 carbon atoms, or a substituted or unsubstituted linked aromatic group in which two to five of these aromatic rings are linked to each other, specific examples thereof are the same as in the case of $Ar^1$ and $Ar^{11}$ except that two to five of these aromatic rings are linked to each other.

p, r, and s represent the number of substitutions, and each independently represent an integer of 0 to 4. These are each preferably an integer of 0 to 3, and further preferably 0 to 2. q represents an integer of 0 to 2, preferably represents an integer of 0 to 1.

$Ar^5$ and $Ar^{51}$ independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other. Preferred is a substituted or unsubstituted aromatic hydrocarbon group having 6 to 10 carbon atoms, a substituted or unsubstituted aromatic heterocyclic group having 3 to 12 carbon atoms, or a substituted or unsubstituted linked aromatic group in which two to seven of these aromatic rings are linked to each other.

In the case of $Ar^5$ and $Ar^{51}$ being each an unsubstituted aromatic hydrocarbon group, an unsubstituted linked aromatic group, and an unsubstituted linked aromatic group, specific examples thereof are the same as in the case of $Ar^1$ and $Ar^{11}$. Preferred is a group generated from pyridine, pyrimidine, triazine, dibenzofuran, dibenzothiophene, carbazole, benzene, naphthalene, or a compound formed by linking two to seven of these aromatic groups to each other.

$L^5$ and $L^{51}$ independently represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group. It is preferred that at least one of $L^5$ and $L^{51}$ is a substituted or unsubstituted nitrogen-containing 6-membered ring, or a substituted or unsubstituted ring-fused aromatic heterocyclic group in which nitrogen-containing 6-membered rings are fused.

Specific examples of the unsubstituted nitrogen-containing 6-membered ring, or the unsubstituted ring-fused aromatic heterocyclic group containing a nitrogen-containing 6-membered ring include pyridine, pyrimidine, triazine, quinoline, isoquinoline, quinoxaline, naphthyridine, or phenazine.

Specific examples of the unsubstituted aromatic hydrocarbon group or the aromatic heterocyclic group are the same as in the case where $Ar^1$ and $Ar^{11}$ are each the group except that the group is (r+1)-valent or (s+1)-valent. Preferred is a group generated from pyridine, pyrimidine, triazine, quinoline, isoquinoline, quinoxaline, naphthyridine, phenazine, dibenzofuran, dibenzothiophene, carbazole, benzene, or naphthalene.

Specific examples of the compounds represented by the general formula (5) are described below, but the compounds are not limited to these exemplified compounds.

[C 54]

5-1

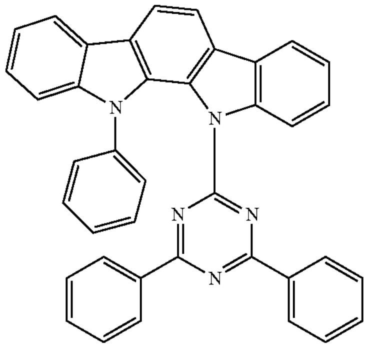

5-2

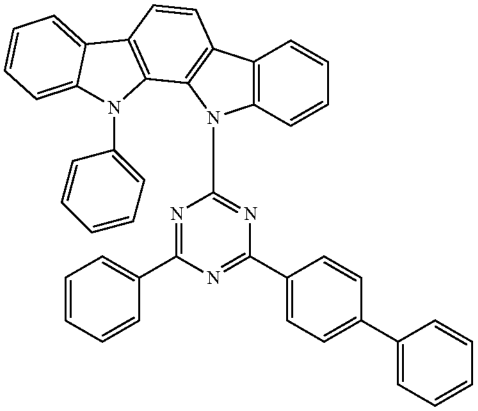

5-3

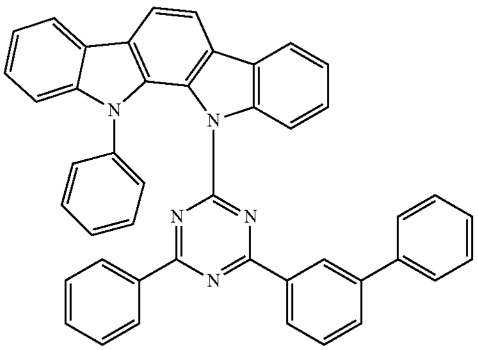

-continued
5-4
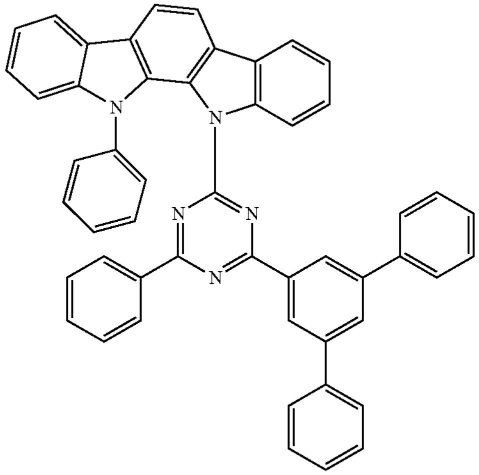
5-5
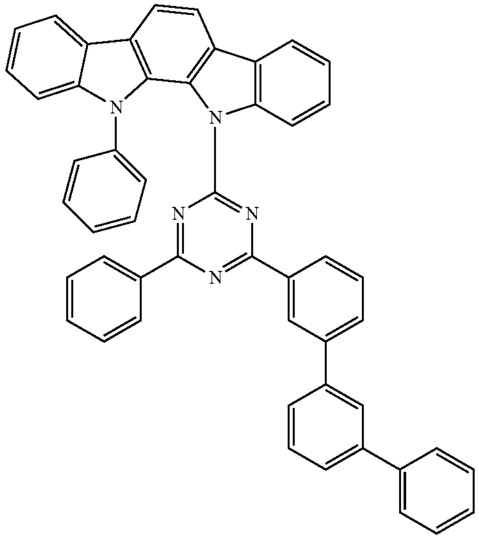
5-6
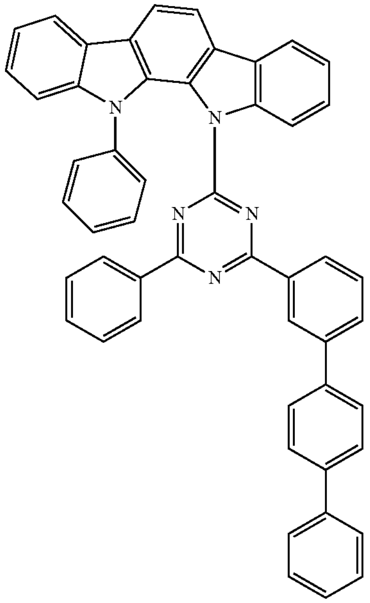
-continued
[C 55]
5-7
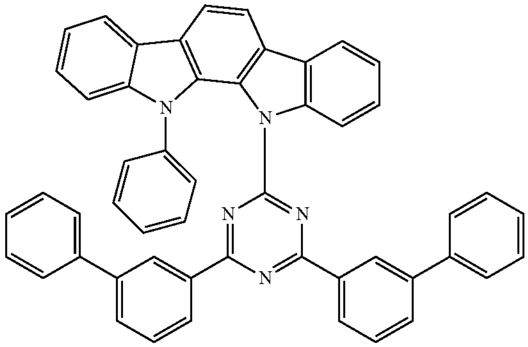
5-8
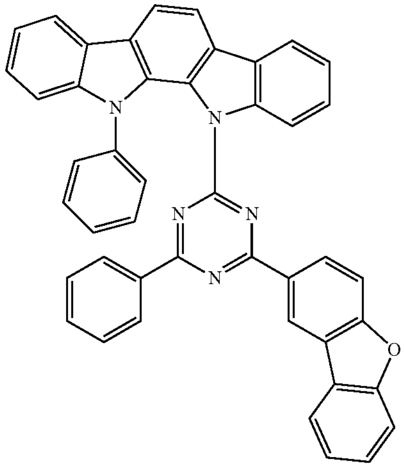
5-11
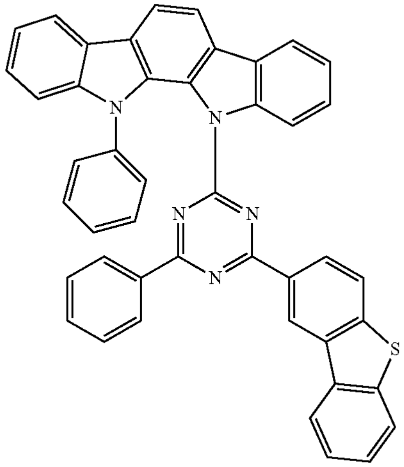

-continued
[C 56]
5-12
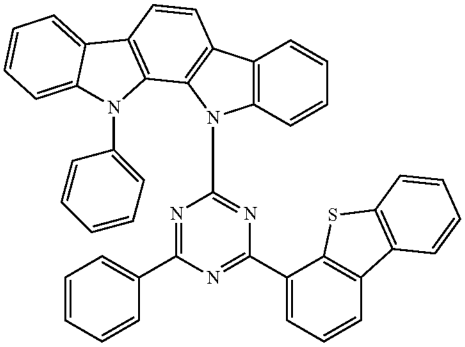
5-13
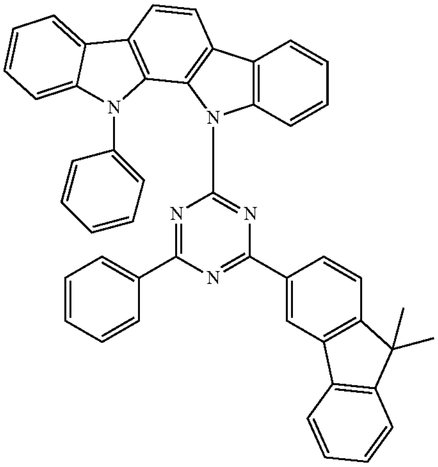
5-14
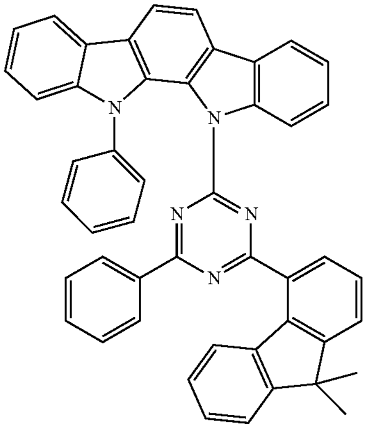
-continued
5-15
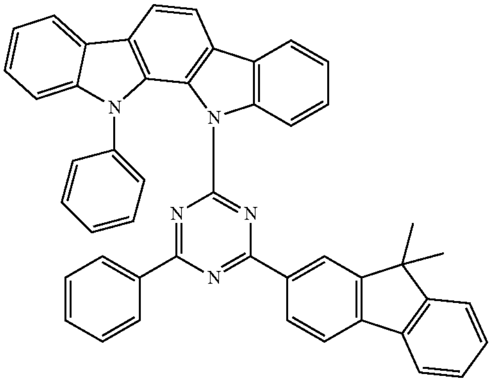
5-16
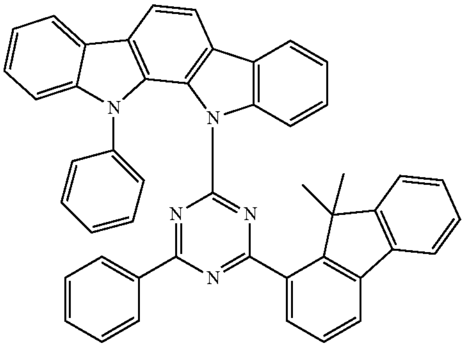
5-17
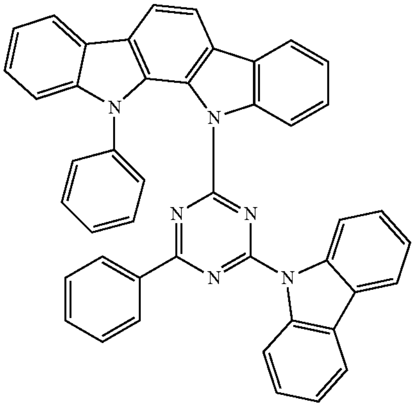
5-18
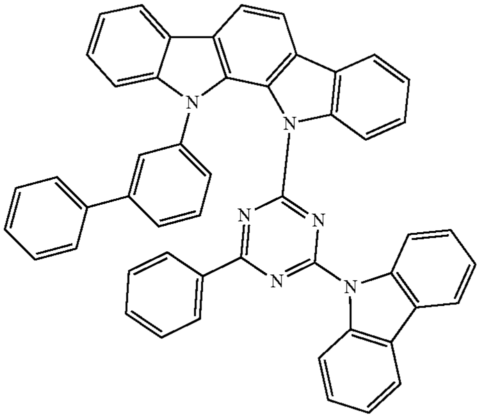

-continued
[C 57]
5-19
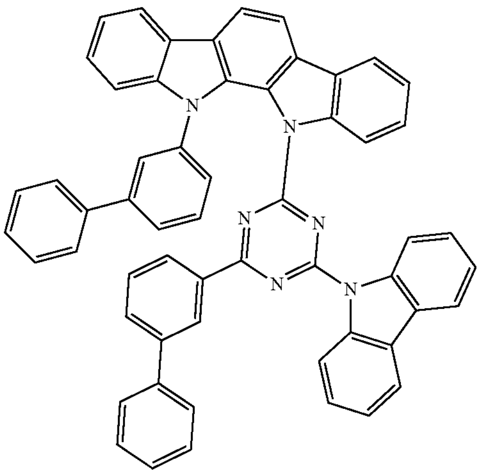
5-20
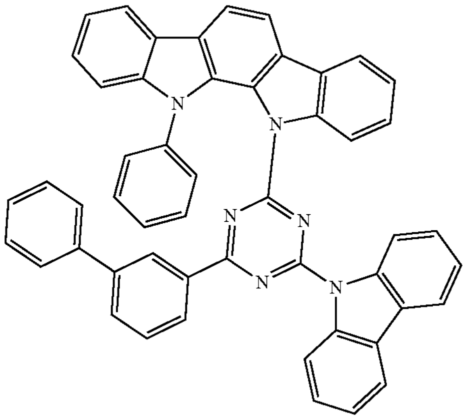
5-21
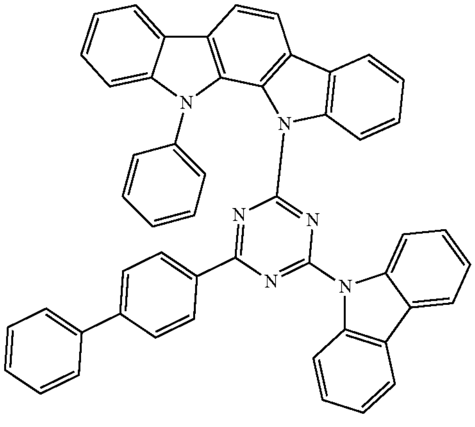
-continued
5-22
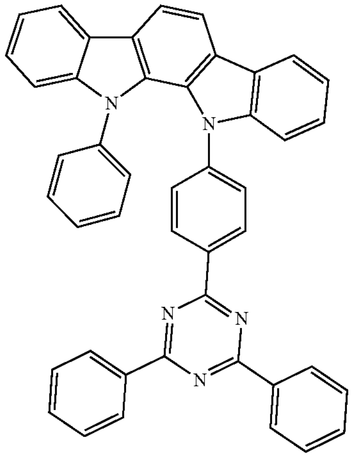
5-23
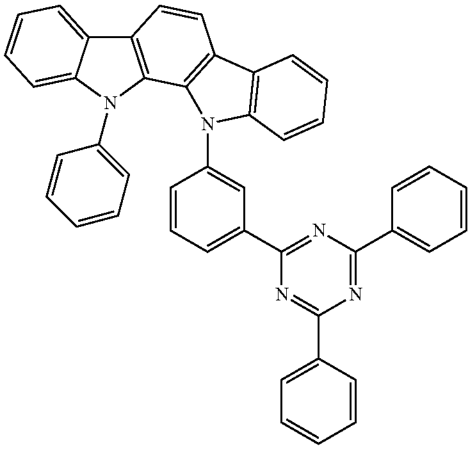
5-24
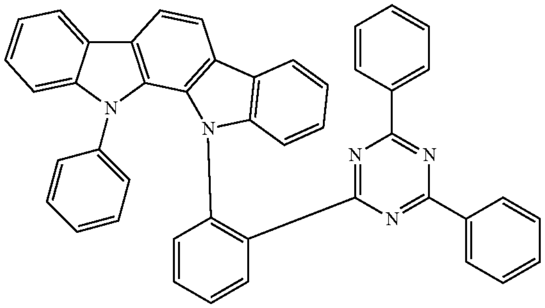

-continued
[C 58]
5-25
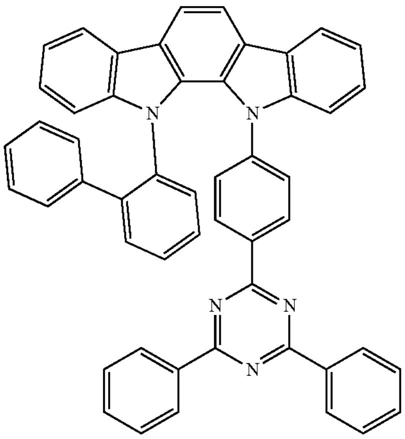
5-26
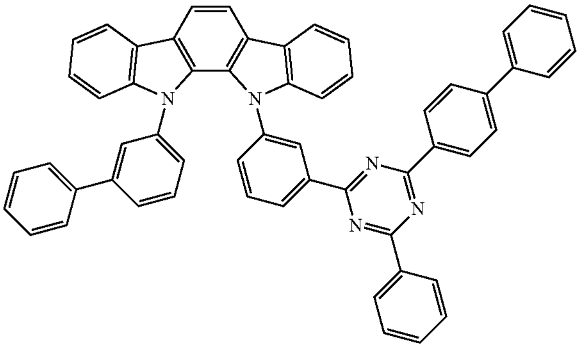
5-27
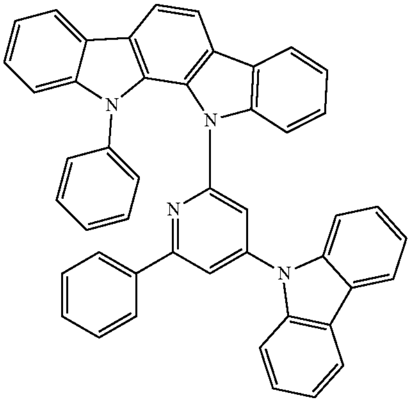
-continued
5-28
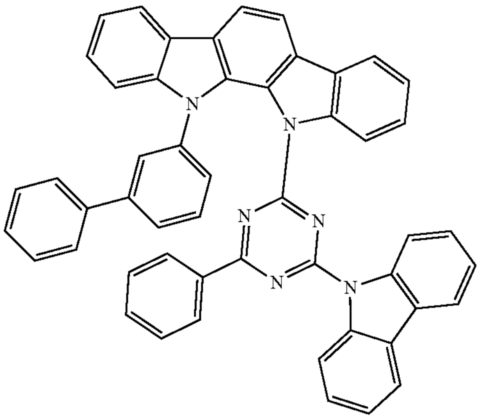
5-29
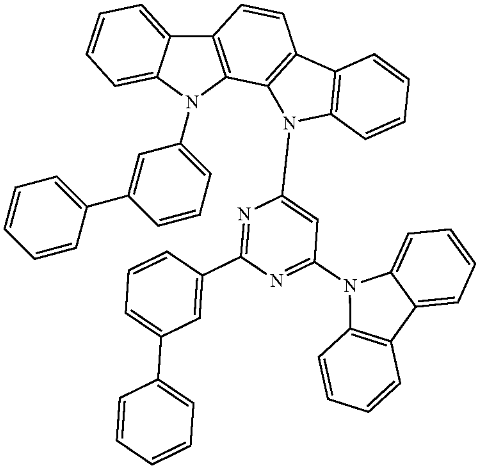
5-30
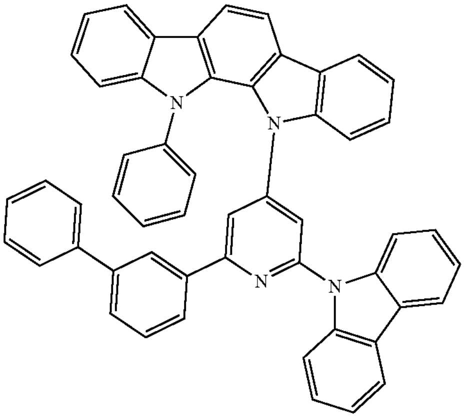

-continued
5-31
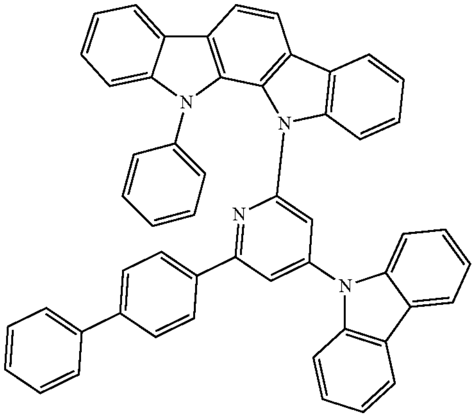
5-32
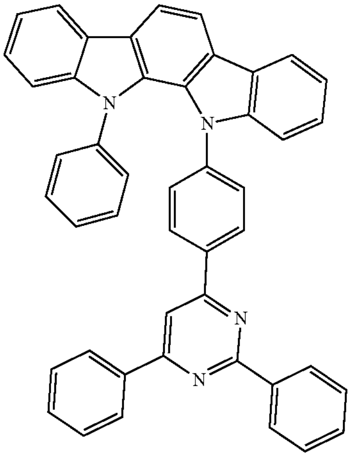
[C 59]
5-33
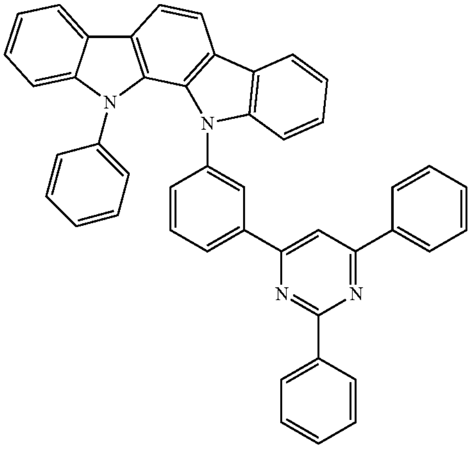
-continued
5-34
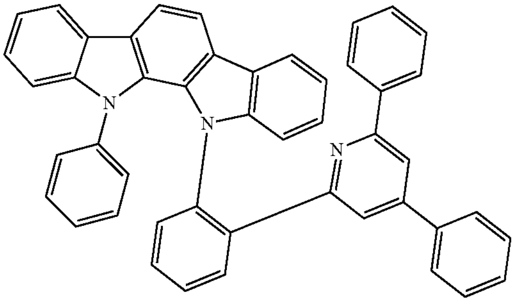
5-35
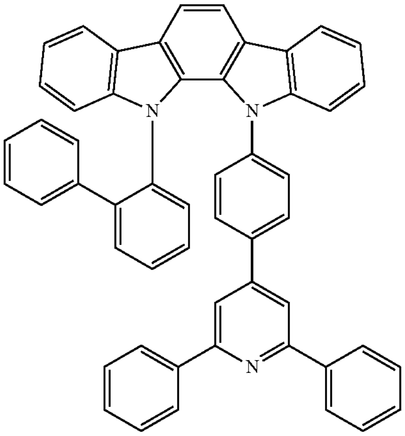
5-36
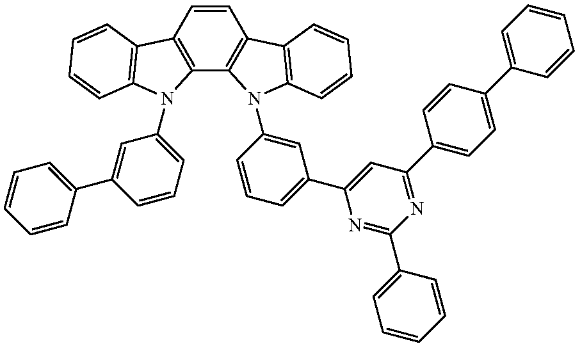
5-37
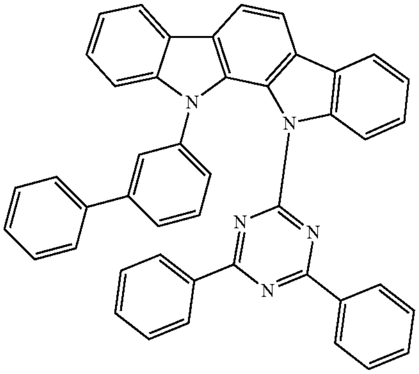

-continued
5-38
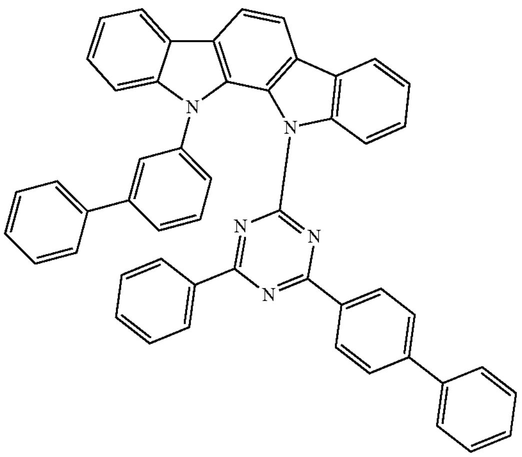
5-39
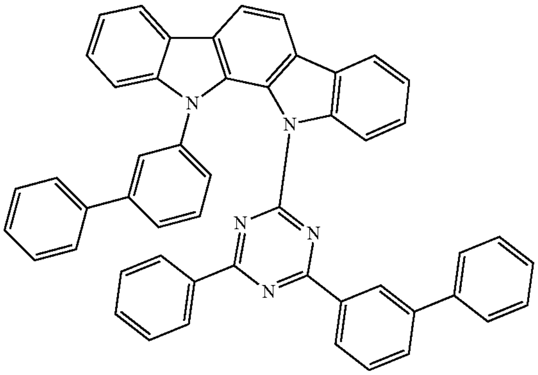
5-40
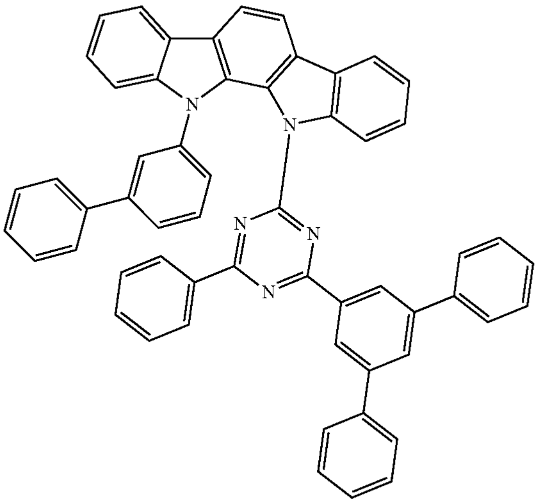
-continued
[C 60]
5-41
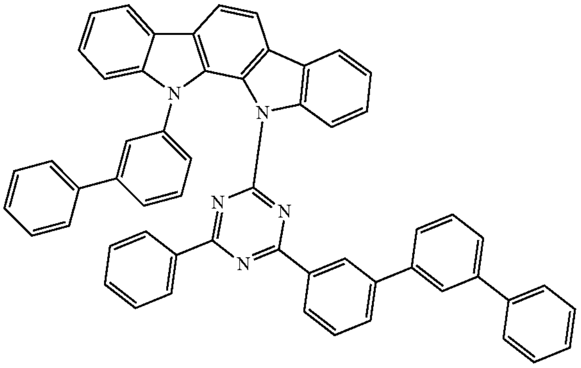
5-42
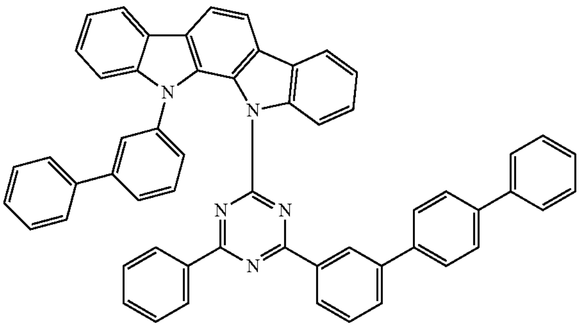
5-43
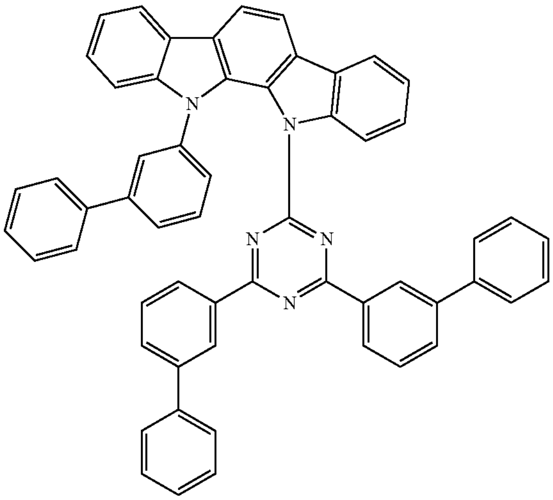

-continued
5-44
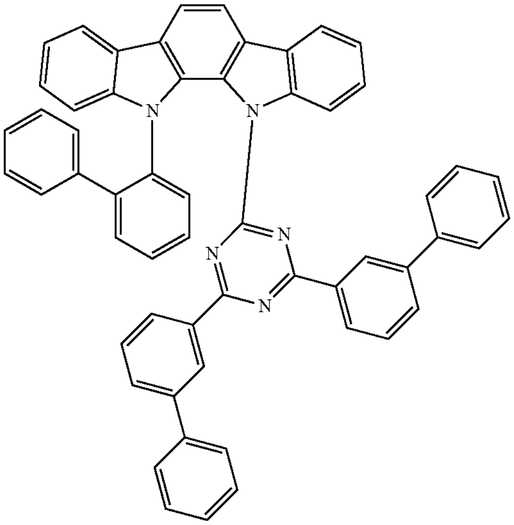
5-45
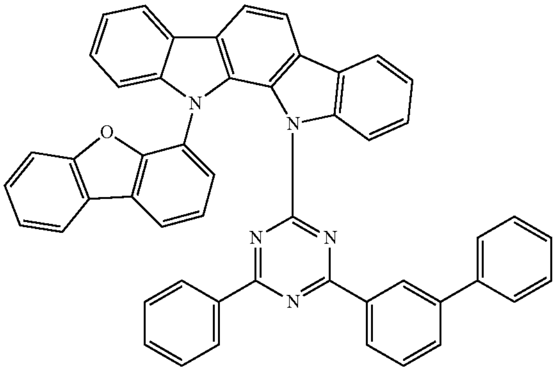
5-46
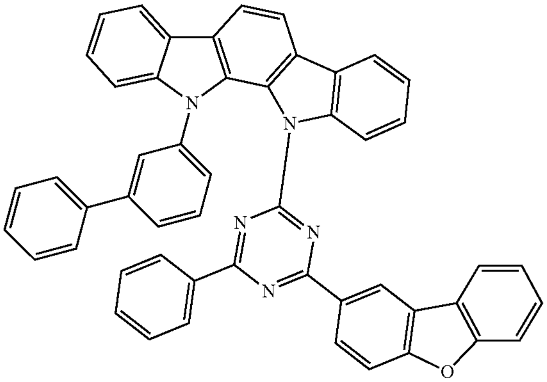
-continued
[C 61]
5-47
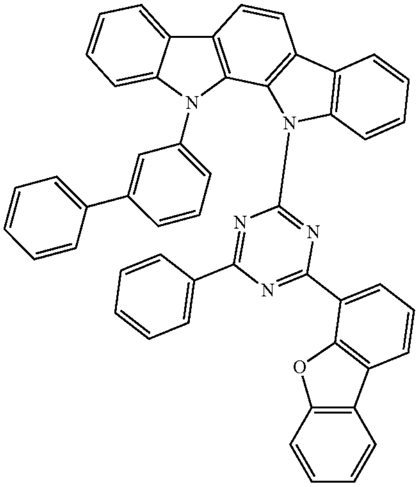
5-48
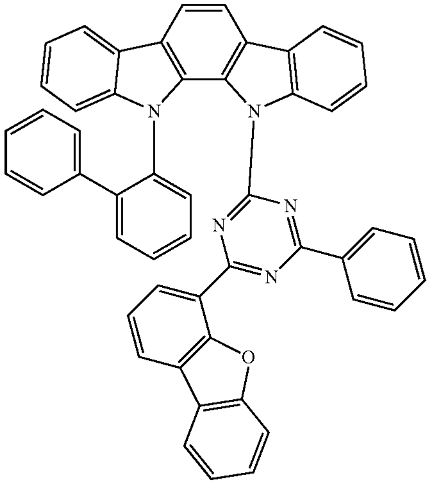
5-49
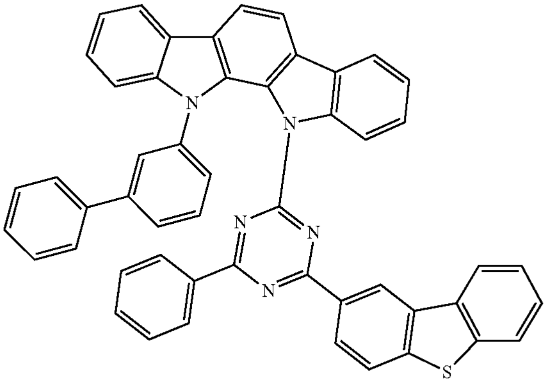

-continued
5-50
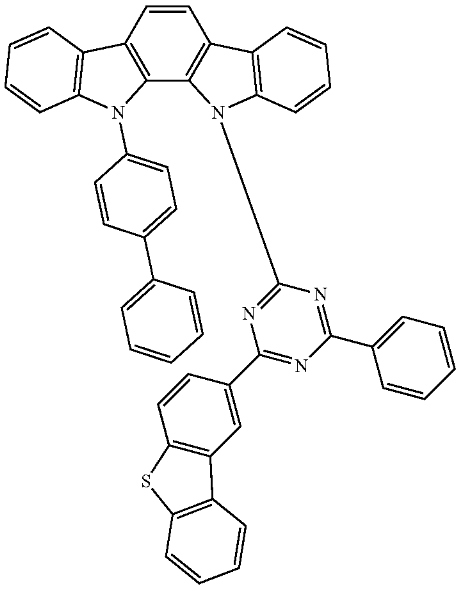
5-51
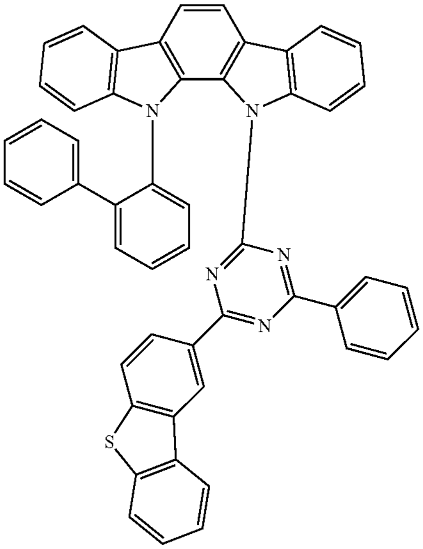
5-52
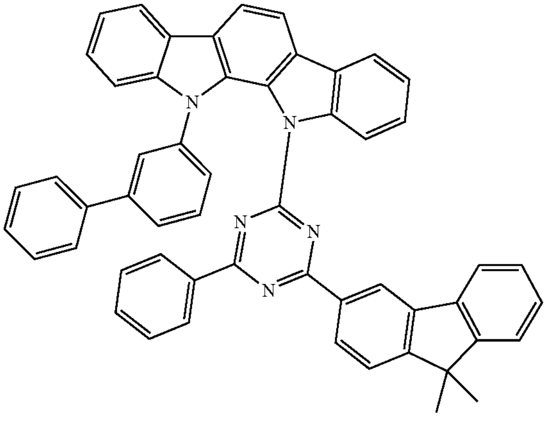
-continued
5-53
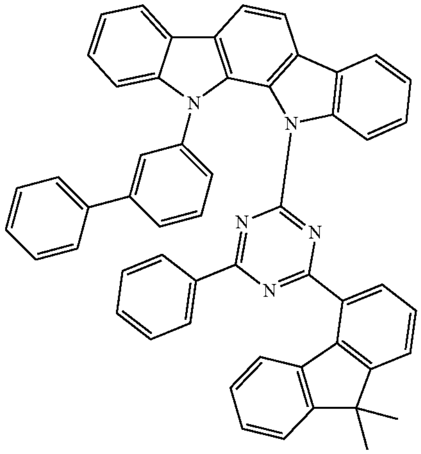
[C 62]
5-54
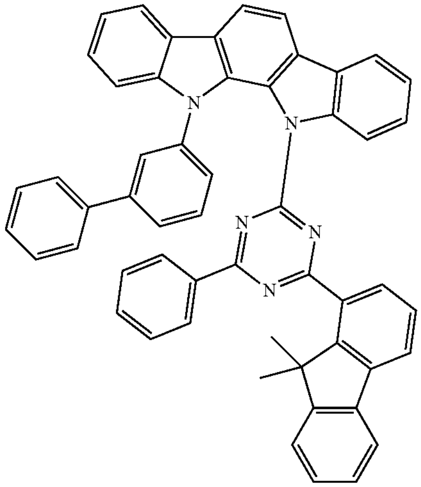
5-55
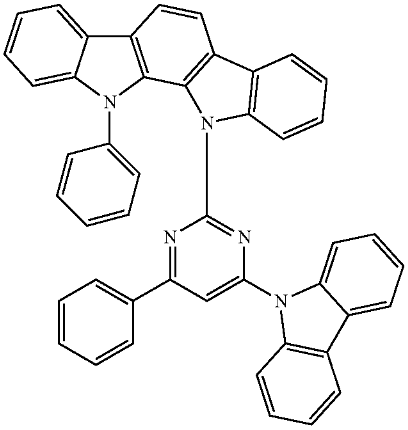

-continued
5-56
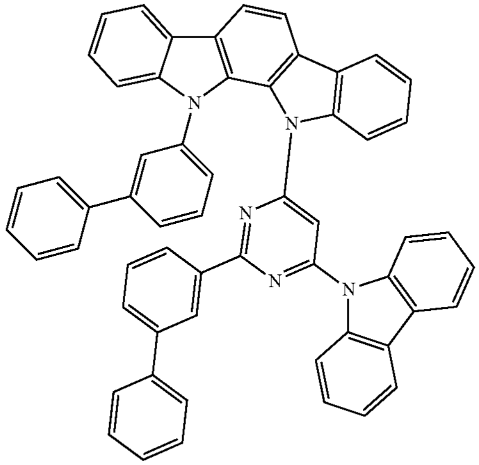
5-57
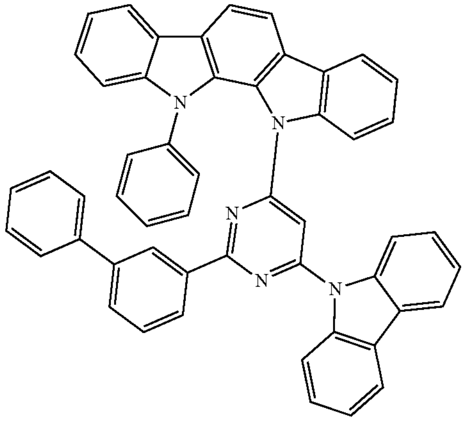
5-58
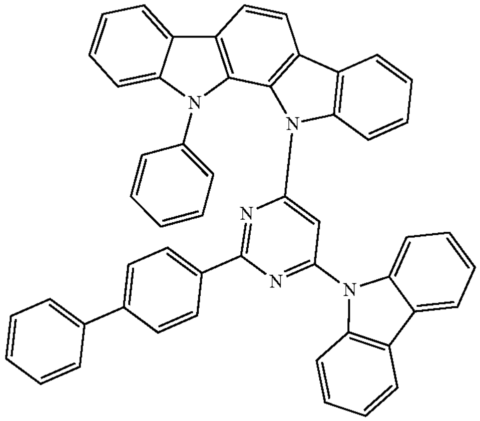
-continued
5-59
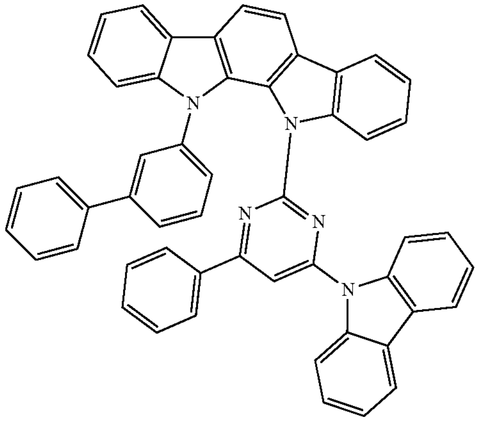
5-60
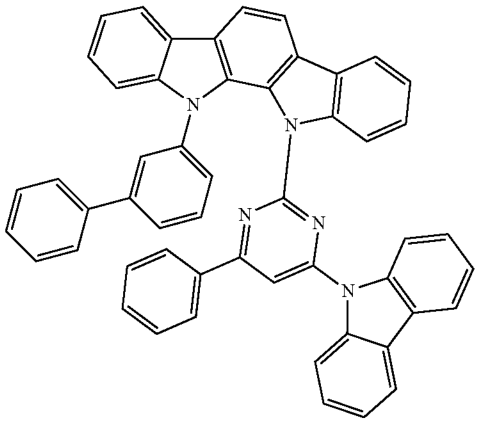
5-61
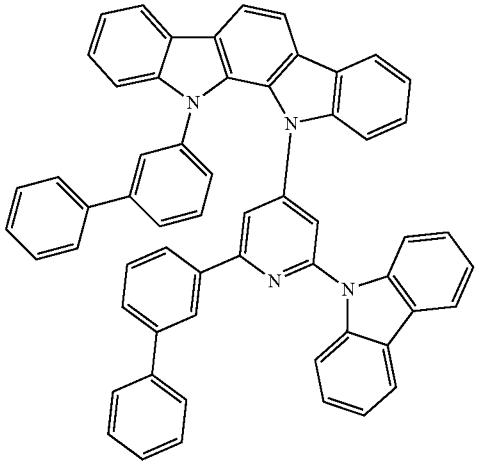

-continued
[C 63]
5-62
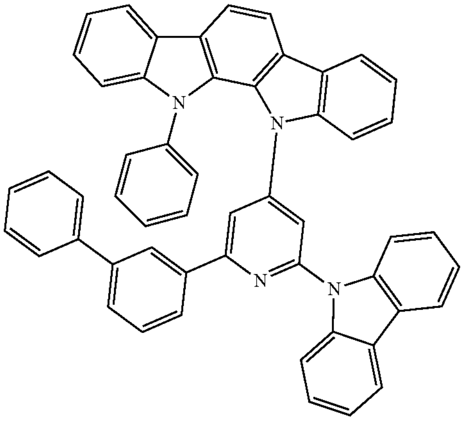
5-63
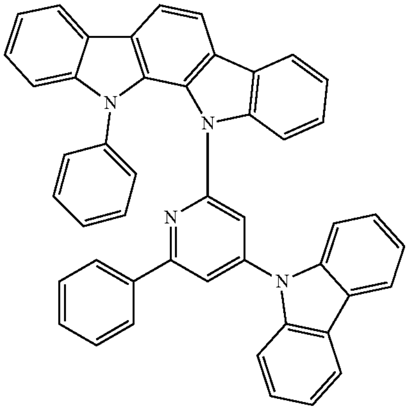
5-64
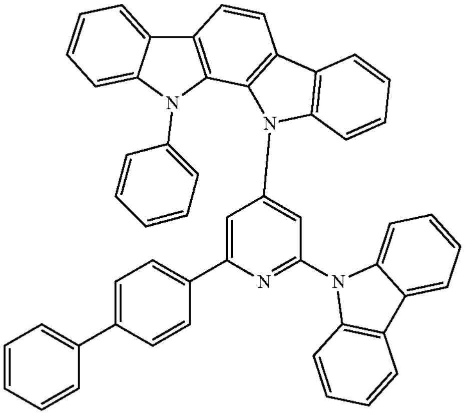
5-65
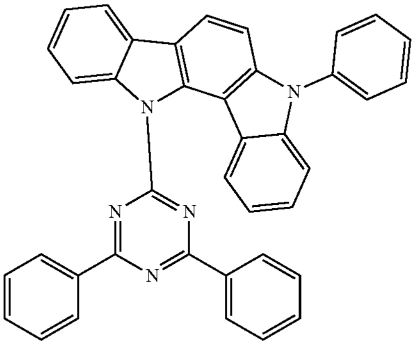
-continued
5-66
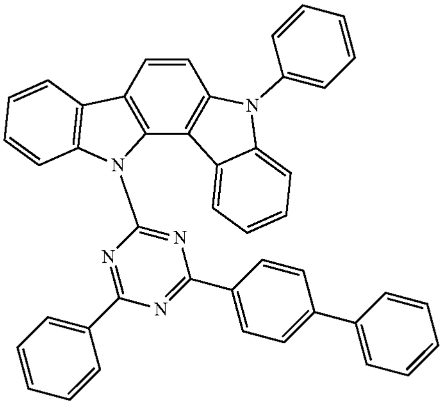
5-67
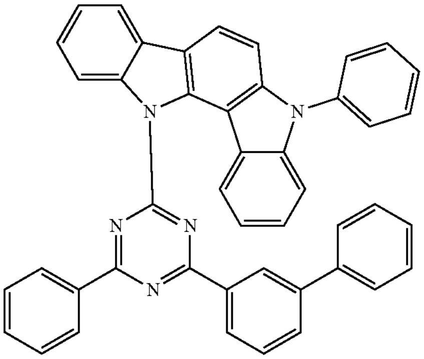
5-68
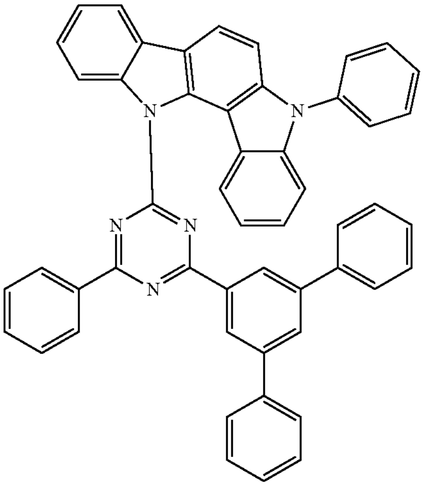

-continued
5-69
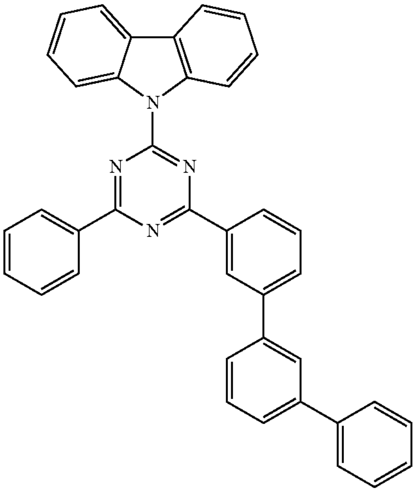
[C 64]
5-70
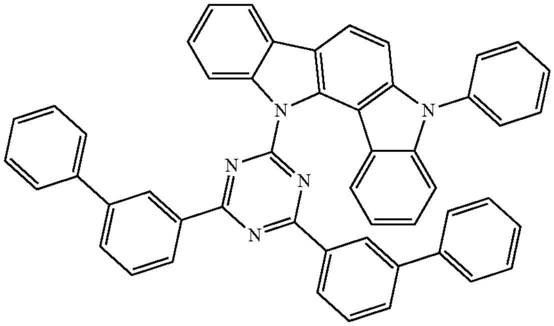
5-71
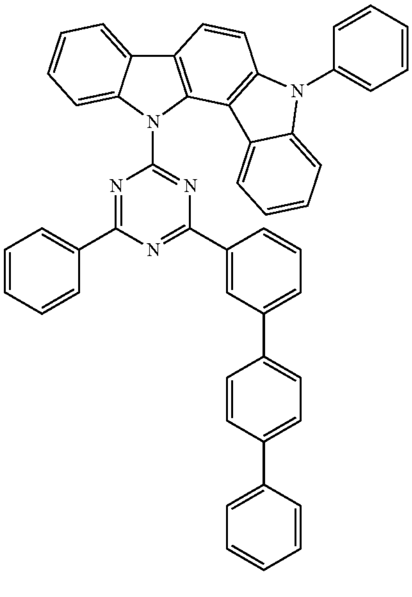
-continued
5-72
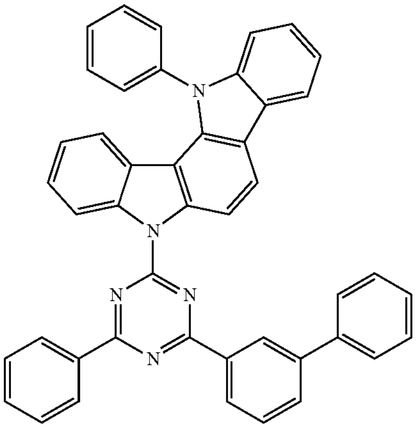
5-72b
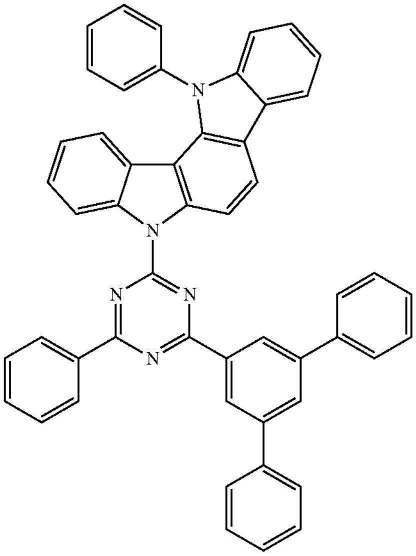
5-73
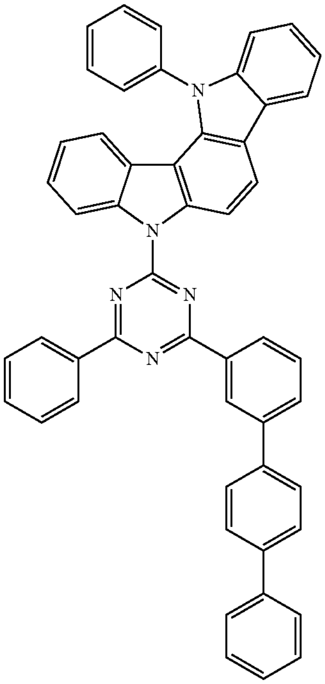

-continued
5-74
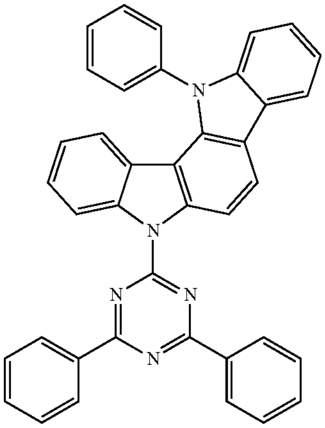
5-75
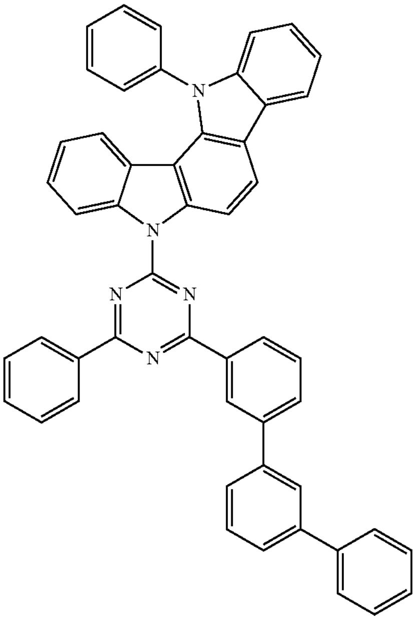
5-76
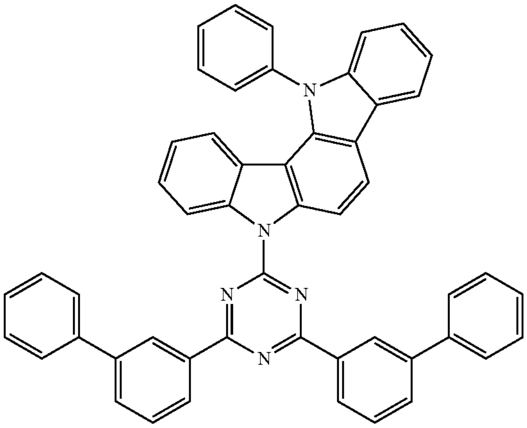
-continued
5-77
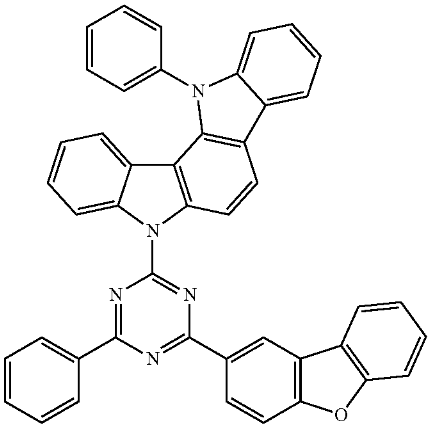
5-78
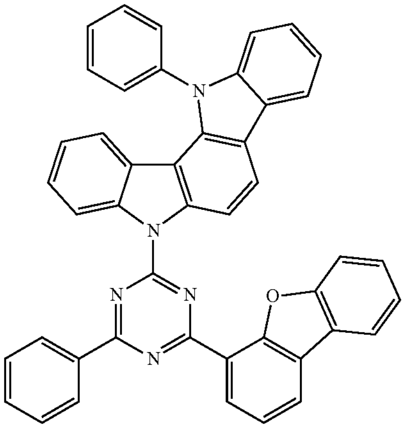
5-79
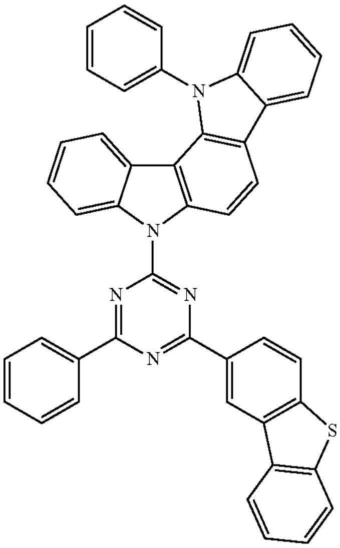

-continued
5-80
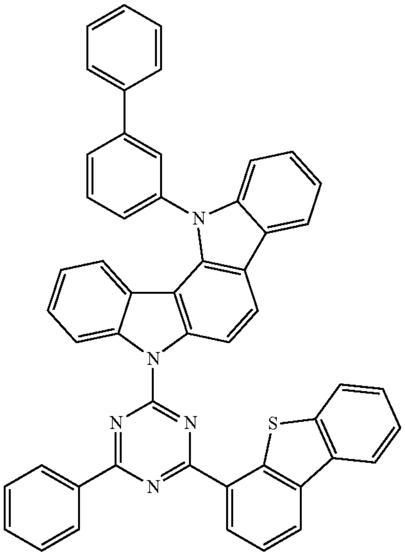
[C 66]
5-81
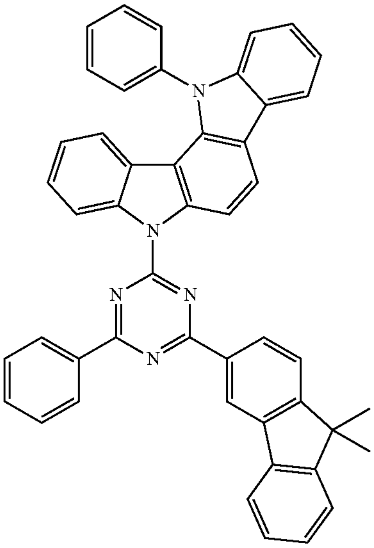
5-82
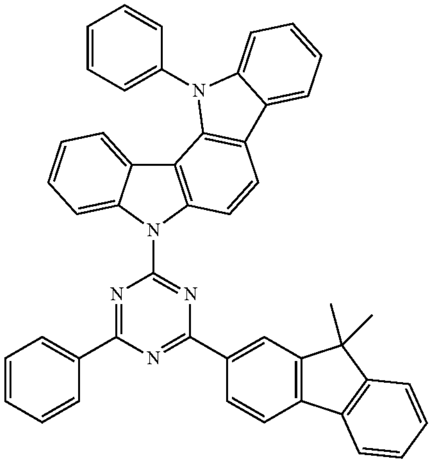
-continued
5-83
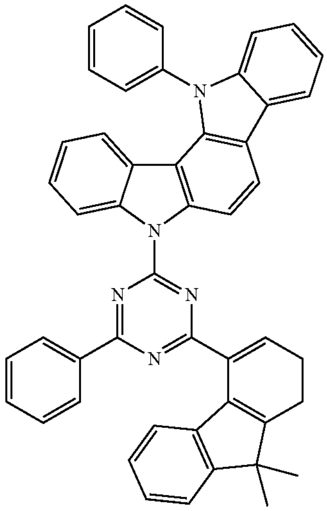
5-84
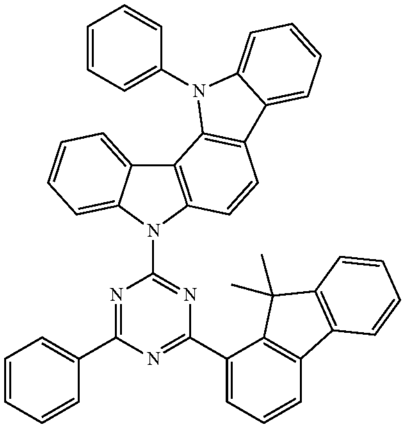
5-85
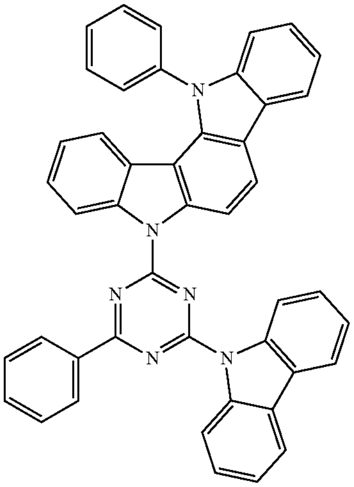

-continued
5-86
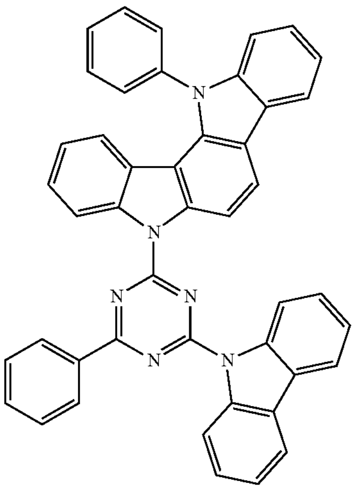
5-87
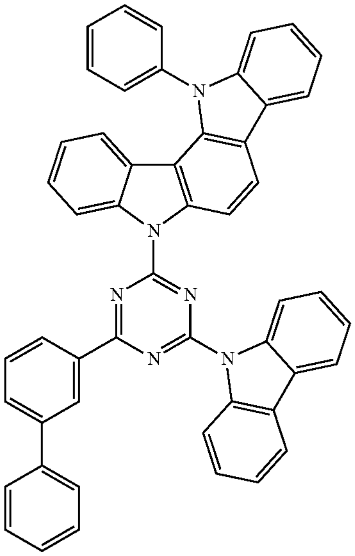
5-88
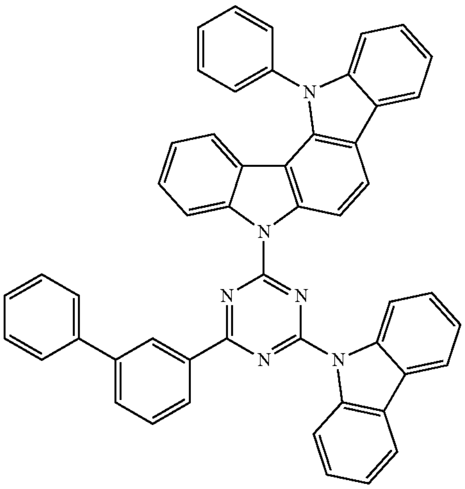
-continued
5-89
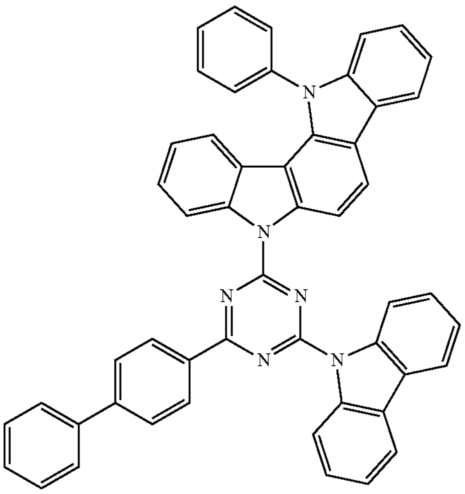
5-90
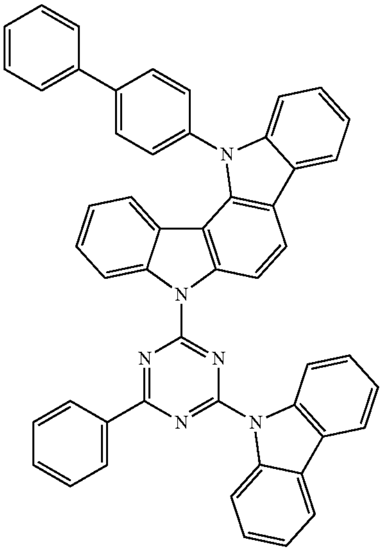
5-91
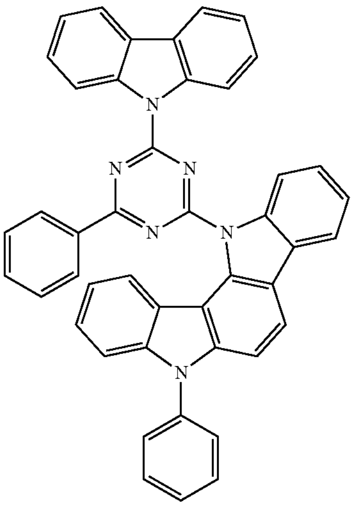

-continued
5-92
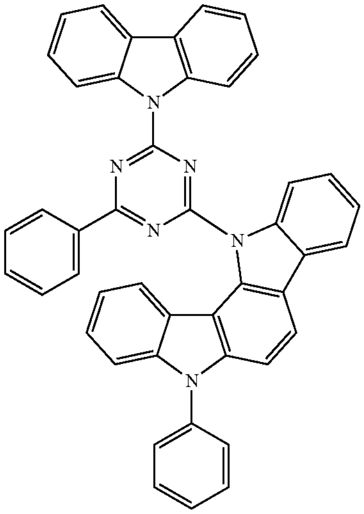
5-93
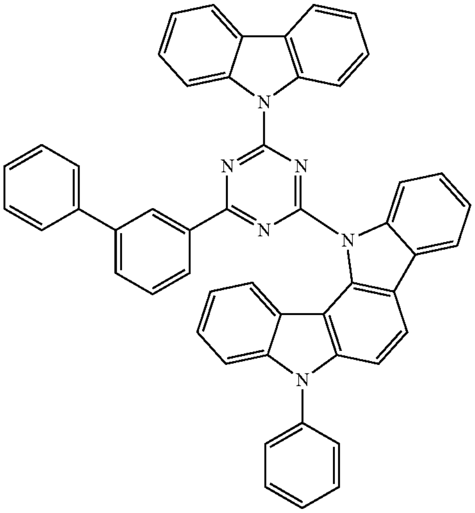
5-94
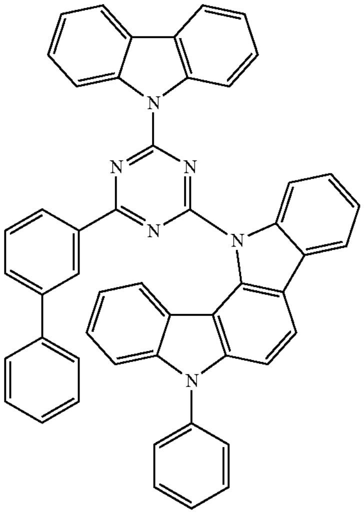
-continued
[C 67]
5-95
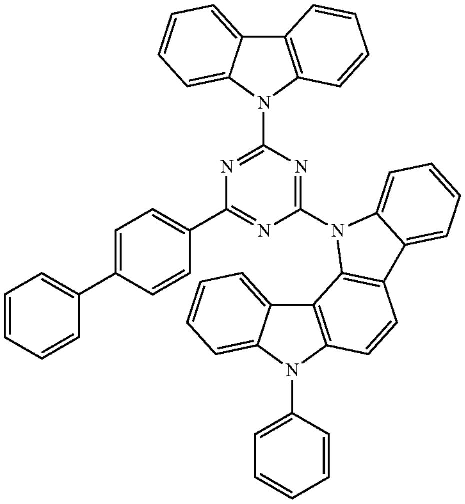
5-96
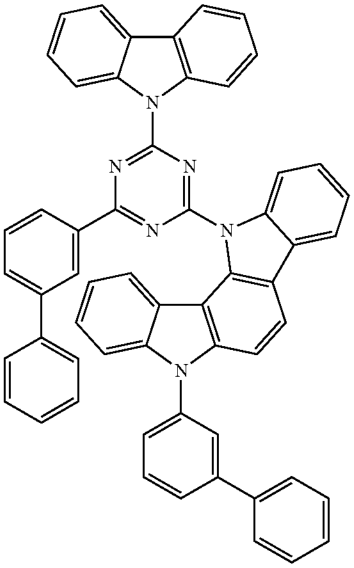
5-97
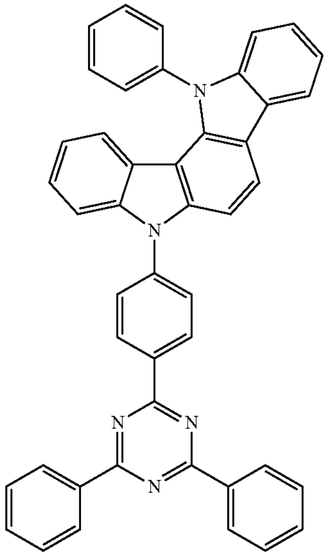

-continued
5-98
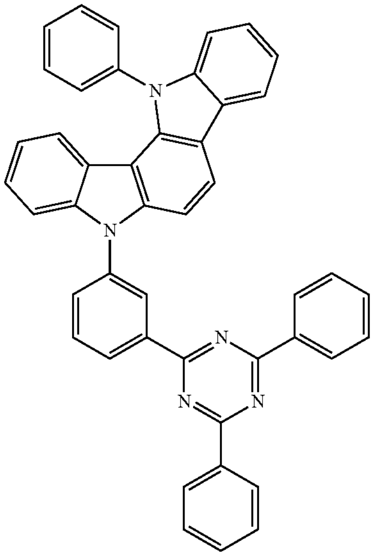
5-99
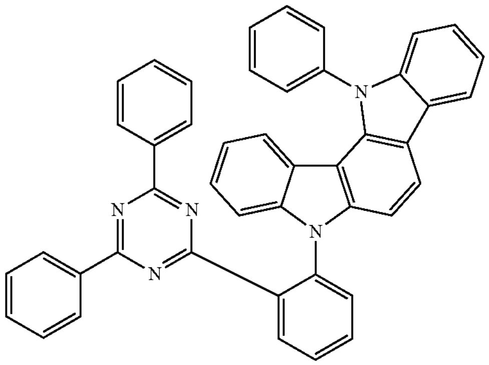
5-100
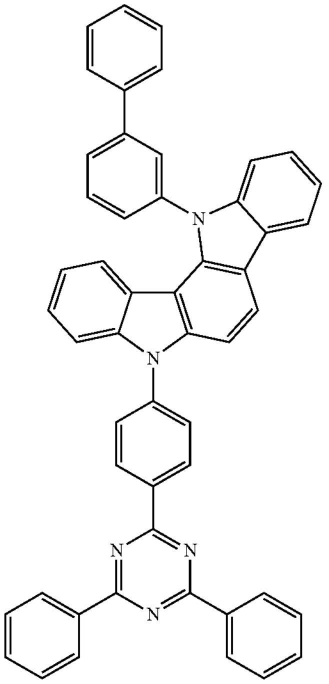
-continued
5-101
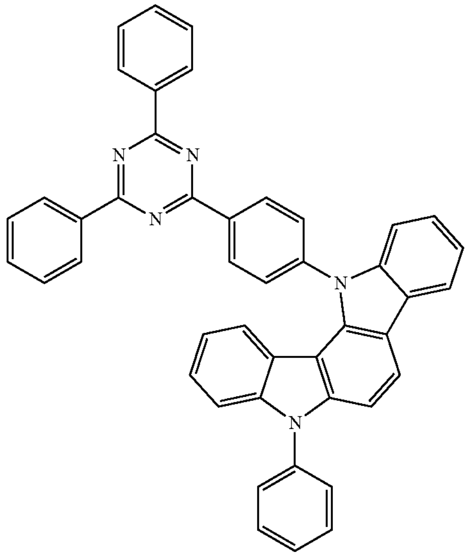
[C 68]
5-102
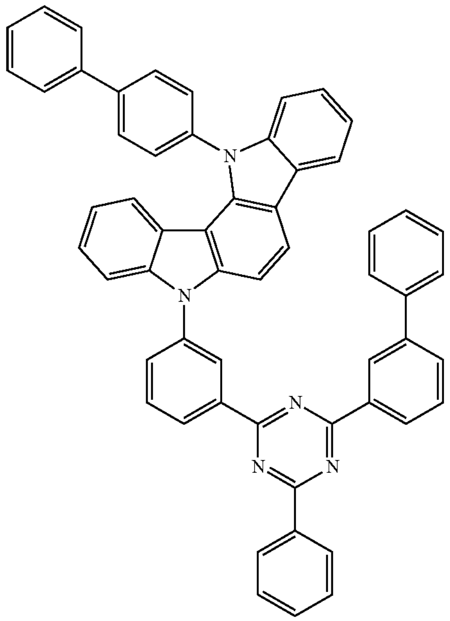

-continued
5-103
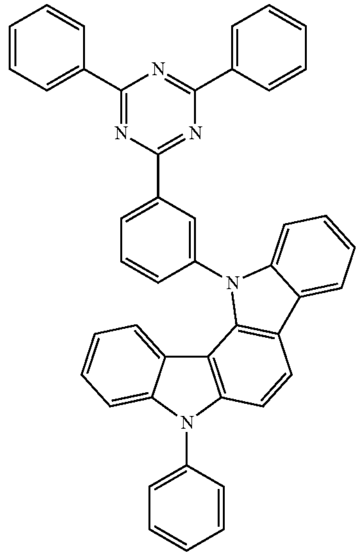
5-104
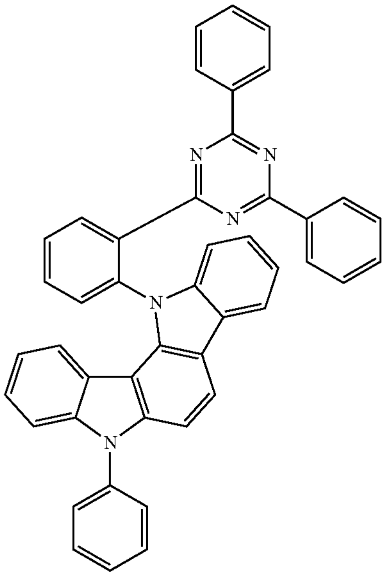
-continued
5-105
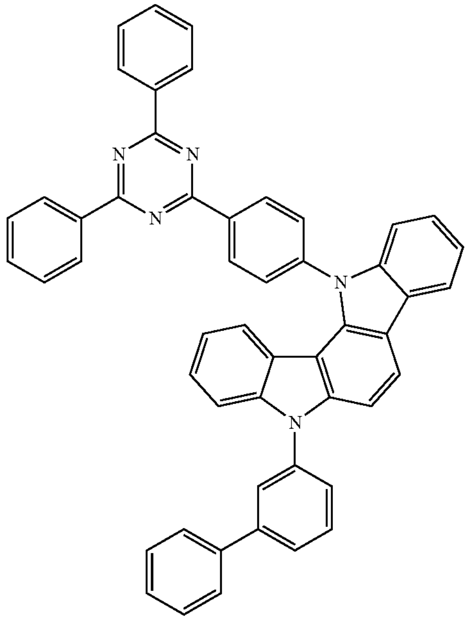
5-106
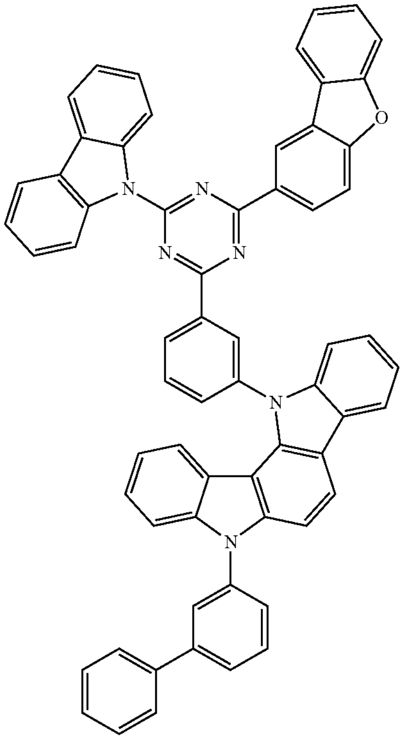

-continued
5-107
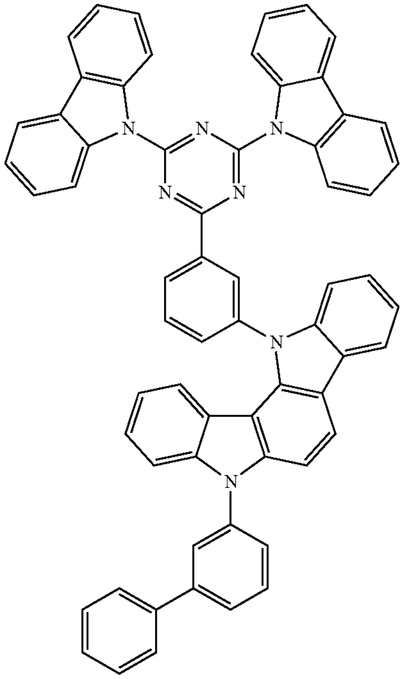
5-108
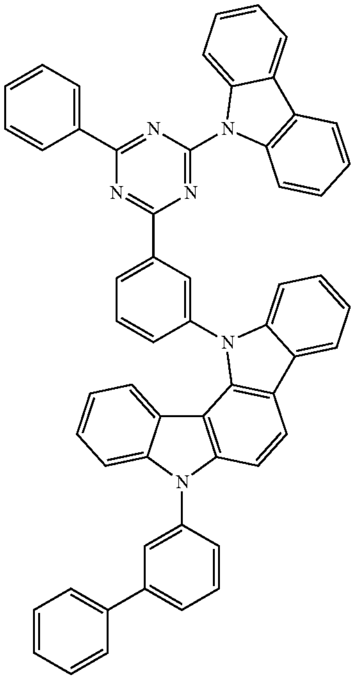
-continued
[C 69]
5-109
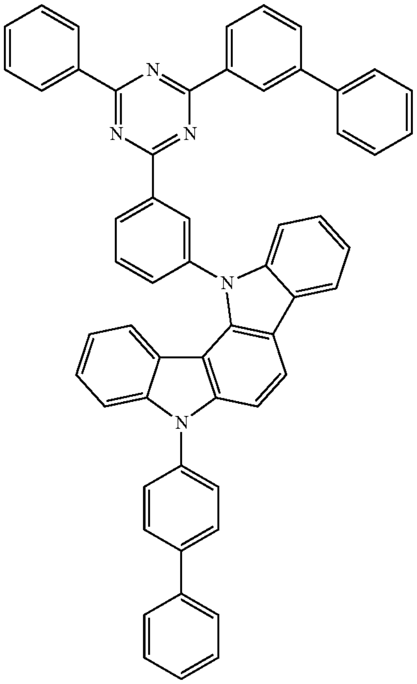
5-110
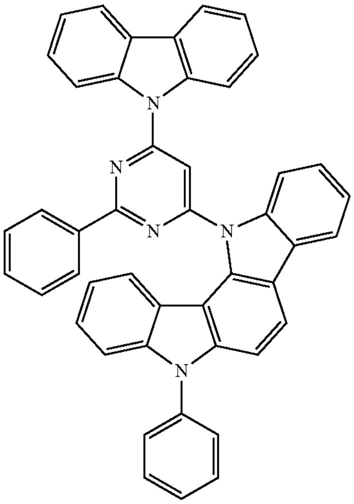

-continued
5-111
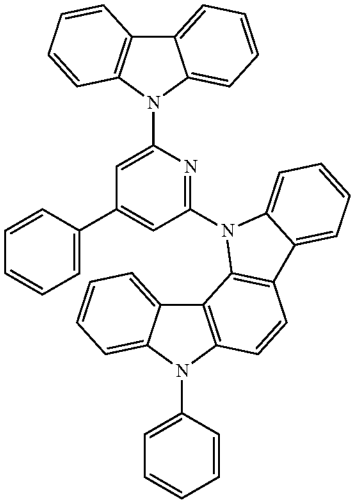
5-112
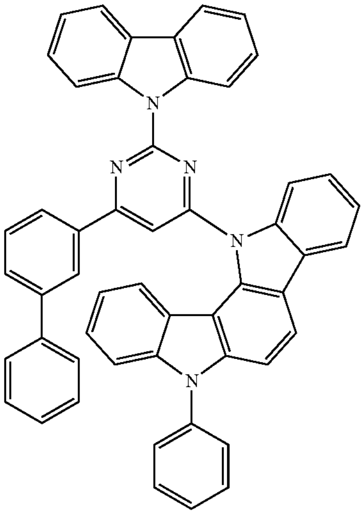
5-113
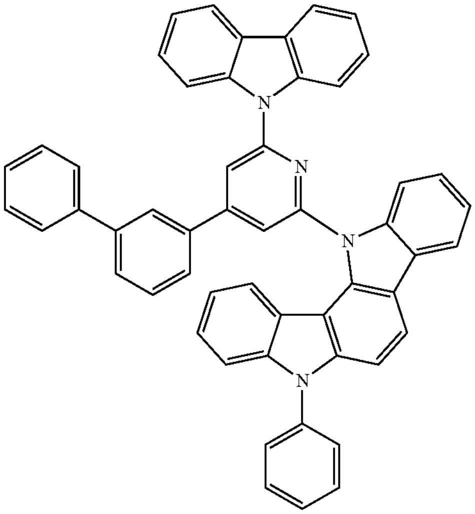
-continued
5-114
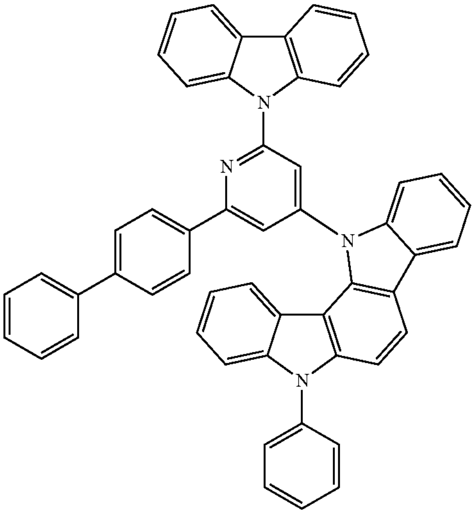
5-115
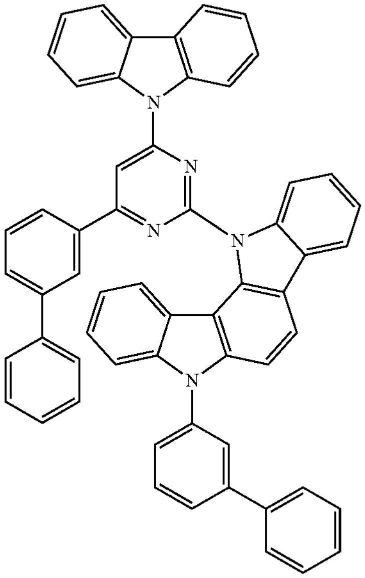

[C 70]
5-116
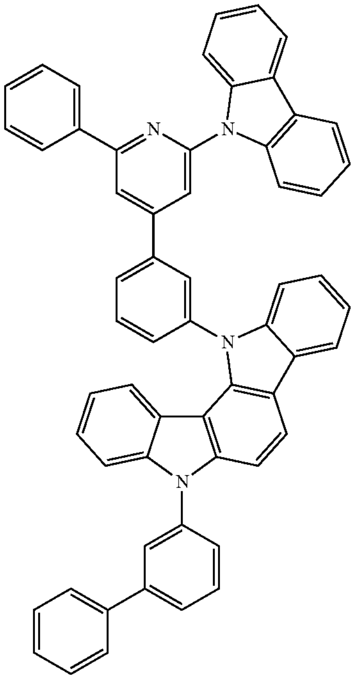
5-117
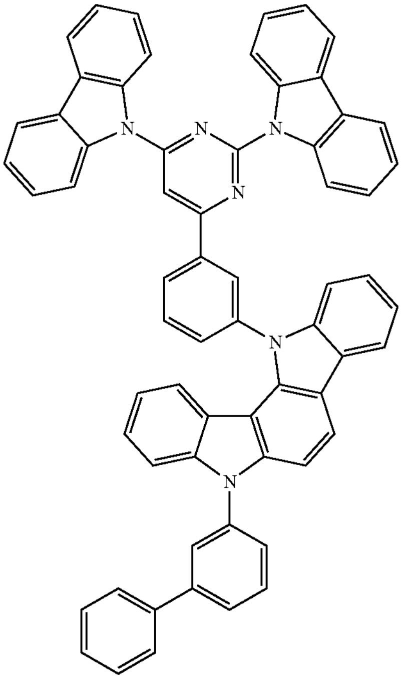
5-118
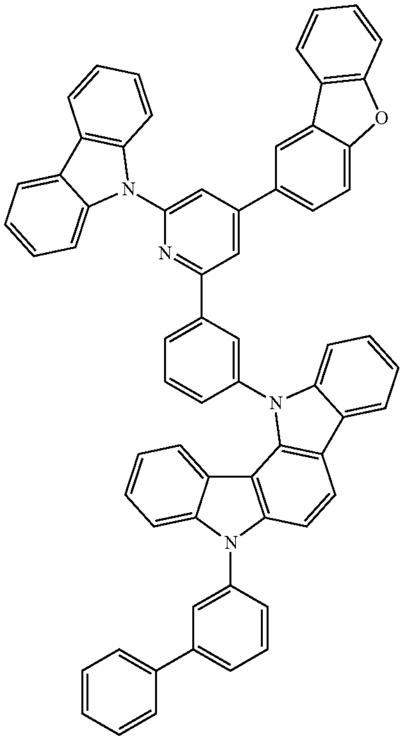
5-119
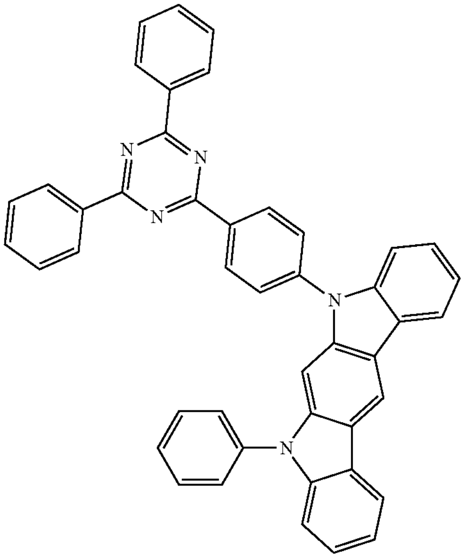

-continued
5-120
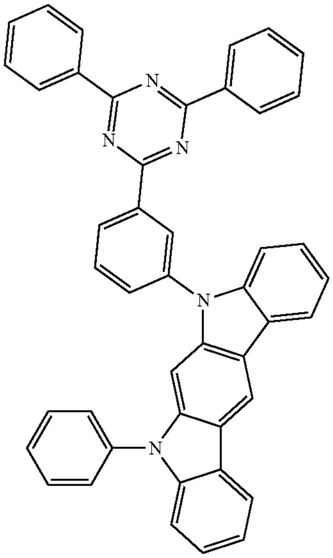
5-121
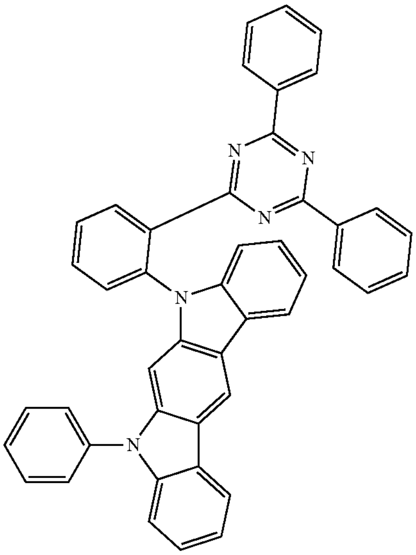
-continued
5-122
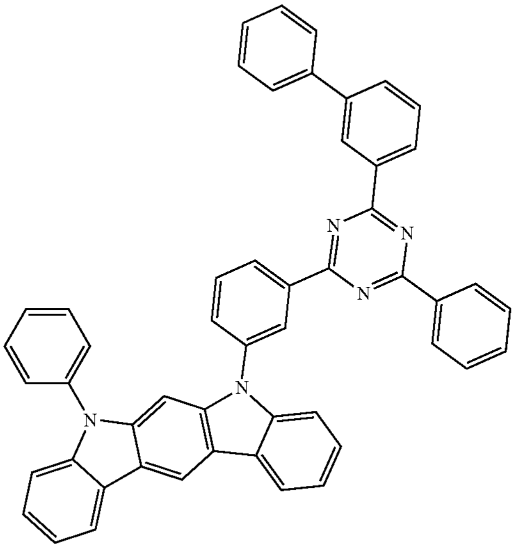
[C 71]
5-123
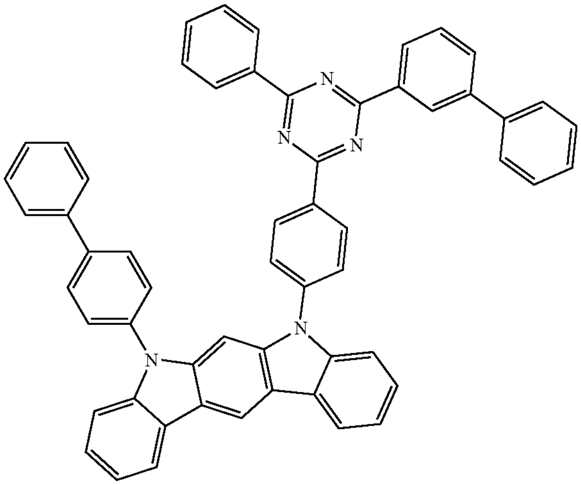

-continued
5-124
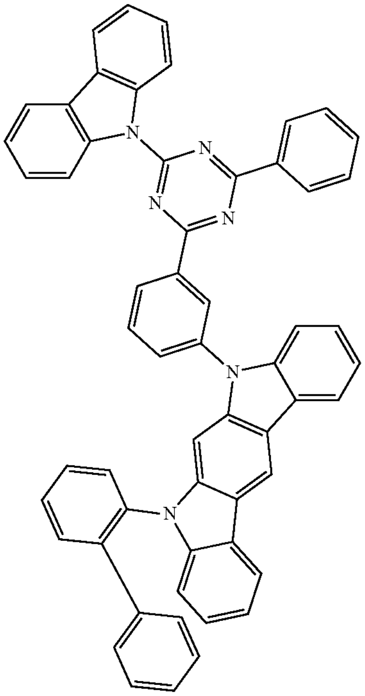
5-125
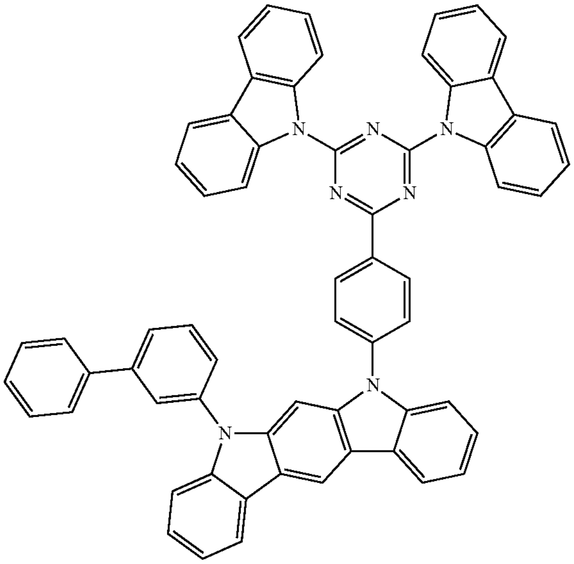
-continued
5-126
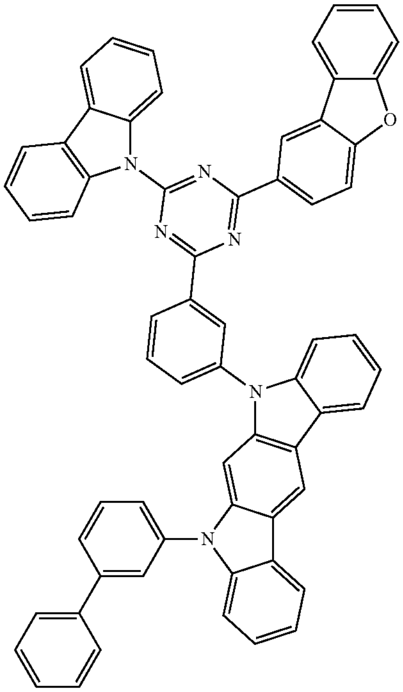
5-127
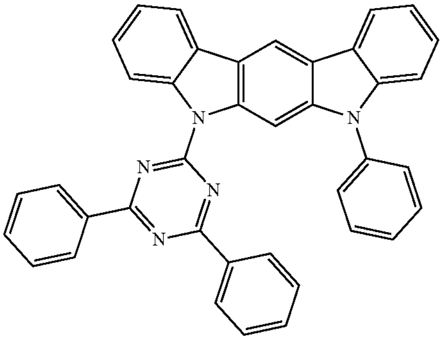
5-128
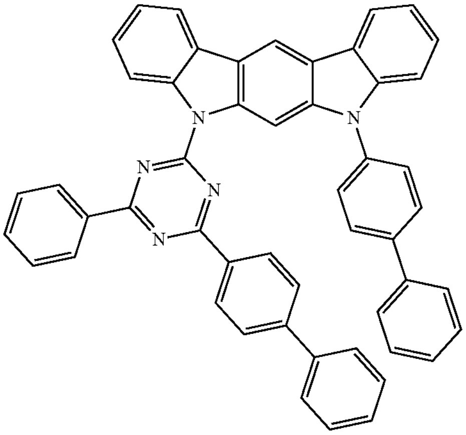

[C 72]
5-129
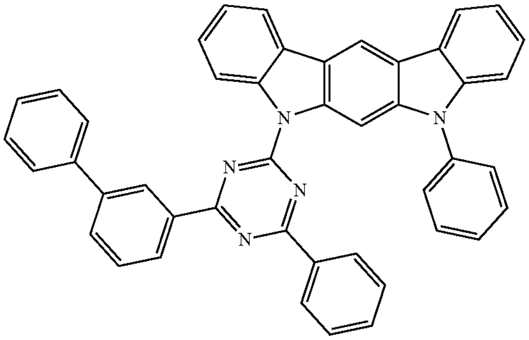
5-130
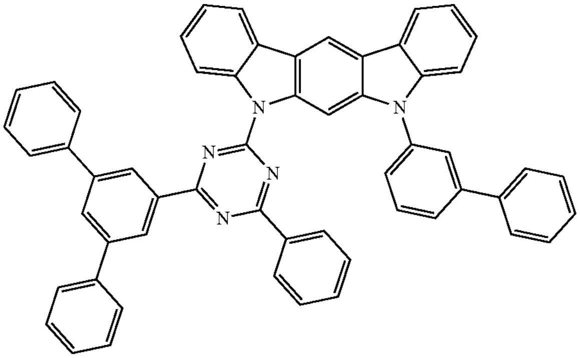
5-131
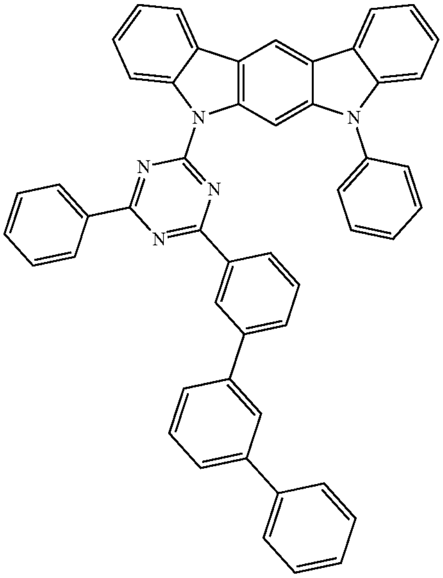
5-132
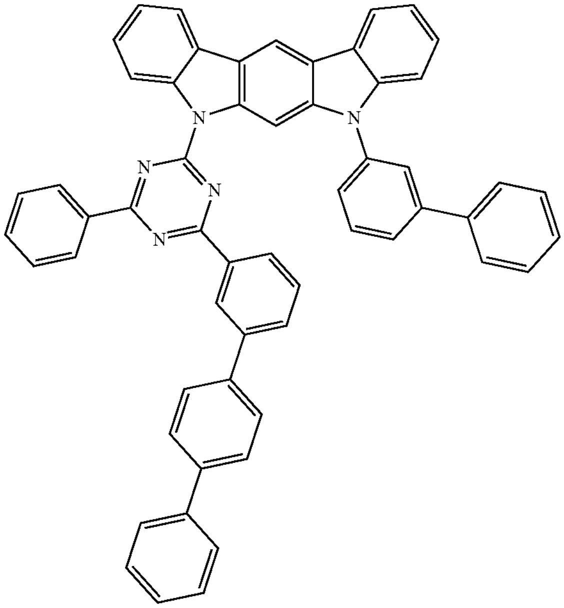
5-133
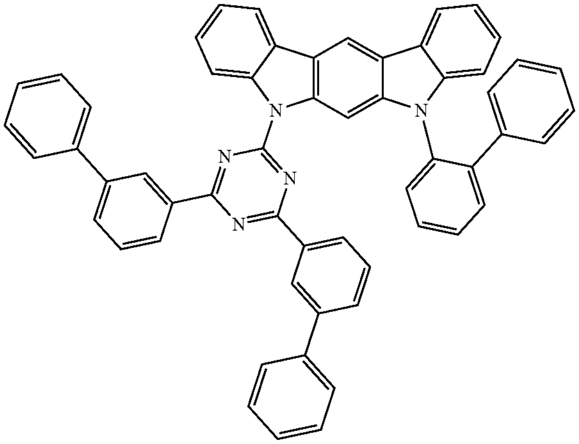
5-134
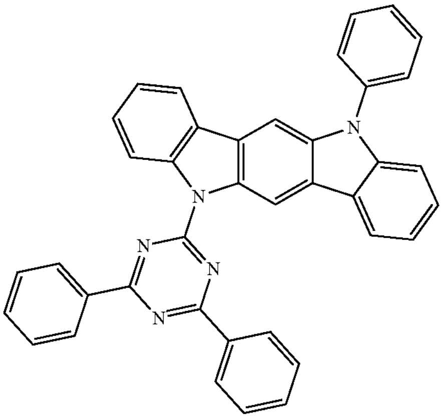

-continued
5-135
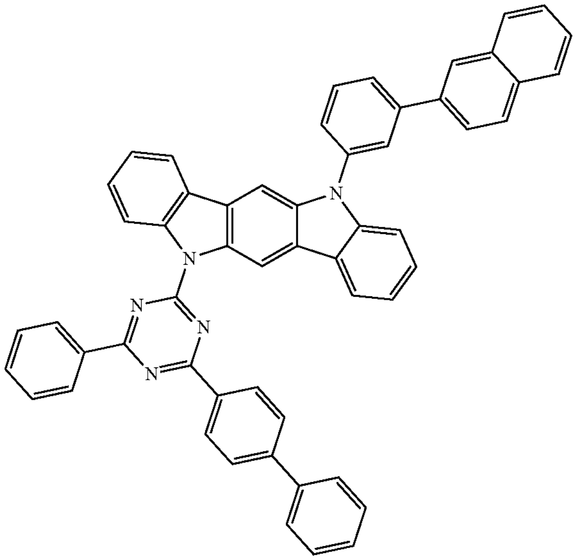
5-136
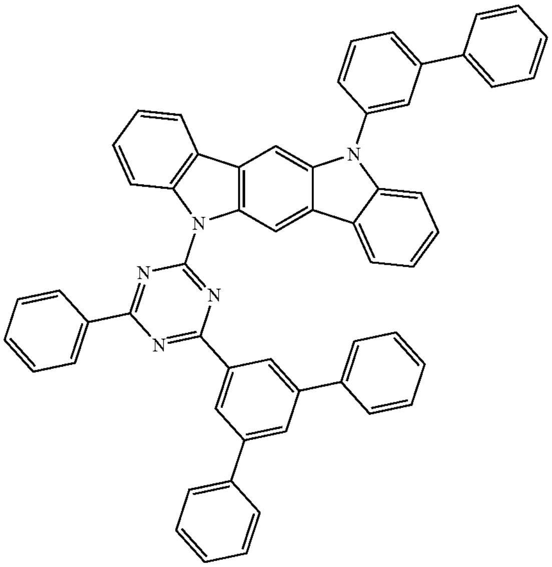
[C 73]
5-137
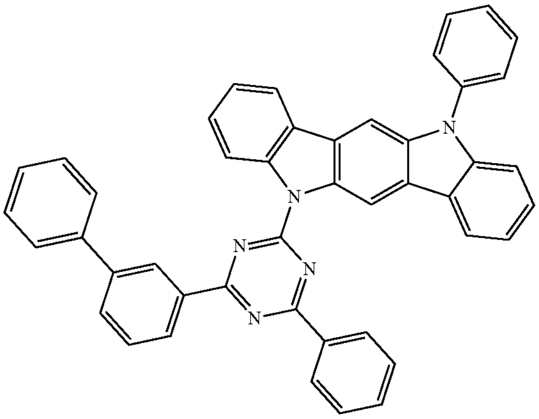
-continued
5-138
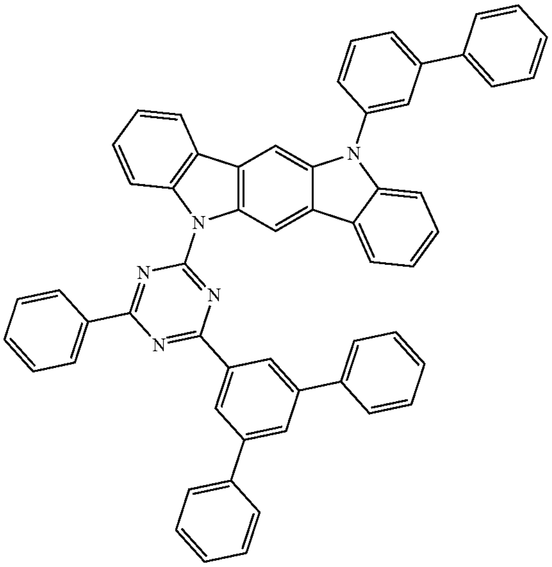
5-139
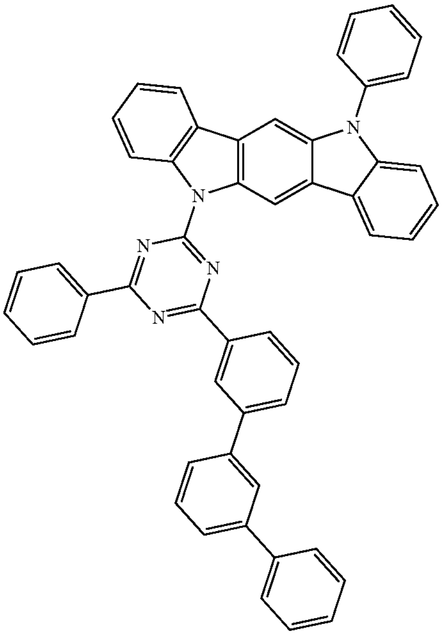

-continued
5-140
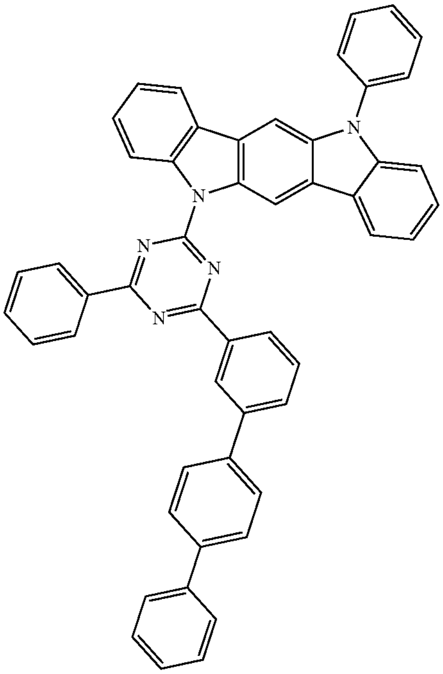
5-141
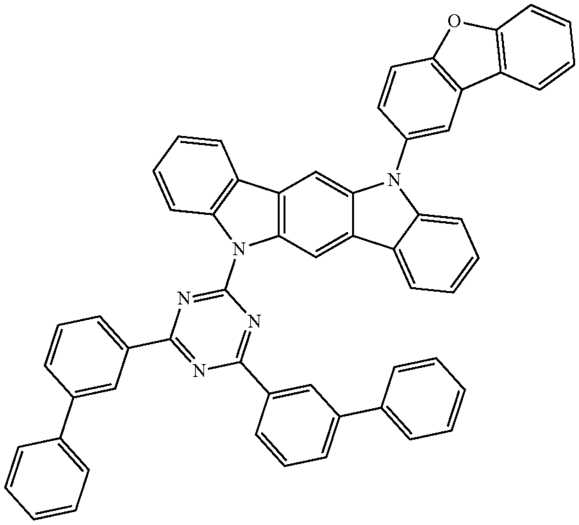
-continued
5-142
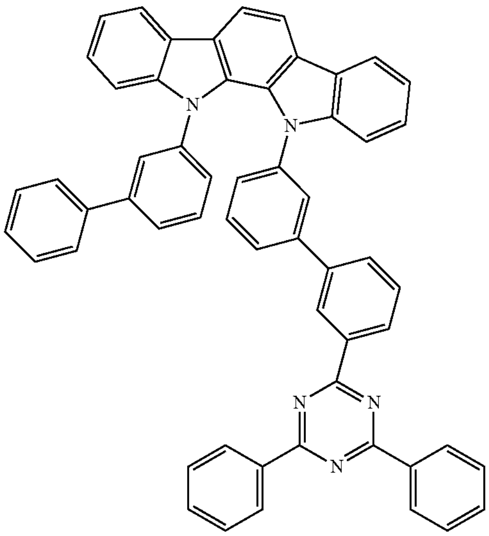
5-143
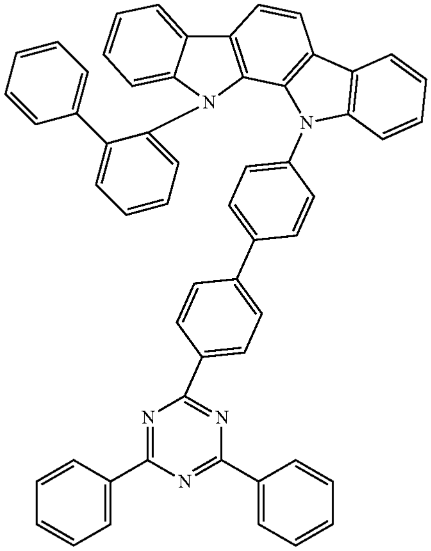
5-144
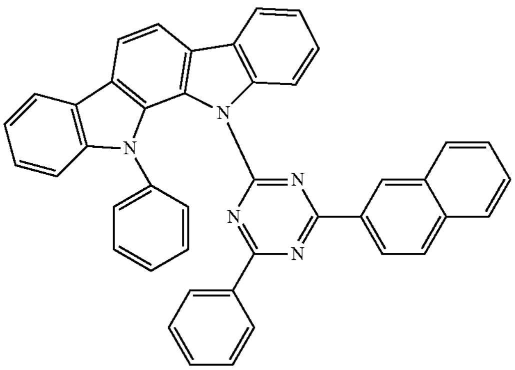

-continued
[C 74]
5-145
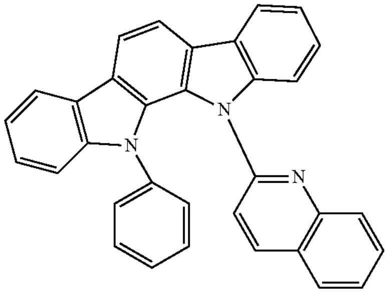
5-146
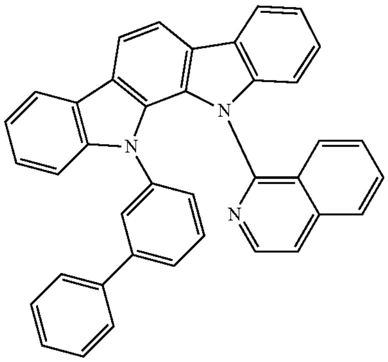
5-147
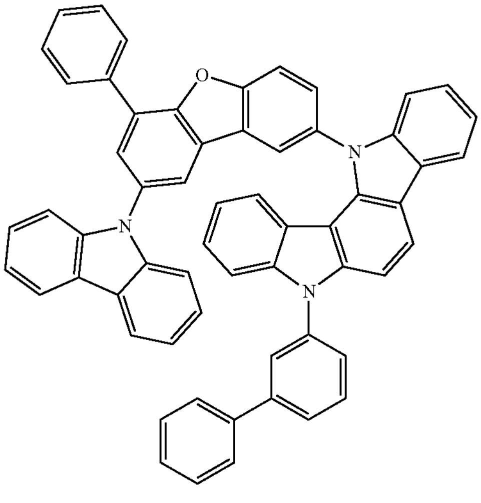
-continued
5-148
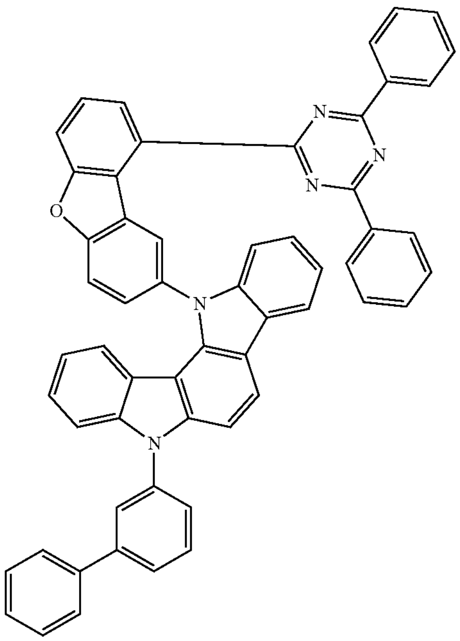
5-149
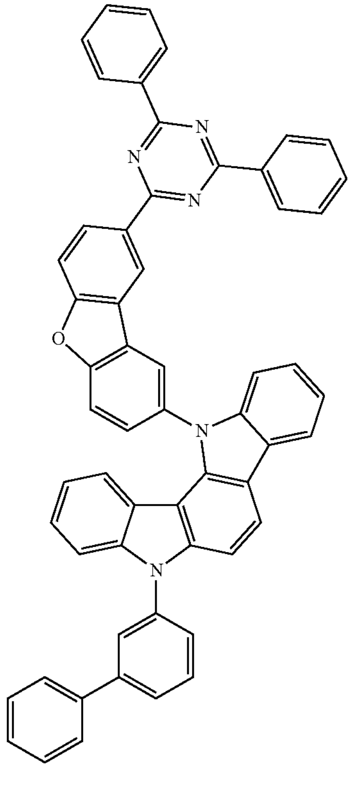

-continued 5-150

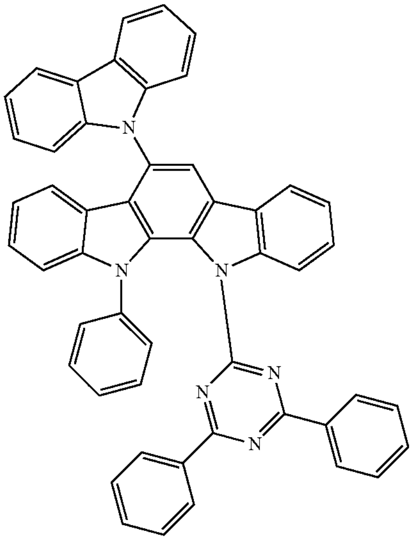

5-151

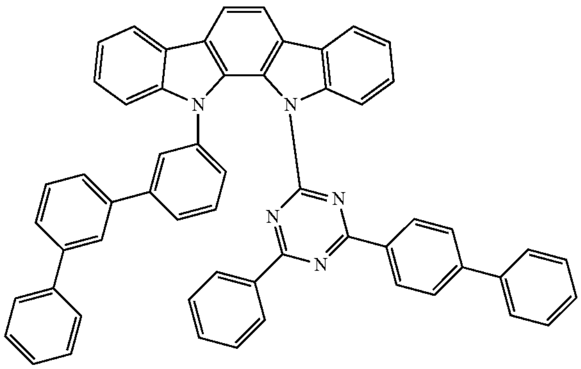

5-152

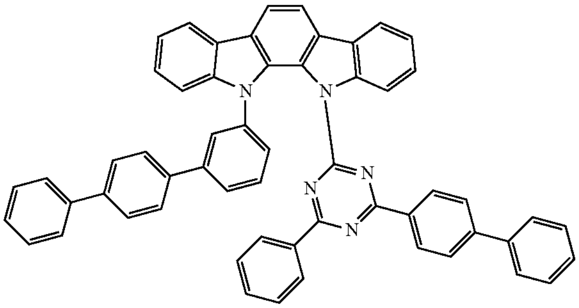

A method for producing an organic electroluminescent device of the present invention is a method for forming a light-emitting layer by vapor deposition of a host material composition including the first host material, the second host material and the third host material, and a light-emitting dopant material.

A host material composition of the present invention is a host material composition for use in the method for producing an organic electroluminescent device. The host material composition may include the first host material, the second host material and the third host material, and may include other material such as a dopant material, as necessary.

The first host material, the second host material, the third host material and the light-emitting dopant material which are, for example, vapor deposited from different individual vapor deposition sources can be used; however, it is preferable to premix them as a host material composition (also referred to as "premixture".) before vapor deposition and to vapor deposit the premixture simultaneously from one vapor deposition source to thereby form a light-emitting layer. In this case, it is preferred to premix the host material, or the light-emitting dopant material and the host material may be mixed, and when there is a large difference in temperatures to provide desired vapor pressure, vapor deposition may be performed from another vapor deposition source.

The premixing method is desirably a method that can allow for mixing as uniformly as possible, and examples thereof include pulverization and mixing, a heating and melting method under reduced pressure or under an atmosphere of an inert gas such as nitrogen, and sublimation, but not limited thereto.

The first host material has a LUMO energy of −1.95 eV or less, and is a host material having the lowest LUMO energy among the first, second and third host materials. The third host material has a LUMO energy of −1.94 to −1.77 eV, and is a material having the next lowest LUMO energy to the first host material. The second host material has a LUMO energy of −1.54 eV or more, and is a host material having the highest LUMO energy among the first, second and third host materials.

In addition, regarding the mixing ratio (weight ratio) among the first host material, the second host material and the third host material, the proportion of the first host material is larger than 1.0 wt % and less than 30 wt % and the proportion of the third host material is larger than 5.0 wt % and less than 80 wt % based on the first host material, the second host material and the third host material in total. It is preferred that the proportion of the first host material is 2 to 20 wt % and the proportion of the third host material is 10 to 70 wt %, and it is more preferred that the proportion of the first host material is 5 to 20 wt % and the proportion of the third host material is 10 to 60 wt %. The proportion of the second host material is a value obtained by subtracting the proportions of the first host material and the third host material from 100 wt %, and is preferably 19 to 80 wt %.

Each of the triplet excitation (T1) energies of the first host material, the second host material and the third host material is preferably 2.55 eV or more.

The LUMO energies and the T1 energies can be obtained by quantum chemical calculation. The LUMO energy prescribed herein is a value calculated by performing structure optimization calculation at the B3LYP/6-31G* level with molecular orbital method program Gaussian 03 according to the density functional theory (DFT).

Next, the structure of the organic electroluminescent device of the present invention will be described by referring to the drawing, but the structure of the organic electroluminescent device of the present invention is not limited thereto.

The FIGURE is a cross-sectional view showing a structure example of an organic electroluminescent device generally used for the present invention, in which there are indicated a substrate 1, an anode 2, a hole injection layer 3, a hole transport layer 4, a light-emitting layer 5, an electron transport layer 6, and a cathode 7. The organic electroluminescent device of the present invention may have an exciton blocking layer adjacent to the light-emitting layer and may have an electron blocking layer between the light-emitting layer and the hole injection layer. The exciton blocking layer can be inserted into either of the anode side and the cathode side of the light-emitting layer and inserted into both sides at the same time. The organic electroluminescent device of the present invention has the anode, the light-emitting layer, and the cathode as essential layers, and preferably has a hole injection transport layer and an electron injection transport layer in addition to the essential layers, and further preferably has a hole blocking layer between the light-emitting layer and the electron injection transport layer. Note that the hole injection transport layer refers to either or both of a hole injection layer and a hole transport layer, and the electron injection transport layer refers to either or both of an electron injection layer and an electron transport layer.

A structure reverse to that of The FIGURE is applicable, in which a cathode 7, an electron transport layer 6, a light-emitting layer 5, a hole transport layer 4, and an anode 2 are stacked on a substrate 1 in this order. In this case, layers may be added or omitted as necessary.

——Substrate——

The organic electroluminescent device of the present invention is preferably supported on a substrate. The substrate is not particularly limited, and those conventionally used in organic electroluminescent devices may be used, and substrates made of, for example, glass, a transparent plastic, or quartz may be used.

——Anode——

Regarding an anode material for an organic electroluminescent device, it is preferable to use a material selected from a metal, an alloy, an electrically conductive compound or a mixture thereof having a large work function (4 eV or more).

Specific examples of such an electrode material include a metal such as Au, and a conductive transparent material such as CuI, indium tin oxide (ITO), $SnO_2$, and ZnO. In addition, an amorphous material such as IDIXO ($In_2O_3$—ZnO), which is capable of forming a transparent conductive film, may be used. Regarding the anode, such an electrode material is used to form a thin film by, for example, a vapor-deposition or sputtering method, and a desired shape pattern may be formed by a photolithographic method; or if the pattern accuracy is not particularly required (about 100 μm or more), a pattern may be formed via a desired shape mask when the electrode material is vapor deposited or sputtered. Alternatively, when a coatable substance such as an organic conductive compound is used, a wet film formation method such as a printing method or a coating method may be used. For taking emitted light from the anode, it is desired to have a transmittance of more than 10%, and the sheet resistance for the anode is preferably several hundreds Ω/□ or less. The film thickness is selected usually within 10 to 1000 nm, preferably within 10 to 200 nm though depending on the material.

——Cathode——

Meanwhile, regarding a cathode material, preferable to a material selected from a metal (an electron injection metal), an alloy, an electrically conductive compound, or a mixture thereof having a small work function (4 eV or less) are used. Specific examples of such an electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among these, from the viewpoint of the electron injectability and the durability against oxidation and the like, a mixture of an electron injection metal and a second metal which is a stable metal having a larger work function value is suitable, and examples thereof include a magnesium/silver mixture, a magnesium/aluminum mixture, a magnesium/indium mixture, an aluminum/aluminum oxide mixture, a lithium/aluminum mixture and aluminum. The cathode can be produced by forming a thin film by a method such as vapor-depositing or sputtering of such a cathode material. In addition, the sheet resistance of cathode is preferably several hundreds Ω/□ or less. The film thickness is selected usually within 10 nm to 5 μm, preferably within 50 to 200 nm. Note that for transmission of emitted light, if either one of the anode and cathode of the organic electroluminescent device is transparent or translucent, emission luminance is improved, which is convenient.

In addition, formation of a film of the above metal with a thickness of 1 to 20 nm on the cathode, followed by formation of a conductive transparent material described in the description on the anode thereon, enables production of a transparent or translucent cathode, and application of this enables production of a device wherein an anode and a cathode both have transmittance.

——Light-Emitting Layer——

The light-emitting layer is a layer that emits light after excitons are generated when holes and electrons injected from the anode and the cathode, respectively, are recombined. The light-emitting layer contains an organic light-emitting dopant material and a host material.

As a host material, the first host material, the second host material and the third host material are used.

Regarding the compound represented by the general formula (1) as the first host material, one kind thereof may be used, or two or more kinds thereof may be used. Likewise, regarding the carbazole compound or indolocarbazole compound represented by the general formulas (2) to (4) as the second host material, one kind thereof may be used, or two or more kinds thereof may be used. Regarding to the compound represented by the general formula (5), as the third host material, one kind thereof may be used, or two or more kinds thereof may be used.

If necessary, a material other than the first host material, the second host material and the third host material may be added.

When a plurality of the host materials, or the host materials and a dopant are premixed and used, it is desirable that a difference in 50% weight reduction temperature ($T_{50}$) be small in order to produce an organic electroluminescent device having favorable characteristics with high reproducibility. The 50% weight reduction temperature is a temperature at which the weight is reduced by 50% when the temperature is raised to 550° C. from room temperature at a rate of 10° C./min in TG-DTA measurement under a nitrogen stream reduced pressure (1 Pa). It is considered that vaporization due to evaporation or sublimation the most vigorously occurs around this temperature.

The difference in 50% weight reduction temperatures of the materials for use in the premixture is preferably within 15° C. and more preferably within 12° C.

The premixing method is desirably a method that can allow for mixing as uniformly as possible, and examples thereof include pulverization and mixing, a heating and melting method under reduced pressure or under an atmosphere of an inert gas such as nitrogen, and sublimation, but not limited thereto.

The forms of the hosts and the premixture thereof may be powdery, stick-shaped, or granular.

When a phosphorescent dopant is used as a light-emitting dopant material, preferred is a phosphorescent dopant including an organic metal complex containing at least one metal selected from ruthenium, rhodium, palladium, silver, rhenium, osmium, iridium, platinum and gold. Specifically, iridium complexes described in J. Am. Chem. Soc. 2001, 123, 4304 and JP2013-530515A are preferably used, but the phosphorescent dopant is not limited thereto.

Regarding the phosphorescent dopant material, only one kind thereof may be contained in the light-emitting layer, or two or more kinds thereof may be contained. A content of the phosphorescent dopant material is preferably 0.10 to 30 wt % and more preferably 1.0 to 20 wt % with respect to the host material.

The phosphorescent dopant material is not particularly limited, and specific examples thereof include the following.

[C 75]

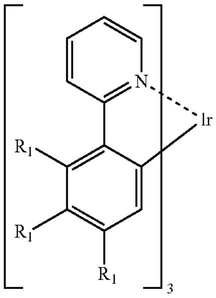

$R_1$: H, $CH_3$, $CF_3$, F

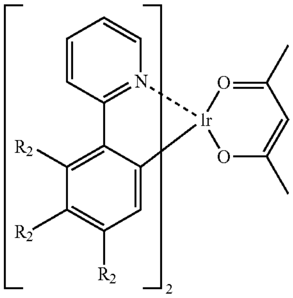

$R_2$: H, F

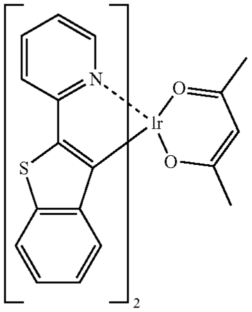

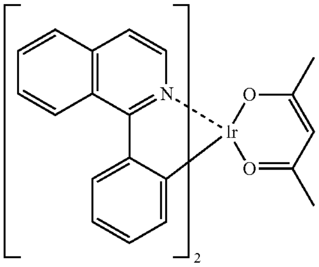

-continued

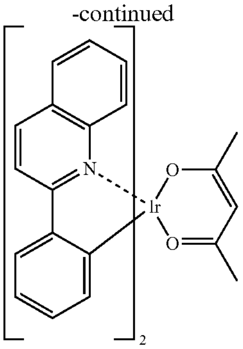

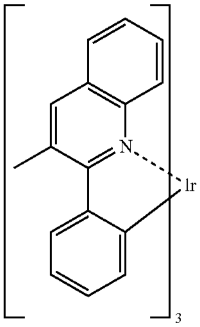

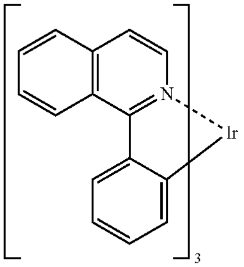

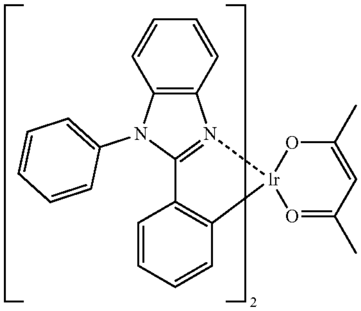

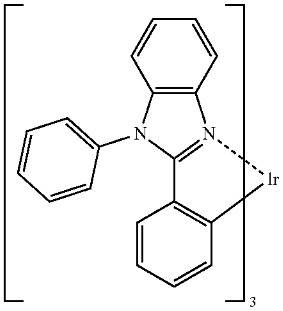

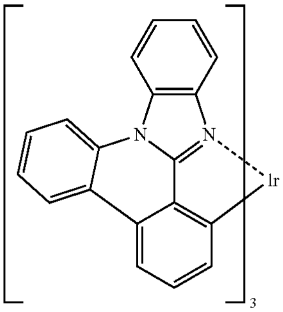

-continued
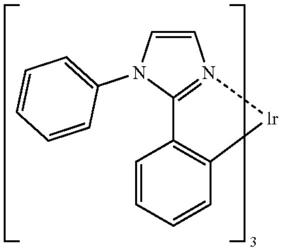
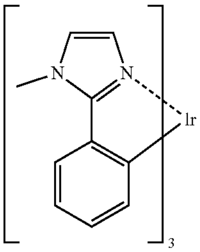
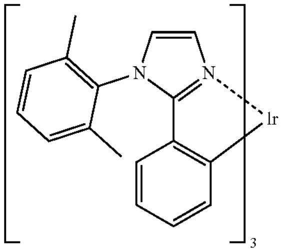
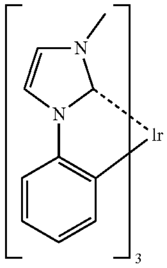
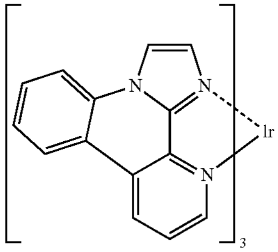
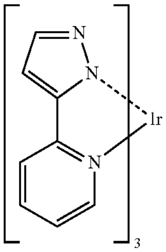
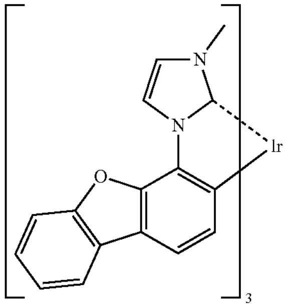
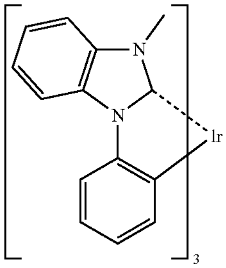
-continued
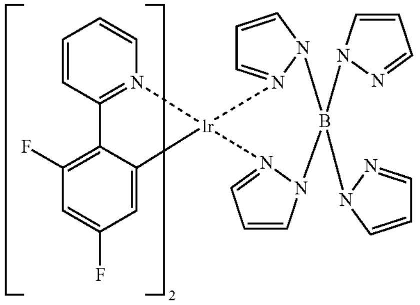
[C 76]
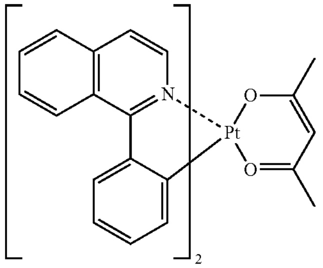
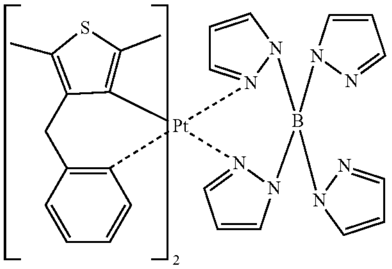
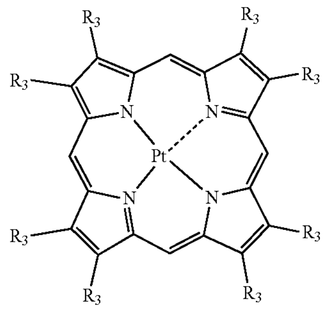
$R_3$: $CH_3$, $CH_2CH_3$
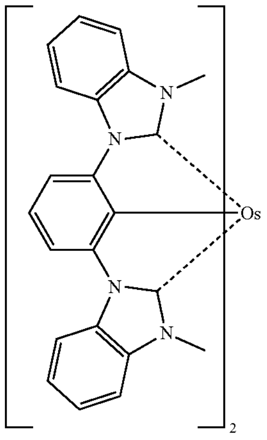

-continued

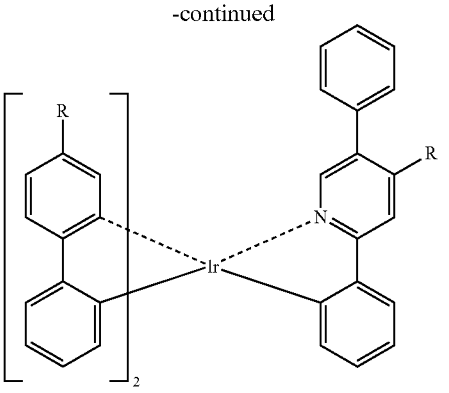

R: H, $CH_3$, $CD_3$

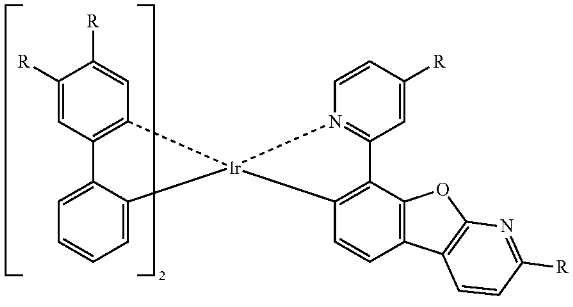

R: H, $CH_3$, $CD_3$

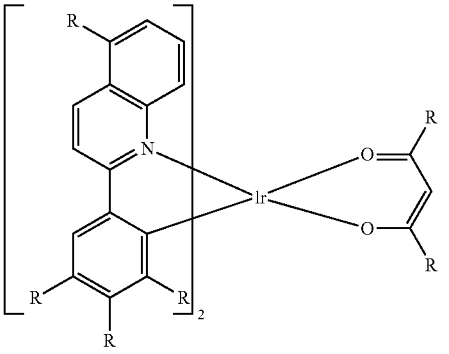

R: H, $CH_3$, $C_4H_9$, $CD_3$

When a fluorescence-emitting dopant is used as the light-emitting dopant material, the fluorescence-emitting dopant is not particularly limited. Examples thereof include benzoxazole derivatives, benzothiazole derivatives, benzimidazole derivatives, styrylbenzene derivatives, polyphenyl derivatives, diphenylbutadiene derivatives, tetraphenyl butadiene derivatives, naphthalimido derivatives, coumarin derivatives, fused aromatic compounds, perinone derivatives, oxadiazole derivatives, oxazine derivatives, aldazine derivatives, pyrrolidine derivatives, cyclopentadiene derivatives, bisstyryl anthracene derivatives, quinacridone derivatives, pyrrolopyridine derivatives, thiadiazolopyridine derivatives, styrylamine derivatives, diketopyrrolopyrrole derivatives, aromatic dimethylidine compounds, metal complexes of 8-quinolinol derivatives or metal complexes of pyromethene derivatives, rare earth complexes, various metal complexes represented by transition metal complexes, polymer compounds such as polythiophene, polyphenylene, and polyphenylene vinylene, and organosilane derivatives. Preferred examples thereof include fused aromatic derivatives, styryl derivatives, diketopyrrolopyrrole derivatives, oxazine derivatives, pyromethene metal complexes, transition metal complexes, and lanthanoid complexes. More preferable examples thereof include naphthalene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthalene, hexacene, naphtho[2,1-f]isoquinoline, α-naphthaphenanthridine, phenanthrooxazole, quinolino[6,5-f]quinoline, and benzothiophanthrene. These may have an alkyl group, an aryl group, an aromatic heterocyclic group, or a diarylamino group as a substituent.

Regarding the fluorescence-emitting dopant material, only one kind thereof may be contained in the light-emitting layer, or two or more kinds thereof may be contained. A content of the fluorescence-emitting dopant material is preferably 0.1% to 20% and more preferably 1% to 10% with respect to the host material.

When a thermally activated delayed fluorescence-emitting dopant is used as the light-emitting dopant material, the thermally activated delayed fluorescence-emitting dopant is not particularly limited. Examples thereof include: metal complexes such as a tin complex and a copper complex; indolocarbazole derivatives described in WO2011/070963A; cyanobenzene derivatives and carbazole derivatives described in Nature 2012, 492, 234; and phenazine derivatives, oxadiazole derivatives, triazole derivatives, sulfone derivatives, phenoxazine derivatives, and acridine derivatives described in Nature Photonics 2014, 8,326.

The thermally activated delayed fluorescence-emitting dopant material is not particularly limited, and specific examples thereof include the following.

[C 77]

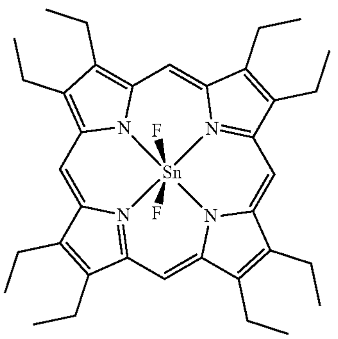

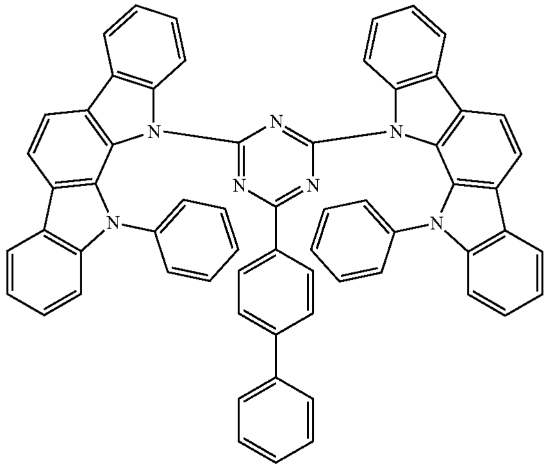

-continued

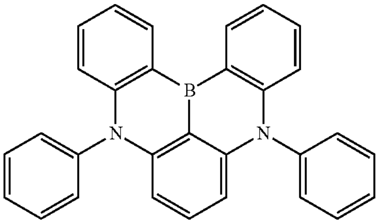

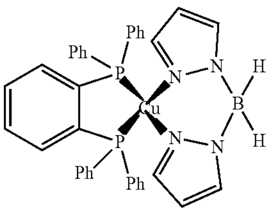

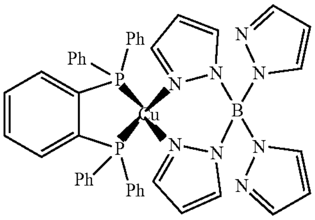

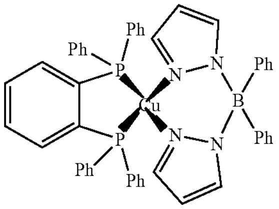

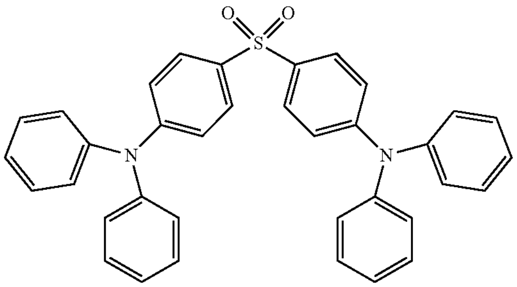

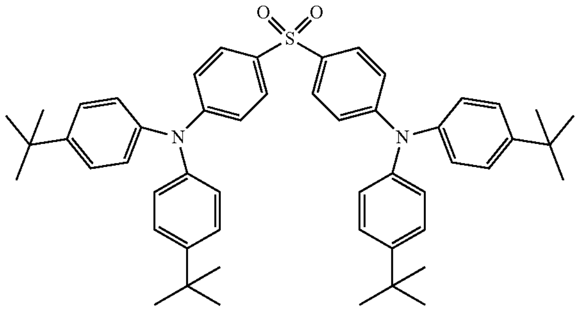

-continued

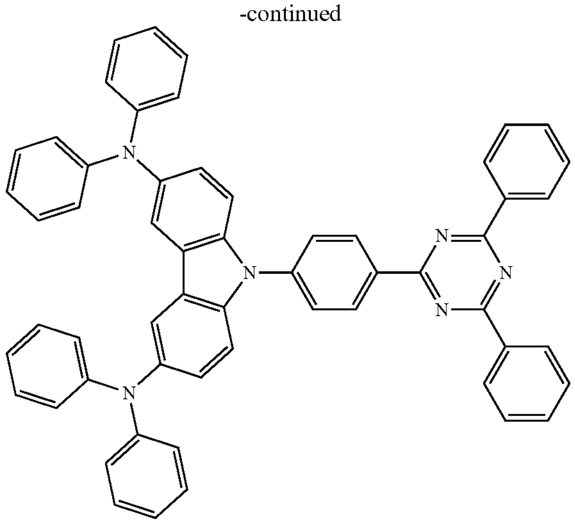

Regarding the thermally activated delayed fluorescence-emitting dopant material, only one kind thereof may be contained in the light-emitting layer, or two or more kinds thereof may be contained. In addition, the thermally activated delayed fluorescence-emitting dopant may be used by mixing with a phosphorescent dopant and a fluorescence-emitting dopant. A content of the thermally activated delayed fluorescence-emitting dopant material is preferably 0.10% to 50% and more preferably 1.0% to 30% with respect to the host material.

——Injection Layer——

The injection layer is a layer that is provided between an electrode and an organic layer in order to lower a driving voltage and improve emission luminance, and includes a hole injection layer and an electron injection layer, and may be present between the anode and the light-emitting layer or the hole transport layer, and between the cathode and the light-emitting layer or the electron transport layer. The injection layer can be provided as necessary.

——Hole Blocking Layer——

The hole blocking layer has a function of the electron transport layer in a broad sense, and is made of a hole blocking material having a function of transporting electrons and a significantly low ability to transport holes, and can block holes while transporting electrons, thereby improving a probability of recombining electrons and holes in the light-emitting layer.

For the hole blocking layer, a known hole blocking layer material can be used.

——Electron Blocking Layer——

The electron blocking layer has a function of a hole transport layer in a broad sense and blocks electrons while transporting holes, thereby enabling a probability of recombining electrons and holes in the light-emitting layer to be improved.

Regarding the material of the electron blocking layer, a known electron blocking layer material can be used and a material of the hole transport layer to be described below can be used as necessary. A film thickness of the electron blocking layer is preferably 3 to 100 nm, and more preferably 5 to 30 nm.

——Exciton Blocking Layer——

The exciton blocking layer is a layer for preventing excitons generated by recombination of holes and electrons in the light-emitting layer from being diffused in a charge transport layer, and insertion of this layer allows excitons to be efficiently confined in the light-emitting layer, enabling the luminous efficiency of the device to be improved. The exciton blocking layer can be inserted, in a device having two or more light-emitting layers adjacent to each other, between two adjacent light-emitting layers.

Regarding the material of the exciton blocking layer, a known exciton blocking layer material can be used. Examples thereof include 1,3-dicarbazolyl benzene (mCP) and bis(2-methyl-8-quinolinolato)-4-phenylphenolato aluminum (III) (BAlq).

——Hole Transport Layer——

The hole transport layer is made of a hole transport material having a function of transporting holes, and the hole transport layer can be provided as a single layer or a plurality of layers.

The hole transport material has either hole injection, transport properties or electron barrier properties, and may be an organic material or an inorganic material. For the hole transport layer, any one selected from conventionally known compounds can be used. Examples of such a hole transport material include porphyrin derivatives, arylamine derivatives, triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styryl anthracene derivatives, fluorenone derivatives, hydrazone derivatives, stilbene derivatives, silazane derivatives, an aniline copolymer, and a conductive polymer oligomer, and particularly a thiophene oligomer. Use of porphyrin derivatives, arylamine derivatives, or styrylamine derivatives preferred. Use of arylamine compounds is more preferred.

——Electron Transport Layer——

The electron transport layer is made of a material having a function of transporting electrons, and the electron transport layer can be provided as a single layer or a plurality of layers.

The electron transport material (which may also serve as a hole blocking material) may have a function of transferring electrons injected from the cathode to the light-emitting layer. For the electron transport layer, any one selected from conventionally known compounds can be used, and examples thereof include polycyclic aromatic derivatives such as naphthalene, anthracene, and phenanthroline, tris(8-quinolinolato)aluminum(III) derivatives, phosphine oxide derivatives, nitro-substituted fluorene derivatives, diphenylquinone derivatives, thiopyrandioxide derivatives, carbodiimide, (fluorenylidene)methane derivatives, anthraquinodimethane and anthrone derivatives, bipyridine derivatives, quinoline derivatives, oxadiazole derivatives, benzimidazole derivatives, benzothiazole derivatives, and indolocarbazole derivatives. In addition, a polymer material in which the above material is introduced into a polymer chain or the above material is used for a main chain of a polymer can be used.

EXAMPLES

Hereafter, the present invention will be described in detail by referring to Examples, but the present invention is not limited these Examples and can be implemented in various forms without departing from the gist thereof.

"%" expressing the compounding proportion and the concentration means "wt %".

Example 1

The LUMO energy and the T1 energy of each compound used for a first host material, a second host material and a third host material were calculated by performing structure optimization calculation at the B3LYP/6-31G* level with molecular orbital method program Gaussian 03 according to the density functional theory (DFT). Results are shown in Table 1.

The LUMO energy and the T1 energy of each compound used in Comparative Examples are shown in Table 1.

TABLE 1

| Compound | LUMO (eV) | T1 (eV) |
|---|---|---|
| 1-326 | −2.01 | 2.68 |
| 1-327 | −1.98 | 2.70 |
| 1-217 | −2.00 | 2.66 |
| 1-6 | −1.98 | 2.75 |
| 3-21 | −0.94 | 2.97 |
| 3-33 | −0.96 | 2.96 |
| 4-69 | −1.32 | 3.16 |
| 2-3 | −0.98 | 3.01 |
| 2-51 | −1.26 | 2.65 |
| 2-2 | −0.98 | 3.01 |
| 2-43 | −0.99 | 3.00 |
| 5-2 | −1.93 | 2.73 |
| 5-3 | −1.88 | 2.81 |
| 5-38 | −1.92 | 2.73 |
| 5-151 | −1.93 | 2.73 |
| 5-152 | −1.93 | 2.73 |
| A | −2.02 | 2.38 |
| B | −1.20 | 3.01 |
| C | −2.15 | 2.49 |

Example 2

On a glass substrate on which an anode made of ITO with a film thickness of 110 nm was formed, respective thin films were stacked by a vacuum evaporation method at a degree of vacuum of $4.0\times10^{-5}$ Pa. First, HAT-CN was formed with a thickness of 25 nm as a hole injection layer on ITO, and next, NPD was formed with a thickness of 30 nm as a hole transport layer. Next, HT-1 was formed with a thickness of 10 nm as an electron blocking layer. Then, compound 1-326 as a first host material, compound 3-21 as a second host material, compound 5-2 as a third host material and $Ir(ppy)_3$ as a light-emitting dopant were co-vapor deposited from different vapor deposition sources, respectively, to form a light-emitting layer with a thickness of 40 nm. In this case, co-vapor deposition was performed under vapor deposition conditions such that the concentration of $Ir(ppy)_3$ was 10% and the concentration of the host material was 90% (the ratio among the first host material, the second host material and the third host material was 5%:70%:25%). Next, ET-1 was formed with a thickness of 20 nm as an electron transport layer. Further, LiF was formed with a thickness of 1 nm as an electron injection layer on the electron transport layer. Finally, Al was formed with a thickness of 70 nm as a cathode on the electron injection layer to produce an organic electroluminescent device.

Examples 3 to 17

Organic electroluminescent devices were produced in the same manner as in Example 2 except that the first host material, the second host material and the third host material, and the proportions of the first host material, the second host material and the third host material were as shown in Table 2.

The luminance, driving voltage, luminous efficiency and lifetime characteristics of each of the organic electroluminescent devices produced in Examples 2 to 17 are shown in Table 2. In the table, the luminance, driving voltage, and luminous efficiency are values obtained at a driving current of 20 mA/cm$^2$, and exhibit initial characteristics. LT70 is a time period taken for a reduction in luminance to 70% of an initial luminance of 9000 cd/m$^2$, and represents lifetime characteristics. The same also applies to the following table.

The numbers in brackets in each column of the first host, the second host, and the third host are compounding proportions.

TABLE 2

| Example | First host | Second host | Third host | Luminance (cd/m$^2$) | Voltage (V) | Power efficiency (lm/W) | LT70 (h) |
|---|---|---|---|---|---|---|---|
| 2 | 1-326 (5%) | 3-21 (70%) | 5-2 (25%) | 11,830 | 4.4 | 42.1 | 3,270 |
| 3 | 1-326 (10%) | 3-21 (70%) | 5-2 (20%) | 11,520 | 4.3 | 41.9 | 3,300 |
| 4 | 1-326 (20%) | 3-21 (70%) | 5-2 (10%) | 11,510 | 4.1 | 43.9 | 3,250 |
| 5 | 1-326 (10%) | 3-21 (80%) | 5-2 (10%) | 12,330 | 4.3 | 40.1 | 3,460 |
| 6 | 1-326 (10%) | 3-33 (70%) | 5-3 (20%) | 12,140 | 4.4 | 43.2 | 3,220 |
| 7 | 1-327 (10%) | 4-69 (70%) | 5-2 (20%) | 11,830 | 4.6 | 40.2 | 3,560 |
| 8 | 1-327 (20%) | 4-69 (70%) | 5-2 (10%) | 11,840 | 4.4 | 42.1 | 3,500 |
| 9 | 1-217 (10%) | 2-3 (70%) | 5-3 (20%) | 12,330 | 4.4 | 43.9 | 3,720 |
| 10 | 1-217 (20%) | 2-3 (70%) | 5-3 (10%) | 12,350 | 4.2 | 46.0 | 3,700 |
| 11 | 1-327 (10%) | 2-51 (70%) | 5-3 (20%) | 12,160 | 4.4 | 43.3 | 3,040 |
| 12 | 1-6 (10%) | 2-3 (70%) | 5-38 (20%) | 11,970 | 4.2 | 44.6 | 4,040 |
| 13 | 1-6 (10%) | 2-3 (80%) | 5-38 (10%) | 11,830 | 4.4 | 42.1 | 4,070 |
| 14 | 1-6 (10%) | 2-3 (70%) | 5-151 (20%) | 11,330 | 4.6 | 38.5 | 3,520 |
| 15 | 1-327 (10%) | 2-2 (70%) | 5-38 (20%) | 11,470 | 4.4 | 40.8 | 4,020 |
| 16 | 1-6 (10%) | 2-43 (70%) | 5-152 (20%) | 11,220 | 1.4 | 39.3 | 3,380 |
| 17 | 1-6 (3%) | 2-43 (70%) | 5-152 (27%) | 11,340 | 4.6 | 38.6 | 3,520 |

Example 18

The 50% weight reduction temperatures ($T_{50}$) of compounds used as the first host material, the second host material and the third host material were measured. Results are shown in Table 3.

TABLE 3

| Compound | $T_{50}$ [° C.] |
|---|---|
| 1-6 | 312 |
| 2-3 | 315 |
| 5-151 | 312 |
| 2-2 | 279 |
| 5-38 | 278 |
| 2-43 | 316 |
| 5-152 | 311 |
| 1-327 | 273 |

Example 19

Premixture H1 was prepared by weighing first host material 1-6 (0.10 g), second host material 2-3 (0.70 g) and third host material 5-151 (0.20 g) and mixing them with grinding in a mortar.

On a glass substrate on which an anode made of ITO with a film thickness of 110 nm was formed, respective thin films were stacked by a vacuum evaporation method at a degree of vacuum of $4.0\times10^{-5}$ Pa. First, HAT-CN was formed with a thickness of 25 nm as a hole injection layer on ITO, and next, NPD was formed with a thickness of 30 nm as a hole transport layer. Next, HT-1 was formed with a thickness of 10 nm as an electron blocking layer. Then, premixture H1 and $Ir(ppy)_3$ as a light-emitting dopant were co-vapor deposited from different vapor deposition sources, respectively, to form a light-emitting layer with a thickness of 40 nm. In this case, co-vapor deposition was performed under vapor deposition conditions such that the concentration of $Ir(ppy)_3$ was 10% and the concentration of the host material was 90%. Next, ET-1 was formed with a thickness of 20 nm as an electron transport layer. Further, LiF was formed with a thickness of 1 nm as an electron injection layer on the electron transport layer. Finally, Al was formed with a thickness of 70 nm as a cathode on the electron injection layer to produce an organic electroluminescent device.

Examples 20 to 23

Premixtures H2 to H5 were prepared in the same manner as in Example 19 except that the types and the compounding proportions of the first host material, the second host material and the third host material were as shown in Table 4.

Organic electroluminescent devices were produced in the same manner as in Example 19 except that premixtures H2 to H5 were used.

TABLE 4

| Premixture | First host | Second host | Third host |
|---|---|---|---|
| H1 | 1-6 (10%) | 2-3 (70%) | 5-151 (20%) |
| H2 | 1-6 (20%) | 2-3 (70%) | 5-151 (10%) |
| H3 | 1-327 (10%) | 2-2 (70%) | 5-38 (20%) |
| H4 | 1-327 (20%) | 2-2 (70%) | 5-38 (10%) |
| H5 | 1-6 (10%) | 2-43 (70%) | 5-152 (20%) |

Evaluation results of the organic electroluminescent devices in produced Examples 19 to 23 are shown in Table 5.

TABLE 5

| Example | Premixture | Luminance ($cd/m^2$) | Voltage (V) | Power efficiency (lm/W) | LT70 (h) |
|---|---|---|---|---|---|
| 19 | H1 | 11,300 | 4.4 | 40.2 | 3,790 |
| 20 | H2 | 11,230 | 4.2 | 41.8 | 3,850 |
| 21 | H3 | 11,480 | 4.2 | 42.8 | 4,050 |
| 22 | H4 | 11,450 | 4.0 | 44.8 | 4,040 |
| 23 | H5 | 11,280 | 4.3 | 41.1 | 3,830 |

Comparative Examples 1 to 5

Organic electroluminescent devices were produced in the same manner as in Example 2 except that the types and the compounding proportions of the first host material, the second host material and the third host material were as shown in Table 6.

Evaluation results of the produced organic electroluminescent devices are shown in Table 6.

TABLE 6

| Comparative Example | First host | Second host | Third host | Luminance ($cd/m^2$) | Voltage (V) | Power efficiency (lm/W) | LT70 (h) |
|---|---|---|---|---|---|---|---|
| 1 | — | 3-33 (70%) | 5-3 (30%) | 11,070 | 4.9 | 35.4 | 3,210 |
| 2 | — | 2-43 (70%) | 5-152 (30%) | 11,150 | 4.9 | 35.6 | 3,460 |
| 3 | 1-6 (30%) | 2-3 (70%) | — | 10,900 | 4.0 | 42.6 | 2,450 |
| 4 | A (10%) | B (70%) | C (20%) | 530 | 4.3 | 1.9 | 2,150 |
| 5 | — | 2-3 (70%) | 5-2 (10%) 5-151 (20%) | 11,200 | 5.0 | 35.1 | 3,580 |

Comparative Examples 7 to 8

Premixture H6 to H7 were prepared in the same manner as in Example 19 except that the types and the compounding proportions of the host materials were as shown in Table 7.

TABLE 7

| Premixture | Second host | Third host |
|---|---|---|
| H6 | 2-3 (70%) | 5-151 (30%) |
| H7 | 2-3 (70%) | 5-152 (10%) 5-151 (20%) |

Organic electroluminescent devices were produced in the same manner as in Example 19 except that premixtures H6 to H7 were used.

Evaluation results of the produced organic electroluminescent devices are shown in Table 8.

TABLE 8

| Comparative Example | Premixture | Luminance ($cd/m^2$) | Voltage (V) | Power efficiency (lm/W) | LT70 (h) |
|---|---|---|---|---|---|
| 8 | H6 | 11,230 | 4.9 | 35.9 | 3,600 |
| 9 | H7 | 11,250 | 4.9 | 35.9 | 3,550 |

It can be seen from the foregoing that Examples, while exhibit lifetime characteristics comparable with or more than those of Comparative Examples, exhibit improved driving voltage and power efficiency. In other words, the present invention realizes an organic electroluminescent device having simultaneously respective characteristics of lifetime characteristics, driving voltage, and power efficiency at favorable levels.

Compounds used in Examples and Comparative Examples are shown below.
[C 34]
HAT-CN
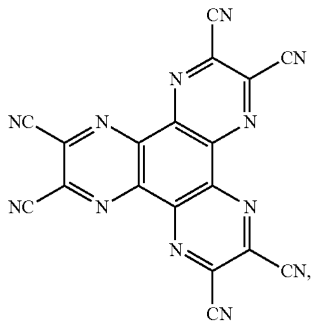
NPD
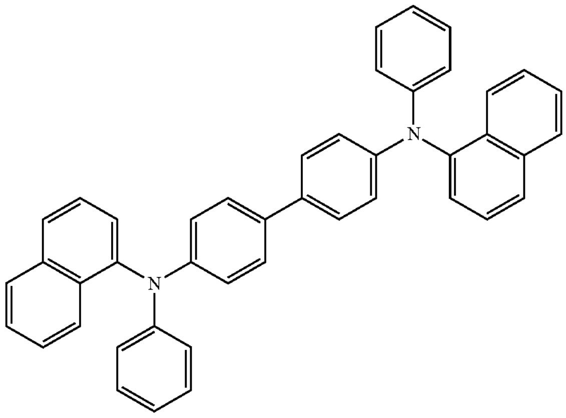
,
HT-1
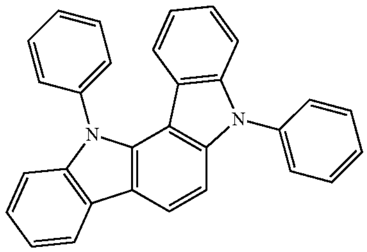
,
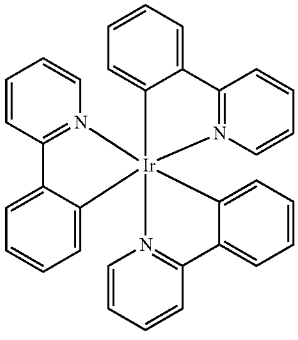
,
Ir(ppy)3
-continued
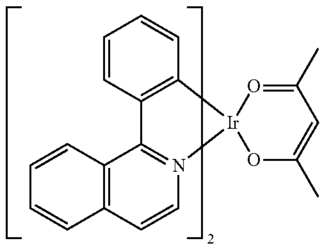
Ir(piq)2acac
ET-1
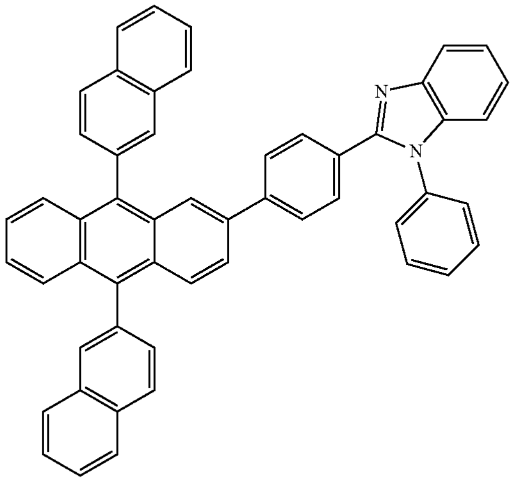
A
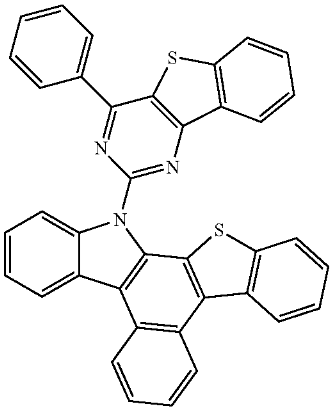

-continued

B

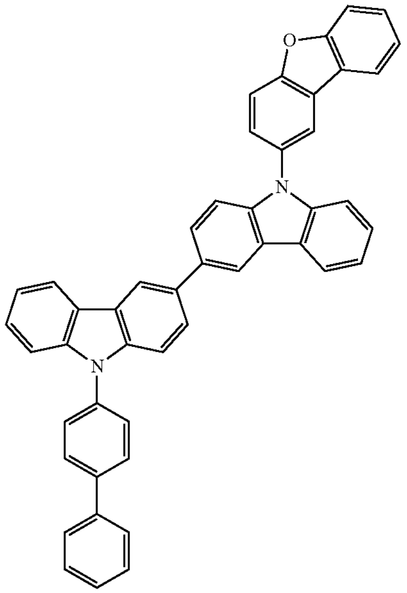

C

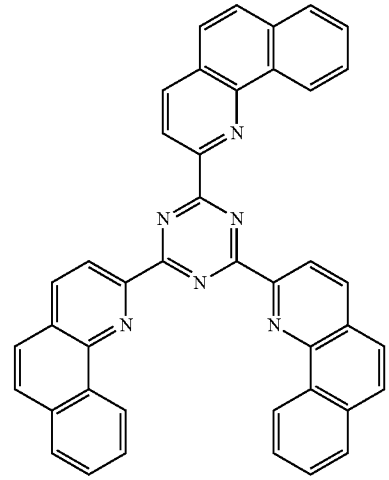

The invention claimed is:

1. An organic electroluminescent device comprising one or more light-emitting layers between an anode and a cathode opposed to each other, wherein at least one of the light-emitting layers contains a host material comprising a first host material, a second host material and a third host material, and a light-emitting dopant material, a LUMO energy of the first host material is −1.95 eV or less, a LUMO energy of the second host material is −1.54 eV or more, and LM2≥LM3≥LM1 is satisfied under the assumption that LUMO energies of the first host material, the second host material and the third host material are LM1, LM2 and LM3, respectively, wherein the LUMO energies of the first, second, and third host materials are calculated by performing structure optimization calculation at the B3LYP/6-31G* level with the molecular orbital method program Gaussian 03 according to the density functional theory (DFT).

2. The organic electroluminescent device according to claim 1, wherein the LUMO energy of the third host material is −1.94 to −1.77 eV.

3. The organic electroluminescent device according to claim 1, wherein triplet excitation (T1) energies of the first host material, the second host material and the third host material are each 2.55 eV or more as calculated using the program Gaussian 03 according to density functional theory (DFT) at the B3LYP/6-31G* level.

4. The organic electroluminescent device according to claim 1, which is an organic electroluminescent device comprising one or more light-emitting layers between an anode and a cathode opposed to each other, wherein at least one of the light-emitting layers contains a first host material, a second host material and a third host material, and a light-emitting dopant material, and at least three materials selected from the first host material, the second host material, the third host material, and the light-emitting dopant contained in the light-emitting layers are vapor deposited from one vapor deposition source.

5. The organic electroluminescent device according to claim 4, wherein the first host material, the second host material and the third host material are vapor deposited from one vapor deposition source.

6. The organic electroluminescent device according to claim 1, wherein the light-emitting dopant material is a material emitting fluorescence including thermally activated delayed fluorescence.

7. The organic electroluminescent device according to claim 1, wherein the light-emitting dopant material is a phosphorescence-emitting material.

8. The organic electroluminescent device according to claim 1, wherein the first host material is a compound represented by the following general formula (1):

(1)

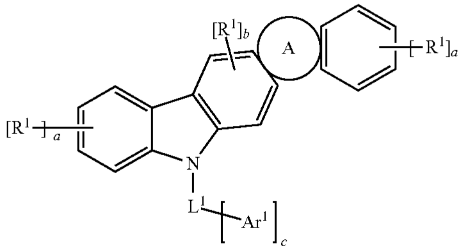

(1a)

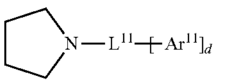

wherein a ring A is a heterocycle represented by formula (1a) and the ring A is fused to an adjacent ring at any position, $R^1$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, a, c and d each independently represent an integer of 0 to 4, and b represents an integer of 0 to 2, $L^1$ and $L^{11}$ independently represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group, and $Ar^1$ and $Ar^{11}$ each independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other.

9. The organic electroluminescent device according to claim 8, wherein at least one of $L^1$ and $L^{11}$ is a substituted or unsubstituted nitrogen-containing 6-membered ring group, or a substituted or unsubstituted ring-fused aromatic heterocyclic group containing a nitrogen-containing 6-membered ring.

10. The organic electroluminescent device according to claim 8, wherein the general formula (1) is the following formula (11):

(11)

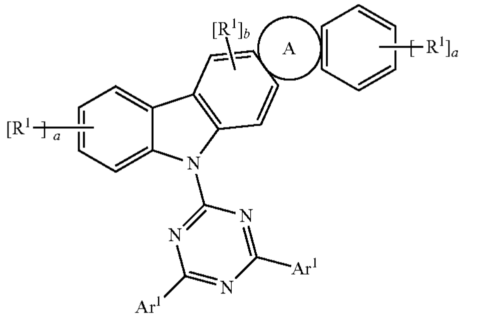

wherein $R^1$, ring A, $Ar^1$, a, and b are as defined for the general formula (1).

11. The organic electroluminescent device according to claim 10, wherein formula (11) is a compound represented by the following formula (12) or formula (13):

(12)

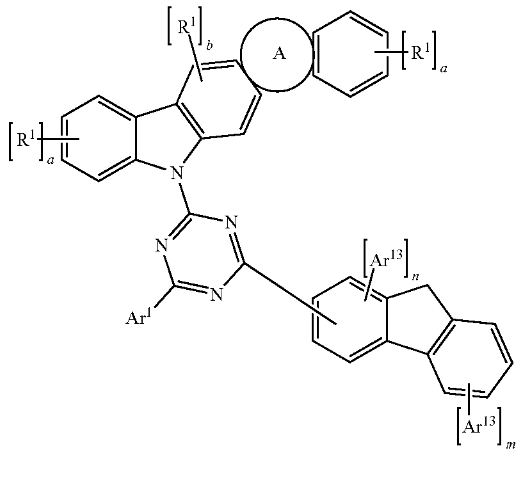

-continued (13)

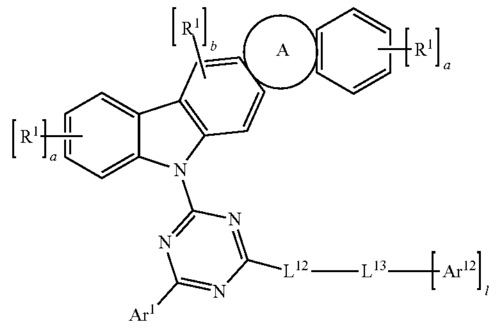

wherein $R^1$, ring A, $Ar^1$, a and b are as defined for the general formula (1), Y represents O, S, $NAr^{14}$, or $CAr^{15}Ar^{16}$, $Ar^{13}$, $Ar^{14}$, $Ar^{15}$, and $Ar^{16}$ each independently represent an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, m represents an integer of 0 to 4, n represents an integer of 0 to 3, and 1 represents an integer of 0 to 4, $L^{12}$ represents a substituted or unsubstituted aromatic hydrocarbon group having 6 to 30 carbon atoms, $L^{13}$ represents a nitrogen-containing 6-membered ring group, and $Ar^{12}$ independently represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other.

12. The organic electroluminescent device according to claim 1, wherein the second host material is a compound represented by the following general formula (2), general formula (3), or general formula (4):

(2)

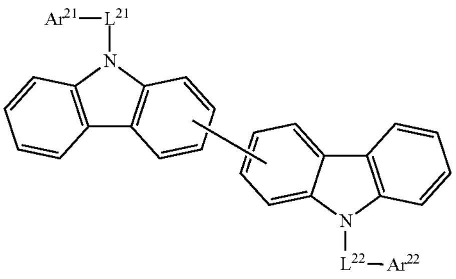

wherein $Ar^{21}$ and $Ar^{22}$ independently represent hydrogen, deuterium, a substituted or unsubstituted aromatic hydrocarbon group having 6 to 14 carbon atoms, a substituted or unsubstituted aromatic heterocyclic group having 3 to 17 carbon atoms, or a substituted or unsubstituted linked aromatic group in which two of the aromatic rings are linked to each other; and $L^{21}$ and $L^{22}$ independently represent a direct bond or a phenylene group;

(3)

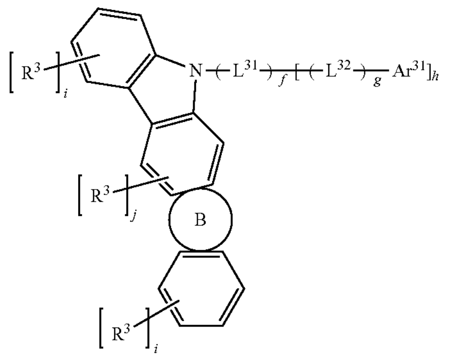

(3a)

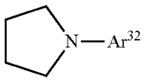

wherein a ring B is a heterocycle represented by formula (3a) and the ring B is fused to an adjacent ring at any position, $R^3$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, $L^{31}$ independently represents a substituted or unsubstituted aromatic hydrocarbon group having 6 to 30 carbon atoms, or a substituted or unsubstituted aromatic heterocyclic group having 3 to 17 carbon atoms, $L^{32}$ independently represents a substituted or unsubstituted aromatic hydrocarbon group having 6 to 10 carbon atoms, $Ar^{31}$ represents a substituted or unsubstituted aromatic hydrocarbon group having 6 to 10 carbon atoms, a substituted or unsubstituted carbazolyl group, or a substituted or unsubstituted linked aromatic group in which two to five of these aromatic rings are linked to each other, $Ar^{32}$ represents a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, i represents an integer of 0 to 4, and j represents an integer of 0 to 2, f is the number of repetitions, and represents an integer of 1 to 3, g is the number of repetitions and independently represents an integer of 0 to 3, and h represents the number of substitutions and represents an integer of 0 to 7;

(4)

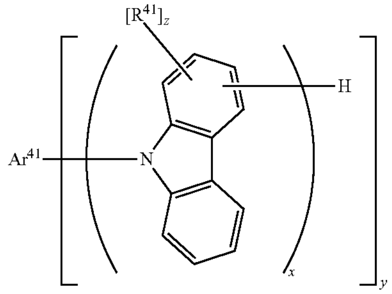

wherein $Ar^{41}$ represents a substituted or unsubstituted aromatic hydrocarbon group having 6 to 30 carbon atoms, a substituted or unsubstituted aromatic heterocyclic group having 3 to 17 carbon atoms, or a linked aromatic group in which two to five of these aromatic rings are linked; when $Ar^{41}$ has a hydrogen atom, the hydrogen atom may be replaced by deuterium, $R^{41}$ each independently represents deuterium, an aliphatic hydrocarbon group having 1 to 10 carbon atoms, a substituted or unsubstituted aromatic hydrocarbon group having 6 to 30 carbon atoms, or a substituted or unsubstituted aromatic heterocyclic group having 3 to 17 carbon atoms, provided that $R^{41}$ is not a carbazolyl group, x is the number of repetitions and independently represents an integer of 1 to 4, and at least one x is an integer of 2 to 4; y is the number of substitutions and independently represents an integer of 1 to 4; and when x and y is 2 or more, a plurality of carbazolyl groups may be the same or different; and z is an integer of 0 to 3.

13. The organic electroluminescent device according to claim 1, wherein the third host material is a compound represented by general formula (5):

(5)

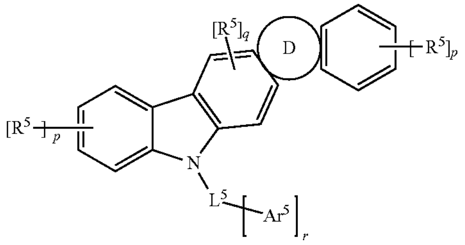

(5a)

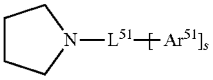

wherein a ring D is a heterocycle represented by formula (5a) and the ring D is fused to an adjacent ring at any position, $R^5$ independently represents deuterium, an aliphatic hydrocarbon group having 1 to 10 carbon atoms, a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to five of these aromatic rings are linked to each other, p, r and s each independently represent an integer of 0 to 4, and q represents an integer of 0 to 2, $L^5$ and $L^{51}$ independently represent a substituted or unsubstituted aromatic hydrocarbon group having 6 to 30 carbon atoms, or a substituted or unsubstituted aromatic heterocyclic group having 3 to 17 carbon atoms, and at least one thereof represents the aromatic heterocyclic group, and $Ar^5$ and $Ar^{51}$ each independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group in which two to seven of these aromatic rings are linked to each other.

14. The organic electroluminescent device according to claim 13, wherein at least one of $L^5$ and $L^{51}$ represents a substituted or unsubstituted nitrogen-containing 6-membered ring or ring-fused aromatic heterocyclic group containing a nitrogen-containing 6-membered ring.

15. The organic electroluminescent device according to claim 13, wherein the third host material is a compound represented by the following formula (51):

(51)

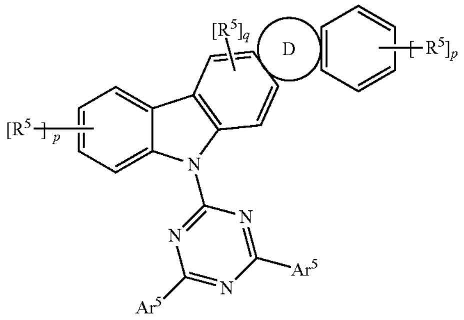

wherein $R^5$, D, $Ar^5$, p, and q are as defined for the general formula (5).

16. The organic electroluminescent device according to claim 15, wherein a proportion of the first host material is larger than 1.0 wt % and less than 30 wt % and a proportion of the third host material is larger than 5.0 wt % and less than 80 wt % based on the first host material, the second host material and the third host material in total.

17. A method for producing an organic electroluminescent device comprising one or more light-emitting layers between an anode and a cathode opposed to each other, at least one of the light-emitting layers comprising a host material comprising a first host material, a second host material and a third host material, and a light-emitting dopant material, the method comprising forming each of the light-emitting layers by vapor depositing the light-emitting dopant material and a host material composition in which a LUMO energy of the first host material is −1.95 eV or less, a LUMO energy of the second host material is −1.54 eV or more, and LM2≥LM3≥LM1 is satisfied under the assumption that LUMO energies of the first host material, the second host material and the third host material are LM1, LM2 and LM3, respectively, wherein the LUMO energies of the first, second, and third host materials are calculated by performing structure optimization calculation at the B3LYP/6-31G* level with the molecular orbital method program Gaussian 03 according to the density functional theory (DFT).

18. A host material composition for use in the method for producing an organic electroluminescent device according to claim 17.

* * * * *